US012678472B2

(12) United States Patent
Cordier et al.

(10) Patent No.: US 12,678,472 B2
(45) Date of Patent: Jul. 14, 2026

(54) METHOD FOR SELECTIVE RECOVERY OF HYDROPHOBIC COMPOUNDS

(71) Applicant: Grow Biotech PLC, London (GB)

(72) Inventors: Christopher James Cordier, London (GB); Sadaf Saad Anjum, London (GB); Henry Alexander Fisher, London (GB); Benjamin Thomas Langley, London (GB); Ian Joseph Atkinson, Cochrane (CA); Laurence Busch Hansen, London (GB)

(73) Assignee: Grow Biotech PLC, London (GB)

( * ) Notice: Subject to any disclaimer, the term of this patent is extended or adjusted under 35 U.S.C. 154(b) by 1034 days.

(21) Appl. No.: 17/735,505

(22) PCT Filed: Nov. 4, 2020

(86) PCT No.: PCT/GB2020/052792

§ 371 (c)(1),
(2) Date: May 3, 2022

(87) PCT Pub. No.: WO2021/090003

PCT Pub. Date: May 14, 2021

(65) Prior Publication Data

US 2022/0363658 A1     Nov. 17, 2022

Related U.S. Application Data

(60) Provisional application No. 62/930,459, filed on Nov. 4, 2019.

(51) Int. Cl.
*C07D 311/80* (2006.01)
*A61K 36/185* (2006.01)
*C07C 37/68* (2006.01)

(52) U.S. Cl.
CPC ........ *A61K 36/3482* (2024.05); *C07C 37/685* (2013.01); *C07D 311/80* (2013.01)

(58) Field of Classification Search
CPC .................................................. C07D 311/80
See application file for complete search history.

(56) References Cited

U.S. PATENT DOCUMENTS

| | | |
|---|---|---|
| 2006/0078955 A1 | 4/2006 | Lin et al. |
| 2022/0023771 A1 | 1/2022 | Cannazza et al. |

FOREIGN PATENT DOCUMENTS

| | | |
|---|---|---|
| CN | 1589246 A | 3/2005 |
| CN | 104353431 A | 2/2015 |
| CN | 107383115 A | 11/2017 |
| CN | 109833312 A | 6/2019 |
| CN | 110204426 A | 9/2019 |
| DE | 102012105613 A1 | 1/2014 |
| KR | 20050039328 A | 4/2005 |
| WO | 2020121218 A2 | 6/2020 |
| WO | 2020168421 A1 | 8/2020 |

OTHER PUBLICATIONS

Yu et al., "Molecular Recognition and Assembly of Supramolecular Chemical Synthesis Receptors," Nankai University Press, 2001, p. 286.
Chinese Patent Application No. CN202080077114, Office Action and Search Report dated Apr. 8, 2023. English Translation not available.
Yuqing, et al., "Cross-linking of B-cyclodextrin Polymers With Hexamethylene Diisocyanate Underultrasonic Irradiation," Chemical Industry and Engineering Progress, 2011, pp. 1900-1905.
Zainal-Abidin, Mohamad Hamdi, et al. "New Horizons in the Extraction of Bioactive Compounds using Deep Eutectic Solvents: A Review," Analytica Chimica Acta (2017).
Zulfiqar, Fazila, et al. "Cannabisol, a novel $\Delta^9$-THC dimer possessing a unique methylene bridge, isolated from Cannabis sativa," Tetrahedron Letters 53 (2012) 3560-3562.
International Patent Application No. PCT/GB2020/052792, International Preliminary Report on Patentability dated Jan. 25, 2022.
International Patent Application No. PCT/GB2020/052792, International Search Report and Written Opinion dated Feb. 1, 2021.
Ahmed, S. A.; Ross, S. A.; Slade, D.; Radwan, M. M.; Zulfigar, F.; ElSohly, M. A. "Cannabinoid Ester Constituents from High-Potency Cannabis sativa," J. Nat. Prod. 2008, 71(4), 536-542.
Al-Zouabi, et al. "Butane hash oil and dabbing: insights into use, amateur production techniques, and potential harm mitigation," Substance Abuse and Retaliation. 2018: 9 91-101.
Ameh, S. J.; Obodozie, O. O.; Babalola, P. C.; Gamaniel, K. S. Br. J. Pharmacol. Res. 2011, 1(4), 99-123.
Anderson, R. P.; Zechar, K. Respir. Med. Case Rep. 2019, 26, 171-173.
Arslan et al., "Enantioselective Sorption of Some Chiral Carboxylic Acids by Various Cyclodextrin-Grafted Iron Oxide Magnetic Nanoparticles, " Tetrahedron Asymmetry, 2013, vol. 24(17), pp. 982-989.
Azmir, J. et al. "Techniques for extraction of bioactive compounds from plant materials: A review," Journal of Food Engineering, 117 (2013) 426-436.

(Continued)

*Primary Examiner* — John S Kenyon
(74) *Attorney, Agent, or Firm* — Daniel A. Blasiole; DeWitt LLP

(57) ABSTRACT

A method of selectively recovering a hydrophobic target substance. The method is applied to a solution of the target substance in a hydrophobic solvent. An insoluble polysaccharide is combined with the solution, the solution is passed over the insoluble polysaccharide or otherwise exposed to the insoluble polysaccharide. A hydrophilic solvent, which is less hydrophobic than the hydrophobic solvent, is combined with the solution or combined with the hydrophobic target substance and the insoluble polysaccharide after evaporation of the hydrophobic solvent to facilitate binding of the insoluble polysaccharide with the target substance rather than remaining in solution in the hydrophobic solvent. The cyclic polysaccharide is isolated from the solution. A dissociation solvent is combined with the cyclic polysaccharide for solubilizing the target substance from the cyclic polysaccharide and recovering the target substance.

30 Claims, 65 Drawing Sheets

(56) References Cited

OTHER PUBLICATIONS

Berman, Paul, et al. "A new ESI-LC/MS approach for comprehensive metabolic profiling of phytocannabinoids in Cannabis," Scientific Reports (2018) 8:14280.

Braganca de Carvalho, Lucas, et al. "Cyclodextrin/silica hybrid adsorbent for removal of methylene blue in aqueous media," J Incl Phenom Marcocycl Chem. (2014) 78:77-87.

Cai, Changyong et al. "Green extraction of cannabidiol from industrial hemp (*Cannabis sativa* L.) using deep eutectic solvents coupled with further enrichment and recovery by macroporous resin." Journal of Molecular Liquids (2018).

Claude, Berengere, et al. "Selective solid-phase extraction of a triterpene acid from a plant extract by molecularly imprinted polymer," Talanta 75 (2008) 344-350.

Cordier, Christopher, et al. "Natural products as an inspiration in the diversity-oriented synthesis of bioactive compound libraries," Nat. Prod. Rep., 2008, 25, 719-737.

Crini, Gregorio. "Review: A History of Cyclodextrins," Chemical Reviews (2014).

Davison, Emma K. & Brimble, Margaret A. "Natural product derived privileged scaffolds in drug discovery," Current Opinion in Chemical Biology (2019) 52:1-8.

Del Valle, E.M. Martin. "Cyclodextrins and their uses: a review," Process Biochemistry (2003).

Doorenbos, Norman J. et al. "Cultivation, Extraction, and Analysis of *Cannabis Sativa* L.," Part I. Annals New York Academy of Sciences. (1971).

Gaoni, Yehiel & Mechoulam, Raphael. "The Isolation and Structure of Δ1-Tetrahydrocannabinol and Other Neutral Cannabinoids from Hashish," Journal of the American Chemical Society, 93:1 (1971) 217-224.

Gilbert, Benjamin & Alves, Lucio Ferreira. "Synergy in Plant Medicines," Current Medicinal Chemistry, 2003, 10, 13-20.

Grof, Christopher P. L. "Cannabis, from plant to pill," Br J Clin Pharmacol (2018) 84, 2463-2467.

Hazekamp, Arno & Verpoorte, Rob. "Structure elucidation of the tetrahydrocannabinol complex with randomly methylated β-cyclodextrin," European Journal of Pharmaceutical Sciences, 29 (2006) 340-347.

Křížek, Tomáš et al. "Menthol-based hydrophobic deep eutectic solvents: towards greener and efficient extraction of phytocannabinoids," Journal of Cleaner Production (2018).

Lewis, Melissa M. et al. "Chemical Profiling of Medical Cannabis Extracts," ACS Omega, 2017, 2, 6091-6103.

Li, Gang & Lou, Hong-Ziang. "Strategies to diversify natural products for drug discovery," Med Res Rev. 2017: 1-40.

Loftsson, Thorsteinn & Brewster, Marcus E. "Pharmaceutical Applications of Cyclodextrins. 1. Drug Solubilization and Stabilization." Journal of Pharmaceutical Sciences, vol. 85, No. 10 (1996) 1017-1025.

Loomis, W.D., & Battaile, J. "Plant Phenolic Compounds and the Isolation of Plant Enzymes," Phytochemistry, 1966, vol. 5, 423-438.

Machado, Bruna Aparecida Souza, et al. "Supercritical Fluid Extraction Using CO2: Main Applications and Future Perspectives," Separation Science and Technology, 2013, 48:18, 2741-2760.

Mannila, Janne et al. "Precipitation Complexation Method Produces Cannabidiol/β-Cyclodextrin Inclusion Complex Suitable for Sublingual Administration of Cannabidiol," Journal of Pharmaceutical Sciences, vol. 96, No. 2 (2007) 312-319.

Moon et al., "Validated Gas Chromatographic-Mass Spectrometric Analysis of Urinary Cannabinoids Purified With a Calcium-hardened B-Cyclodextrin Polymer", Journal of Chromatography A, Elsevier, Sep. 2008, vol. 1204(1), pp. 87-92.

Morin-Crini, Nadia et al. "Water-soluble β-cyclodextrin-epichlorohydrin polymers for removal of pollutants from aqueous solutions by sorption processes using batch studies: A review of inclusion mechanisms." Progress in Polymer Science 78 (2018) 1-23.

Moulahcene, Lamia, et al. "New Polymer Inclusion Membrane Containing β-Cyclodextrin Polymer: Application for Pharmaceutical Pollutant Removal from Waste Water," Int. J. Environ. Res. Public Health, 2019, 16, 414.

Ogawa, Noriko et al. "Physicochemical Characterization of Cyclodextrin-Drug Interactions in the Solid State and the Effect of Water on These Interactions," Journal of Pharmaceutical Sciences (2015).

Otta, K. et al. "Cyclodextrin—Cellulose Copolymers," Proceedings of the Fourth International Symposium on Cyclodextrins, 1988 by Kluwer Academic Publishers, 139-143.

Peng, Xiao, et al. "Green extraction of five target phenolic acids from Lonicerae japonicae Flos with deep eutectic solvent," Separation and Purification Technology, (2015).

Philippova, Olga et al. "Magnetic polymer beads: Recent trends and developments in synthetic design and applications," European Polymer Journal, 47 (2011) 542-559.

Pushpangadan, P. et al. "Handbook of herbs and spices," Woodhead Publishing Limited, Second Edition, vol. 1 (2012).

Radosevic, Kristina, et al. "Natural deep eutectic solvents as beneficial extractants for enhancement of plant extracts bioactivity," LWT—Food Science and Technology, 73, 2016, 45-54.

Rajewski, Roger A. & Stella, Valentina J. "Pharmaceutical Applications of Cyclodextrins. 2. In Vivo Drug Delivery," Journal of Pharmaceutical Sciences, vol. 85, No. 11 (1996) 1142-1169.

Rates, S.M.K. "Plants as source of drugs," Toxicon 39 (2001) 603-613.

Rovetto, Laura J. & Aieta, Niccolo V. "Supercritical carbon dioxide extraction of cannabinoids from *Cannabis sativa* L.," J. of Supercritical Fluids, 129, 2017, 16-27.

Ruesgas-Ramon, Mariana, et al. "Application of Deep Eutectic Solvents (DES) for phenolic compounds extraction: overview, challenges, and opportunities," J. Agric. Food Chem., 2017.

Russo, Ethan B. "Taming THC: potential cannabis synergy and phytocannabinoid-terpenoid entourage effects," British Journal of Pharmacology (2011), 163, 1344-1364.

Sexton, Michelle et al. "Evaluation of Cannabinoid and Terpenoid Content: Cannabis Flower Compared to Supercritical CO2 Concentrate," Planta Med (2017).

Starmans, Dick A.J. & Nijhuis, Herry H. "Extraction of secondary metabolites from plant material: A review," Trends in Food Science & Technology, vol. 7 1996.

Still, W. Clark, et al. "Rapid Chromatographic Technique for Preparative Separations with Moderate Resolution," J. Org. Chem., vol. 43, No. 14, 1978, 2923-2925.

Turner, C. E. et al. "Constituents of Cannabis sativa," Journal of Medicinal Plant Research, 1979, vol. 37, 217-225.

Yamasaki, Hirohito, et al. "Efficient phenol removal of wastewater from phenolic resin plants using crosslinked cyclodextrin particles," Journal of Chemical Technology and Biotechnology, 81: 1271-1276 (2006).

Yamasaki, Hirohito, et al. "Preparation of crosslinked B-cyclodextrin polymer beads and their application as a sorbent for removal of phenol from wastewater," Journal of Chemical Technology and Biotechnology, 83: 991-997 (2008).

Ying, Zhang et al. "Macroporous Resin Adsorption for Purification of Flavonoids in Houttuynia cordata Thunb.," Chin. J. Chem. Eng., 15(6), 872-876 (2007).

Yue, Daran, et al. "A Continuous Procedure Based on col. Chromatography to Purify Anthocyanins from Schisandra chinensis by a Macroporous Resin plus Gel Filtration Chromatography," Molecules, 2016, 21, 204.

VARIATION OF
CYCLODEXTRIN CORE:
n = 5 ($\alpha$), 6 ($\beta$), 7 ($\gamma$)

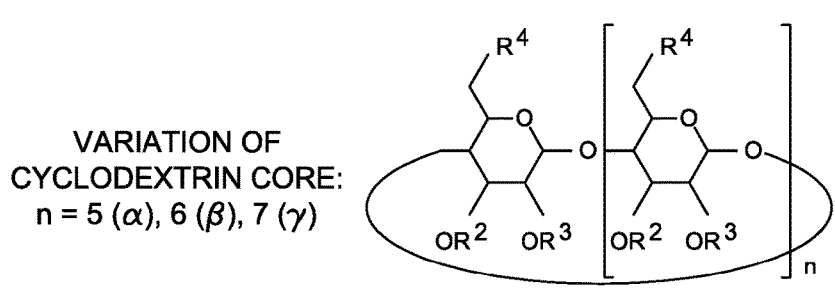

VARIATION TO C6-POLYMERIC MATRIX:
FOR HDI-CDPs, $R^4$=H OR

FOR ECH-CDP, $R^4$=H OR

FOR Si-CDPs,
FOR MNP-CDPS,
FOR MEM-CDPs, $R^4$=H OR

FOR Si-CDPs, R=POLYMERIC SILICA
FOR MNP-CDPs, R=MAGNETIC
NANOPARTICLE HYDROXYLS
FOR MEM-CDPs, R=MEMBRANE-
BASED HYDROXYLS

VARIATION OF $R^2$/$R^3$ SITES:
ESTERS:
$R^2$/$R^3$= H OR COR
CARBAMOYL:
$R^2$/$R^3$= H OR CONHR
ALKYL:
$R^2$/$R^3$=H OR ALKYL UNIT
ARYL:
$R^2$/$R^3$= H OR ARYL UNIT
R=H OR WIDE VARIETY OF COMMERCIAL OPTIONS AVAILABLE

VARIATION TO POLYMER LINKAGE:
FOR LINKAGE 1, R=

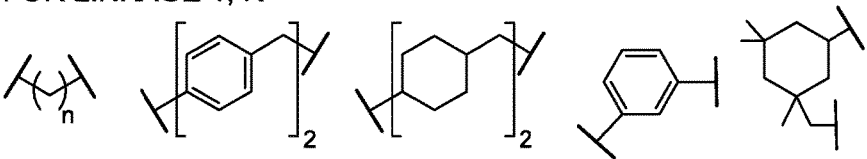

FOR LINKAGE 2, R=

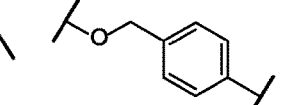

ETHER-        AMINO-        CARBAMATE-        HYDROXY        BENZYL
TETHER        TETHER        TETHER            PROPYL-TETHER  ETHER-TETHER

FIG. 1

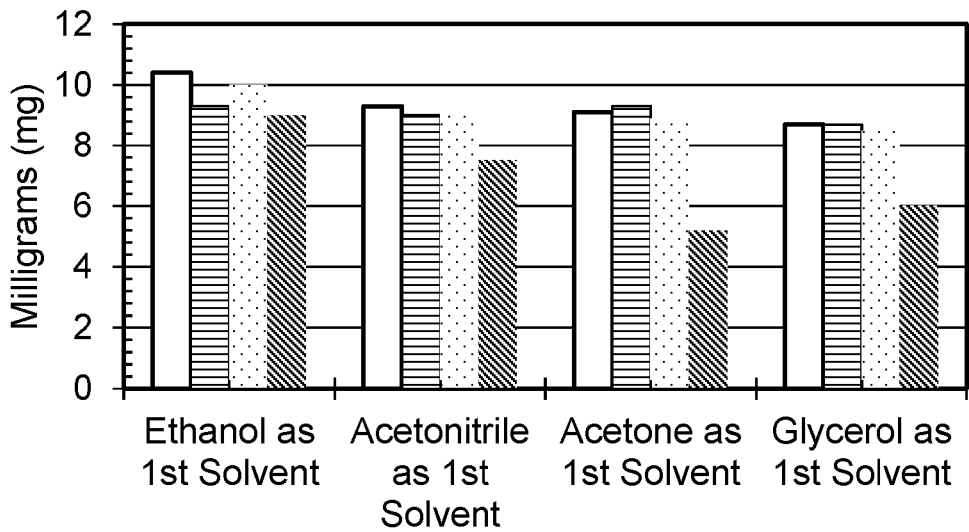
Fig. 83
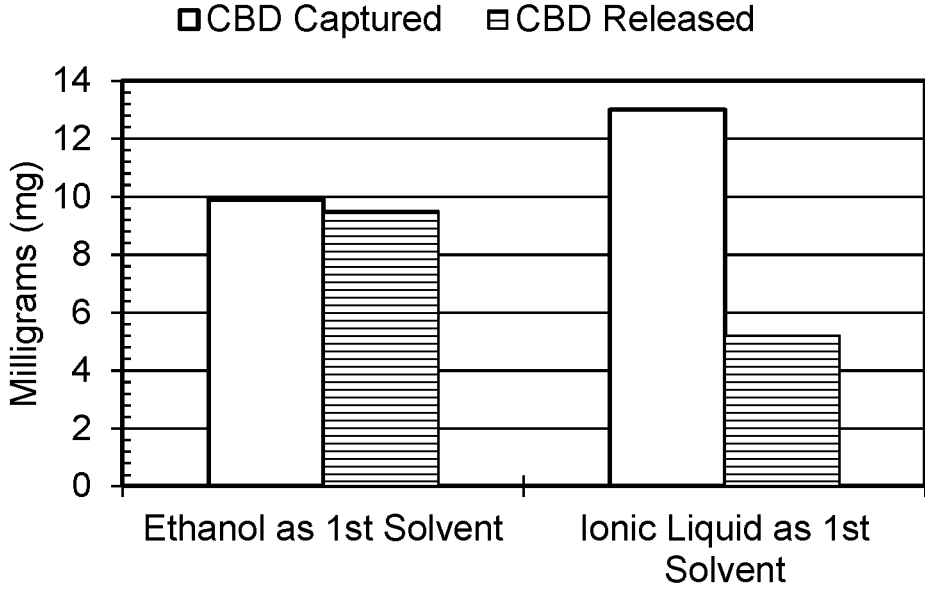
Fig. 84

Xanthumol
Flavanone
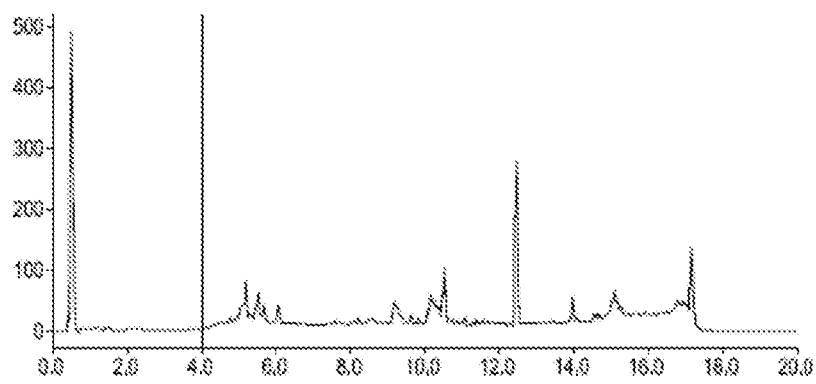
Mw = 354
Fig. 103　　　　　　　　　　Fig. 104
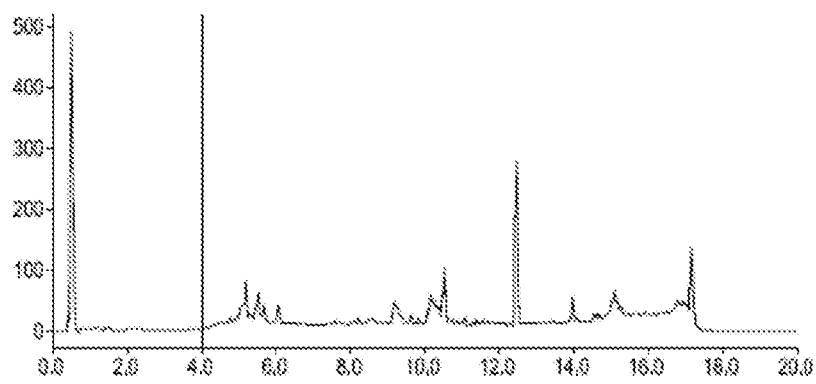
Fig. 105
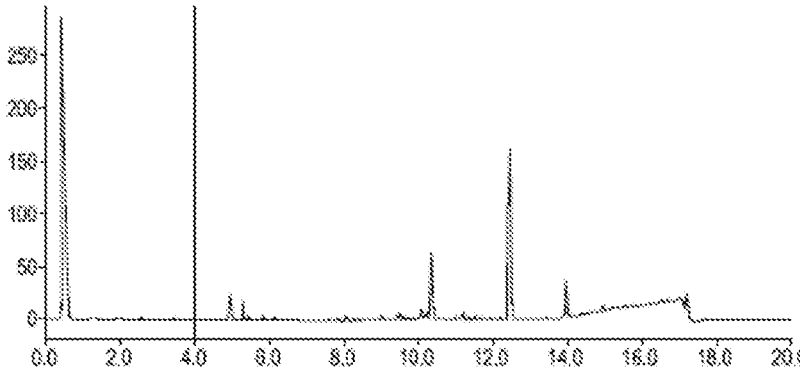
Fig. 106

METHOD FOR SELECTIVE RECOVERY OF HYDROPHOBIC COMPOUNDS

FIELD

The present disclosure relates to selective recovery of hydrophobic compounds.

BACKGROUND

A significant portion of all drugs prescribed worldwide are natural products sourced from plants. Of 252 drugs described as essential by the World Health Organisation, 11% are exclusively from plant origin and a significant number of the rest are synthetic compounds prepared from naturally occurring precursors. Herbal medicines are treated differently in medicine, pharmacology, and regulatory guidelines than drugs based on isolation and administration of purified active pharmaceutical ingredients ("API") from plant sources. Clinical trials involving medicines derived from a single API provide health care practitioners with the confidence to prescribe drugs for which there is evidence of efficacy, safety, and reproducible results. The comparative dearth of scientific verification of many herbal medicines may, in the worst-case scenario, be harmful to health, potentially through complications with existing medicines. These concerns may curtail the potential of using whole plant material, or crude extracts, as medicines and hence constrict the therapeutic potential of pharmacological interventions using herbal medicines, despite certain herbal treatments undergoing some degree of clinical certification for efficacy.

One hurdle in bridging the divide between whole plant medicines and contemporary pharmacological standards is the identification of active chemical components of the plant. Extraction and purification of bioactive substances from plant matter has been an active area of investigation since before the introduction of current pharmacological standards and remains a crucial tool in the pharmacologist toolkit today. This approach has allowed the introduction of many widely prescribed essential medicines that are based on a single chemical component of plant origin. There are instances, however, in which no single active chemical component can be identified for a given herbal medicine, even though evidence exists demonstrating the crude whole plant extract is effective in treating a specific disease state. In such cases, thorough analysis of plant extract fractions has shown that more than one active ingredient is required to elicit the desired pharmacological response either in vitro or in vivo.

*Cannabis*-based medicines are an example of synergy in treatments involving plant derived bioactive substances. *Cannabis sativa* produces over 140 structurally distinct phytocannabinoids comprising approximately a dozen subclasses based on structural similarity, in addition to a variety of flavanones, terpenoids and other minor constituents that are known to act in concert. This synergistic response to multiple bioactive substances is commonly referred to as the 'entourage effect' and is absent when a single phytocannabinoid is administered alone. Administration of a single API such as delta-9-tetrahydrocannabinol ("THC") can in certain indications lead to an unsatisfying therapeutic outcome with adverse effects including inebriation and short-term memory impairment. As such, deployment of THC in combination with another phytocannabinoid, cannabidiol ("CBD"), has been shown to improve the therapeutic outcome for some conditions and to ameliorate some unwanted side effects.

While the assumption that a single active chemical compound should be responsible for a given therapeutic response has been substantially overturned, the complexity of synergies possible when administering plant-based medicines is enormous when such a large variety of chemical constituents are biosynthesized as by *C. sativa*. To capitalize on medicinal benefits of this synergy, two approaches have arisen toward broadening the application of *cannabis*-derived medicines: reconstituting a mixture of active components using purified samples of each constituent, and accurately measuring the content of all bioactive ingredients in a whole plant *cannabis* extract.

As alluded to above, one ab initio tactic involves attempting to recreate a mixture of APIs in relative quantities that either replicate their natural abundance or can be modified at will to improve outcome or patient experience. A clear advantage of this method is that the therapeutic response can be definitively attributed to the phytocannabinoids added to the reconstituted mixture. As such, regulatory compliance can be navigated through straightforward adaption of current single-API approaches. However, current barriers to full implementation of this approach include: access to all phytocannabinoids in highly purified form is practically very challenging; limited understanding of the relevance of minor bioactive constituents often present in very low quantities below easily detectable levels; high commercial costs of available phytocannabinoids; and the vast range of permutations that exist when attempting to combine these ingredients to simulate the synergistic effect. Future developments that will enable this goal to be realized will include the development of highly efficient extraction technologies that provide the medical and pharmacological communities with cost-effective analytically pure samples of all phytocannabinoids, flavanones, phenylpropanoids and terpenoids.

The alternative approach involves utilizing the broad range of bioactive constituents present in *cannabis* extracts accessed using current extraction technologies. The effects of administered medicines can be attributed to the unique chemical fingerprint of the extract. This strategy has the benefit that many minor phytocannabinoids can be administered that cannot be easily accessed in sufficient quantities using conventional extraction methods. Conversely, administration of such a broad range of potentially bioactive ingredients presents a complicated challenge that regulatory authorities need to navigate to ensure safe and effective medicines are introduced to the market. Crucial barriers to implementation of this strategy include a lack of authentic samples for analytical confirmation of minor phytocannabinoid content, batch-to-batch variability of metabolite quantities based on plant genetics, growing conditions, harvesting times and extraction method, and inability to detect and accurately measure the levels of minor components that can have either a beneficial influence on synergistic behaviour or a deleterious effect on therapeutic outcome.

In many cases, the regulatory requirements pertaining to analysis of whole plant extracts of *C. sativa* focus on inebriating phytocannabinoids such as THC, and analysis laboratories do not always possess suitable authentic samples for complete phytocannabinoid profiling. The expense associated with full metabolite profiling leads to wide variability of many minor phytocannabinoids and is often overlooked entirely and results in low patient confidence and low physician confidence in medical utility. As with the ab initio approach to synergistic medical administrations, key technological improvements that will improve the whole plant extract ("WPE") strategy include the introduction of analytical standard samples or analytical standards of all phytocannabinoids in highly purified form such that in-depth analysis of whole plant extracts can be accurate, low-cost, and routine.

Natural product extraction from botanic sources remains a vibrant area of investigation for pharmacological, pharmaceutical, and medicinal researchers. Natural products chemical architectures provide researchers with a wealth of privileged scaffolds for use in drug discovery, starting points for chemical diversification toward novel libraries, and inspiration for de novo synthesis of natural product-like libraries. To continue and expand the benefit of natural products in the development of new medicines, new approaches to the extraction, isolation, and purification of naturally occurring small molecules is crucial and often requires techniques, protocols, and strategies to be tailored to the target compound of interest.

Previous approaches to extraction of phytocannabinoids and other metabolites found in *C. sativa* have involved the use of conventional organic solvents, supercritical fluid, butane and related volatile organic media. Deep eutectic solvents and ionic liquids have been used for the extraction of plant metabolites from plant matter, including from *C. sativa*. Each of the above approaches provide an extraction technique that can be somewhat tailored to the isolation of certain plant metabolite subclasses from other natural product classes but also presents unique challenges. Selectivity for phytocannabinoids of interest, isolation or removal of fatty acids and waxes, infrastructural requirements, pre-extraction requirements such as drying and wax winterization procedures, or post-extraction treatments such as solvent removal operations all require bespoke solutions.

A common challenge to most conventional extraction methods is the necessity to dry plant material prior to extraction using a non-aqueous solvent. Drying is a hugely costly process since it requires reducing water content from the harvested plant, which can be 70-90% humidity, to closer to 5-15% water content. Disruptive new technology will use innovative solutions that bypass this energy and cost-intensive impediment. One strategy that circumvents the necessity for arduous drying protocols, is water-steam distillations, that have found some utility in the extraction of plant metabolites in some specific applications. For example, isolation of essentials oils and terpenoids have benefited from steam distillation techniques but such approaches have not been widely functional for more structurally complex or chemically sensitive compounds that are sensitive to heat or suffer from bespoke challenges associated with physico-chemical tolerance to water environments.

Ethanol extracts of *cannabis* have the benefit of using a sustainable, renewable solvent that is generally regarded as safe even if trace quantities are present when consumed. This solvent can be effective at removing many plant metabolites from the whole plant biomass but comes at the cost of requiring multiple processing operations downstream of the initial extraction. For an organic solvent, ethanol is highly polar and as such removes not only the highly lipophilic components such as phytocannabinoids extracted from *cannabis* but also unwanted water-soluble compounds such as chlorophyll. Post extraction processing is generally more extensive and labour intensive than extractions using alternative protocols and solvents. Ethanol has a notably higher boiling point compared with shorter hydrocarbons such as butane or propane and this property makes solvent removal slower, more difficult, and costly.

Supercritical fluid technology, particularly using carbon dioxide, is an area of continuing improvement within the field of natural product extraction from plant material. This method of extraction has been particularly well utilized within the *cannabis* industry for the isolation of phytocannabinoids, flavonoids, phenylpropanoids, terpenoids, and other constituents of value for patients and consumers. Supercritical carbon dioxide extraction systems have the advantage of being non-flammable, and can be performed at temperatures that can be attenuated for the isolation of temperature-sensitive plant metabolites. A major disadvantage of super critical fluid extraction is the high barrier to entry by means of investment in costly infrastructure requirements and the maintenance of said instruments by technically skilled personnel. The use of such a setup does not negate any of the pre- and post-extraction operations mentioned above for ethanol extraction. Supercritical fluid extraction functions as a wide-net capture method without providing highly selective operating conditions for the isolation of specific plant metabolites. In addition, while the use of supercritical methods may be described as a solvent-free extraction approach, a solvent is frequently required during post-extraction operations when unwanted extracted compounds are removed in order to prepare pharmaceutical-grade active components.

Isolation of plant metabolites using highly lipophilic solvents such as hydrocarbons presents an attractive option when target molecules demonstrate non-optimal solubility in more polar media. A major disadvantage with this technology is the use of highly flammable material that represents an explosion risk. In addition, hydrocarbon-based extracts are more likely to contain trace solvent residues. In applications to the *cannabis* industry, this drawback can lead to flavour anomalies and potentially as lung irritation.

Deep eutectic solvents ("DES"), natural deep eutectic solvents ("NADES"), and ionic liquids ("IL") have been used for the extraction of plant metabolites from plant material. Within this context, such solvents have been used in the extraction of phytocannabinoids from *C. sativa* plant matter. These solvents are non-trivial to remove and as such isolation of purified samples of phytocannabinoids from these solvents post-extraction from the plant matter presents a barrier to their application.

There exists a number of peer-reviewed literature articles pertaining to the application of deep eutectic solvents and ionic liquids for the extraction of plant metabolites, including phytocannabinoids and specific applications for the isolation of broader classes of phenolic compounds from various plant sources.

In one approach to circumvent solvent removal challenges when performing extractions using DESs, NADESs, or ILs, such solvent mixtures have been used in conjunction with macroporous polymeric capturing devices to remove extracted natural products from these non-volatile solvents. Macroporous resins have been used in extraction protocols more generally, including the isolation of flavonoids from plant material following supercritical fluid extraction.

SUMMARY

Plant derived medicinal products are crucial tools to complement pharmacological treatments utilising single component APIs, as well as being a source and starting point for new APIs. Treatment using herbal extracts often benefit from synergistic behaviours of multiple active species produced by the plant but suffer from limitations regarding formulations, dosing irregularities, and chemovar variabilities. Comprehensive chemical analysis of whole plant extracts is often expensive and complicated by a lack of accuracy in determining levels of minor constituents that may be relevant to the overall therapeutic outcome. Access to standard analytical samples of minor plant constituents may greatly improve the regulatory oversight for these treatments and provide medical practitioners with greater confidence when prescribing whole plant medicines. Efforts to isolate each bioactive component with a view to consistently providing an accurately prepared mixture of active ingredients may overcome extract irregularities but demands commercial access to all active species in highly purified form in order to reconstitute that which is observed in the crude plant extract.

Contemporary approaches to extraction of plant metabolites, such as phytocannabinoids, have involved the use of conventional alcohols, organic solvents, supercritical fluids, hydrocarbons and related volatile organic media. Less conventional approaches include employing deep eutectic solvents and ionic liquids for extraction of plant metabolites from plant biomass and have also been applied to phytocannabinoid isolation. The above approaches do not provide a highly tunable approach to the separation of various plant metabolites subclasses from unwanted natural product classes, or for the isolation of specific compounds from said mixtures. Non-specific extractions of this kind can capture a wide variety of compound classes from the plant, such as fatty acids, waxes, and chlorophyll; crucially, these techniques do not benefit from chemical structure-based specificity. Often the strategies used in extractions require high infrastructure costs, highly flammable solvents, and expensive pre- and post-extraction treatments. Such approaches may ultimately provide insufficient quantities of minor phytocannabinoids at highly inflated prices. The pharmacological understanding and expansion of plant-based medicines requires new extraction technologies that can be tailored to specific metabolites of interest that are easy to operate, provides bioactive compounds in high purity, and substantially reduces costs.

In view of the shortcomings in extraction technology, there is motivation to produce an approach to capturing plant metabolites, such as polyphenolics, phytocannabinoids, terpenoids, or other plant metabolites that utilizes and expands upon the known guest-host molecular interactions governing encapsulation into cyclic polysaccharides such as cyclodextrins.

Polysaccharide mixtures have been used to improve the water solubility of phytocannabinoid and whole plant extracts of *cannabis*, allowing greater control over dosing and formulation. Applications of cyclic polysaccharides, such as cyclodextrins, have shown structure-dependent guest-host molecular interactions between the sugar (host) and the phytocannabinoid (guest) in resulting inclusion complexes, conceptually similar to a lock and key. Silica-bound cyclodextrins and derivatives, have been utilized previously for their ability to selectively bind small molecules in a structure-dependent manner when constructed into chromatography columns but have not been optimized for phytocannabinoid extraction applications. In addition, polymeric cyclic polysaccharides, such as cyclodextrins, have been used to remove phenolic compounds during water purification, including with selectivity for certain phenols based on chemical structures but have not been utilized as a tool for plant metabolite extraction.

Cyclodextrins contained within polymeric matrices used for phenol decontamination from water have not been utilized in the extraction of plant metabolites from plant matter.

The method provided herein applies structure-specific guest-host molecular interactions between hydrophobic compounds, such as phytocannabinoids or other plant metabolites, and the polysaccharide. Cyclodextrins, derivatives, or similar cyclic polysaccharides are applied as a polymeric framework that permits capture, release, and hence purification of plant metabolites from a solution of whole plant extract.

In the method disclosed herein, cyclodextrins, including α-cyclodextrin, β-cyclodextrin and γ-cyclodextrins, or similar cyclic polysaccharides, are incorporated into polymeric frameworks that permit facile separation of bound target compounds from unwanted plant debris or undesired plant metabolites. Different cavity sizes may be applied for the capture of plant metabolites based on guest-host compatibility due to molecular size and shape.

Cyclic polysaccharides may be applied as an insoluble polymeric material, ground to a fine powder, milled into beads, appended to magnetic nanoparticles or insoluble magnetic beads. Such polymers may be added to crude extracts of plant material derived from conventional organic solvents, water, deep eutectic solvents, ionic liquids, or a mixture thereof, following filtration of plant debris. Attenuation of the solvent mixture promotes capture of compounds of interest, and filtration or other recovery of the insoluble polysaccharide permits physical exclusion of target metabolites from the solvent. Suspension of metabolite-bound polymers in a dissociation solvent, or application of heat, promotes release of captured metabolites as purified compounds.

The cyclic polysaccharide-containing polymer may be embedded onto a chromatography medium or other insoluble matrix, which may be used in a slurry, coated to a surface such as silica gel, embedded within a chromatography device or otherwise applied to selective recovery of hydrophobic compounds. The chromatography medium may be applied in a chromatography column for use with instrument including high-pressure liquid chromatography, supercritical fluid chromatography or manual chromatography applications. This chromatography medium may be used in direct substitution with conventional silica gel or contained within chromatography devices such as a chromatography column for use with instrument including high-pressure liquid chromatography, supercritical fluid chromatography, manual chromatography applications or related approaches, for chromatographic separation of plant metabolites from unwanted plant material or metabolites, or from the solvent mixture itself. Elution using solvents that perturb the binding affinity of the target molecule to the capture device allowing release of target molecules in highly purified or enriched form. Where chromatography is applied, the insoluble polysaccharides are provided with at least two cyclic polysaccharides for each subunit that is attached to the immobile phase.

Cyclic polysaccharides may be bound, such as by covalent attachment, to a fibrous chromatography matrix such as glass fibre, cellulosic material or alternative matrices. Fibrous material of this kind can be used to pack chromatography columns, or used as a polymer inclusion membrane or alternatives for recovery of hydrophobic target molecules from whole plant extracts derived from conventional organic solvents, water, deep eutectic solvents, ionic liquids or a mixture thereof, following filtration of plant debris, with elution of solution-phase unwanted plant metabolites. Upon sequestering of the cyclic polysaccharides bound to the hydrophobic target molecules from the unwanted plant metabolites that remain in solution, elution from the matrix may be promoted by addition of hydrophobic solvents, such as conventional organic solvents, aqueous mixtures, deep eutectic solvents, natural deep eutectic solvents or ionic liquids, or the application of heat, to disrupt the guest-host environment and promote release of metabolites of interest into solution in purified or enriched quantities.

Solvents that interrupt the non-covalent binding interactions between hydrophobic target molecules and a given cyclic polysaccharide host may be applied to recover the hydrophobic target molecules. When these interactions are interfered with, the binding affinity of the hydrophobic target molecule with the cyclic polysaccharide is substantially reduced and the encapsulation process is overturned, releasing target compounds into solution, or in vapour form if applying heat, thereby allowing recovery of the hydrophobic target molecule. Such dissociation solvents may include conventional organic solvents, supercritical fluids, water, deep eutectic solvents, ionic liquids, or a mixture thereof.

Upon release of target molecules bound to cyclic polysaccharide units of the polymeric devices, a cleaning solvent may be used to strip away any compounds still bound to the polymeric matrix. At this stage, the cyclic polysaccharide offers the same binding motifs that were present prior to any capturing and as such can be reused multiple times using a sequence of capture, release, and cleaning, based on solvent choice.

In a first aspect, herein provided is a method of selectively recovering a hydrophobic target substance. The method is applied to a solution of the target substance in a hydrophobic solvent. An insoluble polysaccharide is combined with the solution, the solution is passed over the insoluble polysaccharide or otherwise exposed to the insoluble polysaccharide. A hydrophilic solvent, which is less hydrophobic than the hydrophobic solvent, is combined with the solution or combined with the hydrophobic target substance and the insoluble polysaccharide after evaporation of the hydrophobic solvent to facilitate binding of the insoluble polysaccharide with the target substance rather than remaining in solution in the hydrophobic solvent. The cyclic polysaccharide is isolated from the solution. A dissociation solvent is combined with the cyclic polysaccharide for solubilizing the target substance from the cyclic polysaccharide and recovering the target substance.

In a further aspect, herein provided is a method of selectively recovering a hydrophobic target substance, the method comprising: providing a solution comprising the target substance in a first solvent; combining cyclic polysaccharide with the solution, the cyclic polysaccharide being insoluble in the solution; combining a second solvent with the solution, the second solvent being less hydrophobic than the first solvent for facilitating binding of the cyclic polysaccharide with the target substance; isolating the cyclic polysaccharide from the solution; and combining a dissociation solvent with the cyclic polysaccharide for recovering the target substance.

In some embodiments, providing the solution comprises combining bulk plant material with the first solvent and separating the bulk plant material from the first solvent. In some embodiments, the bulk plant material comprises material from *Cannabis sativa*. In some embodiments, the first solvent comprises an organic solvent. In some embodiments, the organic solvent is selected from the group consisting of acetone, acetonitrile, tetrahydrofuran, glycerol, DMSO, dichloromethane and chloroform. In some embodiments, the organic solvent comprises an alcohol. In some embodiments, the alcohol is selected from the group consisting of methanol, ethanol, n-propyl alcohol and isopropyl alcohol. In some embodiments, the organic solvent comprises a hydrocarbon. In some embodiments, the hydrocarbon is selected from the group consisting of n-hexane, butane and propane. In some embodiments, the first solvent comprises a eutectic solvent. In some embodiments, the eutectic solvent is selected from the group consisting of glucose syrup, and acetic acid mixed with menthol. In some embodiments, the first solvent comprises an ionic liquid. In some embodiments, the ionic liquid comprises 1-butyl-3-methylimidazolium tetrafluoroborate. In some embodiments, the second solvent comprises water. In some embodiments, the second solvent comprises a chelating agent. In some embodiments, combining a second solvent with the solution comprises evaporating at least a portion of the first solvent prior to combining the second solvent with the solution. In some embodiments, the cyclic polysaccharide comprises cyclodextrin. In some embodiments, the cyclodextrin comprises a cyclodextrin selected from the group consisting of α-cyclodextrin, β-cyclodextrin and γ-cyclodextrin. In some embodiments, the cyclodextrin is cross-linked with hexamethylene diisocyanate. In some embodiments, the cyclic polysaccharide comprises beads that are insoluble in the solution and isolating the cyclic polysaccharide from the comprises filtering the beads out of the solution. In some embodiments, the beads comprise a magnetic substance and isolating the cyclic polysaccharide from the comprises magnetically attracting the magnetic substance. In some embodiments, the cyclic polysaccharide comprises nanoparticles of a magnetic substance and isolating the cyclic polysaccharide from the comprises magnetically attracting the magnetic substance. In some embodiments, the cyclic polysaccharide comprises a powder that is insoluble in the solution. In some embodiments, the cyclic polysaccharide comprises a gel matrix that is insoluble in the solution. In some embodiments, the cyclic polysaccharide comprises a membrane material. In some embodiments, the dissociation solvent is more hydrophobic than the first solvent. In some embodiments, the dissociation solvent comprises a solvent selected from the group consisting of methanol, ethanol, n-propyl alcohol and isopropyl alcohol, other alcohols, acetone, acetonitrile, tetrahydrofuran, glycerol, DMSO, dichloromethane, chloroform, other organic solvents, n-hexane, butane, propane, other hydrocarbons, glucose syrup, acetic acid mixed with menthol, other eutectic solvents, 1-butyl-3-methylimidazolium tetrafluoroborate and other ionic liquids. In some embodiments, the cyclic polysaccharide is added to the solution before combining the second solvent with the solution. In some embodiments, the cyclic polysaccharide is added to the solution after combining the second solvent with the solution.

In a further aspect, herein provided is a method of selectively recovering a hydrophobic target substance comprising: providing a solution comprising the target substance in a first solvent; combining a second solvent with the solution, the second solvent being less hydrophobic than the first solvent to facilitate binding of the target substance with a cyclic polysaccharide; exposing the solution to a chromatography medium, the chromatography medium comprising the cyclic polysaccharide for binding to the target substance; and combining a dissociation solvent with the chromatography medium for eluting the target substance in an eluted solution. The polysaccharide is bound with the chromatography medium in subunits of at least two cyclic polysaccharide structures per subunit.

In some embodiments, providing the solution comprises combining bulk plant material with the first solvent and separating the bulk plant material from the first solvent. In some embodiments, the bulk plant material comprises material from *Cannabis sativa*. In some embodiments, the first solvent comprises an organic solvent. In some embodiments, the organic solvent is selected from the group consisting of acetone, acetonitrile, tetrahydrofuran, glycerol, DMSO, dichloromethane and chloroform. In some embodiments, the organic solvent comprises an alcohol. In some embodiments, the alcohol is selected from the group consisting of methanol, ethanol, n-propyl alcohol and isopropyl alcohol. In some embodiments, the first solvent comprises a hydrocarbon. In some embodiments, the hydrocarbon is selected from the group consisting of n-hexane, butane and propane. In some embodiments, the first solvent comprises a eutectic solvent. In some embodiments, the eutectic solvent is selected from the group consisting of glucose syrup, and acetic acid mixed with menthol. In some embodiments, the first solvent comprises an ionic liquid. In some embodiments, the ionic liquid comprises 1-butyl-3-methylimidazolium tetrafluoroborate. In some embodiments, the second solvent comprises water. In some embodiments, the second solvent comprises a chelating agent. In some embodiments, the cyclic polysaccharide comprises cyclodextrin. In some embodiments, the cyclodextrin comprises a cyclodextrin selected from the group consisting of α-cyclodextrin, β-cyclodextrin and γ-cyclodextrin. In some embodiments, the cyclodextrin is cross-linked with hexamethylene diisocyanate. In some embodiments, the cyclic polysaccharide is covalently bound with the chromatography medium. In some embodiments, the cyclic polysaccharide is cross-linked with the chromatography medium by a cross-linking agent. In some embodiments, the cross-linking agent comprises a diisocyanate. In some embodiments, the chromatography medium comprises media selected from the group consisting of cellulose, other carbohydrates and silica. In some embodiments, the dissociation solvent is more hydrophobic than the solution comprising the first solvent and the second solvent. In some embodiments, the dissociation solvent comprises a solvent selected from the group consisting of methanol, ethanol, n-propyl alcohol and isopropyl alcohol, other alcohols, acetone, acetonitrile, tetrahydrofuran, glycerol, DMSO, dichloromethane, chloroform, other organic solvents, n-hexane, butane, propane, other hydrocarbons, glucose syrup, acetic acid mixed with menthol, other eutectic solvents, 1-butyl-3-methylimidazolium tetrafluoroborate and other ionic liquids.

In a further aspect, herein provided is a method of selectively recovering a phytocannabinoid, the method comprising: providing a solution comprising the phytocannabinoid in a hydrophobic solvent; combining cyclodextrin with the solution; combining a hydrophilic solvent with the solution to facilitate binding the cyclodextrin with the phytocannabinoid; isolating the cyclodextrin from the solution; and combining a hydrophobic dissociation solvent to the cyclic polysaccharide for solubilizing the phytocannabinoid In some embodiments, providing the solution comprises combining bulk plant material with the hydrophobic solvent and separating the bulk plant material from the hydrophobic solvent. In some embodiments, the bulk plant material comprises material from *Cannabis sativa*. In some embodiments, the hydrophobic solvent comprises an organic solvent. In some embodiments, the organic solvent is selected from the group consisting of acetone, acetonitrile, tetrahydrofuran, glycerol, DMSO, dichloromethane and chloroform. In some embodiments, the organic solvent comprises an alcohol. In some embodiments, the alcohol is selected from the group consisting of methanol, ethanol, n-propyl alcohol and isopropyl alcohol. In some embodiments, the organic solvent comprises a hydrocarbon. In some embodiments, the hydrocarbon is selected from the group consisting of n-hexane, butane and propane. In some embodiments, the hydrophobic solvent comprises a eutectic solvent. In some embodiments, the eutectic solvent is selected from the group consisting of glucose syrup, and acetic acid mixed with menthol. In some embodiments, the hydrophobic solvent comprises an ionic liquid. In some embodiments, the ionic liquid comprises 1-butyl-3-methylimidazolium tetrafluoroborate. In some embodiments, the hydrophilic solvent comprises water. In some embodiments, the hydrophilic solvent comprises a chelating agent. In some embodiments, combining a hydrophilic solvent with the solution comprises evaporating at least a portion of the hydrophobic solvent prior to combining the hydrophilic solvent with the solution. In some embodiments, the cyclic polysaccharide comprises cyclodextrin. In some embodiments, the cyclodextrin comprises a cyclodextrin selected from the group consisting of α-cyclodextrin, β-cyclodextrin and γ-cyclodextrin. In some embodiments, the cyclodextrin is cross-linked with hexamethylene diisocyanate. In some embodiments, the cyclic polysaccharide comprises beads that are insoluble in the solution and isolating the cyclic polysaccharide from the comprises filtering the beads out of the solution. In some embodiments, the beads comprise a magnetic substance and isolating the cyclic polysaccharide from the comprises magnetically attracting the magnetic substance. In some embodiments, the cyclic polysaccharide comprises nanoparticles of a magnetic substance and isolating the cyclic polysaccharide from the comprises magnetically attracting the magnetic substance. In some embodiments, the cyclic polysaccharide comprises a powder that is insoluble in the solution. In some embodiments, the cyclic polysaccharide comprises a gel matrix that is insoluble in the solution. In some embodiments, the cyclic polysaccharide comprises a membrane material. In some embodiments, the dissociation solvent is more hydrophobic than the hydrophobic solvent. In some embodiments, the dissociation solvent comprises a solvent selected from the group consisting of methanol, ethanol, n-propyl alcohol and isopropyl alcohol, other alcohols, acetone, acetonitrile, tetrahydrofuran, glycerol, DMSO, dichloromethane, chloroform, other organic solvents, n-hexane, butane, propane, other hydrocarbons, glucose syrup, acetic acid mixed with menthol, other eutectic solvents, 1-butyl-3-methylimidazolium tetrafluoroborate and other ionic liquids. In some embodiments, the cyclic polysaccharide is added to the solution before combining the hydrophilic solvent with the solution. In some embodiments, the cyclic polysaccharide is added to the solution after combining the hydrophilic solvent with the solution.

In a further aspect, herein provided is a method of selectively recovering a hydrophobic target substance, the method comprising: providing a solution comprising the target substance; combining a cyclic polysaccharide with the solution, the cyclic polysaccharide being insoluble in the solution; combining a salt with the solution for decreasing the hydrophobicity of the solution to facilitate binding of the cyclic polysaccharide with the target substance; isolating the cyclic polysaccharide bound with the target substance from the solution; and combining a dissociation solvent with the cyclic polysaccharide for recovering the target substance.

In some embodiments, providing the solution comprises combining bulk plant material with the solution and separating the bulk plant material from the solution. In some embodiments, the bulk plant material comprises material from *Cannabis sativa*. In some embodiments, the solution comprises an organic solvent. In some embodiments, the organic solvent is selected from the group consisting of acetone, acetonitrile, tetrahydrofuran, glycerol, DMSO, dichloromethane and chloroform. In some embodiments, the organic solvent comprises an alcohol. In some embodiments, the alcohol is selected from the group consisting of methanol, ethanol, n-propyl alcohol and isopropyl alcohol. In some embodiments, the organic solvent comprises a hydrocarbon. In some embodiments, the hydrocarbon is selected from the group consisting of n-hexane, butane and propane. In some embodiments, the solution comprises a eutectic solvent. In some embodiments, the eutectic solvent is selected from the group consisting of glucose syrup, and acetic acid mixed with menthol. In some embodiments, the solution comprises an ionic liquid. In some embodiments, the ionic liquid comprises 1-butyl-3-methylimidazolium tetrafluoroborate. In some embodiments, the cyclic polysaccharide comprises cyclodextrin. In some embodiments, the cyclodextrin comprises a cyclodextrin selected from the group consisting of α-cyclodextrin, β-cyclodextrin and γ-cyclodextrin. In some embodiments, the cyclodextrin is crosslinked with hexamethylene diisocyanate. In some embodiments, the cyclic polysaccharide comprises beads that are insoluble in the solution and isolating the cyclic polysaccharide from the comprises filtering the beads out of the solution. In some embodiments, the beads comprise a magnetic substance and isolating the cyclic polysaccharide from the comprises magnetically attracting the magnetic substance. In some embodiments, the cyclic polysaccharide comprises nanoparticles of a magnetic substance and isolating the cyclic polysaccharide from the comprises magnetically attracting the magnetic substance. In some embodiments, the cyclic polysaccharide comprises a powder that is insoluble in the solution. In some embodiments, the cyclic polysaccharide comprises a gel matrix that is insoluble in the solution. In some embodiments, the cyclic polysaccharide comprises a membrane material. In some embodiments, the dissociation solvent is more hydrophobic than the solution. In some embodiments, the dissociation solvent comprises a solvent selected from the group consisting of methanol, ethanol, n-propyl alcohol and isopropyl alcohol, other alcohols, acetone, acetonitrile, tetrahydrofuran, glycerol, DMSO, dichloromethane, chloroform, other organic solvents, n-hexane, butane, propane, other hydrocarbons, glucose syrup, acetic acid mixed with menthol, other eutectic solvents, 1-butyl-3-methylimidazolium tetrafluoroborate and other ionic liquids. In some embodiments, the cyclic polysaccharide is added to the solution before combining the second solvent with the solution. In some embodiments, the cyclic polysaccharide is added to the solution after combining the second solvent with the solution.

In a further aspect, herein provided is an insoluble polysaccharide complex comprising a polysaccharide covalently bound with an insoluble polymer by a benzylic ester linker.

In some embodiments, the benzylic ester linker comprises a carboxymethylene group. In some embodiments, the polysaccharide comprises a cyclodextrin.

In a further aspect, herein provided is an insoluble polysaccharide complex comprising: a polysaccharide; a polyethylene glycol linker covalently bound with the polysaccharide; a hydrocarbon carboxylate spacer bound with the linker through a Van der Waals interaction; and a magnetic particle coordinated with the spacer.

In some embodiments, the hydrocarbon carboxylate spacer comprises a monounsaturated hydrocarbon carboxylate. In some embodiments, the polysaccharide comprises a cyclodextrin.

In a further aspect, herein provided is an insoluble polysaccharide complex comprising: a terminal polysaccharide; at least one polysaccharide-linker subunit covalently bound with the terminal polysaccharide, the polysaccharide-linker subunit comprising an intermediate polysaccharide and an intermediate linker; and a matrix linker group covalently bound with at least one of the at least one polysaccharide-linker subunit for binding with a matrix.

In some embodiments, the terminal polysaccharide comprises a cyclodextrin. In some embodiments, the intermediate polysaccharide comprises a cyclodextrin. In some embodiments, the intermediate linker comprises a functional group selected from the group consisting of 2,4-tolyl-diisocyanate and hexamethylene dicarbamate.

In a further aspect, herein provided is a gel matrix for capturing a hydrophobic target molecule comprising an insoluble polysaccharide complex comprising: a terminal polysaccharide; at least one polysaccharide-linker subunit covalently bound with the terminal polysaccharide, the polysaccharide-linker subunit comprising an intermediate polysaccharide and an intermediate linker; and a matrix linker group covalently bound with at least one of the at least one polysaccharide-linker subunit for binding with a matrix. The insoluble polysaccharide complex comprising is bound with a matrix.

In some embodiments, the terminal polysaccharide comprises a cyclodextrin. In some embodiments, the intermediate polysaccharide comprises a cyclodextrin. In some embodiments, the intermediate linker comprises a functional group selected from the group consisting of 2,4-tolyl-diisocyanate and hexamethylene dicarbamate. In some embodiments, the matrix comprises a material selected from the group consisting of a silica gel and a carbohydrate-based gel.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures, in which reference numerals sharing a common final two digits have equivalent meaning across multiple figures (e.g. the hydrophobic solvent vessel 30, 130, 230, 330, 430, etc.).

FIG. 1 is a schematic diagram of the molecular structure of insoluble cyclodextrin polymers;

FIG. 83 shows mg CBD and CBG captured and released in Example 24;

FIG. 84 shows mg CBD captured and released in Example 25;

FIG. 103 shows the chemical structure of xanthumol;

FIG. 104 shows the chemical structure of flavanone;

FIG. 105 shows a time-course HPLC resolution with UV absorption of the reaction mixture before the addition of the cross-linked polymer in Example 50; and FIG. 106 shows a time-course HPLC resolution with UV absorption of the reaction mixture after filtration and flushing of the cross-linked polymer Example 50.

DETAILED DESCRIPTION

Figure 2:
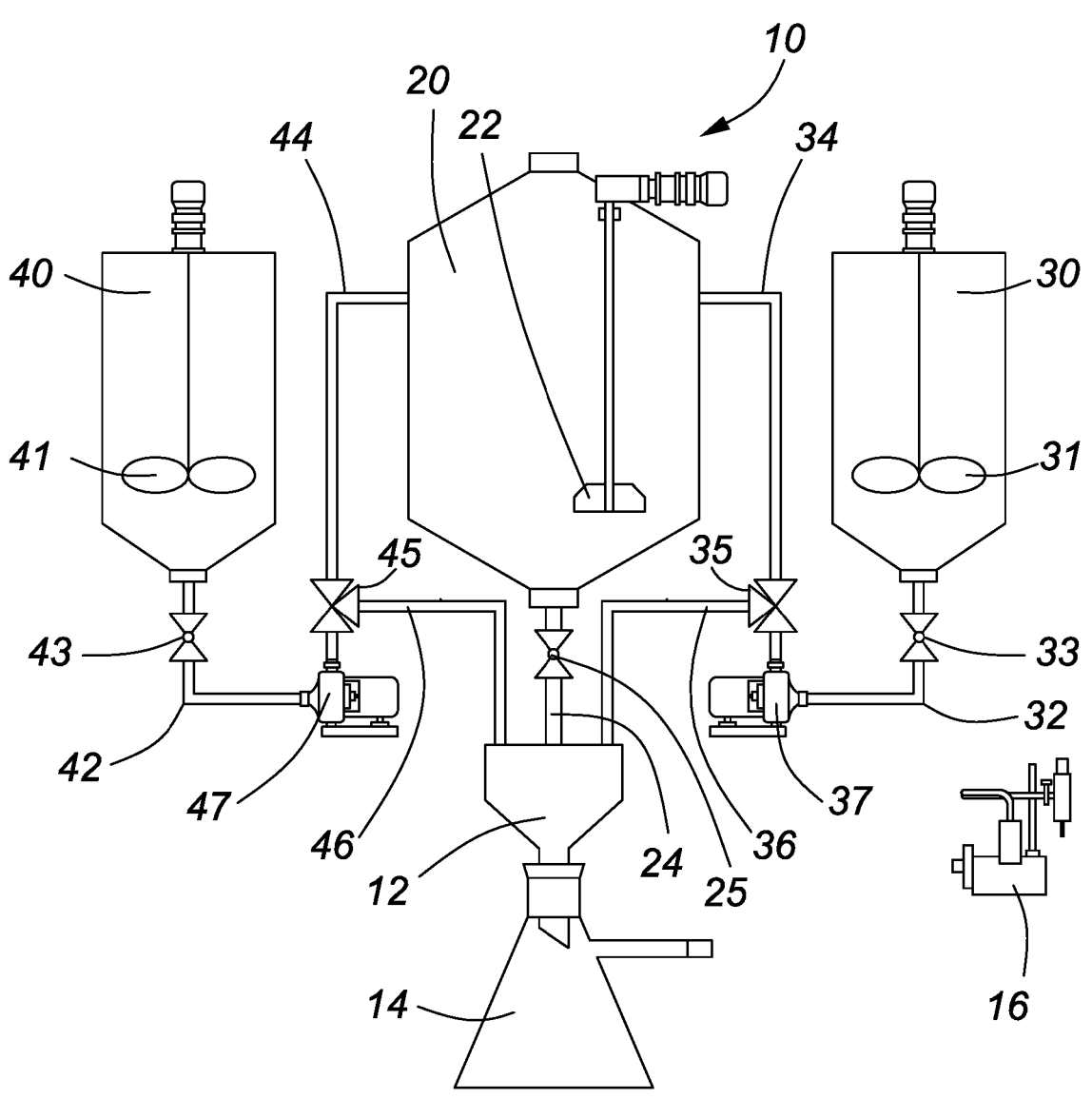
FIG. 2 is a schematic diagram of a hydrophobic compound recovery system.

Generally, the present disclosure provides a method for selective recovery of hydrophobic compounds. The method includes capturing and releasing hydrophobic target molecules. The target molecules may include natural product classes from plant matter, including polyphenolics, terpenoids and phytocannabinoids. The present disclosure describes application of cyclic polysaccharides, including α-cyclodextrin, β-cyclodextrin, γ-cyclodextrin and other cyclic polysaccharides. The cyclic polysaccharides may be covalently linked to a polymeric matrix, a magnetic nanoparticle or a magnetic bead to remain insoluble in both hydrophobic and hydrophilic solutions. The cyclic polysaccharides may be appended to or coated onto surface or mesoporous material such as silica gel, a covalent attachment to a membrane material, or incorporated into a chromatography device such as a chromatography column for use with relevant instrumentation or for manual applications. The cyclic polysaccharides may be appended to insoluble materials or to a chromatography matrix as subunits that include at least two cyclic polysaccharides at each point of attachment to the matrix.

In view of the previously described work and related shortcomings, there is motivation to provide an improved approach to capturing plant metabolites. The method and system provided herein applies and expands upon phytocannabinoid-cyclodextrin encapsulation potential underpinned by the molecular interactions between guest lipophilic small molecules and the cyclic polysaccharide host macromolecular scaffold. Cyclodextrins contained within polymeric matrices have been used for phenol decontamination from water but have not been utilized in the extraction of plant metabolites from plant matter. The method described herein applies molecular recognition and noncovalent bonding interactions within guest-host inclusion complexes of polysaccharides and hydrophobic compounds.

Conventional applications of non-polymeric cyclodextrins within the pharmaceutical industry have centered on their ability to form inclusion complexes with lipophilic drugs. Cyclodextrin-based inclusion complexes facilitate preparing aqueous soluble powdered forms of otherwise highly insoluble drug molecules. These formulations may enhance shelf life or prolongs their stability in vivo during drug administration. Cyclodextrin-inclusion complexes are applied as vehicles for drug delivery whereby powdered material can be pressed into tablets to provide reliably dosed drugs that are not soluble in aqueous solutions or that may otherwise only be available in liquid form. Challenges associated with administration of liquid drugs include dosing difficulties, shelf life irregularities, and limitations associated with administration method.

Cyclodextrins are a family of cyclic oligosaccharides comprised of repeating glucose subunits joined by α-1,4-glucosidic bonds. Cyclic oligosaccharides may include different repeating subunits or alternative linking bonds. For instance, cyclic oligosaccharides comprised of the same monosaccharide, alternating different monosaccharides, or completely distinct monosaccharides contained within a cyclic architecture that is either comprised of glycosidic bonds or formed by means of alternative cyclisation modes known in synthetic organic chemistry. The parent α-1,4-glucose-based cyclodextrins may be formed using six, seven, or eight repeating sugars subunits and are described as α-, β-, and γ-cyclodextrins, respectively.

The macromolecular scaffold cyclodextrins and other cyclic oligosaccharides may be represented as a cone shaped architecture whereby the 6-position hydroxyl groups of glucose subunits are directed toward the narrow region of the cone and the 2-, and 3-hydroxyl groups are positioned near the broader opening. The inner rim of the cyclic oligosaccharide is notably more lipophilic than the outer rim. The inner and outer rims of the cone or torus shaped host are more hydrophilic in behaviour. Structural analysis of complexes between cyclic polysaccharides and hydrophobic target molecules may be applied to rationalize why lipophilic molecules prefer to occupy the inner portion of these host scaffolds with the hydroxyl groups contributing to hydrogen-bonding networks with water-dominant solvent molecules to confer aqueous solubility of the guest-host inclusion complex. Physicochemical characterization of inclusion complexes in solid state using X-ray data, or in solution using nuclear magnetic resonance ("NMR") or other spectral analyses, demonstrates that guest molecules may offer hydrogen-bonding, dipole-dipole, and Van der Waals interactions with the host polysaccharide, thereby driving complex formation and energetically supporting continued complexation when present in aqueous media.

Polysaccharide mixtures have been used to improve the water solubility of phytocannabinoids and whole plant extracts of *cannabis*. Applications of cyclic polysaccharides, such as cyclodextrins, within the context of phytocannabinoid chemistry, have also focused on the solubilisation of such compounds. Varied solubilisation efficacies have been noted for certain phytocannabinoid-cyclodextrin partners, demonstrating some structure-dependent cyclodextrin-phytocannabinoid interactions. In the case of a THC-β-cyclodextrin adduct, the non-covalent interactions responsible for efficient encapsulation into the cyclodextrin core have been partially studied by means of NMR analysis, demonstrating that modifications to said non-covalent interactions may ameliorate this molecular recognition and that tuning of the cyclodextrin architecture may provide selectivity for phytocannabinoids, flavanones, other classes of polyphenolics, or various other metabolites of interest.

Monosaccharides and polysaccharides other than cyclodextrin have been shown to influence of the aqueous solubility of phytocannabinoids and whole plant extracts, demonstrating unique molecular interactions between oligosaccharides and phytocannabinoids responsible for the solubilising behaviour.

Cyclodextrin-based polymers have been used for the capture and removal of phenolic compounds, with some selectivity for certain phenol derivatives, from aqueous media, lipophilic media, and from plant material.

Cyclodextrins have been widely employed as vehicles for administration of small molecules in food additives or in the pharmaceutical industry. However, cyclodextrins have had limited application as capture agents for plant metabolites, including in chromatography for bulk selective recovery of hydrophobic target compounds. Silica-bound cyclodextrins have found application in analytical technologies on monolayers. In the method provided herein, cyclodextrins are used for selective recovery of phytocannabinoids and other compounds from broadly inclusive plant extracts. Polymer-bound cyclodextrins or related cyclic polysaccharides facilitate selective recovery and physical separation of specific plant metabolites from a large mixture of plant constituents, such as would be found in an initial crude plant extract following common extraction methods. In a chromatography column for example, polymeric material facilitates fast flow rates and extraction from wet plant matter.

Cyclodextrin-containing polymers have not been previously employed in chromatographic applications for recovery and purification of the hydrophobic compounds, for instance the use of such polymeric material to pack chromatography columns. Previous applications in chromatography have been limited to HPLC or other analytic techniques. In such applications, mesoporous cyclodextrin-containing material has been created by covalently appending monomeric cyclodextrins to silica gel.

The inside diameter ("ID") of cyclic polysaccharides applied in the method provided herein define the upper size limit of target molecules that can be encapsulated, hence physically separated and isolated. α-cyclodextrin (ID=0.45 nm), β-cyclodextrin (ID=0.60 nm), and γ-cyclodextrin (ID=0.75 nm) each present distinct size restrictions to target molecules, such as specific plant metabolites within a whole plant extract. Target molecules can be divided by their ability to enter and remain within the cavity of the host polysaccharide according to molecular size.

The cyclic polysaccharide may be applied as insoluble polymeric material, such as where the cyclic polysaccharide is reacted with a cross-linking agent. The cross-linking agent may include diisocyanates depicted in FIG. 1, such as hexamethylene diisocyanate ("HDI"). Such polymers can be added to crude extracts of plant material derived from conventional organic solvents, water, deep eutectic solvents, ionic liquids, or a mixture thereof, following filtration of plant debris. Attenuation of the hydrophobicity of the solvent mixture promotes selective retention of hydrophobic target compounds in the cyclic polysaccharide, for example by the slow addition of water to an ethanol plant extract, and filtration of the insoluble polysaccharide permits physical exclusion of target metabolites from the solvent. Suspension of metabolite-bound polymers in more user-friendly solvent mixtures, such as the use of a supercritical carbon dioxide system, or the application of heat, promotes selective release of captured hydrophobic target molecules from the cyclic polysaccharide and into a hydrophobic recovery solvent.

The cyclic polysaccharides may be appended to magnetic nanoparticles, insoluble magnetic beads or powders that can be added to crude extracts of plant material derived from conventional organic solvents, water, deep eutectic solvents, ionic liquids, or a mixture thereof, following filtration of plant debris. The magnetic nanoparticle or magnetic bead can be attached to the cyclic polysaccharide using a variety of synthetic methods or alternative approaches applied in chemical elaboration of nanoparticles or functional magnetic material preparation. The cyclic polysaccharide may be separated from the solvent mixture by magnetic separation. Suspension of metabolite-bound magnetic nanoparticles in a more user-friendly solvent mixture, or the application of heat, promotes release of captured metabolites in highly purified or enriched form.

The cyclic polysaccharide may be bound to a chromatography medium or coated onto a surface such as silica gel. The silica-bound cyclic polysaccharide may be prepared using synthetic methods or using alternative methods applied in preparation of silica-bound organic substrates. The chromatography medium may be used in substitution of conventional silica gel for the purpose of chromatographic separation of target molecules, such as hydrophobic plant metabolites, from each other, from unwanted plant material, or from the solvent mixture itself.

The cyclic polysaccharide may be embedded in a chromatography medium such as a chromatography column for use with high-pressure liquid chromatography ("HPLC"), supercritical fluid chromatography, or related techniques. The cyclic polysaccharide may be used in an analogous manner to conventional chromatography columns by adding a solvent including the target molecule and other compounds to the column and eluting with a gradient, or step-gradient, elution of varying polarity to remove unwanted compounds, such as plant metabolites that adhere less strongly to the cyclic polysaccharide and retaining the target molecules that bind most strongly to the cyclic polysaccharide. Elution using a solvent that disrupts this balance of polymer-bound vs solution-phase occupancy permits selective elution and capture of target molecules.

Solvent mixtures may be used to attenuate the solubility and relative affinity for binding to the cyclic polysaccharide of hydrophobic target molecules from a heterogeneous mixture, such as a particular hydrophobic plant metabolite from a whole plant extract. Some solvents will assist in the binding and selective isolation of particular plant metabolites from the plant biomass while leaving unwanted material in solution or degrading unwanted molecules to prevent binding to the cyclic polysaccharide that has been deployed for the isolation of the hydrophobic target molecules. Examples of such degradation include addition of ethylene-diaminetetraacetic acid ("EDTA"), ethylene glycol-bis(2-aminoethylether)-tetraacetic acid ("EGTA") or other chelating agents to the solution to bind $Mg^{2+}$ coordinated to chlorophyll, or other metal ions coordinated to other molecules, degrading the chemical structure of such molecules and limiting binding of such molecules to the cyclic polysaccharide. Solvent mixtures may be applied whereby an organic solvent, deep eutectic solvent or ionic liquid is applied to dissolve the hydrophobic target compound. Lowering the hydrophobicity of the solvent, such as by adding water, adding a hydrophilic solvent, or adding a salt, favours binding of the target molecule to the cyclic polysaccharide rather than staying in solution, facilitating selective retention of the target molecule.

Filtration of insoluble polymeric material such as cellulose and related biopolymers may be applied to a plant extract, leaving the target molecule in an organic solvent. The cyclic polysaccharide may be added to the solvent to facilitate capture of a target molecule. Slow addition of hydrophilic solvents, such as water, gradually decreases the solubility of the hydrophobic target compounds and provides a driving force for entry into the cyclic polysaccharide cavity due to low solubility in the resultant mixture of organic solvent and hydrophilic solvent.

The choice of initial organic solvent may be tailored to accommodate the solubility of a given natural product class to be extracted as well as the insolubilities of various unwanted plant materials such that unwanted material remains within the plant biomass and is separated during the filtration process. The choice of initial solvent may be governed not only by the ability to exclude plant metabolites from biomass but also due to the physicochemical properties of a resulting solvent-water mixture that are crucial for highly specific encapsulation into the polymer cavities.

Deep eutectic solvents or ionic liquids may be used to solubilize hydrophobic target compounds from plant biomass and biopolymers. Upon addition of water, intermolecular forces governing the properties of these unique solvents may be heavily disrupted, and their ability to solubilize target molecules lowered, driving hydrophobic target compounds into the cyclic polysaccharide cavity. A solvent-water mixture may include an aqueous solution with an agent that destroys the chemical structure of unwanted plant metabolites or constituents such as chlorophyll. For instance, aqueous-soluble chelating agents can bind to the magnesium atom of chlorophyll architecture thereby essentially denaturing the chlorophyll, transforming the molecular structure from one that may bind to a particular cyclic polysaccharide host into one that does not compete for encapsulation with the target molecule of interest.

Dissociation solvents may include any solvent capable of disrupting the intermolecular forces responsible for tight guest-host binding of the target compound within the cyclic polysaccharide and of solubilizing the plant metabolite of interest upon release. Dissociation solvents for recovering the hydrophobic target molecules may include volatile non-toxic solvents such as ethanol that can be easily removed, non-volatile solvents such as dimethyl sulfoxide ("DMSO") that can be used directly as vehicles for delivery of plant metabolites into cell line assays, supercritical fluids such as carbon dioxide, or the application of heat with concomitant trapping of vaporized plant metabolites, such that solvent-free isolates can be attained following return to atmospheric pressure and removal of the gaseous medium.

Solvents used during extraction or release protocols may be recycled by means of closed-loop systems that restrict solvent evaporation and permit re-entry and re-use of solvents for subsequent extraction procedures, thereby reducing waste and cost.

Following an extraction-release protocol, device cleaning protocols may be used to remove unremoved plant metabolites from tanks, columns or other capturing devices and apparatus. This procedure permits re-use of the capturing device and of the cyclic polysaccharide during multiple extraction cycles.

Hydrophobic Compound Recovery System

FIG. 2 shows a hydrophobic compound recovery system 10. The system 10 includes a slurry vessel 20. A filter 12 is in fluid communication with the slurry vessel 20 for receiving fluid from the slurry vessel 20 and filtering material out of the fluid. The filter 12 is shown as a filter funnel but any suitable filter may be applied (e.g. a sintered glass filter, polytetrafluoroethylene membrane filter, etc.) A recovery vessel 14 is in fluid communication with the filter 12 for receiving filtrate that passes through the filter 12. The recovery vessel 14 is shown as a Büchner funnel, but any suitable recovery vessel 14 may be applied (e.g. a flask, Erlenmeyer, round-bottom flask, beaker, test tube, etc.). A processing system 16 may be in fluid communication with the recovery vessel 14 for processing target molecules captured using the filter 12. The slurry vessel 20 is in fluid communication with a hydrophobic solvent vessel 30 for receiving hydrophobic solvent from the hydrophobic solvent vessel 30. The slurry vessel 20 is in fluid communication with a hydrophilic solvent vessel 40 for receiving hydrophilic solvent from the hydrophilic solvent vessel 40.

Each of the slurry vessel 20, the hydrophobic solvent vessel 30 and the hydrophilic solvent vessel 40 may be any suitable fluid vessel appropriate for the size, scale and application of the system 10 (e.g. a tank, pressure-rated tank, etc.).

The hydrophobic solvent may be any suitable hydrophobic solvent in which a target substance is soluble, in which an insoluble polysaccharide for capturing the target substance is insoluble and that will not damage the target substance or the insoluble polysaccharide. For target substances that include phytocannabinoids, suitable hydrophobic solvents may include alcohol (e.g. methanol, ethanol, n-propyl alcohol, isopropyl alcohol, etc.), other polar organic solvents (e.g. acetone, acetonitrile, tetrahydrofuran, glycerol, DMSO, dichloromethane, chloroform, etc.), eutectic solvents (e.g. equimolar mixture of acetic acid and menthol, glucose syrup, etc.), ionic liquids (e.g. 1-butyl-3-methylimidazolium tetrafluoroborate, etc.), supercritical $CO_2$ and hydrocarbons (e.g. n-hexane, butane, propane, etc.). The hydrophobic solvent may include a suitable combination of any of the above solvents.

The hydrophilic solvent may be any suitable hydrophilic solvent in which a target substance is insoluble or poorly soluble, in which an insoluble polysaccharide for capturing the target substance is insoluble and that will not damage the target substance or the insoluble polysaccharide. The hydrophilic solvent may for example include water, brine, salt solutions or buffered solutions, including solutions comprising a chelating agent.

The hydrophobic solvent and the hydrophilic solvent are defined in terms of hydrophobicity and hydrophilicity relative to each other and not necessarily on any particular scale of hydrophobicity and hydrophilicity. For a given hydrophobic target compound and a given sample, the hydrophobic solvent and the hydrophilic solvent may be selected to be miscible with each other for facilitating recovery of the hydrophobic target compound using the insoluble polysaccharide as described above. Where the hydrophobic solvent and the hydrophilic solvent are not miscible with each other to any great degree, the hydrophobic solvent may be evaporated by increasing heat or by decreasing pressure prior to addition of hydrophilic solvent instead of being mixed with the hydrophilic solvent.

Figure 4:
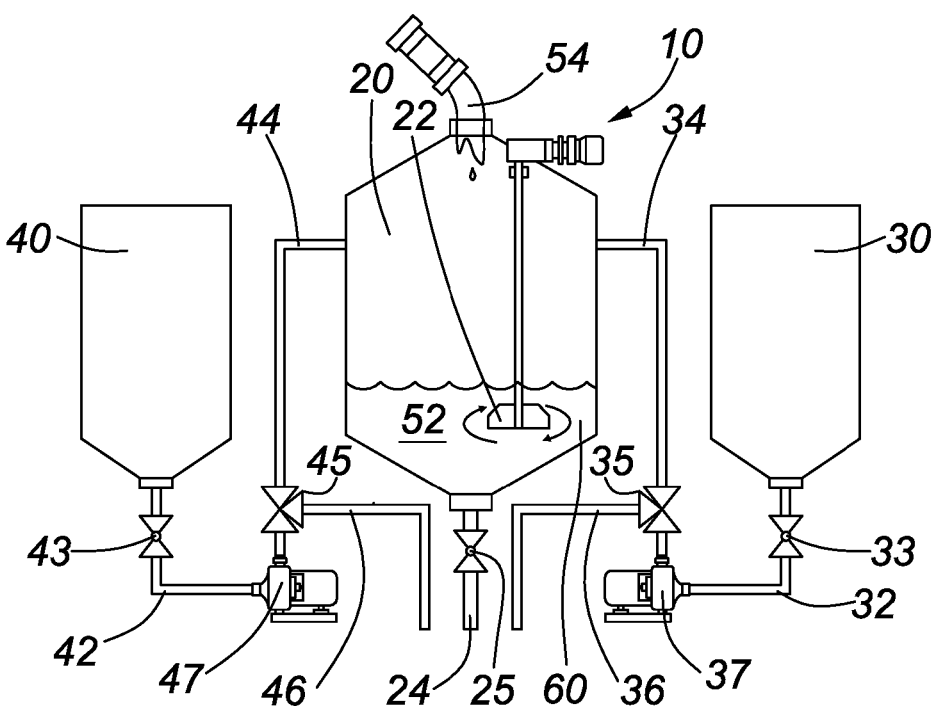
FIG. 4 is a schematic diagram of the system of FIG. 2 with a sample added to the system.

The slurry vessel 20 includes an agitator 22 positioned within the slurry vessel 20. The agitator 22 is for agitating a fluid inside the slurry vessel 20 (e.g. the agitator 22 is shown in FIG. 4 mixing the loaded slurry 52). The agitator 22 is shown as a rotary stirring agitator but any suitable agitator may be used (e.g. cross-flow, a venturi, static agitator, etc.). The slurry vessel 20 is in fluid communication with the filter 12 through a slurry output flow line 24, and fluid communication between the slurry tank 20 and the slurry output flow line 24 may be engaged and disengaged by a output valve 25.

The hydrophobic solvent vessel 30 includes an agitator 31 positioned within the hydrophobic solvent vessel 30. The agitator 31 is for agitating a hydrophobic solvent (e.g. the agitator 31 is shown agitating the hydrophobic solvent 60 in FIG. 3, etc.) inside the hydrophobic solvent vessel 30 to mix the hydrophobic solvent. The hydrophobic solvent vessel 30 is in fluid communication with the slurry vessel 20 and with the filter 12.

The hydrophilic solvent vessel 40 includes an agitator 41 positioned within the hydrophilic solvent vessel 40. The agitator 41 is for agitating a hydrophilic solvent (e.g. the agitator 41 is shown agitating the hydrophilic solvent 70 in FIG. 6, etc.) inside the hydrophilic solvent vessel 40 to mix the hydrophilic solvent. The hydrophilic solvent vessel 40 is in fluid communication with the slurry vessel 20 and with the filter 12.

The hydrophobic solvent vessel 30 may be in fluid communication with the slurry vessel 20 through an upstream hydrophobic solvent flow line 32 and a downstream hydrophobic solvent flow line 34. Fluid communication between the hydrophobic solvent vessel 30 and the slurry vessel 20 may be provided and broken by an upstream hydrophobic solvent valve 33 and a downstream hydrophobic solvent valve 35. Fluid communication between the hydrophobic solvent vessel 30 and the slurry vessel 20 may be driven by a pump 37.

The hydrophobic solvent vessel 30 may be in fluid communication with the filter 12 through an upstream hydrophobic solvent flow line 32 and a hydrophobic solvent rinse flow line 36. Fluid communication between the hydrophobic solvent vessel 30 and the filter 12 may be provided and broken by the upstream hydrophobic solvent valve 33 and the downstream hydrophobic solvent valve 35. Fluid communication between the hydrophobic solvent vessel 30 and the filter 12 may be driven by the pump 37.

The hydrophilic solvent vessel 40 may be in fluid communication with the slurry vessel 20 through an upstream hydrophilic solvent flow line 42 and a downstream hydrophilic solvent flow line 44. Fluid communication between the hydrophilic solvent vessel 40 and the slurry vessel 20 may be provided and broken by an upstream hydrophilic solvent valve 43 and a downstream hydrophilic solvent valve 45. Fluid communication between the hydrophilic solvent vessel 40 and the slurry vessel 20 may be driven by a pump 47.

The hydrophilic solvent vessel 40 may be in fluid communication with the filter 12 through an upstream hydrophilic solvent flow line 42 and a hydrophilic solvent rinse flow line 46. Fluid communication between the hydrophilic solvent vessel 40 and the filter 12 may be provided and broken by the upstream hydrophilic solvent valve 43 and the downstream hydrophilic solvent valve 45. Fluid communication between the hydrophilic solvent vessel 40 and the filter 12 may be driven by the pump 47.

Batch Slurry Protocol

FIGS. 3 to 11 show the system 10 in use to purify a hydrophobic target compound from a sample 54 using an insoluble polysaccharide 50, a hydrophobic solvent 60 and a hydrophilic solvent 70. The hydrophobic solvent 60 is stored in and sourced from the hydrophobic solvent vessel 30. The hydrophilic solvent 70 is stored in and sourced from the hydrophilic solvent vessel 40. For simplicity of review of FIGS. 3 to 11, the hydrophobic solvent 60 and the agitator 31 are shown in the hydrophobic solvent vessel 30 only when the hydrophobic solvent 60 is being supplied to the slurry tank 20. Similarly, and also for simplicity of review of FIGS. 3 to 11, the hydrophilic solvent 70 and the agitator 41 are shown in the hydrophilic solvent vessel 40 only when the hydrophilic solvent 70 is being supplied to the slurry tank 20. In figures where these solvents are not being supplied to the slurry tank 20, the hydrophobic solvent vessel 30 and the hydrophilic solvent vessel 40 are shown without detail.

Figure 3:
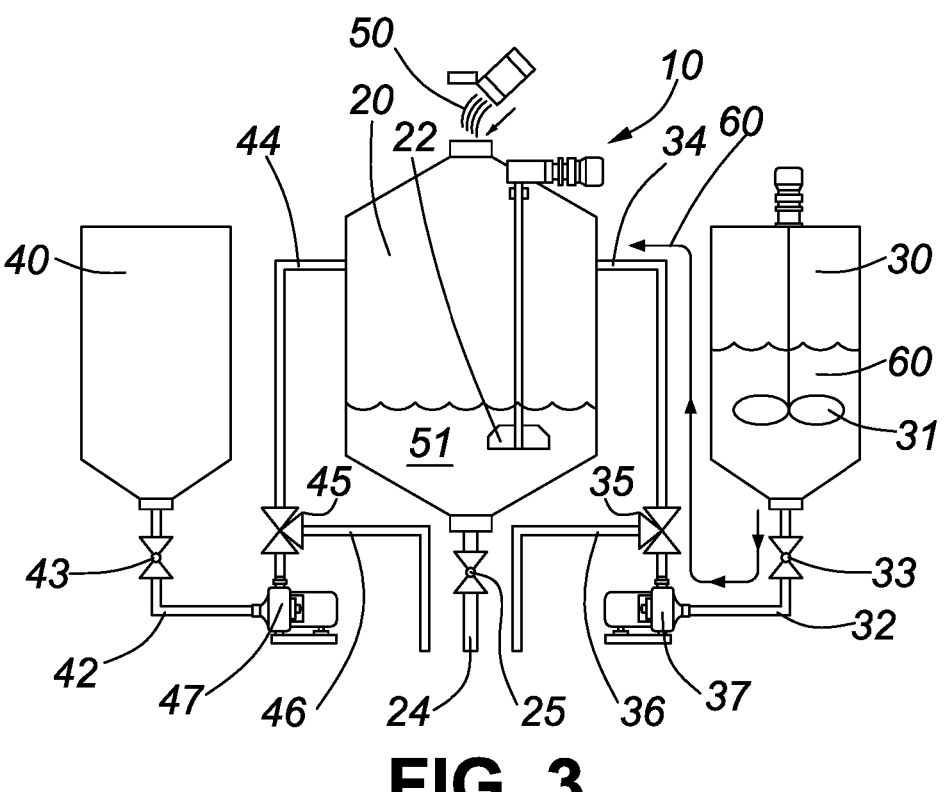
FIG. 3 is a schematic diagram of the system of FIG. 2 with an insoluble polysaccharide added to the system.

In FIG. 3, the insoluble polysaccharide 50, such as a cyclodextrin polymer, is provided into the slurry vessel 20. The insoluble polysaccharide 50 may be supplied dry, for example as a powder, and the slurry vessel 20 may be chilled prior to addition of the insoluble polysaccharide 50.

The insoluble polysaccharide 50 is combined with the hydrophobic solvent 60 in the slurry vessel 20 to provide a slurry 51. The hydrophobic solvent 60 may be provided to the slurry vessel 20 from the hydrophobic solvent vessel 30 via the upstream hydrophobic solvent flow line 32 and the downstream hydrophobic solvent flow line 34. The hydrophobic solvent 60 may be provided in a ratio of 75% insoluble polysaccharide 50 to 25% hydrophobic solvent 60. Alternatively, either a portion of the insoluble polysaccharide 50 or all of the insoluble polysaccharide 50 may be added to the slurry vessel 20 after adding the hydrophilic solvent 70 to the slurry vessel 20 (not shown).

FIG. 4 shows the sample 54 being loaded into the slurry vessel 20 and combined with the slurry 51, providing a loaded slurry 52. The slurry vessel 20 may be chilled to between 3° C. and room temperature, such as 4° C., when the sample 54 is added to the slurry vessel 20. In some cases, lower temperatures may also facilitate maintaining liquidity of a low boiling gaseous solvent, such as butane or other shorter hydrocarbon solvents with boiling points below or close to 20° C. In some cases, lower temperatures may also improve the stability of temperature-sensitive hydrophobic target compounds. In some cases, higher temperatures may be applied to decrease solvent viscosity. In some cases, higher temperatures may be used to facilitate in situ decarboxylation of phytocannabinoids, if decarboxylated phytocannabinoids are the target molecule and where decarboxylation was not previous carried out on the sample 54.

Temperature may also be modulated to maintain a temperature range at which supercritical fluids have the appropriate physical properties.

The sample 54 includes at least one hydrophobic target compound. The sample 54 may include for example an extract or other sample from a biological source (e.g. a plant, animal tissue fungi, yeast, bacteria, or other microorganism), mineral samples (e.g. gold salts, gold complexes, copper salts, copper complexes, etc.), chemical waste samples (e.g. hydrocarbon extraction and processing effluent, mining tailings, etc.). The hydrophobic target compound may include any compound that complexes with, binds with or otherwise adheres to the insoluble polysaccharide 50. The hydrophobic target compound may adhere with the insoluble polysaccharide 50 by coordinating within a torus formed by the molecular structure of the insoluble polysaccharide 50, or by binding with the insoluble polysaccharide 50 outside of the torus.

Figure 5:
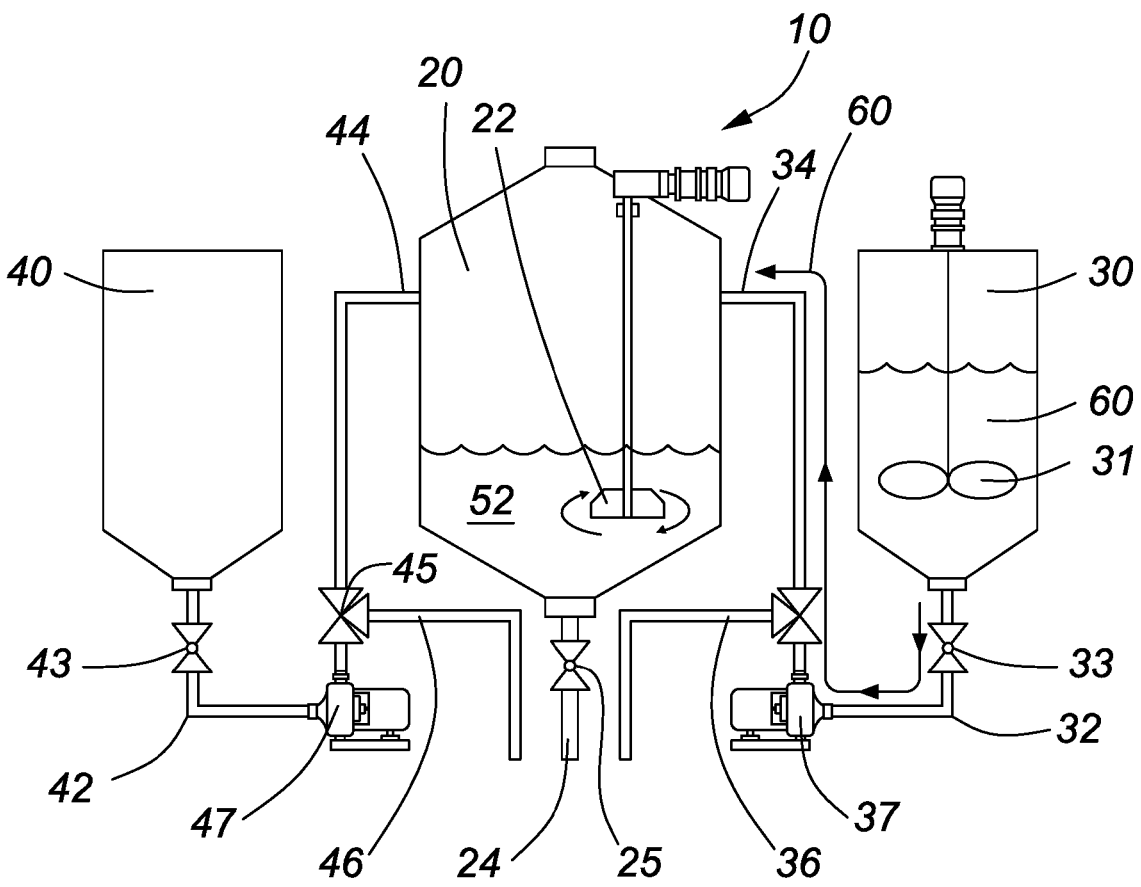
FIG. 5 is a schematic diagram of the system of FIG. 2 with additional hydrophobic solvent added to the system.

FIG. 5 shows additional hydrophobic solvent 60 being added to the slurry vessel 20 to combine with the loaded slurry 52 via the upstream hydrophobic solvent flow line 32 and the downstream hydrophobic solvent flow line 34. The additional hydrophobic solvent 60 may dilute any water that may have been included in the sample 54. The additional hydrophobic solvent 60 may facilitate dissolution of phytocannabinoids or other hydrophobic target compounds that may be present in the sample 54. The loaded slurry 52 may be agitated by the agitator 22.

Figure 6:
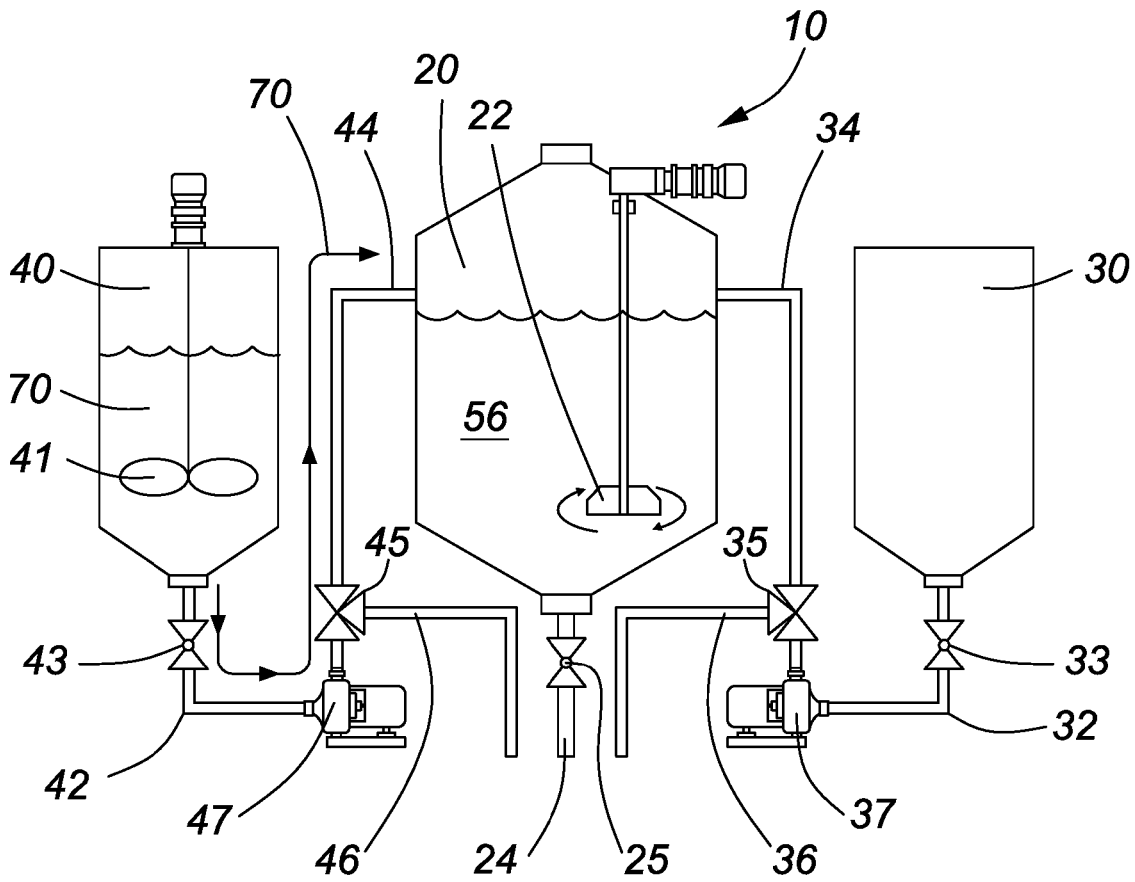
FIG. 6 is a schematic diagram of the system of FIG. 2 with hydrophilic solvent added to the system.

FIG. 6 shows the hydrophilic solvent 70 being added to the flurry tank 20 from the hydrophobic solvent vessel 30. The hydrophilic solvent 70 may be added to the slurry vessel 20 via the upstream hydrophilic solvent flow line 42 and the downstream hydrophilic solvent flow line 44 and combined with the loaded slurry 52 to provide a binding slurry 56. Where the hydrophobic target compound are phytocannabinoids, the sample 54 is an ethanolic extract of *C. sativa* flowers or other trichome-bearing biomass, the hydrophobic solvent 60 is ethanol and the hydrophilic solvent 70 is water, the binding slurry 56 may target a ratio of 30:70 hydrophobic solvent 60 to hydrophilic solvent 70 for driving the hydrophobic target compounds into the insoluble polysaccharide 50 polymer core. Other ratios of hydrophobic solvent 60 to hydrophilic solvent 70 for the binding slurry 56 may be selected for other hydrophobic solvents 60, hydrophilic solvents 70, samples 54 or target hydrophobic compounds. Together, the hydrophobic solvent 60 and the hydrophilic solvent 70 in a ratio that pushes the target hydrophobic target molecule into the insoluble polysaccharide 50 provide a binding solvent 58. The binding solvent 58 may include miscible hydrophobic solvent 60 and hydrophilic solvent 70 or immiscible hydrophobic solvent 60 and hydrophilic solvent 70 separated into two layers.

Figure 7:
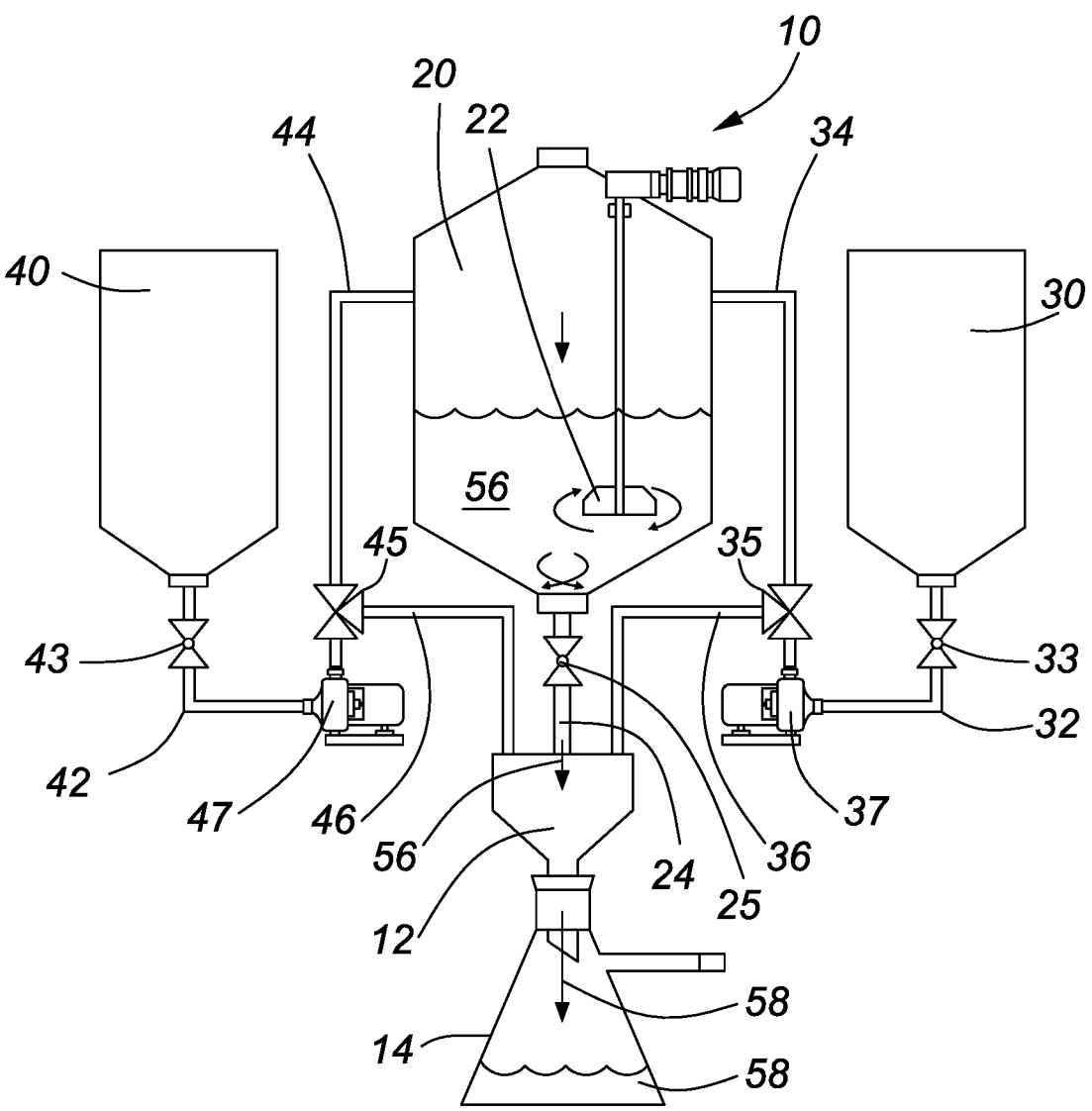
FIG. 7 is a schematic diagram of the system of FIG. 2 while filtering a binding slurry to recover a hydrophobic target compounds.

FIG. 7 shows the binding slurry 56 being run through the filter 12 for filtering and retaining the insoluble polysaccharide 50 with captured hydrophobic target compounds. The binding solvent 58 runs through the filter 12 into the recovery vessel 14. The filter 12 may comprise paramagnetic or other magnetic qualities for magnetically attracting or retaining embodiments of the insoluble polysaccharide 50 bound to a magnetic particle or a magnetic nanoparticle on the filter 12, such as the embodiments of the insoluble polysaccharide 50 shown in FIGS. 14 to 17.

Figure 8:
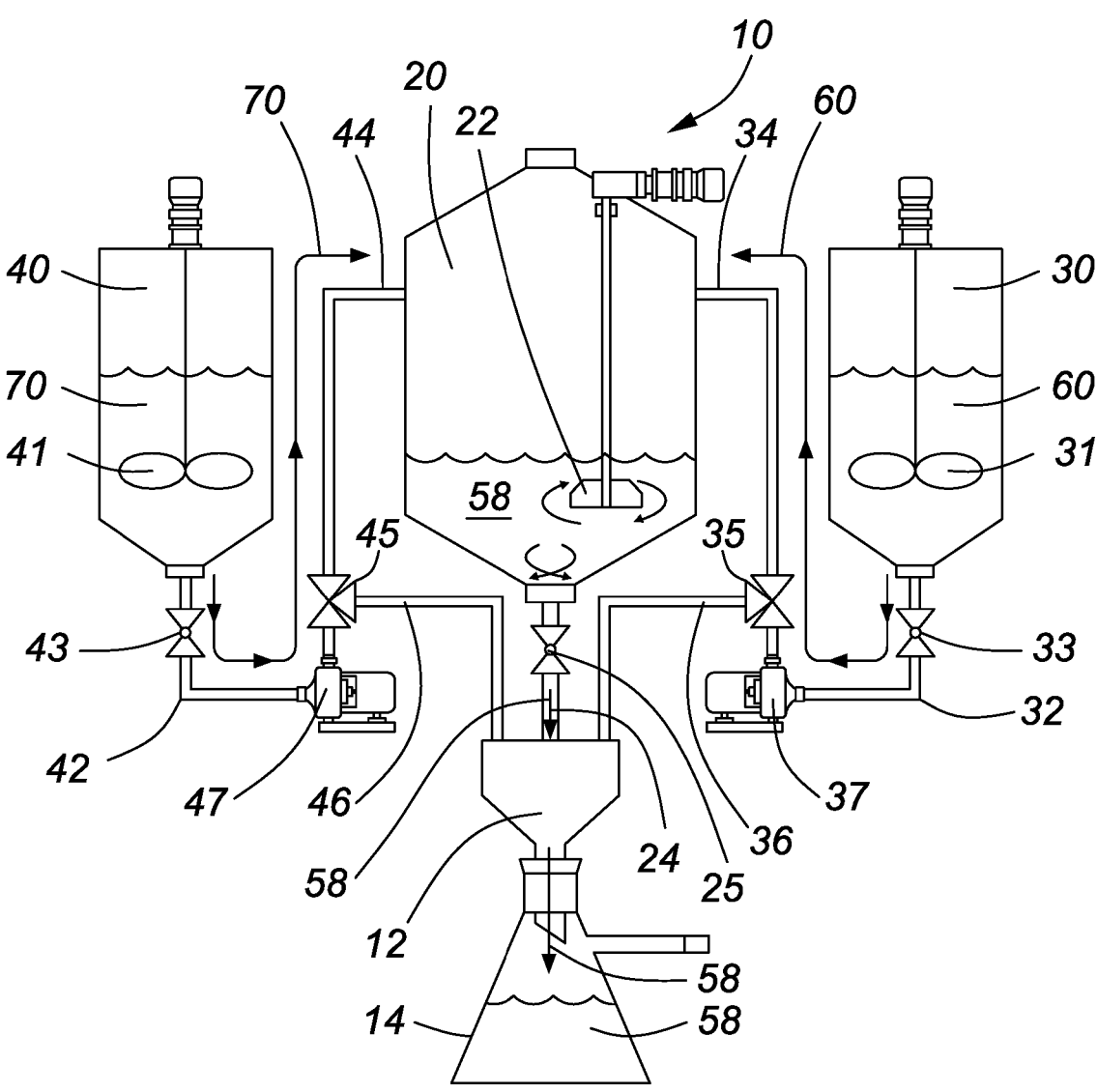
FIG. 8 is a schematic diagram of the system of FIG. 2 while rinsing a filter with both hydrophobic and hydrophilic solvents.

FIG. 8 shows rinsing of the filter 12 with the binding solvent 58 or other ratios of the hydrophobic solvent 60 and the hydrophilic solvent 70 to wash the filter 12. Rinsing with the binding solvent 58 may remove some material (e.g. chlorophyll, CBDA, etc.) that water by itself may not remove. This step may also recover some valuable material that binds less strongly than a target hydrophobic material, such as recovery of CBDA when decarboxylated CBD is the primary hydrophobic target compound. Such valuable material may be repurified through the system 10. Providing the binding solvent 58 to the filter 12 through the downstream hydrophobic solvent flow line 34 and the downstream hydrophilic solvent flow line 44 may rinse out the slurry tank 20. The binding solvent 58 may be provided to the filter 12 by direct application of the hydrophobic solvent 60 and the hydrophilic solvent 70 to the filter 12 through the hydrophobic solvent rinse flow line 36 and the hydrophilic solvent rinse flow line 46.

Figure 9:
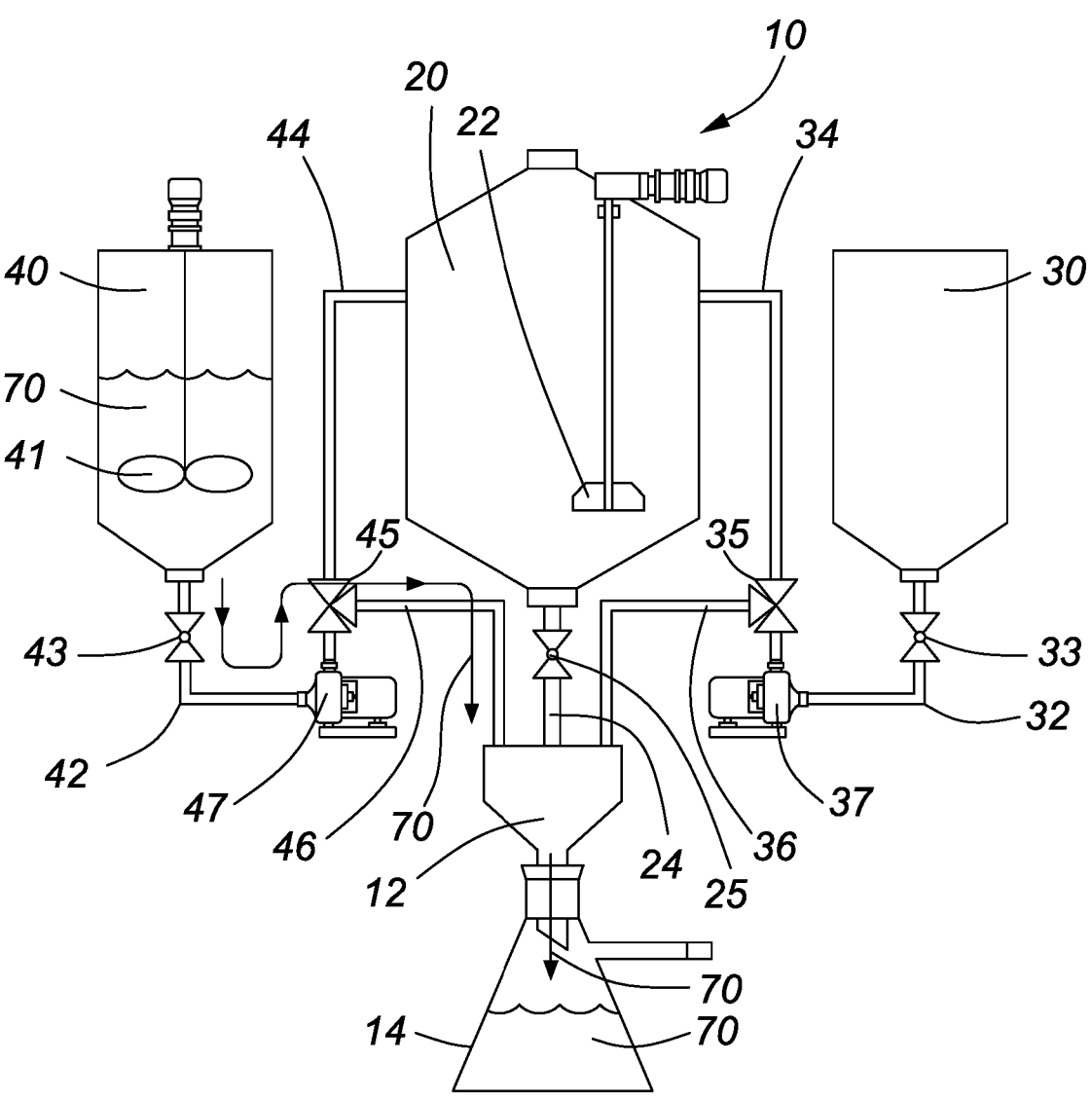
FIG. 9 is a schematic diagram of the system of FIG. 2 while rinsing the filter with hydrophobic solvent.

FIG. 9 shows rinsing of the filter 12 with hydrophilic solvent 70 to wash the filter 12 via the upstream hydrophilic solvent flow line 42 and the hydrophilic solvent rinse flow line 46. An amount of hydrophilic solvent 70 used to wash the filter 12 may be about 3 or 4 times the volume of the binding slurry 56 that was passed through the filter 12.

Figure 10:
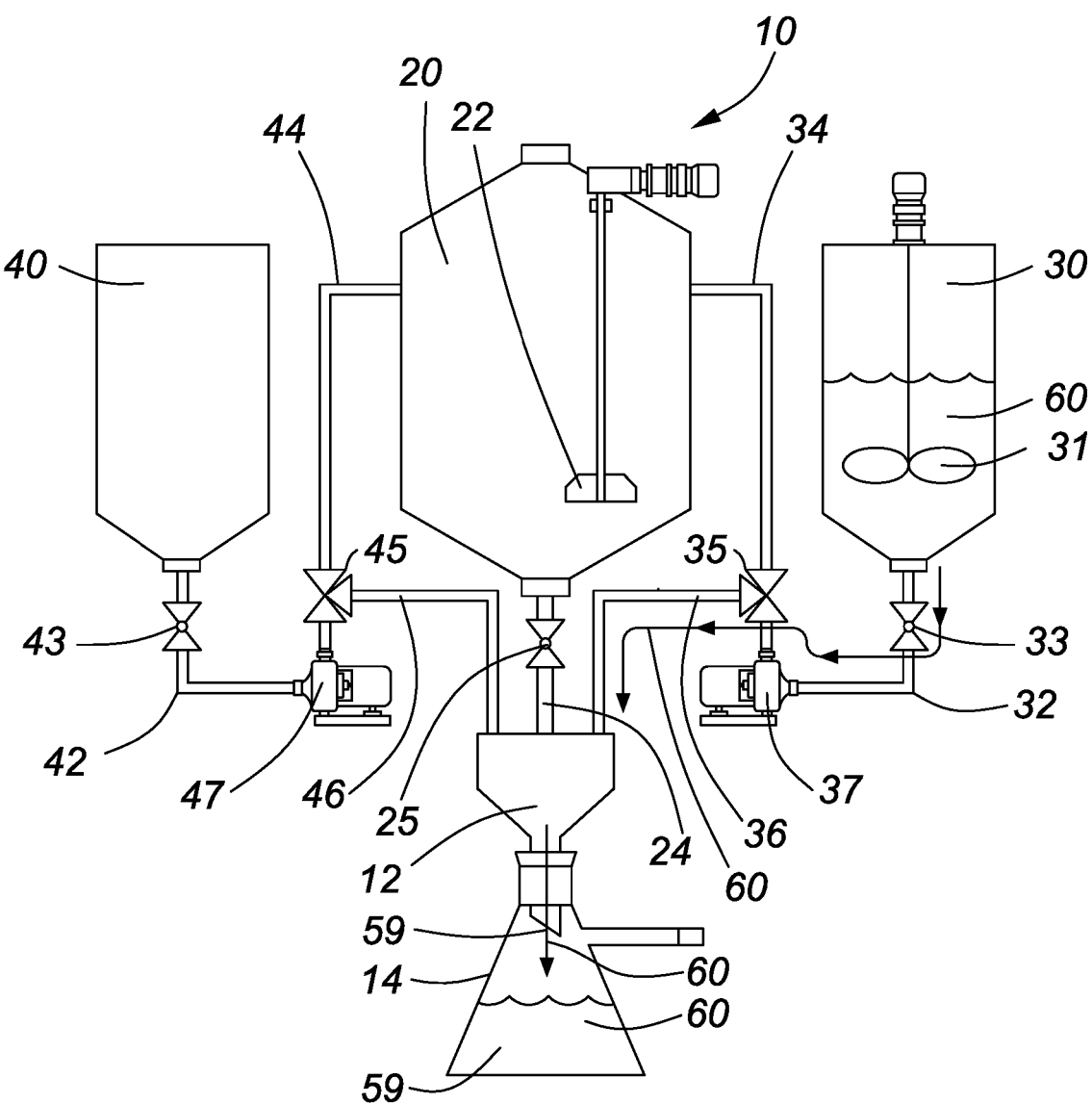
FIG. 10 is a schematic diagram of the system of FIG. 2 while flowing hydrophobic solvent over the filter to dissolve the hydrophobic target compounds.

FIG. 10 shows dissolution of the hydrophobic target compounds by flowing the hydrophobic solvent 60 over the filter 12 to dissociate the hydrophobic target compounds from the insoluble polysaccharide 50 and solubilize the hydrophobic target compounds in the hydrophobic solvent 60. A recovered hydrophobic target compound 59 is recovered in the hydrophobic solvent 60 from the recovery vessel 14 The amount of hydrophobic solvent 60 used to recover the recovered hydrophobic target compound 59 may be selected to provide the recovered hydrophobic target compound 59 at a defined concentration. A hydrophobic solvent other than the hydrophobic solvent 60 may be used to recover the recovered hydrophobic target compound 59.

The insoluble polysaccharide 50 may then be regenerated for reuse by washing the insoluble polysaccharide 50 with a detergent solution, for example 0.1% Triton X-100 at 37° C. for one minute. Solvents that are able to dissociate any hydrophobic compounds from the insoluble polysaccharide 50, such as DMSO, may also be applied for regeneration. Exposure to the detergent solution, to solvent or other regeneration may be followed by re-equilibration with 3 to 5 volumes of ethanol.

Figure 11:
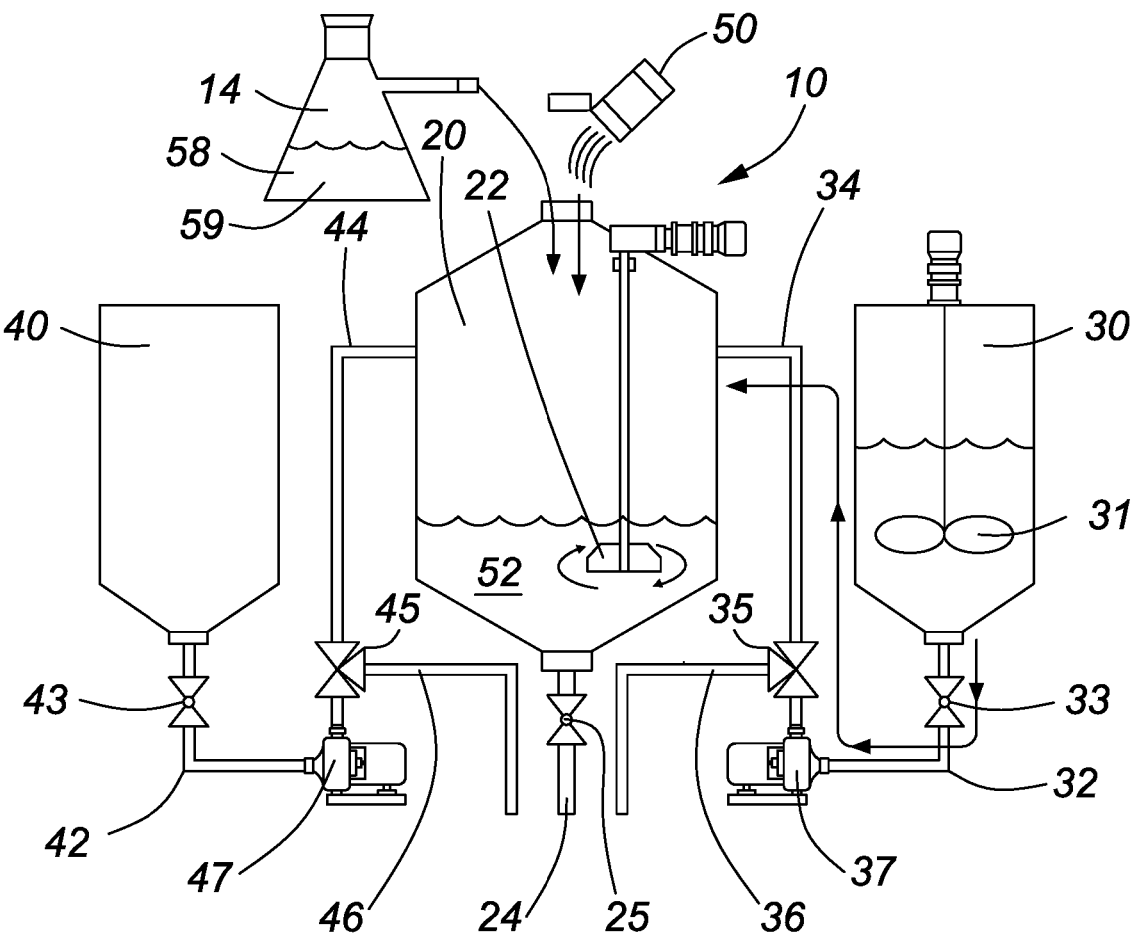
FIG. 11 is a schematic diagram of the system of FIG. 2 with the contents of a recovery vessel added to the system to repeat the process of FIGS. 5 to 10.

FIG. 11 shows that the contents of the recovery vessel 14 after washing of the ethanol extract may then be loaded into the chilled slurry vessel 20 to repeat the batch slurry protocol with an aliquot of unique cyclodextrin polymer (for example α-cyclodextrin or γ-cyclodextrin).

Figure 12:
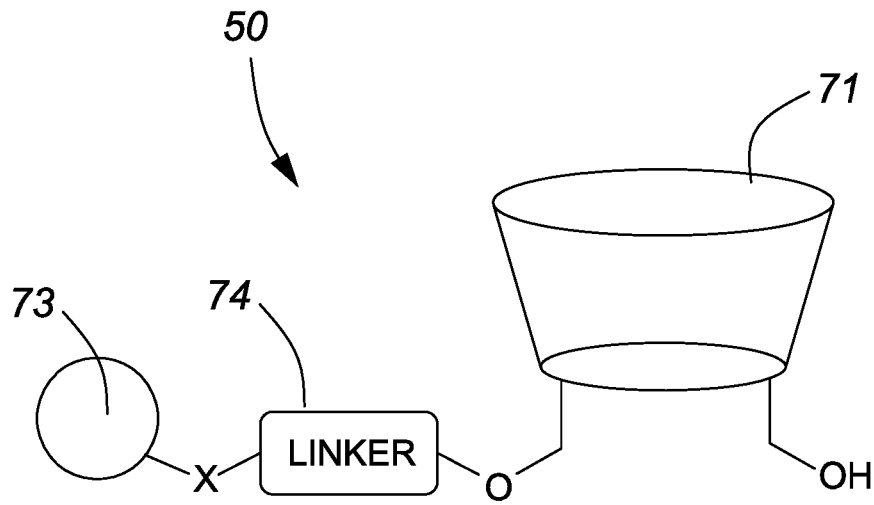
FIG. 12 is a schematic diagram of an insoluble polysaccharide including an insoluble polymer.

FIG. 12 shows an embodiment of the insoluble polysaccharide 50 in which a polysaccharide 71 bound to an insoluble polymer 73, such as an insoluble polymeric bead (e.g. a polystyrene bead, Merrifield polystyrene resin bead, Wang resin bead, etc.). The polysaccharide 71 is bound to the insoluble polymer 73 by a linker 74.

Figure 13:
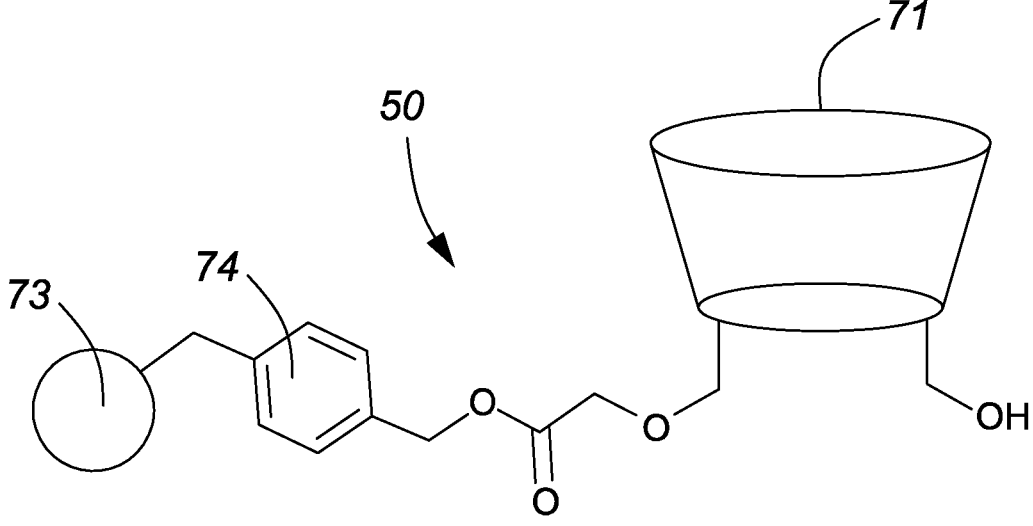
FIG. 13 is a schematic diagram of an insoluble polysaccharide including an insoluble polymer.

FIG. 13 shows an embodiment of the insoluble polysaccharide 50 in which the polysaccharide 71 is bound to the insoluble polymer 73 by the linker 74, and the linker 74 comprises a benzylic ester, in this case a carboxymethylene group.

Figures 14, 15:
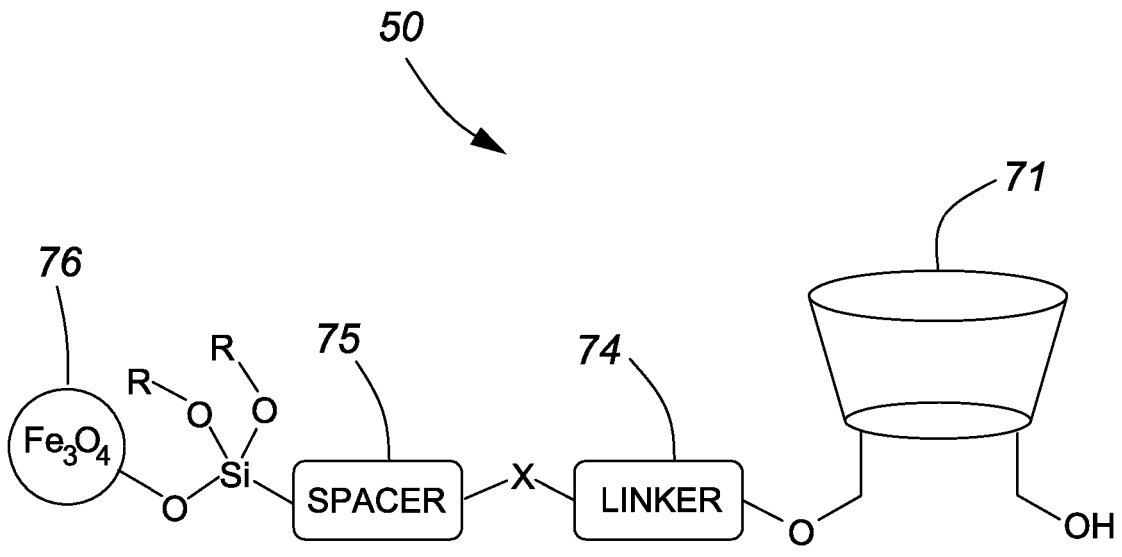
FIG. 14 is a schematic diagram of an insoluble polysaccharide including a magnetic bead.
FIG. 15 is a schematic diagram of an insoluble polysaccharide including a magnetic bead.

FIG. 14 shows an embodiment of the insoluble polysaccharide 50 in which the polysaccharide 71 is bound to a magnetic bead 76 by the linker 74, and by a spacer 75, which may include a silicate group. The magnetic bead 76 may include a micron-sized magnetite particle or other magnetic material.

FIG. 15 shows an embodiment of the insoluble polysaccharide 50 in which the polysaccharide 71 is bound to the magnetic bead 76 by the linker 74, which comprises an amide group, and by the spacer 75, which comprises a propyl group. In FIG. 15, multiple separate spacer groups 75 are bound with the magnetic bead 76 to coordinate multiple insoluble polysaccharides 50 with the magnetic bead 76.

Figures 16, 17:
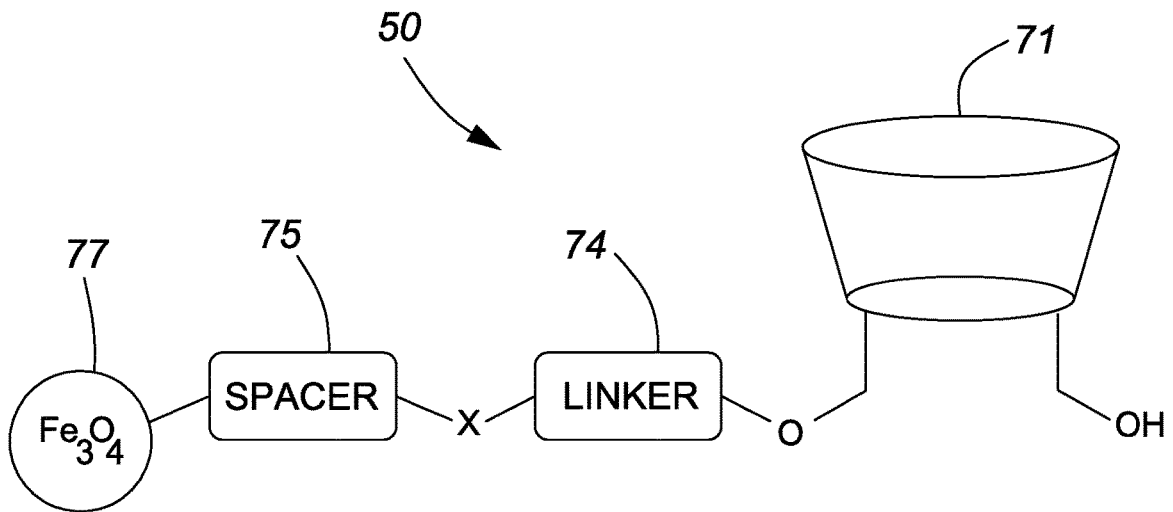
FIG. 16 is a schematic diagram of an insoluble polysaccharide including a magnetic nanoparticle.
FIG. 17 is the molecular structure of an insoluble polysaccharide of including a magnetic nanoparticle.

FIG. 16 shows an embodiment of the insoluble polysaccharide 50 in which the polysaccharide 71 is bound to a magnetic nanoparticle 77 by the linker 74 and the spacer 75. The magnetic nanoparticle 77, may include a micron-sized magnetite particle or other magnetic material.

FIG. 17 shows an embodiment of the insoluble polysaccharide 50 in which the polysaccharide 71 is bound to the magnetic nanoparticle 77 by the linker 74 and the spacer 75. The linker 74 includes a polyethylene glycol linker and amide, which binds non-covalently through Van der Waals hydrophobic interaction with the spacer 75, which includes a monounsaturated hydrocarbon carboxylate. In FIG. 17, multiple separate spacer groups 75 are bound with the magnetic or magnetic nanoparticle 77 to coordinate multiple insoluble polysaccharides 50 with the magnetic nanoparticle 77.

Embodiments of the insoluble polysaccharide 50 shown in FIGS. 12 to 17 may be used in combination, with different filters 12 or other isolation methods being used to target different embodiments of the insoluble polysaccharide 50. For example, the embodiments of the insoluble polysaccharide 50 shown in FIGS. 12 and 13 could be recovered with a filter 12 sized for the particular insoluble polymer 73 used, while at the same time the embodiments of the insoluble polysaccharide 50 shown in FIGS. 14 to 17 could be recovered by application with a magnetic field to the binding slurry 56. The magnetic field could be applied to the binding slurry by using a filter 12 that includes a magnetron or other source of a magnetic field, by immersing a magnetron or other source of a magnetic field in the binding slurry 56 or any suitable method of exposing a magnetic field to the binding slurry such that the magnetic bead 76, or magnetic nanoparticle 77, is drawn toward the magnetic field. If each polysaccharide 71 has a preferred propensity for binding different hydrophobic target molecules, then multiple insoluble polysaccharides 50 of FIGS. 12 to 17 could be used in combination on a given sample 54 and then easily separated, separating different recovered hydrophobic target molecules 59 from the same binding slurry 56.

In addition to the embodiments of the insoluble polysaccharide 50 shown in FIGS. 12 to 17, the embodiments of the insoluble polysaccharide 50 shown in FIGS. 45 to 48 may also be used in the system 10 where the immobile matrix 88 or the silica-based immobile matrix 89 are reduced in size to allow the embodiments of the insoluble polysaccharide 50 shown in FIGS. 45 to 48 to be used in a slurry rather than as part of an immobile phase in a column or other chromatographic separation technique.

Figure 18:
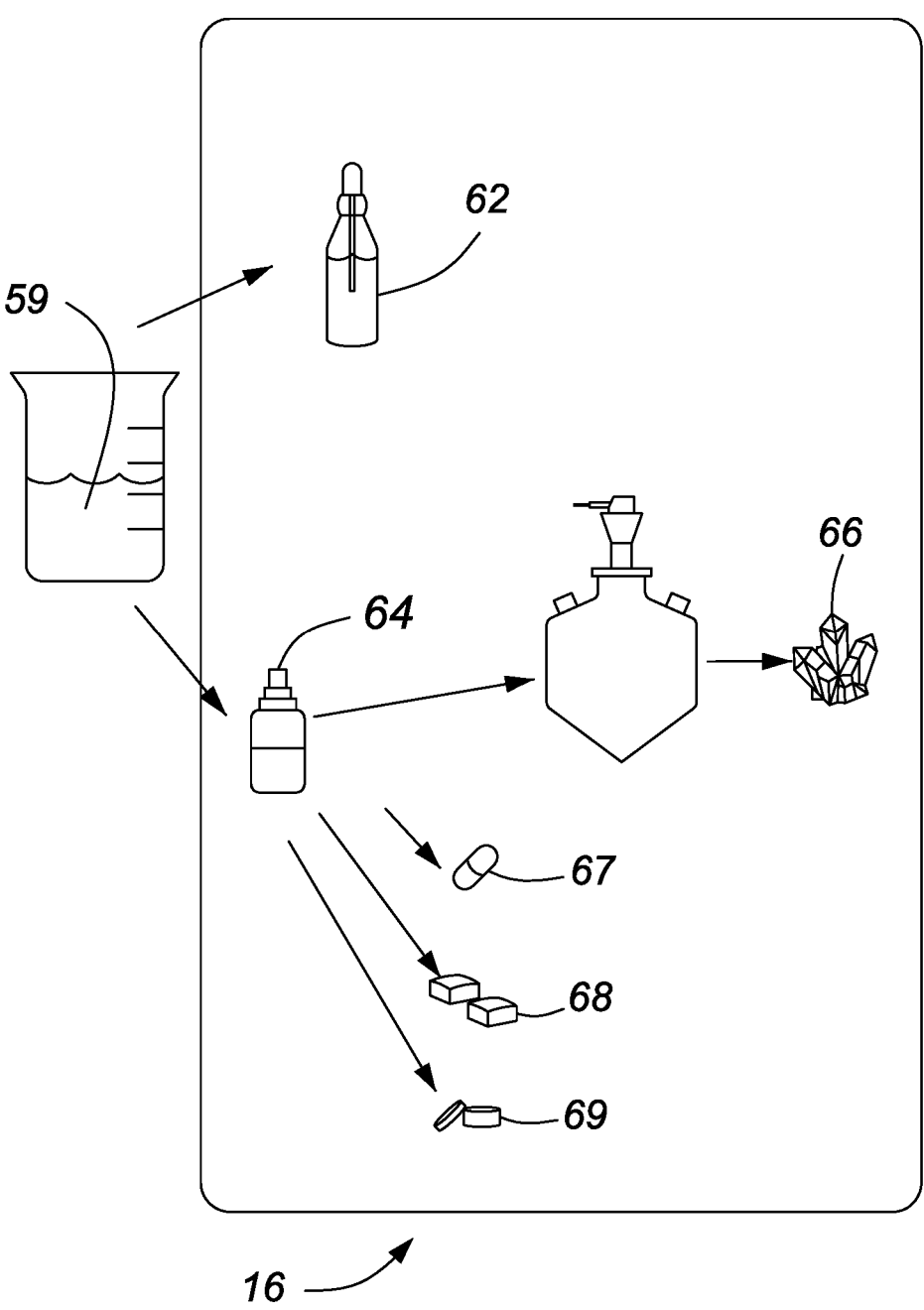
FIG. 18 is a schematic diagram showing processing of recovered target compounds into downstream products.

FIG. 18 shows the recovered target compound 59 recovered from the filter 12 may be provided to the processing system 16 for processing into downstream products for sale to consumers or in business to business transactions. Considering an application where the recovered target compound 59 is from hemp or other *C. sativa* extract, the recovered target compound 59 may be as an input for a tincture 62 (e.g. an ethanol tincture, food oil tincture, etc.). The recovered target compound 59 from hemp or other *C. sativa* extract may be processed with supercritical $CO_2$ or other extraction and formulation to produce a full spectrum extract oil 64 for oil-based products. The full spectrum extract oil 64 may then be further processed for specific phytocannabinoids and crystallized to produce an isolate 66.

Alternatively, the full spectrum extract oil may be used to produce products such as capsules 67, edibles 68 or salves 69.

Column Capture Setup

Figure 19:
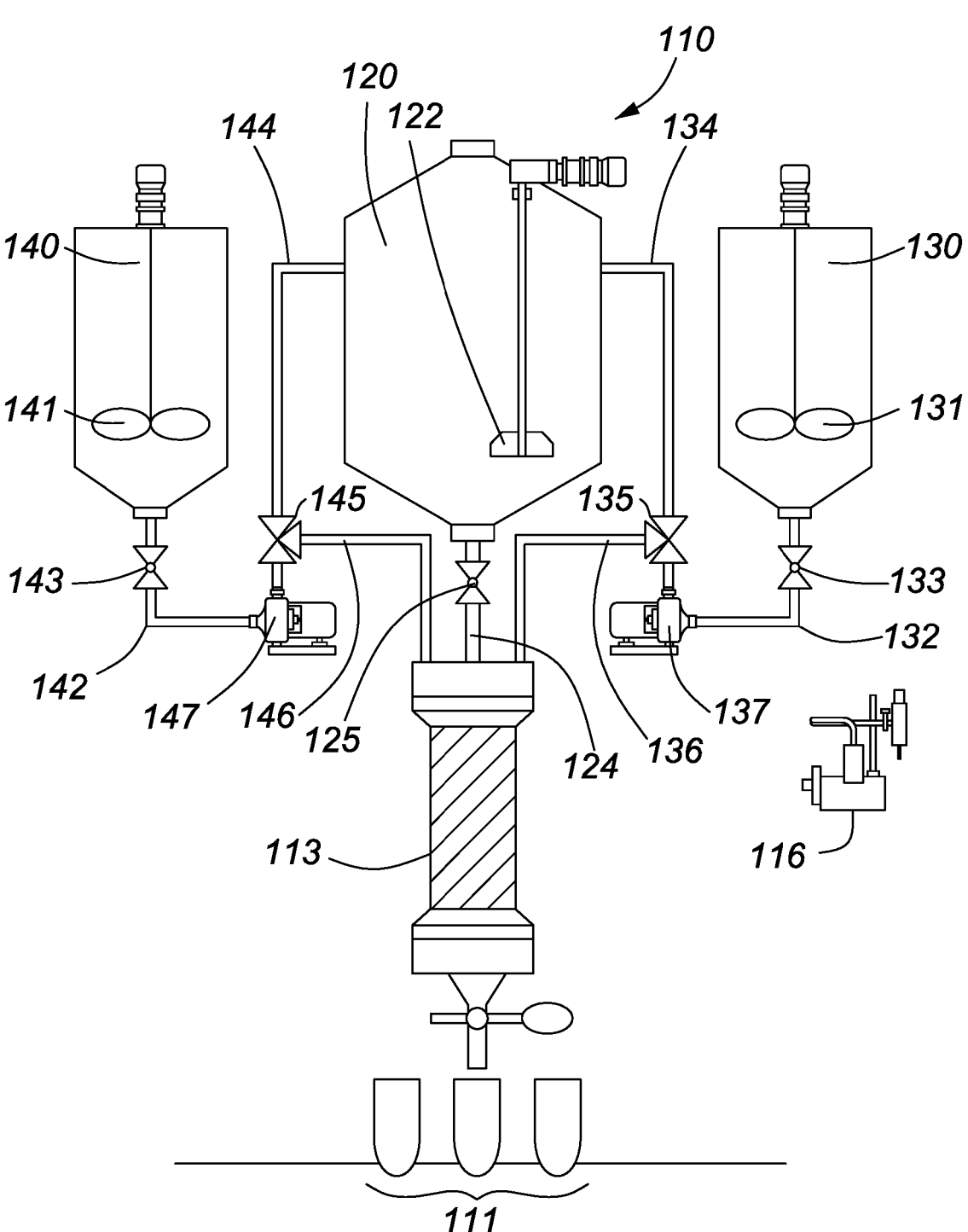
FIG. 19 is a schematic diagram of a hydrophobic compound recovery system.

FIG. 19 shows a hydrophobic compound recovery system 110. The system 110 includes the slurry vessel 120. A column filter 113 is in fluid communication with the slurry vessel 120 for receiving fluid from the slurry vessel 120 and filtering material out of the fluid. A recovery vessel 111 is in fluid communication with the column filter 113 for receiving filtrate that passes through the column filter 113. In the system 110, a series of individual recovery vessels 111 are applied for selective elution from the column filter 113, but a single recovery vessel 111 may be applied. Each recovery vessel 111 may be any suitable recovery vessel may be used (e.g. a flask, Erlenmeyer, round-bottom flask, beaker, test tube, etc.). The processing system 116 may be in fluid communication with the recovery vessel 111 for processing target molecules captured using the column filter 113. The slurry vessel 120 is in fluid communication with the hydrophobic solvent vessel 130 for receiving hydrophobic solvent from the hydrophobic solvent vessel 130. The slurry vessel 120 is in fluid communication with the hydrophilic solvent vessel 140 for receiving hydrophilic solvent from the hydrophilic solvent vessel 140.

Each of the slurry vessel 120, the hydrophobic solvent vessel 130 and the hydrophilic solvent vessel 140 may be any suitable fluid vessel appropriate for the size, scale and application of the system 110 (e.g. a tank, pressure-rated tank, beaker, etc.).

Figure 21:
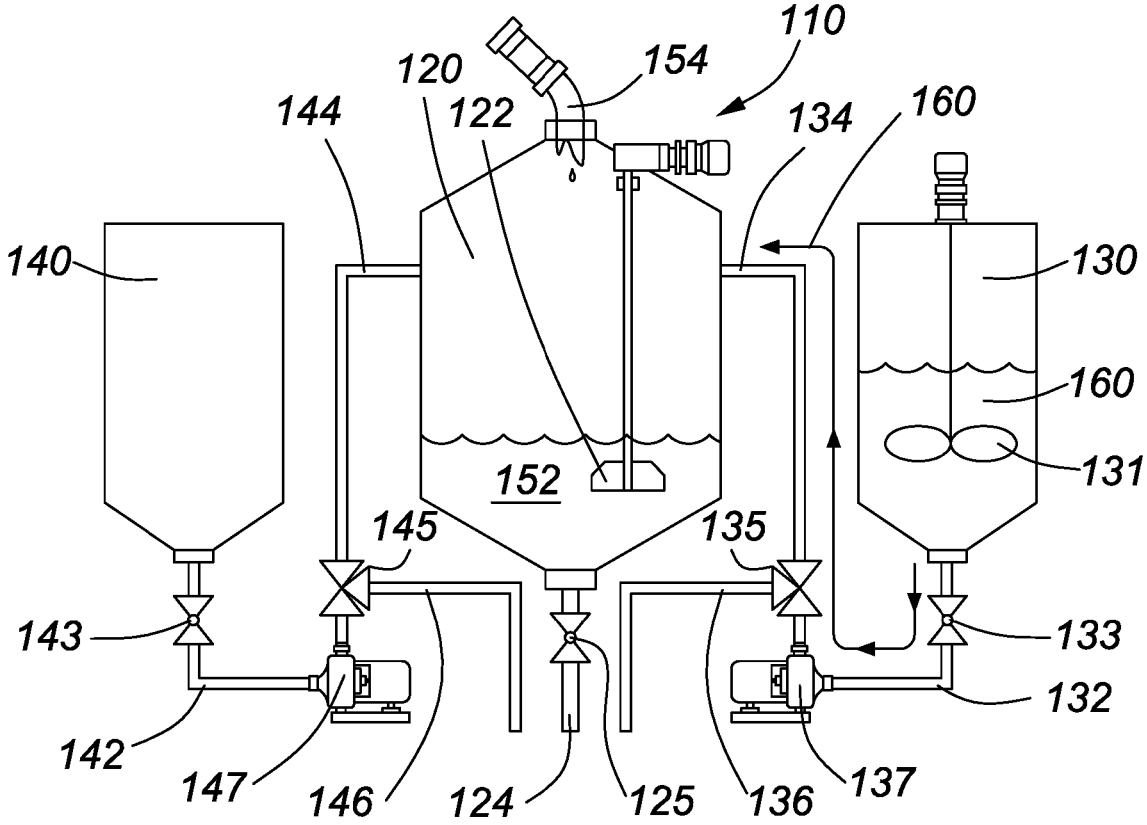
FIG. 21 is a schematic diagram of the system of FIG. 19 with a sample added to the system.

The slurry vessel 120 includes the agitator 122 positioned within the slurry vessel 120. The agitator 122 is for agitating a fluid inside the slurry vessel 120 (e.g. the agitator 122 is shown in FIG. 21 mixing the loaded slurry 152). The agitator 122 is shown as a rotary stirring agitator but any suitable agitator may be used (e.g. cross-flow, a venturi, static agitator, etc.). The slurry vessel 120 is in fluid communication with the column filter 113 through the slurry output flow line 124, and fluid communication between the slurry tank 120 and the slurry output flow line 124 may be engaged and disengaged by the output valve 125.

The hydrophobic solvent vessel 130 includes the agitator 131 positioned within the hydrophobic solvent vessel 130. The agitator 131 is for agitating a hydrophobic solvent (e.g. the agitator 131 is shown agitating the hydrophobic solvent 160 in FIG. 20, etc.) inside the hydrophobic solvent vessel 130 to mix the hydrophobic solvent. The hydrophobic solvent vessel 130 is in fluid communication with the slurry vessel 120 and with the column filter 113.

The hydrophilic solvent vessel 140 includes the agitator 141 positioned within the hydrophilic solvent vessel 140. The agitator 141 is for agitating a hydrophilic solvent (e.g. the agitator 141 is shown agitating the hydrophilic solvent 170 in FIG. 22, etc.) inside the hydrophilic solvent vessel 140 to mix the hydrophilic solvent. The hydrophilic solvent vessel 140 is in fluid communication with the slurry vessel 120 and with the column filter 113.

The hydrophobic solvent vessel 130 may be in fluid communication with the slurry vessel 120 through the upstream hydrophobic solvent flow line 132 and the downstream hydrophobic solvent flow line 134. Fluid communication between the hydrophobic solvent vessel 130 and the slurry vessel 120 may be provided and broken by the upstream hydrophobic solvent valve 133 and the downstream hydrophobic solvent valve 135. Fluid communication between the hydrophobic solvent vessel 130 and the slurry vessel 120 may be driven by the pump 137.

The hydrophobic solvent vessel 130 may be in fluid communication with the column filter 113 through the upstream hydrophobic solvent flow line 132 and the hydrophobic solvent rinse flow line 136. Fluid communication between the hydrophobic solvent vessel 130 and the column filter 113 may be provided and broken by the upstream hydrophobic solvent valve 133 and the downstream hydrophobic solvent valve 135. Fluid communication between the hydrophobic solvent vessel 130 and the column filter 113 may be driven by the pump 137.

The hydrophilic solvent vessel 140 may be in fluid communication with the slurry vessel 120 through the upstream hydrophilic solvent flow line 142 and the downstream hydrophilic solvent flow line 144. Fluid communication between the hydrophilic solvent vessel 140 and the slurry vessel 120 may be provided and broken by the upstream hydrophilic solvent valve 143 and the downstream hydrophilic solvent valve 145. Fluid communication between the hydrophilic solvent vessel 140 and the slurry vessel 120 may be driven by the pump 147.

The hydrophilic solvent vessel 140 may be in fluid communication with the column filter 113 through the upstream hydrophilic solvent flow line 142 and the hydrophilic solvent rinse flow line 146. Fluid communication between the hydrophilic solvent vessel 140 and the column filter 113 may be provided and broken by the upstream hydrophilic solvent valve 143 and the downstream hydrophilic solvent valve 145. Fluid communication between the hydrophilic solvent vessel 140 and the column filter 113 may be driven by the pump 147.

Column Capture Protocol

FIGS. 19 to 28 show the system 110 in use to purify a hydrophobic target compound using insoluble polysaccharides. The hydrophobic solvent 160 is stored in and sourced from the hydrophobic solvent vessel 130. The hydrophilic solvent 170 is stored in and sourced from the hydrophilic solvent vessel 140. For simplicity of review of FIGS. 19 to 28, the hydrophobic solvent 160 and the agitator 131 are shown in the hydrophobic solvent vessel 130 only when the hydrophobic solvent 160 is being supplied to the slurry tank 120. Similarly, and also for simplicity of review of FIGS. 19 to 28, the hydrophilic solvent 170 and the agitator 141 are shown in the hydrophilic solvent vessel 140 only when the hydrophilic solvent 170 is being supplied to the slurry tank 120. In figures where these solvents are not being supplied to the slurry tank 120, the hydrophobic solvent vessel 130 and the hydrophilic solvent vessel 140 are shown without detail.

Figure 20:
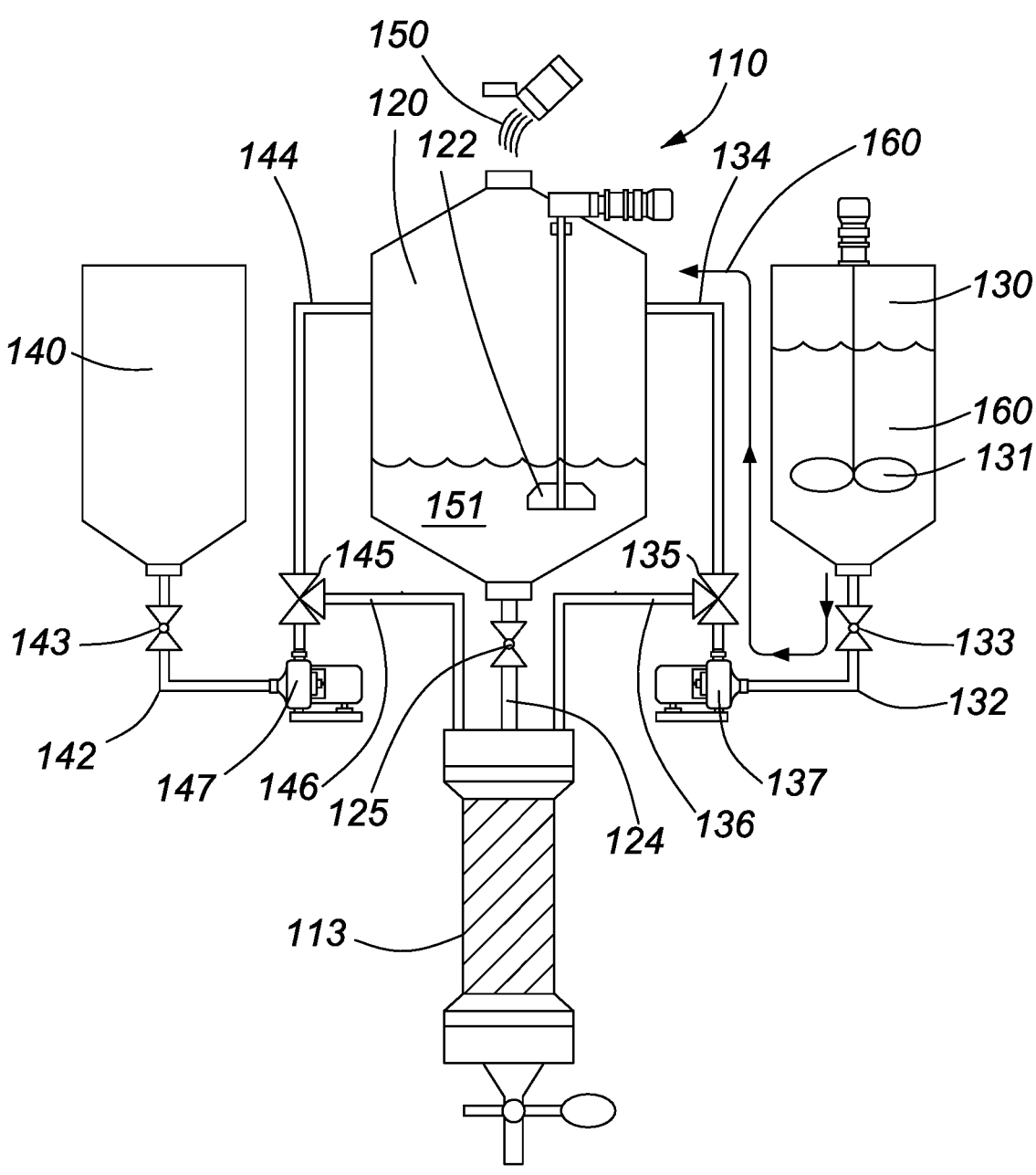
FIG. 20 is a schematic diagram of the system of FIG. 19 with an insoluble polysaccharide added to the system.

In FIG. 20, the insoluble polysaccharide 150, such as a cyclodextrin polymer, is provided into the slurry vessel 120. The insoluble polysaccharide 150 may be supplied dry, for example as a powder, and the slurry vessel 120 may be chilled prior to addition of the insoluble polysaccharide 150. The insoluble polysaccharide 150 is combined with the hydrophobic solvent 160 in the slurry vessel 120 to provide the slurry 151. The hydrophobic solvent 160 may be provided to the slurry vessel 120 from the hydrophobic solvent vessel 130 via the upstream hydrophobic solvent flow line 132 and the downstream hydrophobic solvent flow line 134. The hydrophobic solvent 160 may be provided in a ratio of 75% insoluble polysaccharide 50 to 25% hydrophobic solvent 160.

FIG. 21 shows the sample 154 being loaded into the slurry vessel 120 and combined with the slurry 151, providing the loaded slurry 152. The sample 154 includes at least one hydrophobic target compound.

Figure 22:
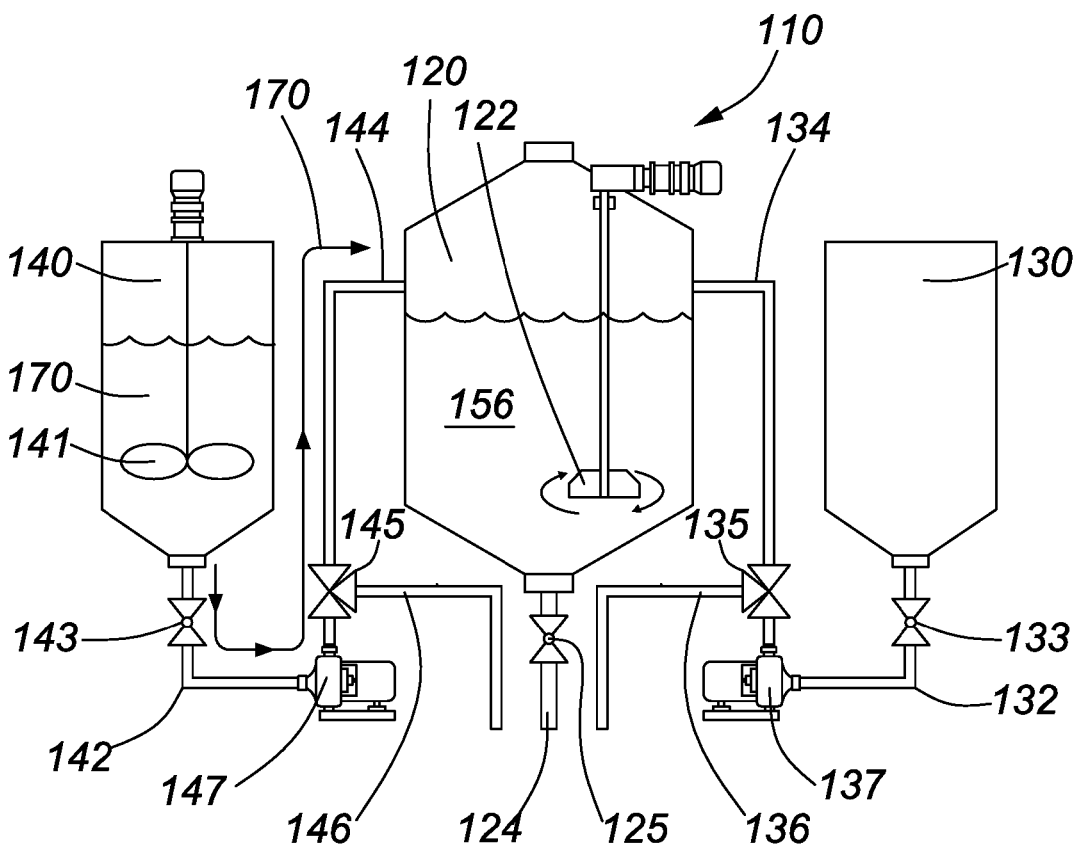
FIG. 22 is a schematic diagram of the system of FIG. 19 with hydrophilic solvent added to the system.

FIG. 22 shows the hydrophilic solvent 170 being added to the slurry vessel 120 from the hydrophobic solvent vessel 130. The hydrophilic solvent 170 may be added to the slurry vessel 120 via the upstream hydrophilic solvent flow line 142 and the downstream hydrophilic solvent flow line 144 and combined with the loaded slurry 152 to provide the binding slurry 156. The binding slurry 156 may include the binding solvent 158 with a ratio of hydrophobic solvent 160 to hydrophilic solvent 170 selected to drive the hydrophobic target compounds into the insoluble polysaccharide 150 polymer core or otherwise bind with the insoluble polysaccharide 150.

A binding solvent 158, which may have a ratio of hydrophobic solvent 160 to hydrophilic solvent 170 similar to the ratio targeted in the binding slurry 156, may be added to an insoluble polysaccharide in to provide a stationary phase solution. The insoluble polysaccharide solution may be poured into the column filter 113 having a glass fibre frit to pack the column filter 113.

Figure 23:
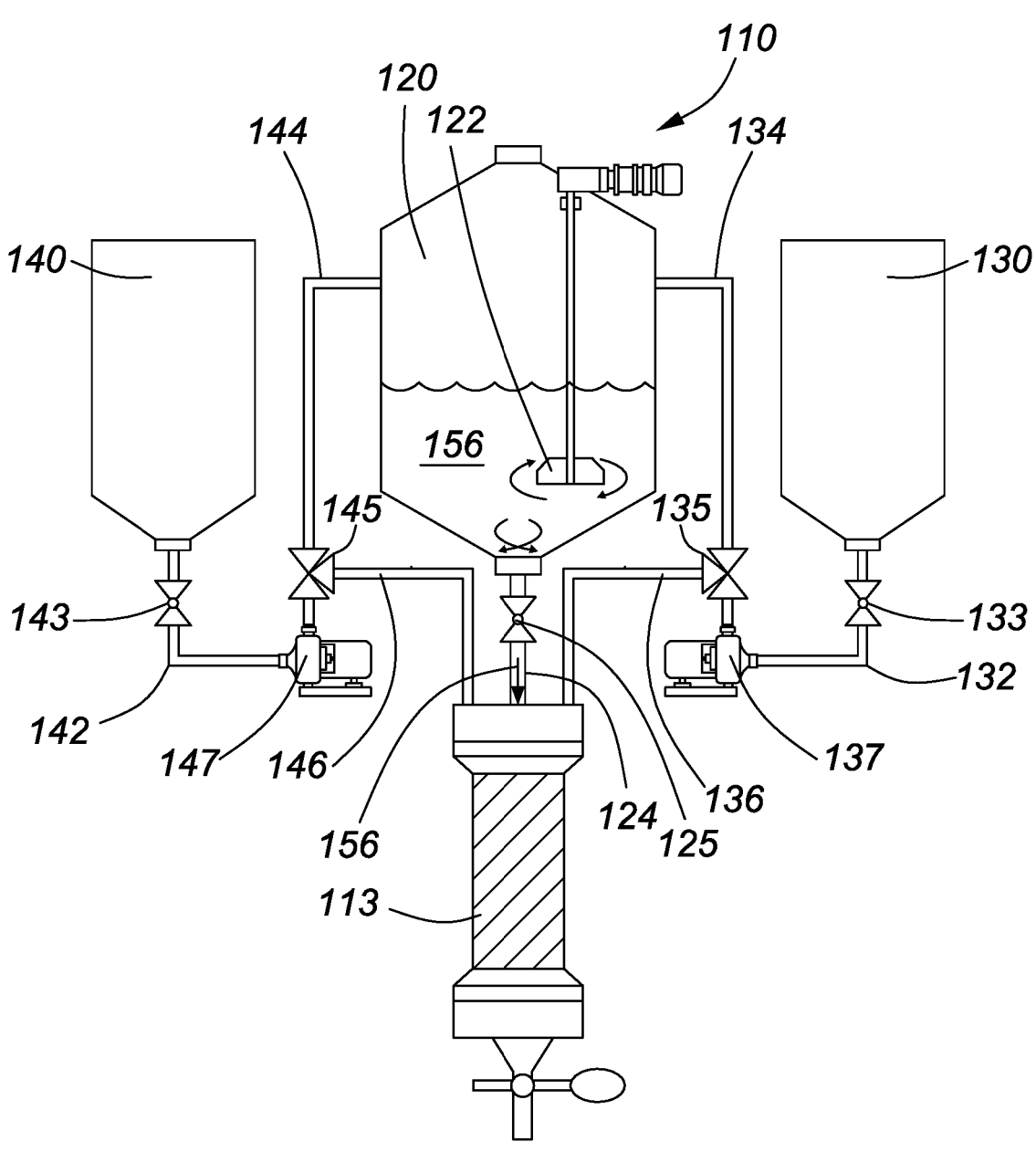
FIG. 23 is a schematic diagram of the system of FIG. 19 while emptying a binding slurry into a column filter.

FIG. 23 shows the binding slurry 156 being emptied into the column filter 113 for loading the insoluble polysaccharide 150 with captured hydrophobic target compounds onto the pre-wetted insoluble polysaccharide stationary phase in the column filter 113, and the hydrophobic target molecules may absorb onto the stationary phase of the column filter 113. Once loaded, load permeate may be collected for storage in a flow-through reservoir (not shown; similar to the flow-through vessels 280 or 380).

Figure 24:
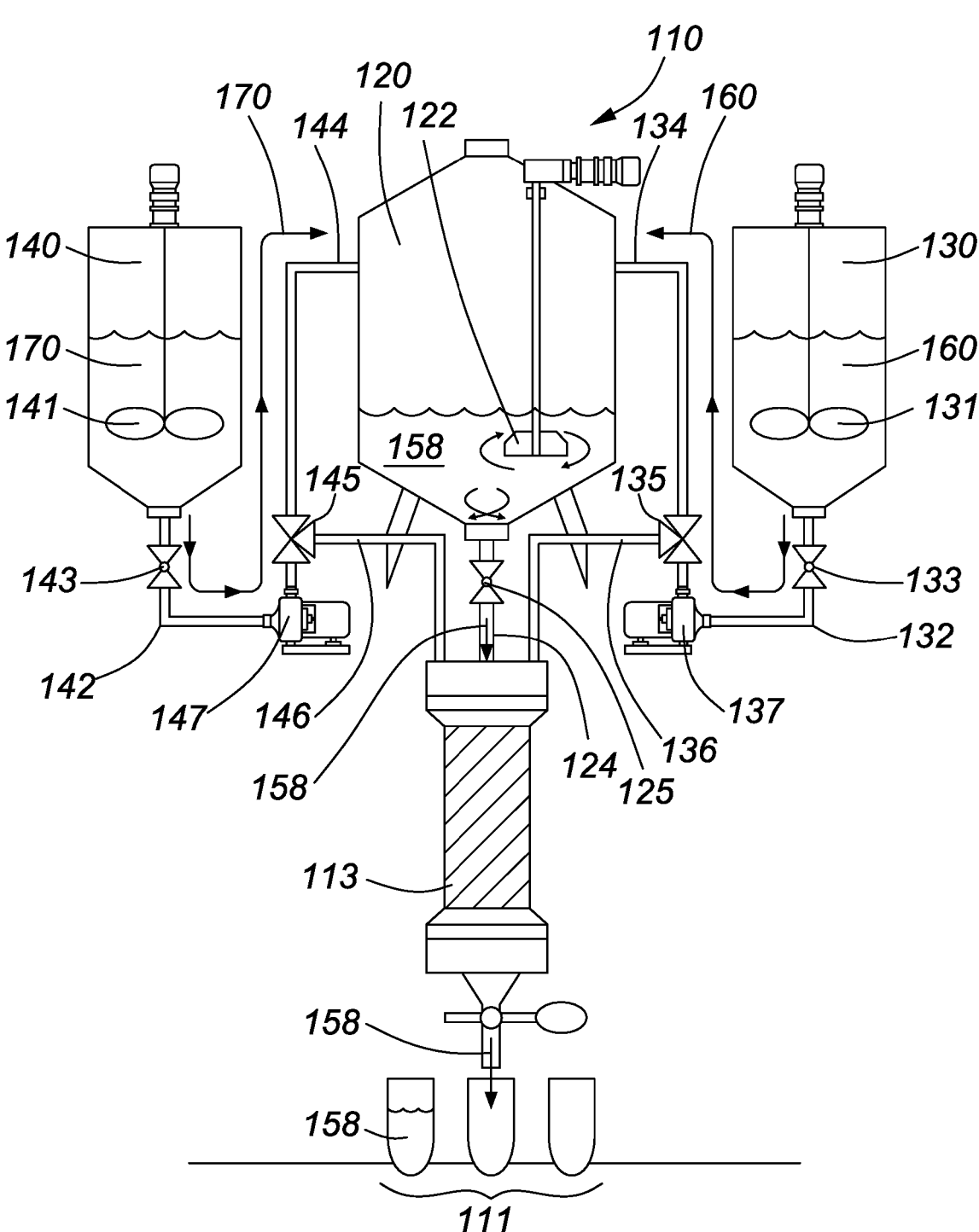
FIG. 24 is a schematic diagram of the system of FIG. 19 while washing a loaded column filter with hydrophobic and hydrophilic solvent.

FIG. 24 shows the loaded column filter 113 being washed with the binding solvent 158 in the slurry vessel 120. The binding solvent 158 may comprise hydrophobic solvent 160 and hydrophilic solvent 170 in the same target ratio as used in the binding slurry 156. The binding solvent 158 passes through the column filter 113 and into the recovery vessels 111. If any insoluble polysaccharide 150 or passes through the column filter 113 with hydrophobic target molecules bound to the insoluble polysaccharide, the insoluble polysaccharide 150 and hydrophobic target molecules maybe recovered from the recovery vessels 111.

Figure 25:
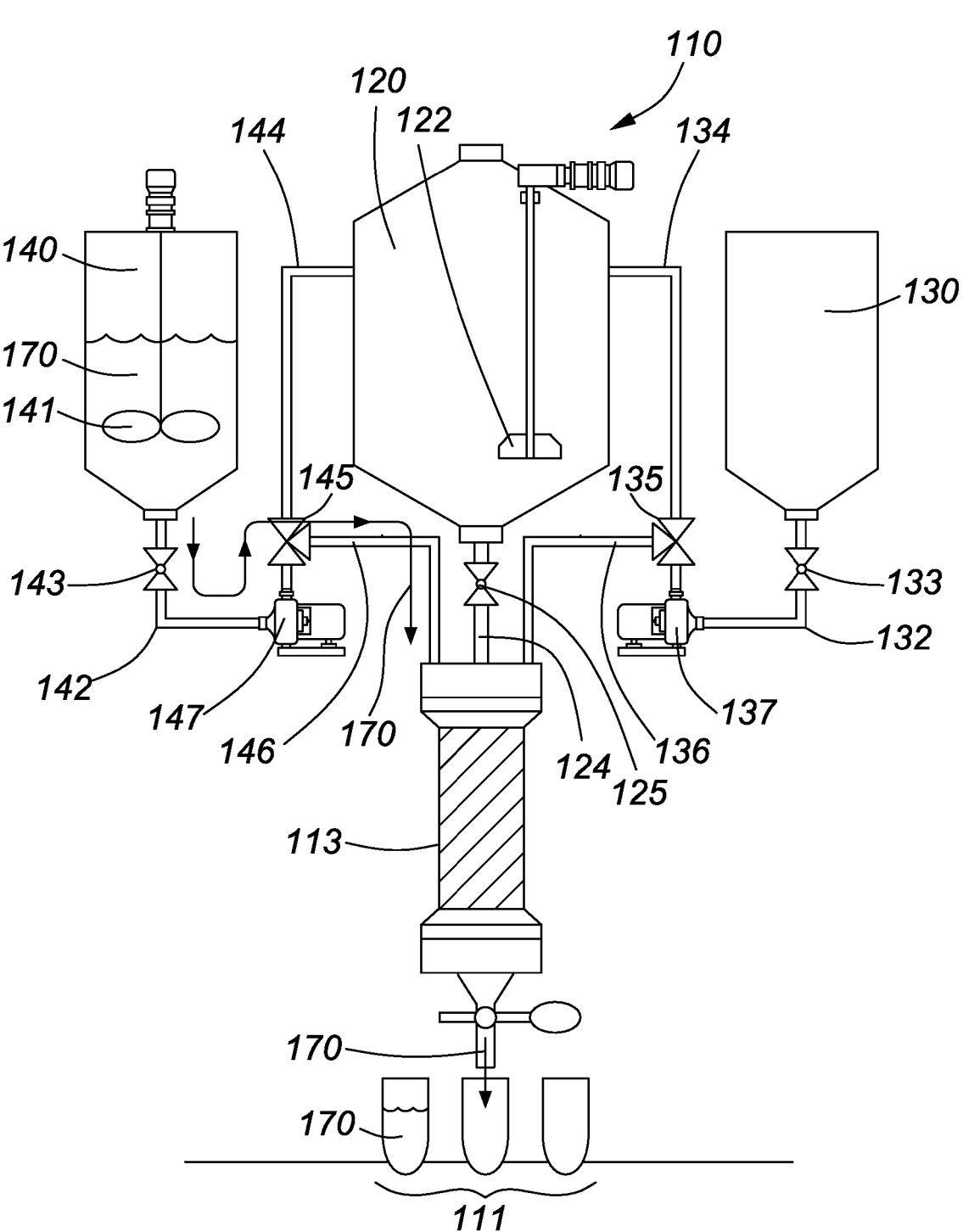
FIG. 25 is a schematic diagram of the system of FIG. 19 while rinsing the loaded column filter with hydrophilic solvent.

FIG. 25 shows rinsing of the column filter 113 with hydrophilic solvent 170 to wash the column filter 113 via the upstream hydrophilic solvent flow line 142 and the hydrophilic solvent rinse flow line 146. An amount of the hydrophilic solvent 170 equal to three or four times the volume of the binding slurry 116 may be passed through the column filter 113 to wash the stationary phase with bound hydrophobic target molecules. The hydrophilic solvent 170 may be collected in the recovery vessels 111.

Figure 26:
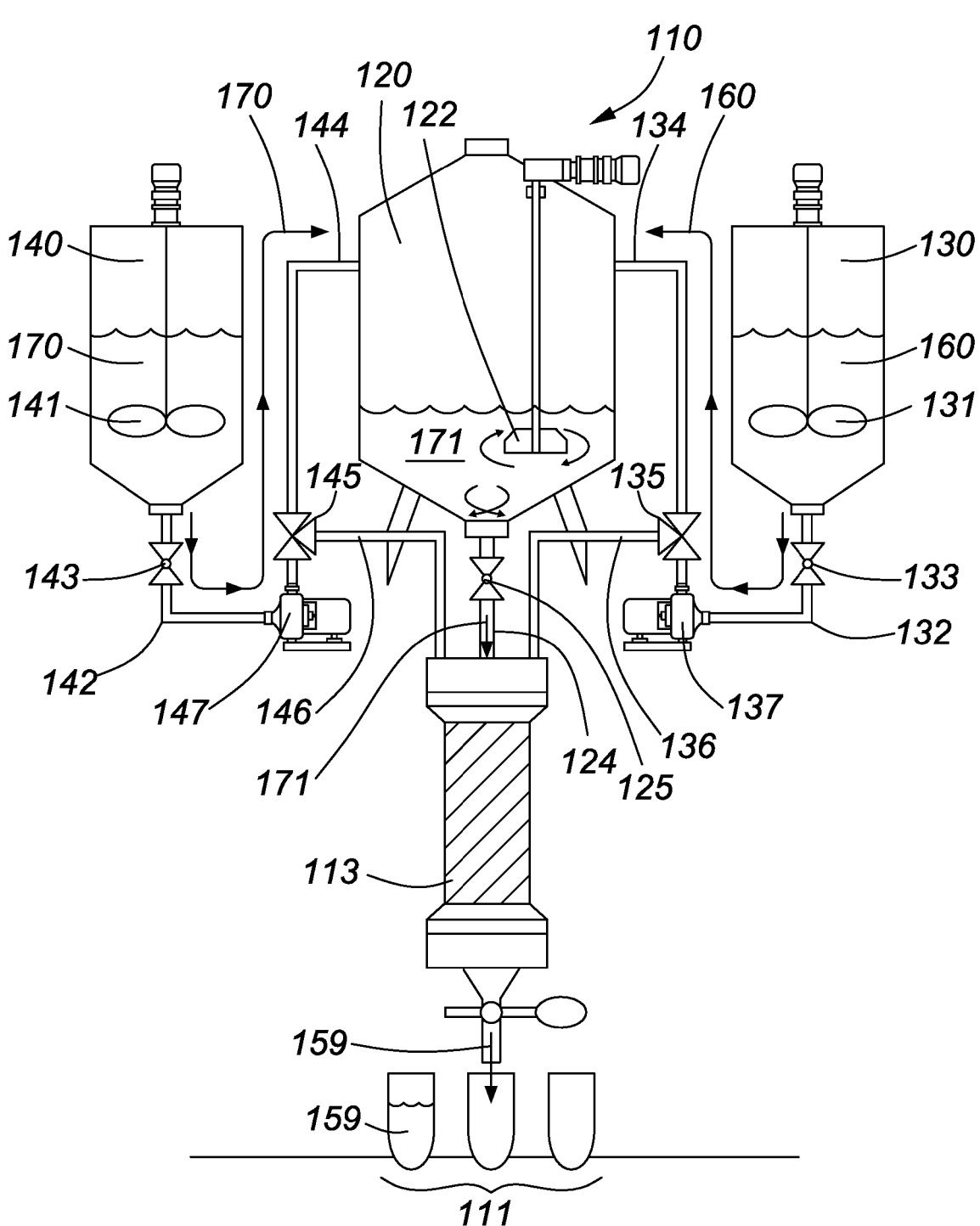
FIG. 26 is a schematic diagram of the system of FIG. 19 while rinsing the loaded column filter with hydrophilic and hydrophobic solvent.

FIG. 26 shows rinsing of the column filter 113 with binding solvent 158, or with other mixtures of the hydrophobic solvent 160 and the hydrophilic solvent 170 to wash the column filter 113 after mixing the hydrophobic solvent 160 and the hydrophilic solvent 170 in the slurry vessel 120. The amount of the hydrophobic solvent 160 included in the mixture of the hydrophobic solvent 160 and the hydrophilic solvent 170 may be increased over time to elute progressively more tightly bound hydrophobic target compounds, providing the recovered hydrophobic target compounds 159. The recovered hydrophobic target compounds 159 may be collected in the recovery vessels 111.

Figure 27:
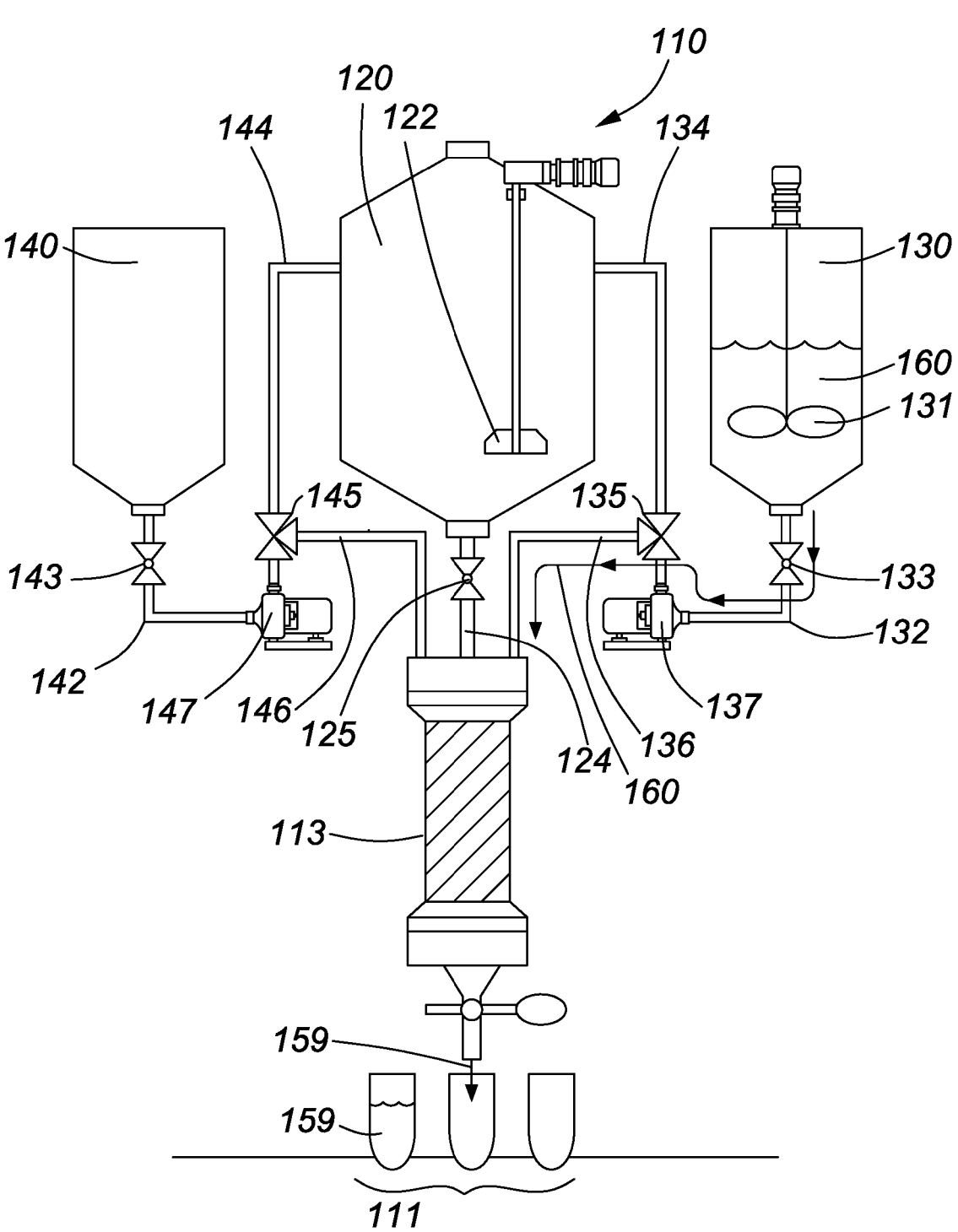
FIG. 27 is a schematic diagram of the system of FIG. 19 while eluting hydrophobic target compounds from the loaded column filter with hydrophobic solvent.

FIG. 27 shows the loaded column filter 113 being eluted with the hydrophobic solvent 160 for dissociating the hydrophobic target compounds from the stationary phase comprising the insoluble polysaccharide 150 and for solubilizing the hydrophobic target compounds in the hydrophobic solvent 160. The column filter 113 is eluted until no more of the hydrophobic target compound is eluted and the output of hydrophobic target compounds is stable. The recovered hydrophobic target compounds 159 may be collected in the recovery vessels 111.

The insoluble polysaccharide 150 may then be regenerated for reuse by washing the insoluble polysaccharide 150 with a detergent solution, for example 0.1% Triton X-100 at 37° C. for one minute. Solvents that are able to dissociate any hydrophobic compounds from the insoluble polysaccharide 150, such as DMSO, may also be applied for regeneration. Exposure to the detergent solution, to solvent or other regeneration may be followed by re-equilibration with 3 to 5 volumes of ethanol.

Figure 28:
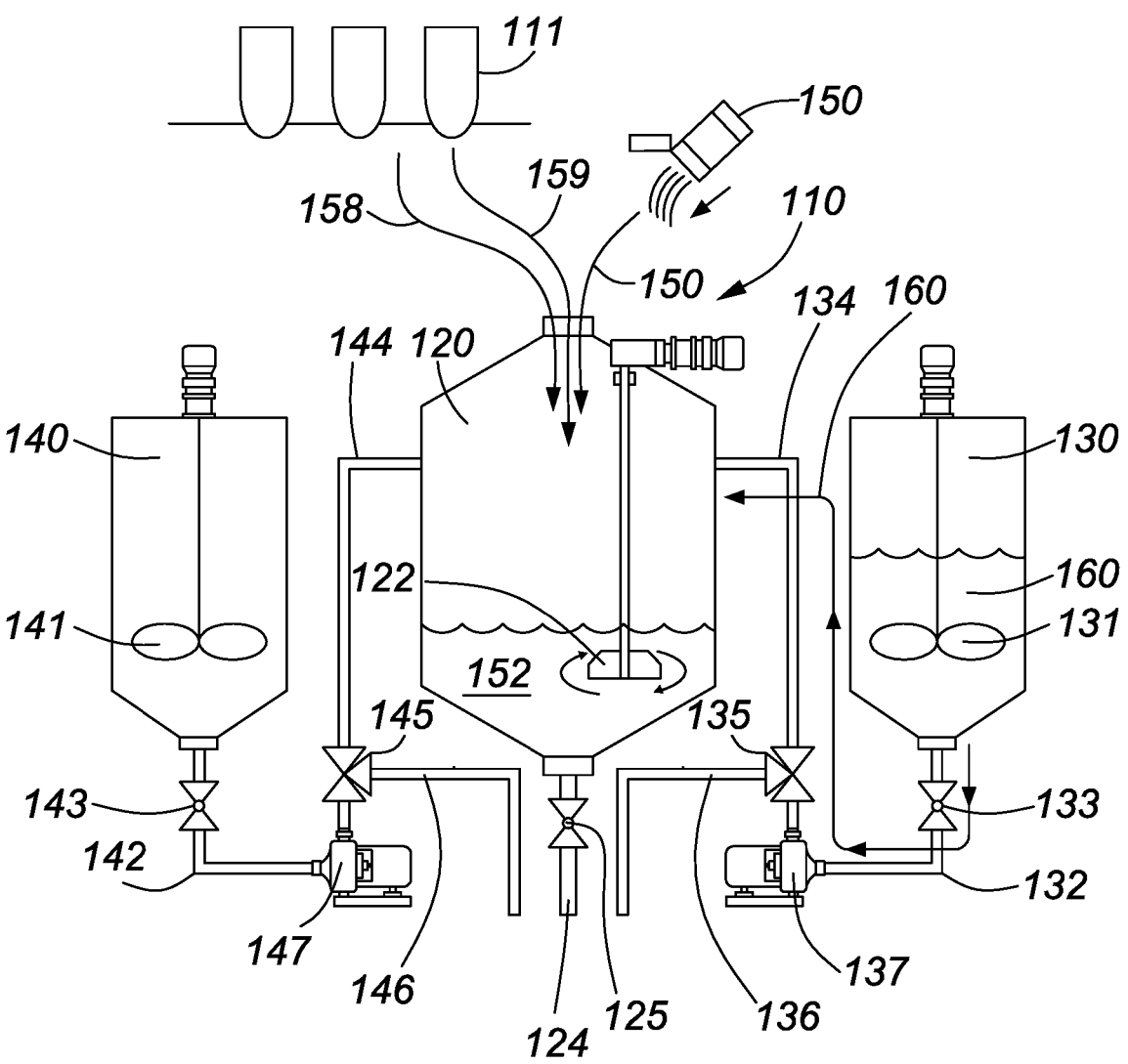
FIG. 28 is a schematic diagram of the system of FIG. 19 with the contents of a recovery vessel added to the system to repeat the process of FIGS. 23 to 27.

FIG. 28 shows that permeate that may have been previously collected in recovery vessel 111 may be loaded into the slurry vessel 120 to repeat the process shown in FIGS. 23 to 27. Where the permeate is passed through the system 110 again, the insoluble polysaccharide 150 used the second time may be different than the insoluble polysaccharide 150 initially used, for example an α-cyclodextrin or γ-cyclodextrin may be used after a β-cyclodextrin.

Immersion Filter Capture Setup

Figure 29:
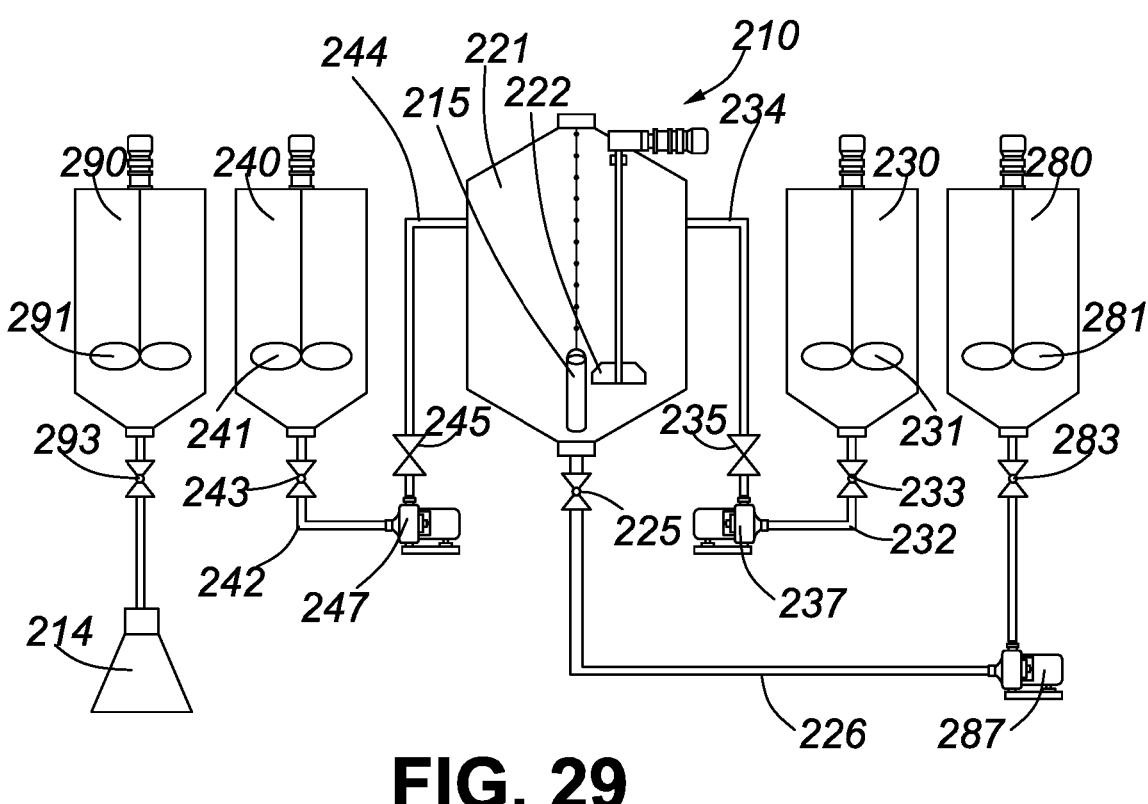
FIG. 29 is a schematic diagram of a hydrophobic compound recovery system.

FIG. 29 shows an hydrophobic compound recovery system 210. The system 210 includes a binding vessel 221. An immersion filter 215 is sized to be housed inside the binding vessel 221 for being in fluid communication with the binding vessel 221, receiving fluid from the binding vessel 221 and filtering material out of the fluid. The immersion filter 215 housing the insoluble polysaccharide 250. The immersion filter 215 may include insoluble polysaccharide bound with a matrix attached to the immersion filter 215, such as the embodiments of the insoluble polysaccharide 50 shown in FIGS. 45 to 48. The immersion filter 215 may include insoluble polysaccharide sequestered within the immersion filter 215 by a pore size smaller than an insoluble polymer 73, magnetic bead 76, magnetic nanoparticle 77 or other insoluble material bound to, complexed with or otherwise adhered to the polysaccharide 71 included in the insoluble polysaccharide 50, such as the embodiments of the insoluble polysaccharide 50 shown in FIGS. 12 to 17.

The immersion filter 215 is sized to receive filtrate that passes through the immersion filter 215. The binding vessel 221 is in fluid communication with the hydrophobic solvent vessel 230 for receiving hydrophobic solvent from the hydrophobic solvent vessel 230. The binding vessel 221 is in fluid communication with the hydrophilic solvent vessel 240 for receiving hydrophilic solvent from the hydrophilic solvent vessel 240. The binding vessel 221 is in fluid communication with a flow-through vessel 280 for storing the binding solution 258 after exposure of the sample 254 to the immersion filter. A wash vessel 290 is in fluid communication with the recovery vessel 214 for receiving waste hydrophilic solvent 270 or binding solvent 258.

Each of the binding vessel 221, the hydrophobic solvent vessel 230 and the hydrophilic solvent vessel 240 may be any suitable fluid vessel appropriate for the size, scale and application of the system 210 (e.g. a tank, pressure-rated tank, etc.).

The binding vessel 221 includes the agitator 222 positioned within the binding vessel 221. The agitator 222 is for agitating a fluid inside the binding vessel 221 (e.g. the propeller shown in FIG. 29) to mix the fluid. The agitator 222 is shown as a rotary stirring agitator but any suitable agitator may be used (e.g. cross-flow, a venturi, static agitator, etc.). The binding vessel 221 is in fluid communication with the immersion filter 215 direct contact with the binding solvent 258.

Figure 30:
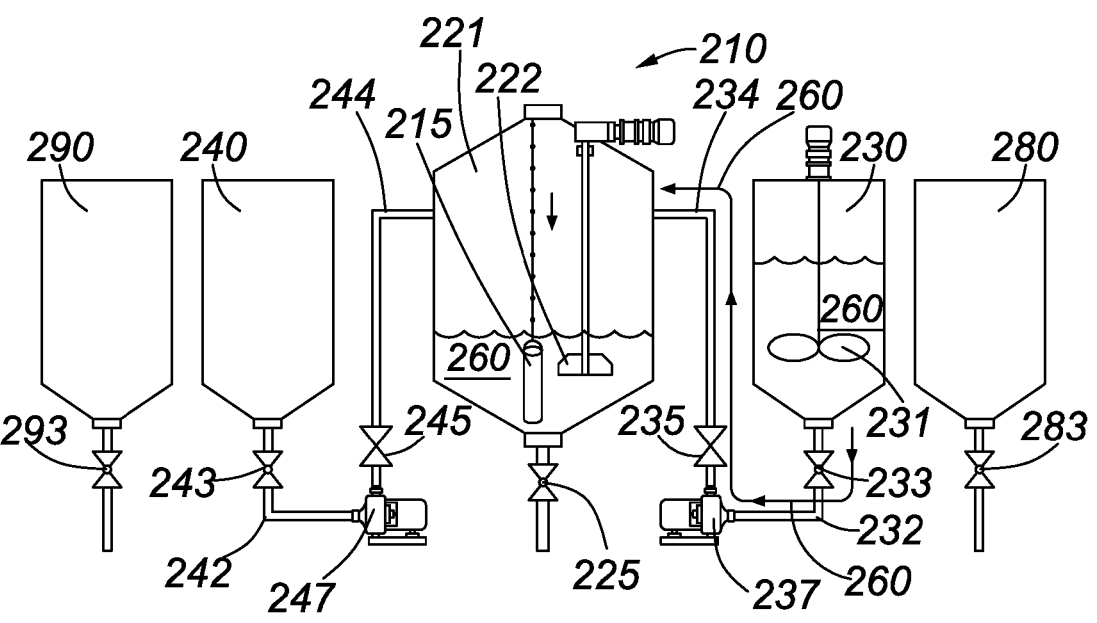
FIG. 30 is a schematic diagram of the system of FIG. 29 with a polysaccharide added to the system in an immersion filter.

The hydrophobic solvent vessel 230 includes the agitator 231 positioned within the hydrophobic solvent vessel 230. The agitator 231 is for agitating a hydrophobic solvent (e.g. the rotary stirring agitator 231 agitating the hydrophobic solvent 260 as shown in FIG. 30) inside the hydrophobic solvent vessel 230 to mix the hydrophobic solvent.

The hydrophobic solvent vessel 230 may be in fluid communication with the binding vessel 221 through the upstream hydrophobic solvent flow line 232 and the downstream hydrophobic solvent flow line 234. Fluid communication between the hydrophobic solvent vessel 230 and the binding vessel 221 may be provided and broken by the upstream hydrophobic solvent valve 233 and the downstream hydrophobic solvent valve 235. Fluid communication between the hydrophobic solvent vessel 230 and the binding vessel 221 may be driven by the pump 237.

The hydrophobic solvent vessel 230 may be in fluid communication with the immersion filter 215 through the upstream hydrophobic solvent flow line 232 and the downstream hydrophobic flow line 234 when the immersion filter 215 is immersed in the liquid contents of the binding vessel 221, for example, the binding solvent 258. Fluid communication between the hydrophobic solvent vessel 230 and the immersion filter 215 may be provided and broken by the upstream hydrophobic solvent valve 233 and the downstream hydrophobic solvent valve 235 and by contact between the immersion filter 215 and the contents of the binding vessel 221. Fluid communication between the hydrophobic solvent vessel 230 and the immersion filter 215 may be driven by the pump 237.

Figure 33:
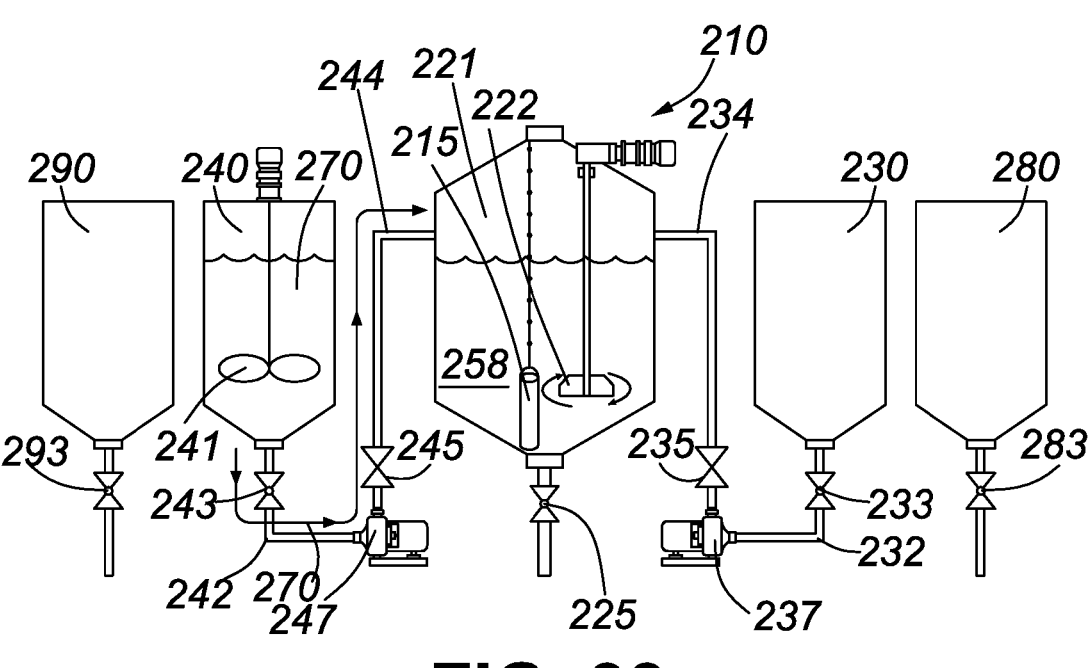
FIG. 33 is a schematic diagram of the system of FIG. 29 with hydrophilic solvent added to the system.

The hydrophilic solvent vessel 240 includes the agitator 241 positioned within the hydrophilic solvent vessel 240. The agitator 241 is for agitating a hydrophilic solvent (e.g. the rotary stirring agitator 241 agitating the hydrophilic solvent 270 as shown in FIG. 33) inside the hydrophilic solvent vessel 240 to mix the hydrophilic solvent 270.

The hydrophilic solvent vessel 240 may be in fluid communication with the binding vessel 221 through the upstream hydrophilic solvent flow line 242 and the downstream hydrophilic solvent flow line 244. Fluid communication between the hydrophilic solvent vessel 240 and the binding vessel 221 may be provided and broken by the upstream hydrophilic solvent valve 243 and the downstream hydrophilic solvent valve 245. Fluid communication between the hydrophilic solvent vessel 240 and the binding vessel 221 may be driven by the pump 247.

The hydrophilic solvent vessel 240 may be in fluid communication with the immersion filter 215 through the upstream hydrophilic solvent flow line 242 and the downstream hydrophilic solvent flow line 244 when the immersion filter 215 is immersed in the liquid contents of the binding vessel 221, for example, the binding solvent 258. Fluid communication between the hydrophilic solvent vessel 240 and the immersion filter 215 may be provided and broken by the upstream hydrophilic solvent valve 243 and the downstream hydrophilic solvent valve 245 and by contact between the immersion filter 215 and the contents of the binding vessel 221. Fluid communication between the hydrophilic solvent vessel 240 and the immersion filter 215 may be driven by the pump 247.

The flow-through vessel 280 may be in fluid communication with the binding vessel 221 through a flow-through line 226. Fluid communication between the flow-through vessel 280 and the binding vessel 221 may be provided and broken by the output valve 225 and a flow-through valve 283. Fluid communication between the flow-through vessel 280 and the binding vessel 221 may be driven by a pump 287.

The flow-through vessel 280 may be in fluid communication with the immersion filter 215 through the upstream hydrophobic solvent flow line 226 when the immersion filter 215 is immersed in the liquid contents of the binding vessel 221, for example, the binding solvent 258. Fluid communication between the flow-through vessel 226 and the immersion filter 215 may be provided and broken by the flow-through valve 283 and by contact between the immersion filter 215 and the contents of the binding vessel 221. Fluid communication between the flow-through vessel 280 and the immersion filter 215 may be driven by the pump 287.

Figure 34:
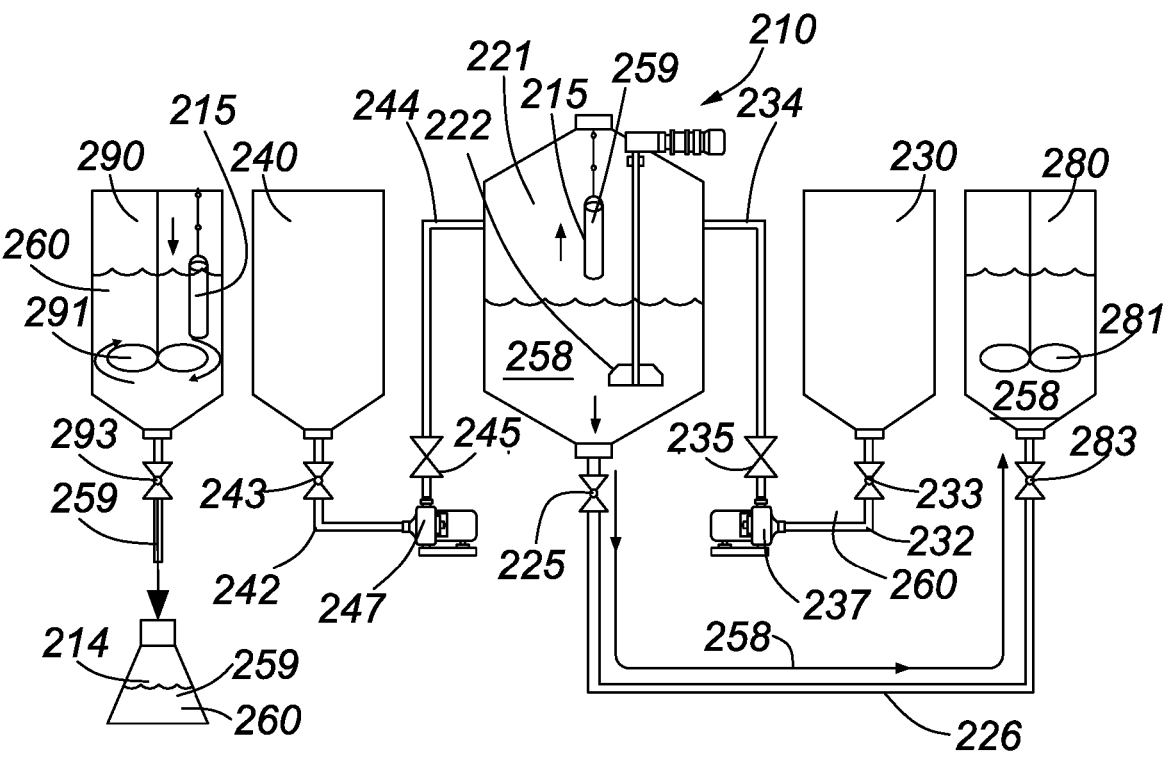
FIG. 34 is a schematic diagram of the system of FIG. 29 while draining the binding solvent into a storage vessel and moving the immersion filter to a wash tank.
Figure 35:
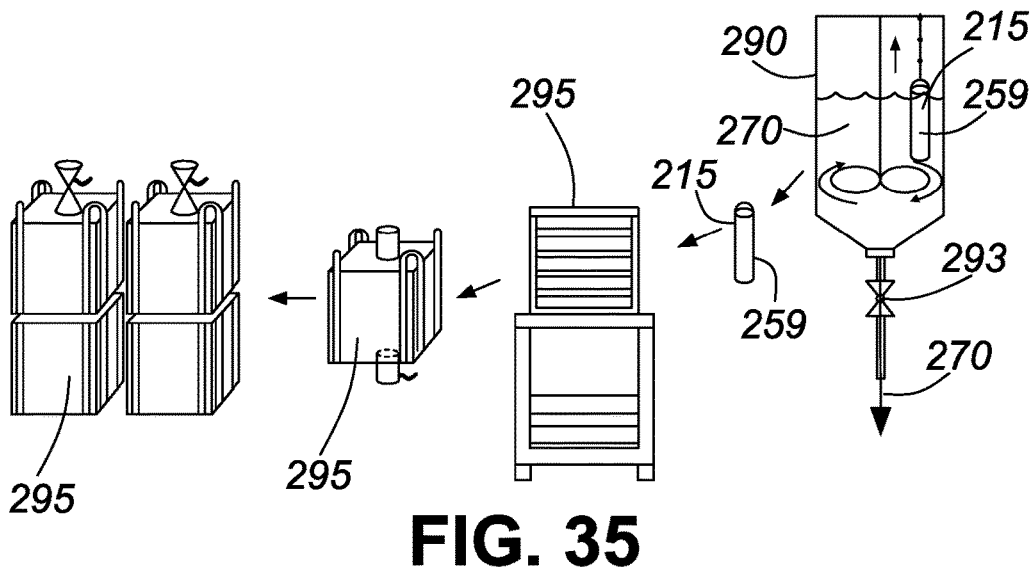
FIG. 35 is a schematic diagram showing storage of the immersion filter of the system of FIG. 29.

The wash vessel 290 need not be in fluid communication with the binding vessel 221. Fluid communication between the wash vessel 290 and the recovery vessel 214 may be provided and broken by a wash vessel valve 293. The immersion filter 215 may be immersed in the hydrophobic solvent 260 in the wash vessel 290 for recovery of the recovered hydrophobic target compound 259 in the recovery vessel 214, as shown in FIG. 34. The immersion filter 215 may be immersed in the binding solvent 258 or the hydrophilic solvent 270 in the wash vessel 290 for washing the immersion filter 215 to maintain binding between the hydrophobic target molecule and the insoluble polysaccharide bound with or otherwise adhered to, or sequestered within, the immersion filter 215, as shown in FIG. 35.

Immersion Filter Capture Protocol

FIGS. 30 to 35 show a system 210 in use to recover a hydrophobic target compound using the immersion filter 215.

In FIG. 30, the immersion filter 215 containing the insoluble polysaccharide 250 is immersed into the hydrophobic solvent 260 to wet the insoluble polysaccharide 250. The hydrophobic solvent 260 may be provided to the binding vessel 221 from the hydrophobic solvent vessel 230. The hydrophobic solvent 260 may be provided in a ratio of 75% insoluble polysaccharide 50 to 25% hydrophobic solvent 260.

Figure 31:
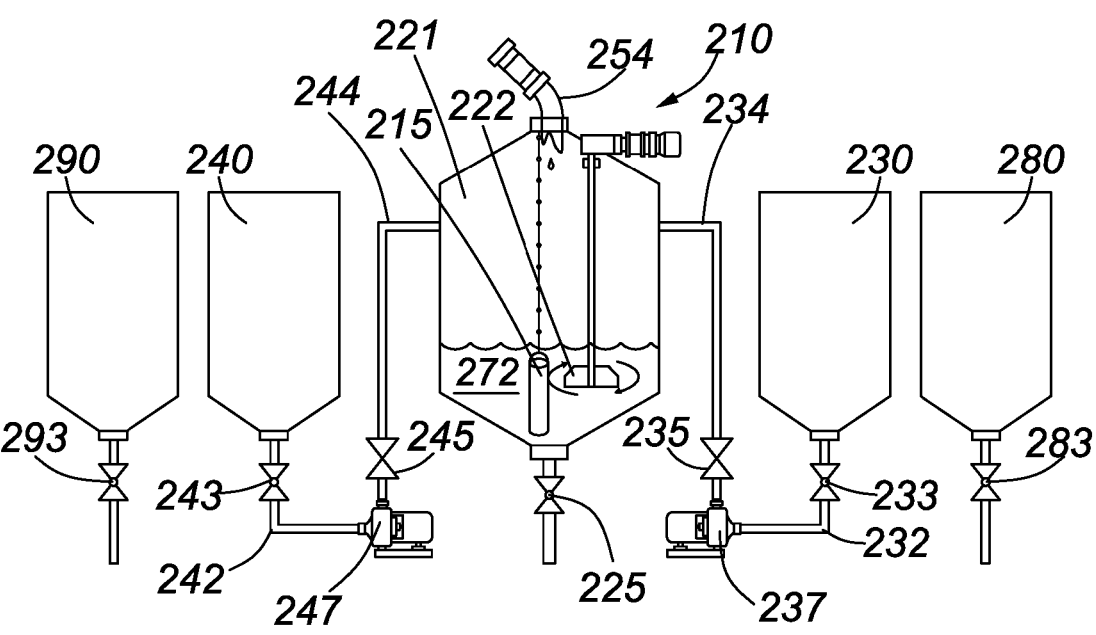
FIG. 31 is a schematic diagram of the system of FIG. 29 with a sample added to the system.

FIG. 31 shows the sample 254 being loaded into the binding vessel 221 and combined with the hydrophobic solvent 260, providing the loaded solution 272. The binding vessel 221 may be chilled to between 3° C. and room temperature, such as to 4° C., when the sample 254 is added to the binding vessel 221. The sample 254 includes at least one hydrophobic target compound.

Figure 32:
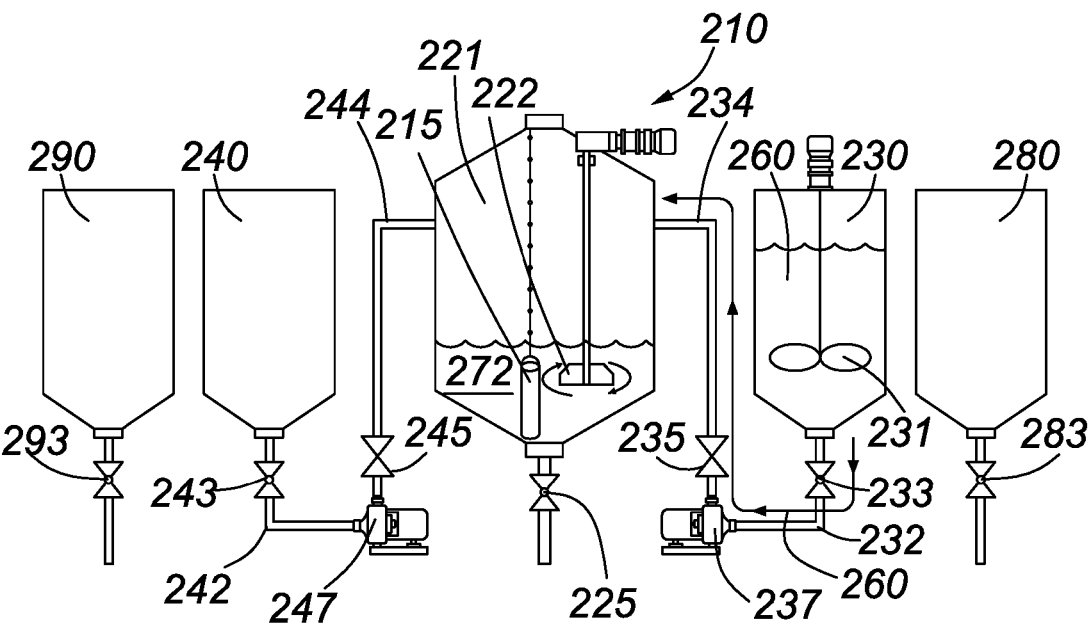
FIG. 32 is a schematic diagram of the system of FIG. 29 with additional hydrophobic solvent added to the system.

FIG. 32 shows additional hydrophobic solvent 260 being added to the binding vessel 221 to combine with the loaded solution 272. The additional hydrophobic solvent 260 may dilute any water that may have been included in the sample 254. The additional hydrophobic solvent 260 may facilitate dissolution into the loaded solution 272 of phytocannabinoids or other hydrophobic target compounds in the sample 254. The loaded solution 272 may be agitated by the agitator 222.

FIG. 33 shows the hydrophilic solvent 270 being added to the binding vessel 221 and combined with the loaded solution 272 to provide the binding solvent 258 and to facilitate binding of the hydrophobic target molecule with the cyclic polysaccharide in the immersion filter 215. The binding solvent 258 may target a ratio of hydrophobic solvent 260 to hydrophilic solvent 270 selected to drive the hydrophobic target compounds into the insoluble polysaccharide polymer core or otherwise bind with the insoluble polysaccharide contained in the immersion filter 215.

FIG. 34 shows the binding solvent 258 being drained into the flow-through vessel 280 via the flow-through line 282. FIG. 34 also shows removal of the immersion filter 215 from the binding vessel 221 and immersing the immersion filter 215 into the contents of the wash tank 290. In FIG. 34, the wash tank 290 contains the hydrophobic solvent 260 for dissolving the hydrophobic target compound in the hydrophobic solvent 260. The hydrophobic solvent 260 then drains through the wash vessel valve 293 and into the recovery vessel, where the recovered hydrophobic target compound 259 may be removed and further processed into downstream products, for example as shown in FIG. 18.

The insoluble polysaccharide in the immersion filter 215 may be regenerated for reuse by emptying the insoluble polysaccharide from the immersion filter 215 and washing the insoluble polysaccharide in a detergent solution, for example 0.1% Triton X-100 at 37° C. for one minute. Solvents that are able to dissociate any hydrophobic compounds from the insoluble polysaccharide, such as DMSO, may also be applied for regeneration. Exposure to the detergent solution, to solvent or other regeneration may be followed by re-equilibration with 3 to 5 volumes of ethanol. Alternatively, the insoluble polysaccharide may remain bound to or sequestered within the immersion filter 215 and regenerated in the immersion filter 215.

Hydrophobic Target Compound Storage

FIG. 35 shows the insoluble polysaccharide 250 contained in the immersion filter 215 being stored in a storage system 295. The hydrophilic solvent 270 is provided to the wash vessel 290. The immersion filter 215 containing the insoluble polysaccharide bound with the recovered hydrophobic target compound 259 is removed from the binding vessel 221 and placed in the wash vessel 290 for immersion in the hydrophilic solvent 270.

The hydrophilic solvent 270 in the wash vessel 290 with the immersion filter 215 immersed in the wash vessel 290 may be mixed for 1 hour to drive hydrophobic target compounds into the insoluble polysaccharide polymer core or otherwise increasing adhering of the hydrophobic target molecule with the insoluble polysaccharide for washing the immersion filter 215 containing the insoluble polysaccharide 250. The hydrophilic solvent 270 may be drained from the wash vessel 290 for reuse or disposal.

The immersion filter 215 is removed from the wash vessel 290 and drained of hydrophilic solvent 270 by hanging to dry, exposing to airflow of atmospheric gases or of inert gases (e.g. argon, etc.) or low-reactivity gases (e.g. $N_2$, etc.).

After drying, the immersion filter 215 including the hydrophobic target compound and the insoluble polysaccharide may be freeze dried or otherwise stabilized and stored in the storage system 295. The immersion filter 215 may be packaged for storage or transport once stabilized and stored, for example, in an opaque bag filled with inert gases (e.g. argon, etc.) or low-reactivity gases (e.g. $N_2$, etc.) for reducing oxidation nor UV light degradation. The immersion filter 215 may be removed from storage and eluted with the hydrophobic solvent 260 or another hydrophobic solvent to solubilize the recovered hydrophobic target compounds 259 from the immersion filter 215 and recover the recovered hydrophobic target compounds 259.

Multiple Immersion Filter Capture Setup

Figure 36:
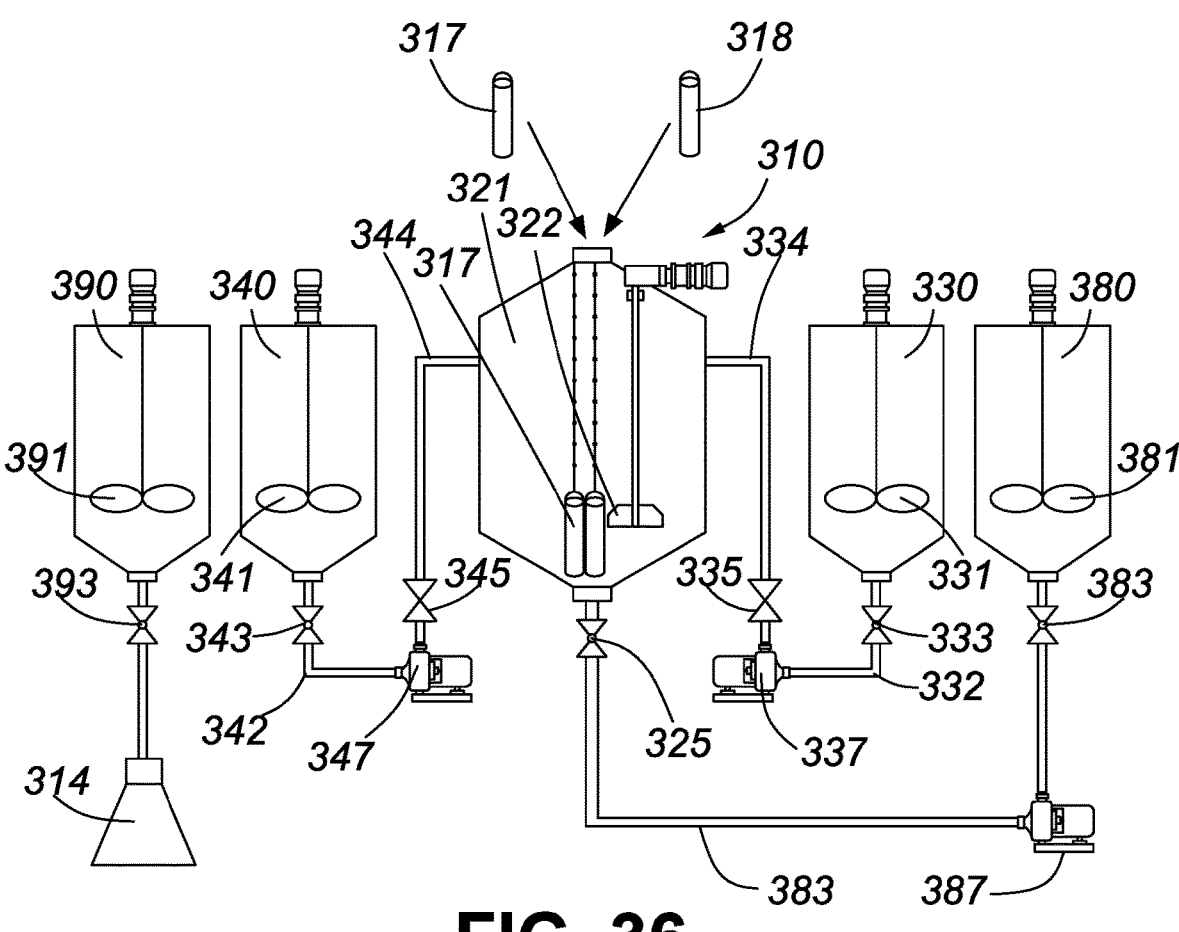
FIG. 36 is a schematic diagram of a hydrophobic compound recovery system with a plurality of immersion filters.

FIG. 36 shows a hydrophobic compound recovery system 310. The system 310 includes the binding vessel 321. A first immersion filter 317 and a second immersion filter 318 that each include insoluble polysaccharide are sized to be housed concurrently inside the binding vessel 321 for being in simultaneous or staged fluid communication with the binding vessel 321 and for receiving fluid from the binding vessel 321 to bind with the insoluble polysaccharide.

The first immersion filter 317 includes a first insoluble polysaccharide and the second immersion filter 318 includes a second insoluble polysaccharide. The first immersion filter 317 and the second immersion filter 318 are sized to receive filtrate that passes through the first immersion filter 317 and the second immersion filter 318, respectively. The binding vessel 321 is in fluid communication with the hydrophobic solvent vessel 330 for receiving hydrophobic solvent from the hydrophobic solvent vessel 330. The binding vessel 321 is in fluid communication with the hydrophilic solvent vessel 340 for receiving hydrophilic solvent from the hydrophilic solvent vessel 340. The binding vessel 321 is in fluid communication with the flow-through vessel 380 for storing the binding solution (not shown; equivalent to the binding solution 258) after exposure of the sample (not shown; equivalent to the sample 254) to the first immersion filter 317 and the second immersion filter 318. The wash vessel 390 is in fluid communication with the recovery vessel 314 for receiving waste hydrophilic solvent (not shown; equivalent to the hydrophilic solvent 270) or binding solvent (not shown; equivalent to the binding solvent 258).

Each of the binding vessel 321, the hydrophobic solvent vessel 330 and the hydrophilic solvent vessel 340 may be any suitable fluid vessel appropriate for the size, scale and application of the system 310 (e.g. a tank, pressure-rated tank, beaker, etc.).

The binding vessel 321 includes the agitator 322 positioned within the binding vessel 321. The agitator 322 is for agitating a fluid inside the binding vessel 321 to mix the fluid. The agitator 322 is shown as a rotary stirring agitator but any suitable agitator may be used (e.g. cross-flow, a venturi, static agitator, etc.). The binding vessel 321 is in fluid communication with the first immersion filters 317 and the second immersion filter 318 to provide direct contact with a solution in the binding vessel 321 (not shown; equivalent to the process shown for the system 210 in FIGS. 30 to 35).

The hydrophobic solvent vessel 330 includes the agitator 331 positioned within the hydrophobic solvent vessel 330. The agitator 331 is for agitating a hydrophobic solvent inside the hydrophobic solvent vessel 330 to mix the hydrophobic solvent. The hydrophobic solvent vessel 330 may be in fluid communication with the binding vessel 321 through the upstream hydrophobic solvent flow line 332 and the downstream hydrophobic solvent flow line 334. Fluid communication between the hydrophobic solvent vessel 330 and the binding vessel 321 may be provided and broken by the upstream hydrophobic solvent valve 333 and the downstream hydrophobic solvent valve 335. Fluid communication between the hydrophobic solvent vessel 330 and the binding vessel 321 may be driven by the pump 337.

The hydrophilic solvent vessel 340 includes the agitator 341 positioned within the hydrophilic solvent vessel 340. The agitator 341 is for agitating a hydrophilic solvent inside the hydrophilic solvent vessel 340 to mix the hydrophilic solvent. The hydrophilic solvent vessel 340 may be in fluid communication with the binding vessel 321, and correspondingly with the first immersion filter 317 and the second immersion filter 318, through the upstream hydrophilic solvent flow line 342 and the downstream hydrophilic solvent flow line 344. Fluid communication between the hydrophilic solvent vessel 340 and the binding vessel 321 may be provided and broken by the upstream hydrophilic solvent valve 343 and the downstream hydrophilic solvent valve 345. Fluid communication between the hydrophilic solvent vessel 340 and the binding vessel 321 may be driven by the pump 347.

The flow-through vessel 380 may be in fluid communication with the binding vessel 321 through the flow-through line 326. Fluid communication between the flow-through vessel 380 and the binding vessel 321 may be provided and broken by the output valve 325 and a flow-through valve 383. Fluid communication between the flow-through vessel 380 and the binding vessel 321 may be driven by the pump 387.

The flow-through vessel 380 may be in fluid communication with the first immersion filter 317 and the second immersion filter 318 through the upstream hydrophobic solvent flow line 326 when the first immersion filter 317 and the second immersion filter 318 are immersed in the liquid contents of the binding vessel 321, for example, the binding solvent (not shown; equivalent to the binding solvent 258). Fluid communication between the flow-through vessel 326, the first immersion filter 317 and the second immersion filter 318, may be provided and broken by the flow-through valve 383 and by contact between the first immersion filter 317 and the second immersion filter 318, and the contents of the binding vessel 321. Fluid communication between the flow-through vessel 380, and the first immersion filter 317 and the second immersion filter 318, may be driven by the pump 387.

The wash vessel 390 need not be in fluid communication with the binding vessel 321. Fluid communication between the wash vessel 390 and the recovery vessel 314 may be provided and broken by a wash vessel valve 393. The first immersion filter 317 and the second immersion filter 318 may be immersed in the hydrophobic solvent (not shown; equivalent to the hydrophobic solvent 260) in the wash vessel 390 for recovery of a recovered hydrophobic target compound (not shown; equivalent to the hydrophobic target compound 259) in the recovery vessel 314. The first immersion filter 317 and the second immersion filter 318 may be immersed in the binding solvent (not shown; equivalent to the binding solvent 258) or the hydrophilic solvent (not shown; equivalent to the hydrophilic solvent 270) in the wash vessel 390 for washing the first immersion filter 317 and the second immersion filter 318 to maintain binding between the hydrophobic target molecule and the insoluble polysaccharide bound with or otherwise adhered to, or sequestered within, the first immersion filter 317 and the second immersion filter 318.

Each of the first immersion filter 317 and the second immersion filter 318 may include a distinct insoluble polysaccharide for binding to a respective distinct hydrophobic target compound. Use of the first immersion filter 317 and the second immersion filter 318 or additional immersion filters simultaneously, may allow for the recovery of a plurality of hydrophobic target compounds simultaneously. For example, unique hydrophobic target compounds can be separately isolated from a plant extract sample as a result of preferential binding to the insoluble polysaccharide contained in each immersion filter.

Column Chromatography Capture Setup

Figure 37:
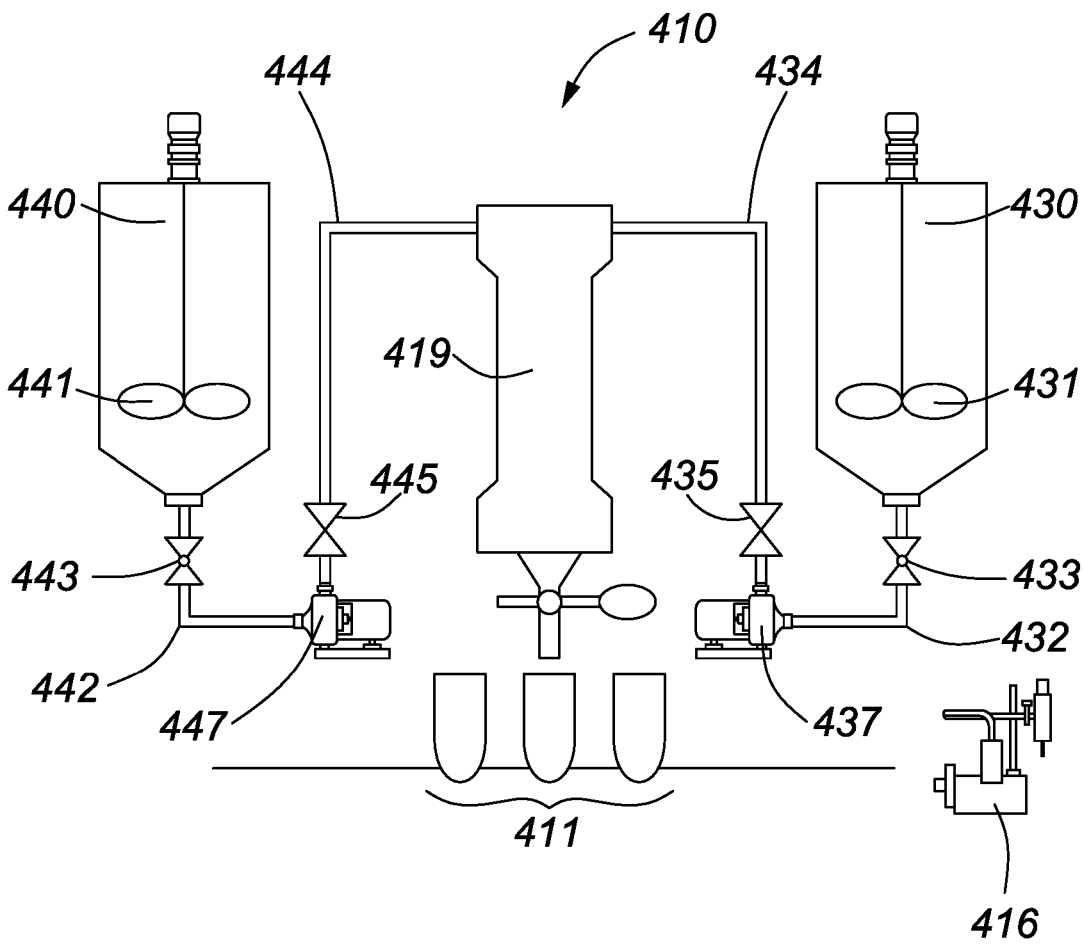
FIG. 37 is a schematic diagram of a column chromatography system.

FIG. 37 shows a column chromatography system 410 for hydrophobic compound recovery. A chromatography column 419 is in fluid communication with the hydrophobic solvent vessel 430 and the hydrophilic solvent vessel 440. Each of the hydrophobic solvent vessel 430 and the hydrophilic solvent vessel 440 may be any suitable fluid vessel appropriate for the size, scale and application of the system 410 (e.g. a tank, pressure-rated tank, etc.). A fractional recovery system 411 or other suitable recovery system may be provided for receiving eluate from the chromatography column 419.

Figure 38:
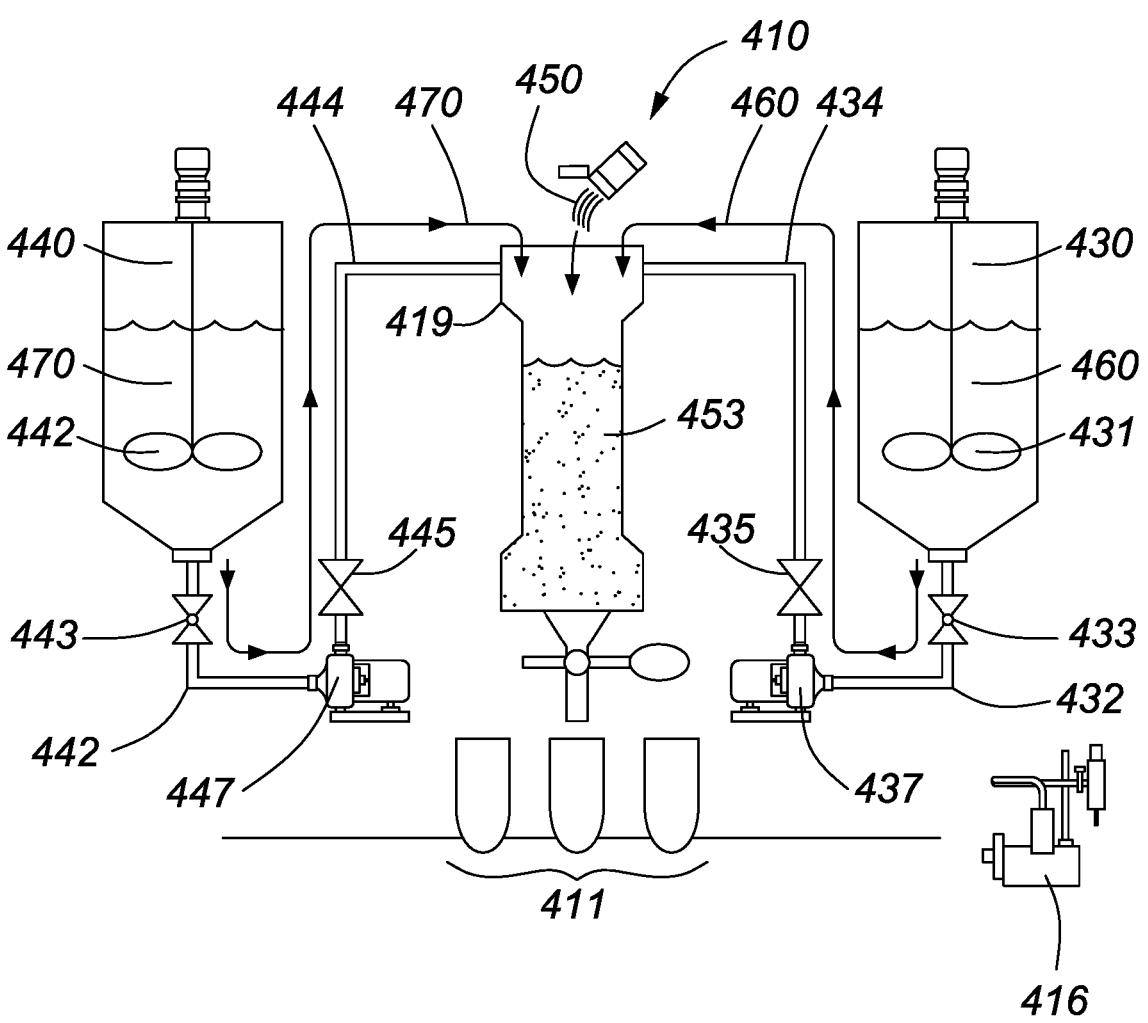
FIG. 38 is a schematic diagram of the system of FIG. 37 with a stationary phase added to the system.

The hydrophobic solvent vessel 430 includes the agitator 431 positioned within the hydrophobic solvent vessel 430. The agitator 431 is for agitating a hydrophobic solvent (e.g. the hydrophobic solvent 460 as shown in FIG. 38) inside the hydrophobic solvent vessel 430 to mix the hydrophobic solvent. The hydrophobic solvent vessel 430 is in fluid communication with the chromatography column 419.

The hydrophobic solvent vessel 430 may be in fluid communication with the chromatography column 419 through the upstream hydrophobic solvent flow line 432 and the downstream hydrophobic solvent flow line 434. Fluid communication between the hydrophobic solvent vessel 430 and the chromatography column 419 may be provided and broken by the upstream hydrophobic solvent valve 433 and the downstream hydrophobic solvent valve 435. Fluid communication between the hydrophobic solvent vessel 430 and the chromatography column 419 may be driven by the pump 437.

The hydrophilic solvent vessel 440 may be in fluid communication with the chromatography column 419 through the upstream hydrophilic solvent flow line 442 and the downstream hydrophilic solvent flow line 444. Fluid communication between the hydrophilic solvent vessel 440 and the chromatography column 419 may be provided and broken by the upstream hydrophilic solvent valve 443 and the downstream hydrophilic solvent valve 445. Fluid communication between the hydrophilic solvent vessel 440 and the chromatography column 419 may be driven by the pump 447.

Column Chromatography Capture Protocol

FIGS. 38 to 44 show the system 410 in use to recover a recovered hydrophobic target molecule 449 using the insoluble polysaccharide 450.

FIG. 38 shows the insoluble polysaccharide 450 being provided to the chromatography column 419 and packed to provide a stationary phase 453. The insoluble polysaccharide includes a carbohydrate, silica or other matrix as further described at FIGS. 45 to 48.

Figure 39:
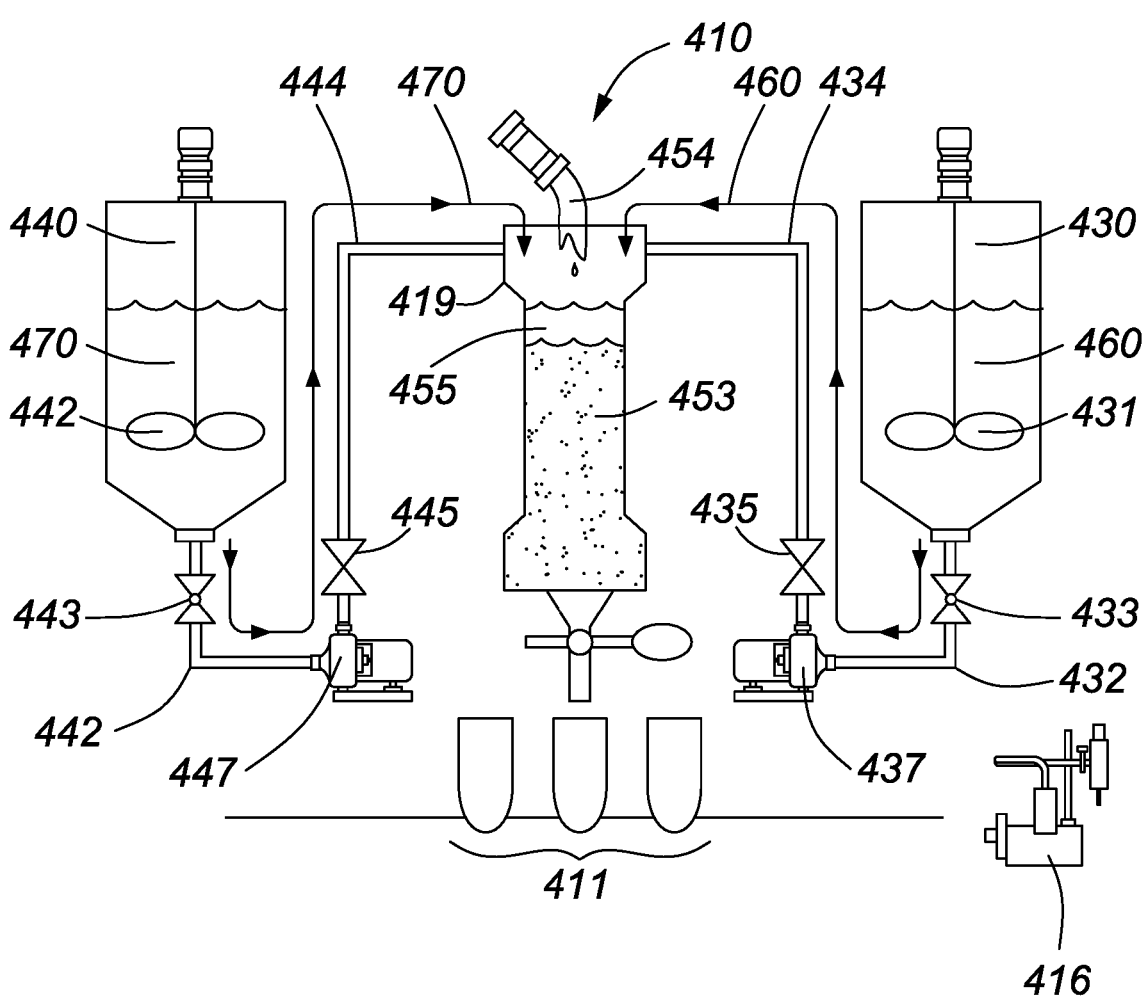
FIG. 39 is a schematic diagram of the system of FIG. 37 with a sample added to the system.

FIG. 39 shows the sample 454 being loaded into the chromatography column 419 for interacting with the stationary phase 453. The sample 454 may comprise a hydrophobic target compound and may be dissolved in the binding solution (not shown; equivalent to the binding solution 258).

The sample 454 may flow into the chromatography column 419 and be eluted as a mobile phase 455. During flow and elution, the hydrophobic solvent 460 and the hydrophilic solvent 470 may be provided to the chromatography column 419 in a proportion selected to facilitate binding of hydrophobic target compounds in the sample 454 to the insoluble polysaccharide 450 in the stationary phase 453.

Figure 40:
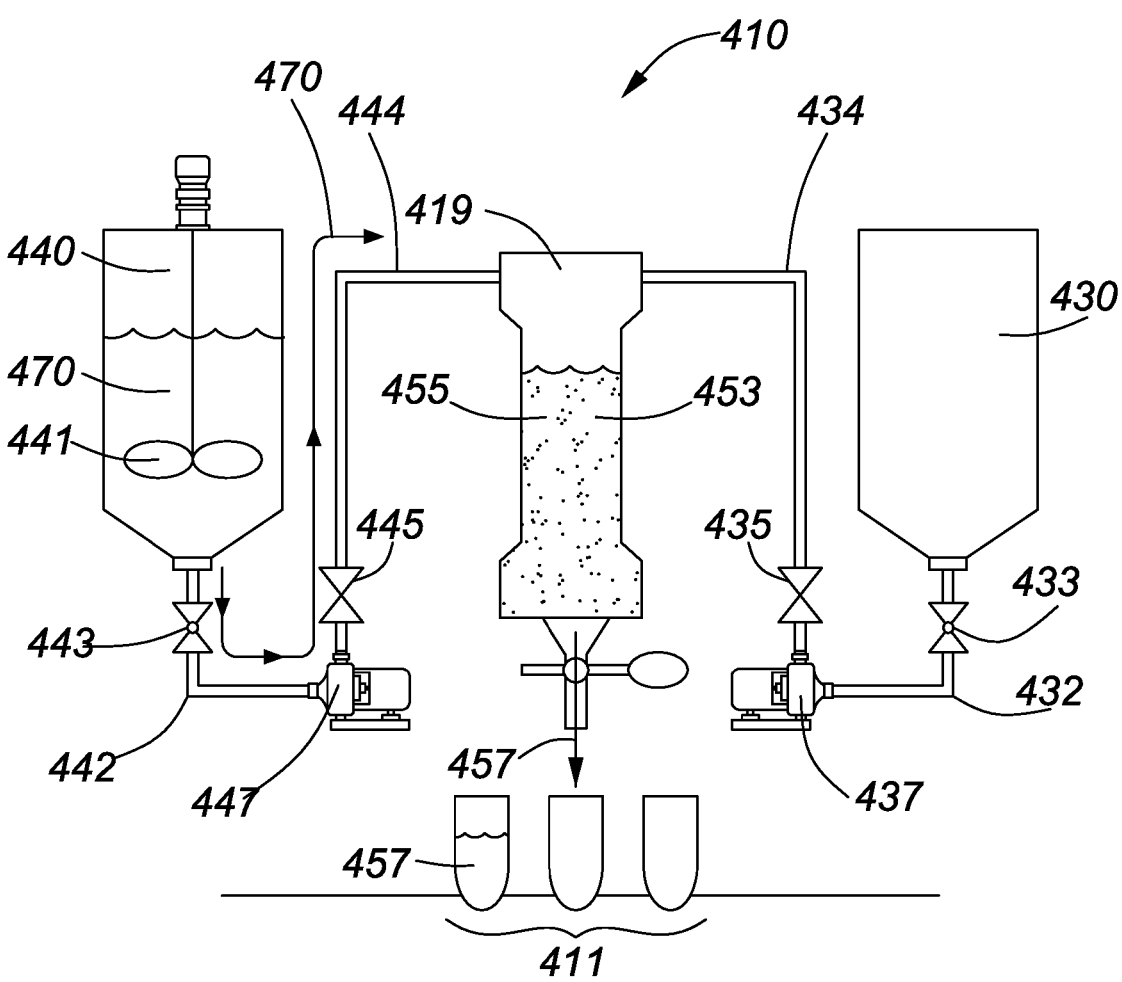
FIG. 40 is a schematic diagram of the system of FIG. 37 with hydrophilic solvent added to the system.

FIG. 40 shows the hydrophilic solvent 470 being added to the chromatography column 419 to further facilitate binding of hydrophobic target compounds in the sample 454 to the insoluble polysaccharide 450 in the stationary phase 453. The hydrophilic solvent 470 and the hydrophobic solvent 460 may flow out of the chromatography column 419 and into the fractional recovery system 411 as eluate 457. The eluate 457 resulting from flow of the hydrophilic solvent 470 alone lacks any significant amount of the hydrophobic target molecule.

Figure 41:
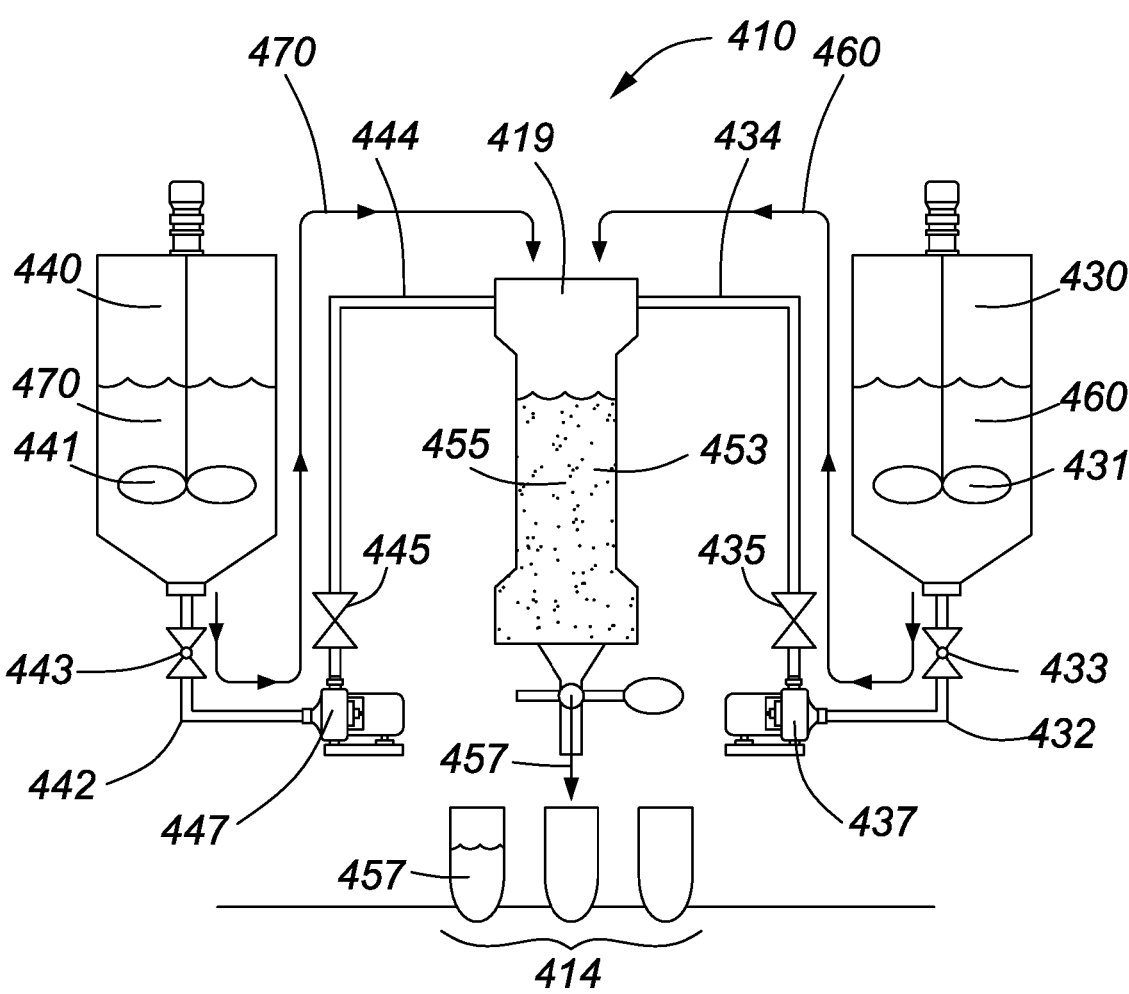
FIG. 41 is a schematic diagram of the system of FIG. 37 while eluting the sample with hydrophobic and hydrophilic solvent.

FIG. 41 shows the sample 454 being be eluted in the mobile phase 455 by a combination of the hydrophobic solvent 460 or the hydrophilic solvent 470. The mobile phase 455 may contain an increasing proportion of the hydrophobic solvent 460 over time as the elution progresses to provide the eluate 457 with an increasing amount of the hydrophobic target molecule. Fractions of the eluate 457 may be collected in separate vessels of the fractional recovery system 411 (e.g. test tubes, etc.). Hydrophobic target compounds may be recovered from the fractions of the eluate 457 by known methods (e.g. example liquid-liquid extraction, evaporation, etc.)

Figure 42:
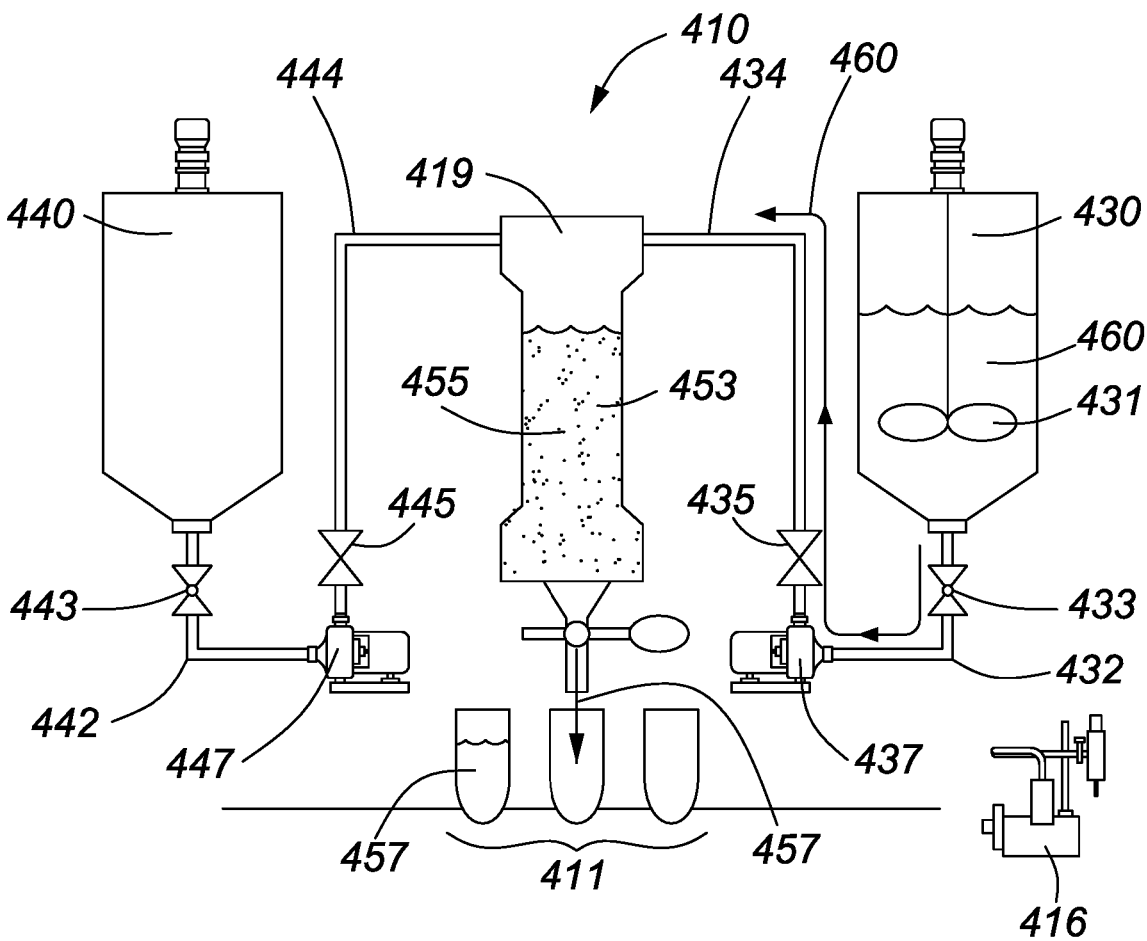
FIG. 42 is a schematic diagram of the system of FIG. 37 while eluting hydrophobic target compounds with hydrophobic solvent.

FIG. 42 shows the mobile phase 455 being eluted from the loaded chromatography column 419 with the hydrophobic solvent 460 alone for dissociating the hydrophobic target compounds from the cyclodextrin polymer stationary phase 453 and for solubilizing the hydrophobic target compounds in the hydrophobic solvent 460. The column filter 419 may be eluted in this manner until no more of the hydrophobic target compound is eluted.

Figure 43:
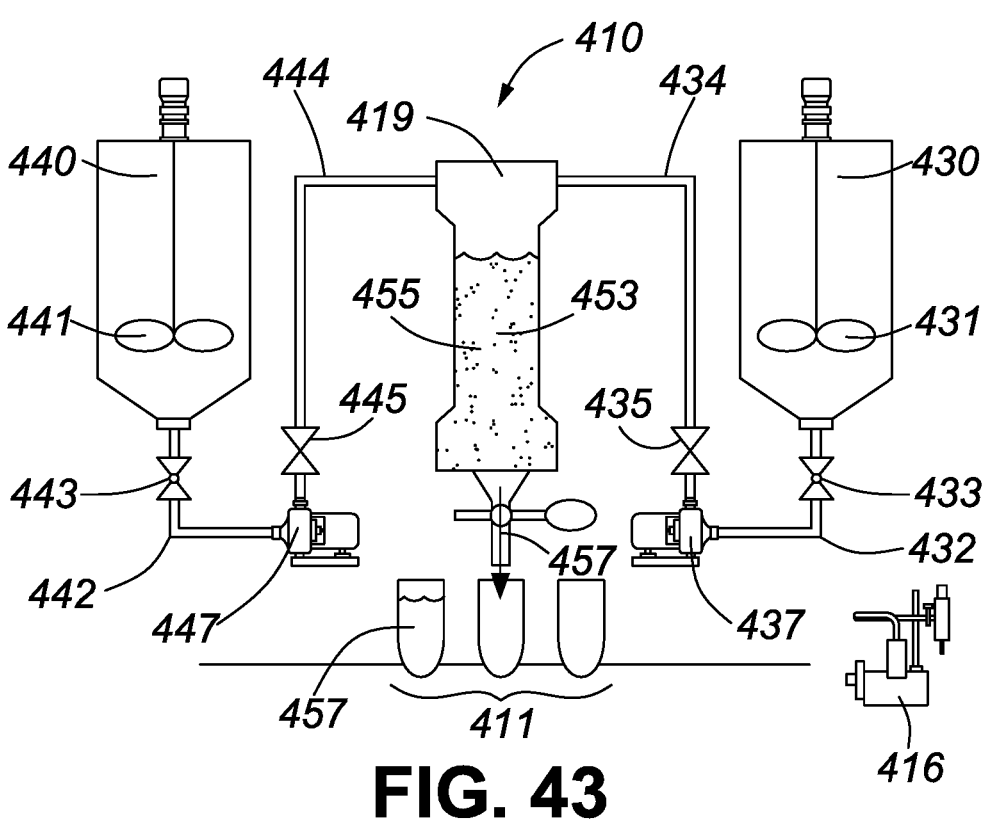
FIG. 43 is a schematic diagram of the system of FIG. 37 while eluting hydrophobic target compounds.

FIG. 43 shows the end of the elution cycle in which the mobile phase 455, at this point predominantly or entirely the hydrophobic solvent 460, is drained into the fractional recovery system 411 as eluate 457.

Figure 44:
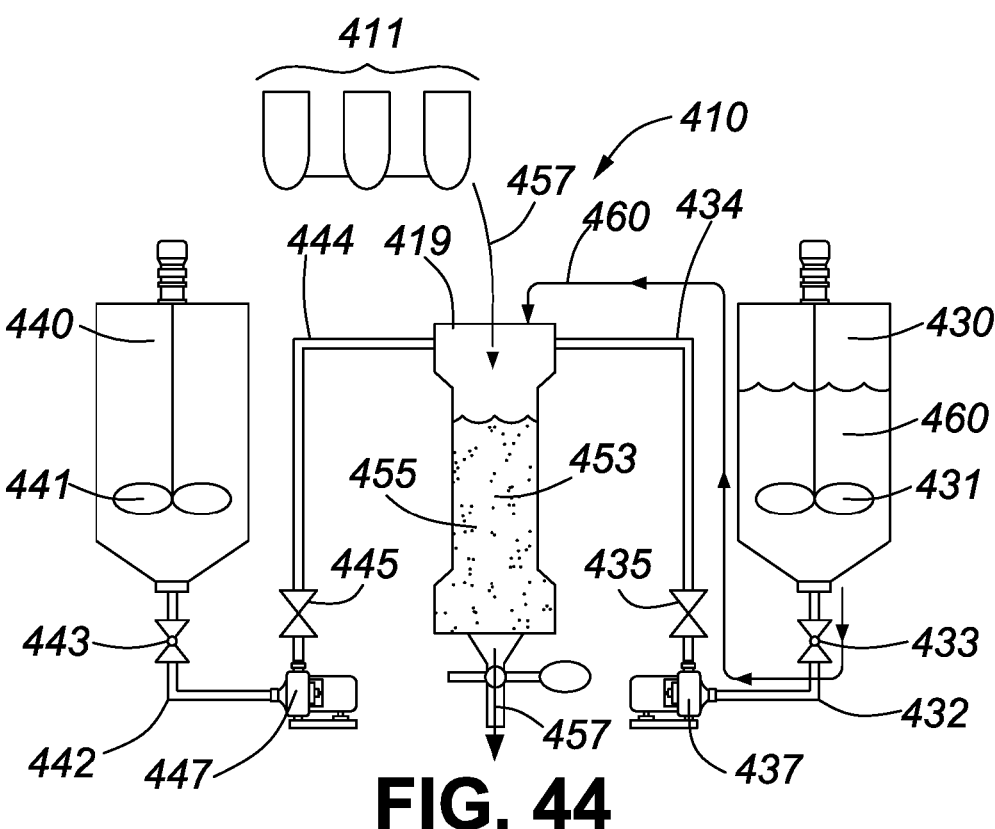
FIG. 44 is a schematic diagram of the system of FIG. 37 with the contents of a recovery vessel added to the system to repeat the process of FIGS. 41 to 43.

FIG. 44 shows some fractions of the eluate 457 being provided back to the chromatography column 419 from the fractional recovery system 411 for further purification.

The insoluble polysaccharide 450 may be regenerated for reuse by washing the insoluble polysaccharide 450 with a detergent solution, for example 0.1% Triton X-100 at 37° C. for one minute. Solvents that are able to dissociate any hydrophobic compounds from the insoluble polysaccharide 450, such as DMSO, may also be applied for regeneration. Exposure to the detergent solution, to solvent or other regeneration may be followed by re-equilibration with 3 to 5 volumes of ethanol.

Figures 45, 46:
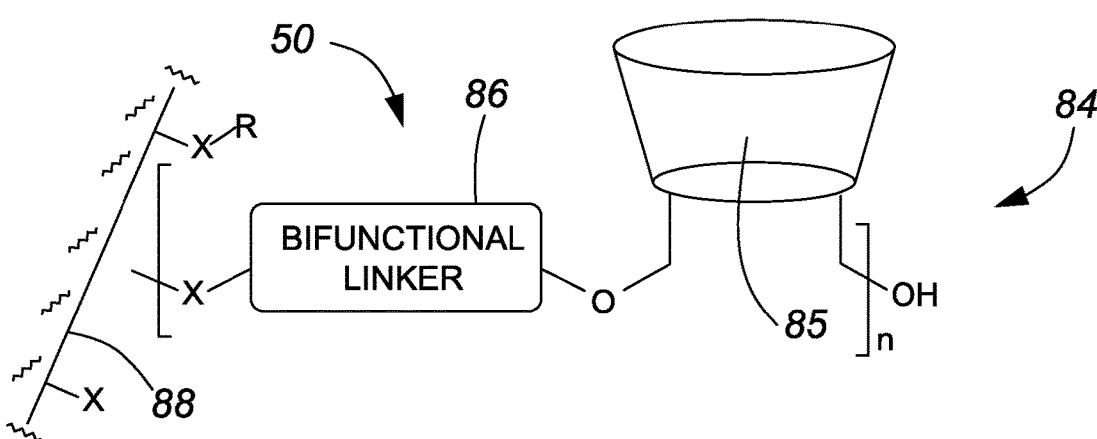
FIG. 45 is a schematic diagram of the molecular structure of a polysaccharide bound to a carbohydrate matrix.
FIG. 46 is a schematic diagram of the molecular structure of a polysaccharide bound to a carbohydrate matrix.

FIG. 45 shows an embodiment of the insoluble polysaccharide 50 in which a polysaccharide-linker subunit 84 bound to an immobile matrix 88 (e.g. cellulose matrix, other carbohydrate matrix, silica matrix, etc.). The immobile matrix 88 may be used as the stationary phase 453 in the system 410. The polysaccharide-linker subunit 84 includes a cyclic polysaccharide 85 bound to a bidirectional linker 86. This embodiment includes at least two polysaccharide subunits 84 (i.e. n=2 or more).

FIG. 46 shows an embodiment of the insoluble polysaccharide 50 in which the polysaccharide-linker subunit 84 includes 2,4-tolyl-diisocyanate as the bidirectional linker 86 and cellulose as the immobile matrix 88. This embodiment includes at least two polysaccharide-linker subunits 84 (i.e. n=2 or more).

Figures 47, 48:
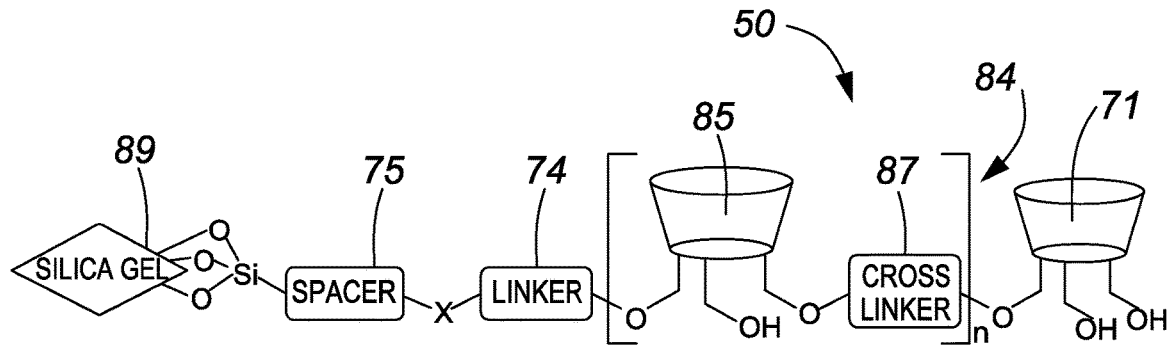
FIG. 47 is a schematic diagram of the molecular structure of a polysaccharide bound to a silica gel.
FIG. 48 is a schematic diagram of the molecular structure of a polysaccharide bound to a silica gel.

FIG. 47 shows an embodiment of the insoluble polysaccharide 50 in which the polysaccharide-linker subunit 84 includes a cross-linker 87 and the cyclic polysaccharide 85. The polysaccharide-linker subunit 84 is bound to the linker 74 and the spacer 75. A silica-based immobile matrix 89 (e.g. a silica gel, mesomorphous silica, amorphous silica, etc.). This embodiment includes at least one polysaccharide-linker subunit 84 (i.e. n=1 or more), in addition to the terminal polysaccharide 71.

FIG. 48 shows an embodiment of the insoluble polysaccharide 50 in which the polysaccharide-linker subunit 84 includes hexamethylene dicarbamate as the cross-linker 87 (which may be reacted from an isocyanate moiety), an amide as the linker 74 and a propyl group as the spacer 75. The immobile matrix 89 is a silica gel (e.g. mesomorphous silica, amorphous silica, etc.). This embodiment includes at least one polysaccharide-linker subunit 84 (i.e. n=1 or more), in addition to the terminal polysaccharide 71.

Any of the embodiments of the insoluble polysaccharide 50 shown in FIGS. 45 to 48, or other immobilized insoluble polysaccharide 50, may be used as the insoluble polysaccharide 450 in the system 410.

Standard Protocol

A standard protocol was followed in all Examples with the variances from the standard protocol as described in each Example. The standard protocol included a plurality of steps. A mass of CBD was dissolved in ethanol to form a stock solution. A reference sample of the stock solution was diluted with ethanol to obtain a target CBD or other target molecule concentration for a reference measurement. A reaction sample was taken from the remaining stock solution. A cross-linked polysaccharide was combined with the reaction sample in a ratio relative to the CBD or other target molecule concentration present in the reaction sample (by mass) as specified in Examples. The cross-linked polymer is HDI-linked cyclodextrin prepared with a ratio of 8:1 HDI to cyclodextrin.

Water is combined with the reaction sample until the reaction sample reaches a target CBD or other target molecule concentration, and a target ethanol to water ratio. The reaction mixture including the water is filtered at a cutoff size of between 75 μm to 4,000 μm aperture size, or exposed to a magnetic field with a neodymium magnet through the wall of a flask, to retrieve the cross-linked polymer bound with CBD or other target molecule concentration. Once retrieved, the cross-linked polymer is flushed with a dissociation solvent for dissolving the target molecule. The dissociation solvent applied in the examples may be methanol, ethanol, isopropanol, a mixtures of aliphatic, aromatic and $CO_2$ fluids, DMSO, butane.

Example 1

Ten milligrams of CBD were dissolved in a 10 mL mixture of 1:1 ethanol to water to produce a reaction mixture with a CBD concentration of 1 mg/mL. A 1 mL aliquot was then taken from the reaction mixture as a reference sample (t=0). One hundred milligrams of the cross-linked polymer was then combined with the reaction mixture for a polymer to CBD ratio of about 10:1 by mass. The reaction mixture was then stirred at room temperature.

One milliliter aliquots were then taken from the reaction mixture and filtered using pipette filtration at 10 minute intervals over 80 minutes (t=10, t=20, t=30, t=40, t=50, t=60, t=70, t=80, t=90). CBD capture data was obtained from the supernatant fluid of these aliquots after filtration. The data point at t=80 was obtained using syringe filtration, which may have filtered out more of the detectable CBD independently of the insoluble polysaccharide through adsorption. The t=90 time point returns to a level consistent with the time points beginning with t=30. About 15% of the CBD, or 1.7 mg was captured with a 10:1 polymer:CBD ratio.

After filtration and recovery of the cross-linked polymer, the cross-linked polymer was flushed with DMSO.

Figure 49:
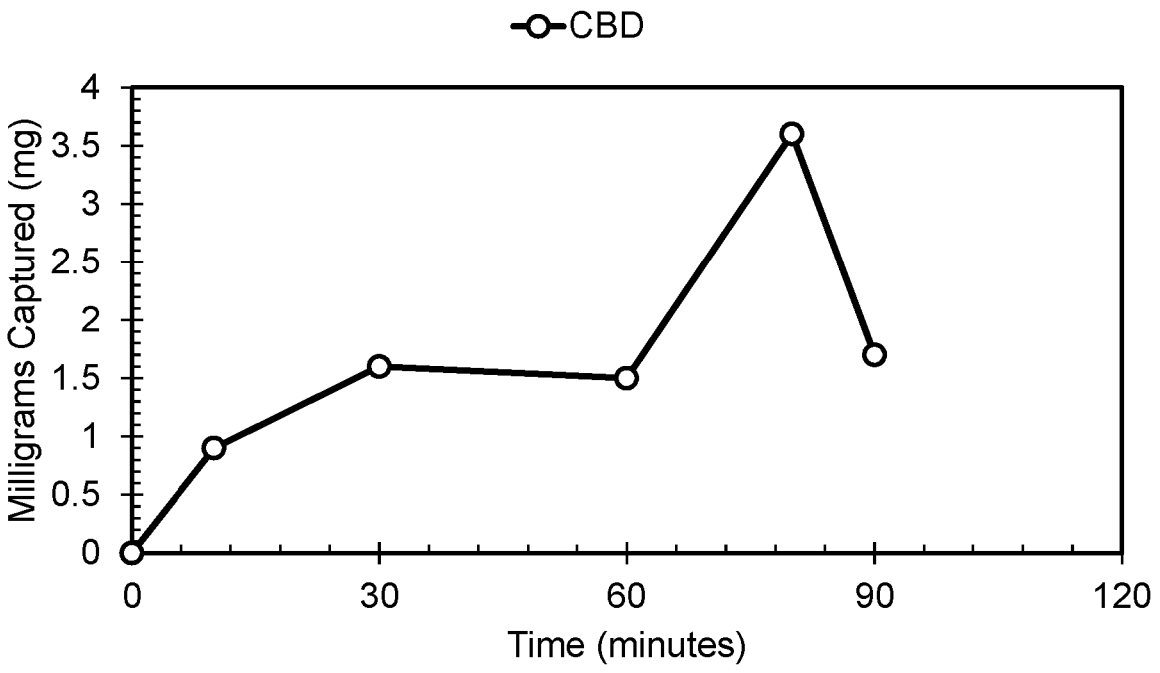
FIG. 49 shows mg of CBD captured over time in Example 1.
Figure 50:
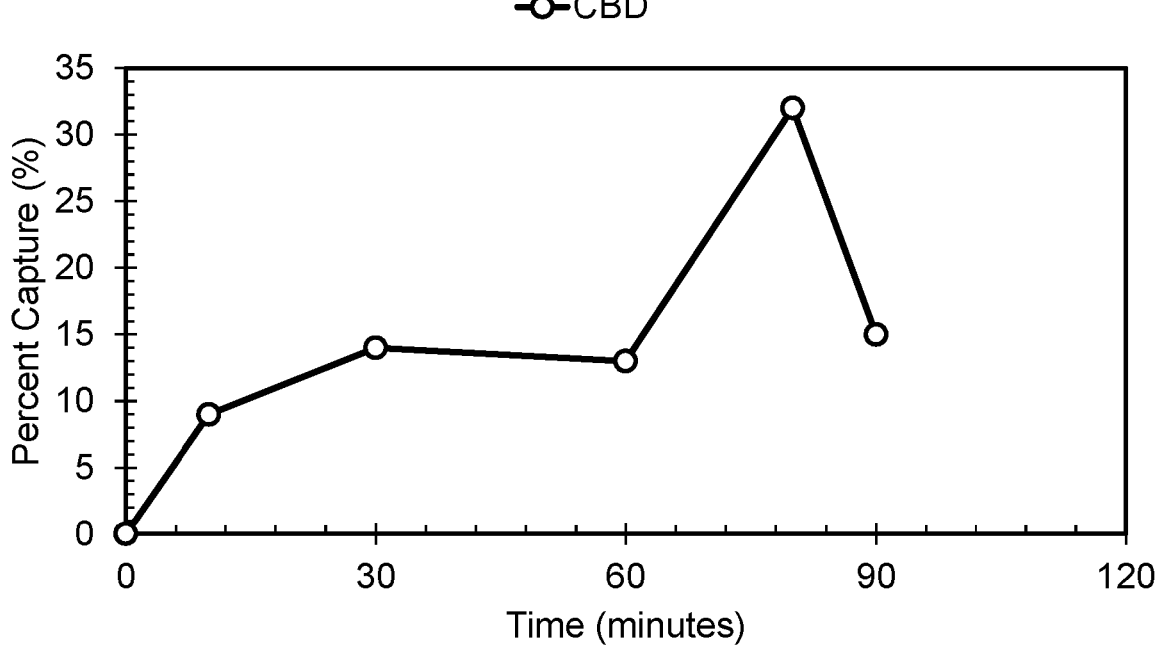
FIG. 50 shows percent of total CBD captured over time in Example 1.

FIGS. 49 and 50 show the milligrams of the CBD captured and percent of total CBD captured, respectively, over the 80 minutes.

Example 2

The protocol of Example 1 was followed. Sixty-eight milligrams of CBD were dissolved in a 1:1 mixture of ethanol and water to produce the reaction mixture with a CBD concentration of 1 mg/mL. Six-hundred and eighty-three milligrams of the cross-linked polymer were then combined with the reaction mixture for a polymer to CBD ratio of approximately 10:1 by mass. The capture was 11.6 mg of the 68 mg of CBD, or about 17%.

Filtration was performed by vacuum filtration using a Büchner funnel.

The cross-linked polymer was collected following filtration and divided into three portions. The first portion was combined with isopropyl alcohol ("IPA") at room temperature, the second with IPA with the application of sonication/heat, and the third with DMSO at room temperature.

Figure 51:
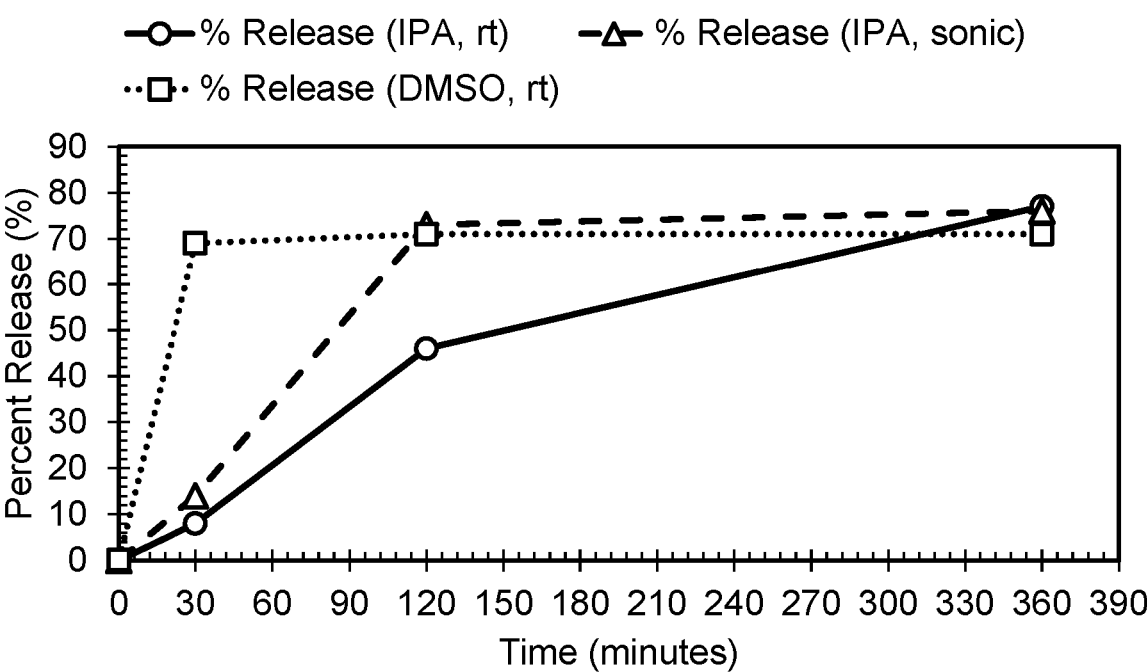
FIG. 51 shows the percentage of CBD release over time in Example 2.

FIG. 51 shows the percentage of CBD release over time for each solvent.

Example 3

The protocol from Example 1 was followed for a first batch with a polymer to CBD ratio of 10:1 by mass. For a second batch, the protocol from Example 1 was followed with a greater amount of cross-linked polymer to reach a polymer to CBD ratio of about 50:1 by mass. Pipette filtration was performed using aliquots collected over the course of more than 100 minutes. After 10 minutes, the 50:1 ratio showed about 4 to 5 times as much capture—about 40 to 45%, or 4.0 to 4.5 mg of CBD for 500 mg of polymer.

Figure 52:
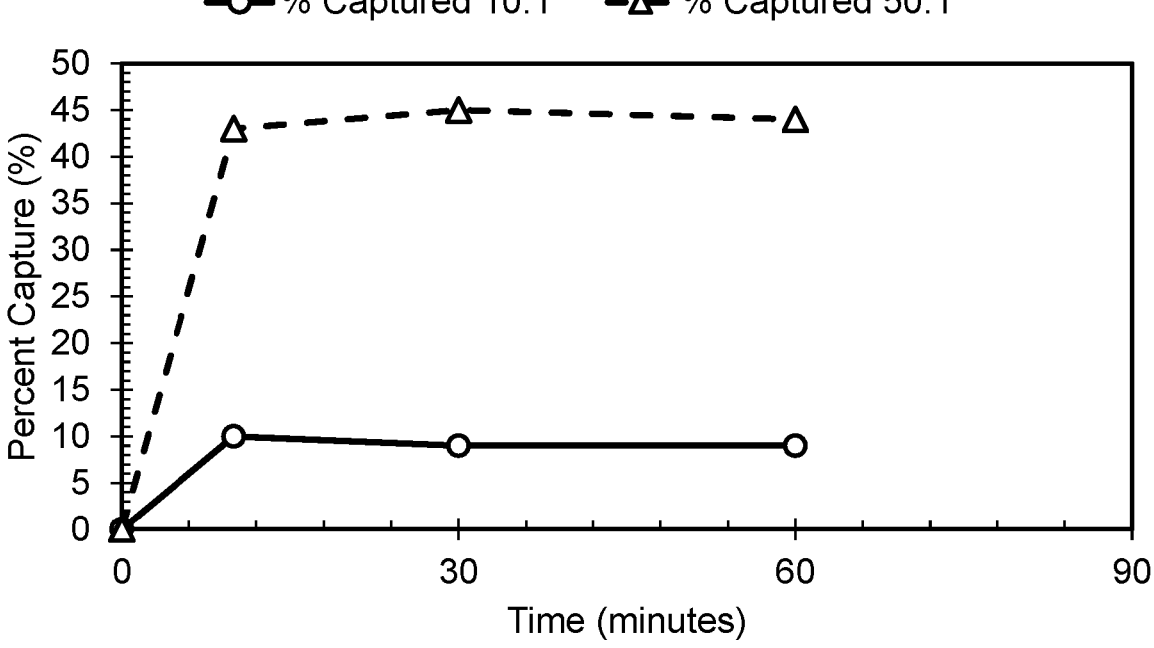
FIG. 52 shows the percentage of CBD captured over time in Example 3.

FIG. 52 shows the percentage of CBD captured over time.

Example 4

The protocol of Example 1 was followed with the additional combination of 10 mg of cannabigerol ("CBG") in the reaction mixture. The cross-linked polymer was combined in a ration of polymer to (CBD and CBG) of 25:1, with 500 mg of polymer to 20 mg of combined CBG and CBD. The dissociation solvent was DMSO. CBG capture was about 45 to 50% (4.5 to 5.0 mg of CBG for 500 mg of polymer). CBG was released into DMSO at room temperature with 104% recovery. No significant selectivity was observed between CBD and CBG. The polymer captured about double the phytocannabinoid weight compared with Example 3.

Figure 53:
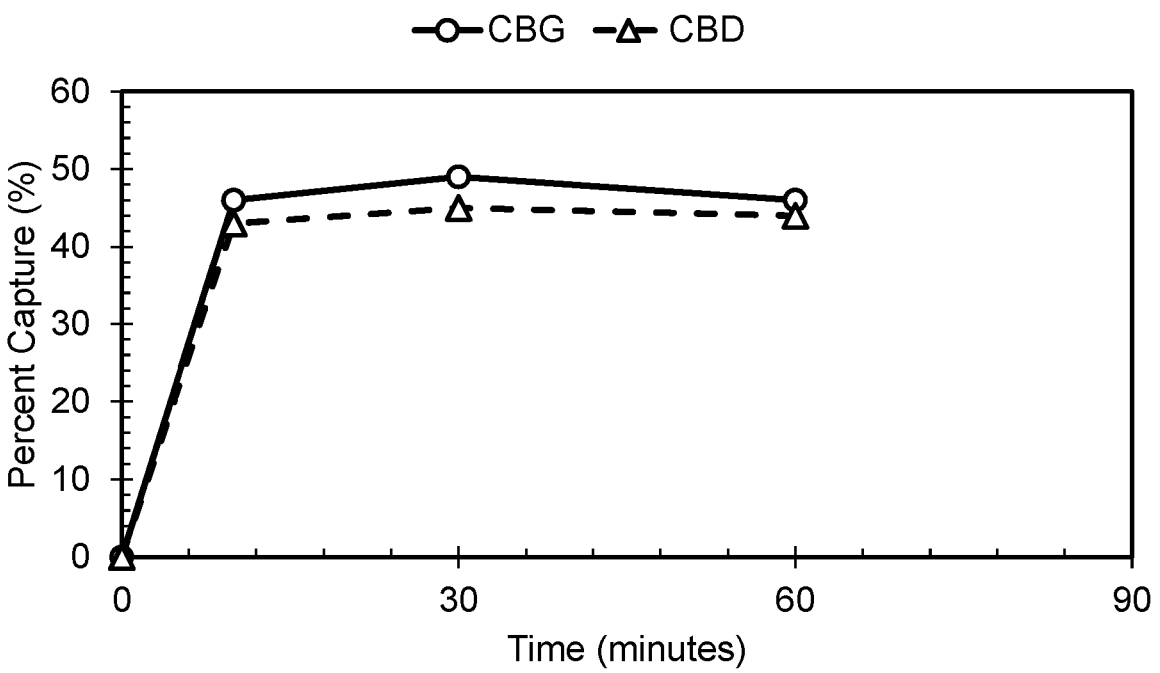
FIG. 53 shows the percentage of CBD and CBG captured over time in Example 4.

FIG. 53 shows the percentage of CBD and CBG captured over time in two separate experiments Example 4.

Figure 54:
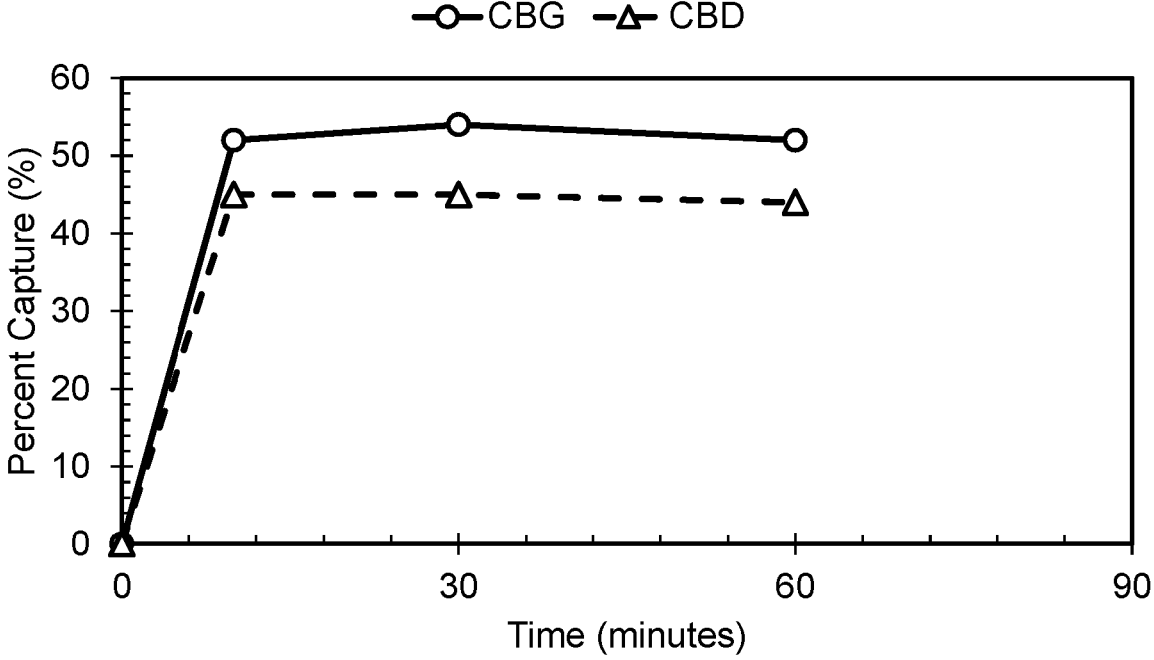
FIG. 54 shows the percentage of CBD and CBG captured over time when CBD and CBG are in competition in Example 4.

FIG. 54 shows the percentage of CBD and CBG captured over time when CBD and CBG are in competition in Example 4.

Example 5

The protocol of Example 1 was followed for four batches. The first batch had an additional combination of 10 mg of vanillin in the reaction mixture. The second batch had an additional combination of 10 mg of olivetol in the reaction mixture. The third batch included 10 mg of vanillin and no CBD. The fourth batch combined 10 mg of olivetol and no CBD. CBD, vanillin and olivetol were recovered.

For each batch, 500 mg of the polymer was combined with the reaction mixture for a polymer to target molecule ratio of 50:1 by mass. Where there is more than one target molecule, the cross-linked polymer was combined with the reaction mixture in a polymer to CBD ratio of 50:1 by mass.

Figure 55:
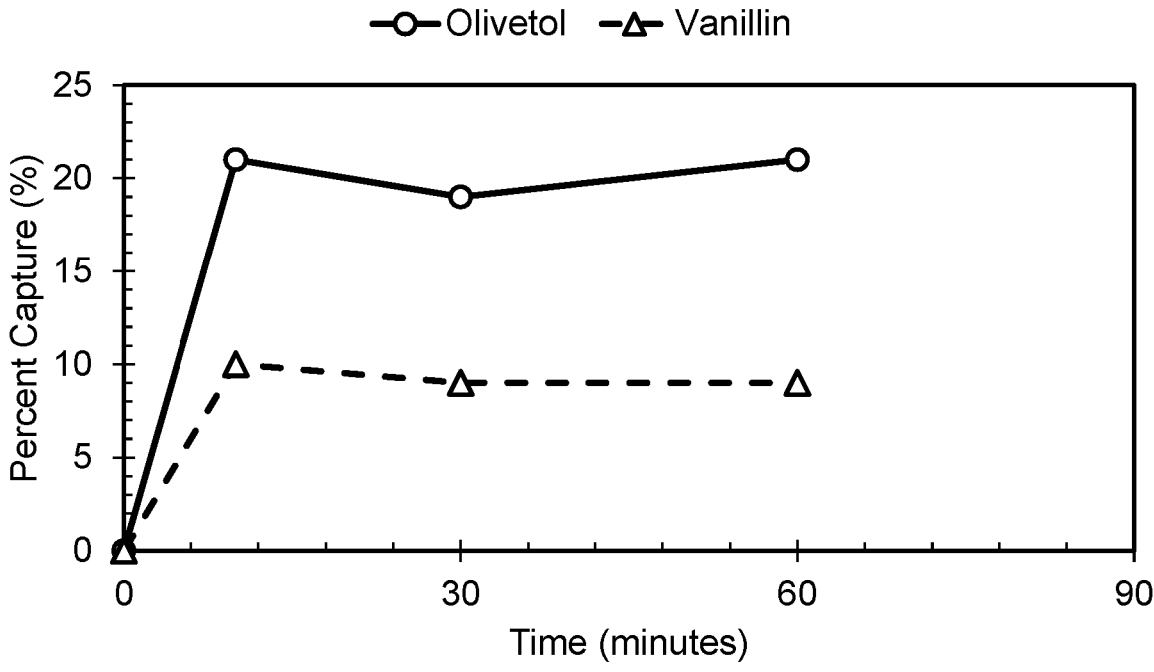
FIG. 55 shows the percentage of vanillin and olivetol captured over time in Example 5.

FIG. 55 shows the percentage capture of olivetol and vanillin over a period of 60 minutes.

Figure 56:
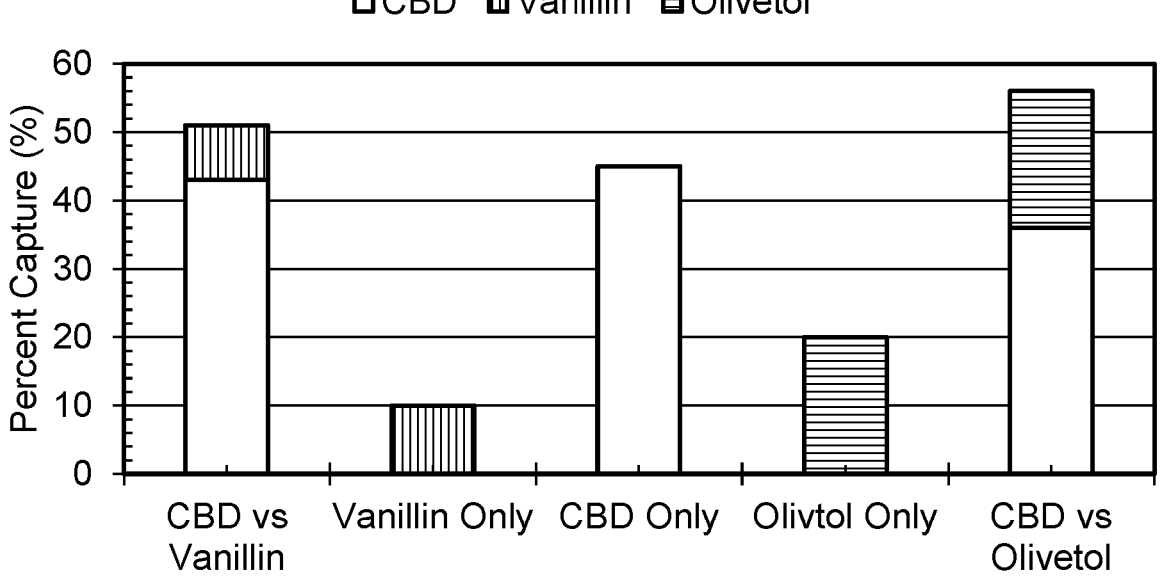
FIG. 56 shows the percentage capture of vanillin, olivetol, and CBD in Example 5.

FIG. 56 shows the percentage capture of CBD, vanillin and olivetol as at 20 to 30 minutes.

Example 6

Five batches of reaction mixture were prepared according to the protocol from Example 1 with the changes described below.

The first batch was prepared by combining 10 mg of CBD with 10 mL of 1:1 ethanol and water to reach a concentration of 1 mg/mL and a polymer to CBD ratio of 10:1 by mass.

The second batch was prepared by combining 10 mg of CBD with 5 mL of 1:1 ethanol and water to reach a concentration of 2 mg/mL and a polymer to CBD ratio of 10:1 by mass.

The third batch was prepared by combining 10 mg of CBD with 10 mL of 1:1 ethanol and water to reach a concentration of 1 mg/mL and a polymer to CBD ratio of 5:1 by mass.

The fourth batch was prepared by combining 20 mg of CBD with 10 mL of 1:1 ethanol and water to reach a concentration of 2 mg/mL and a polymer to CBD ratio of 10:1 by mass.

The fifth batch was prepared by combining 20 mg of CBD with 10 mL of 1:1 ethanol and water to reach a concentration of 2 mg/mL and a polymer to CBD ratio of 5:1 by mass.

Figure 57:
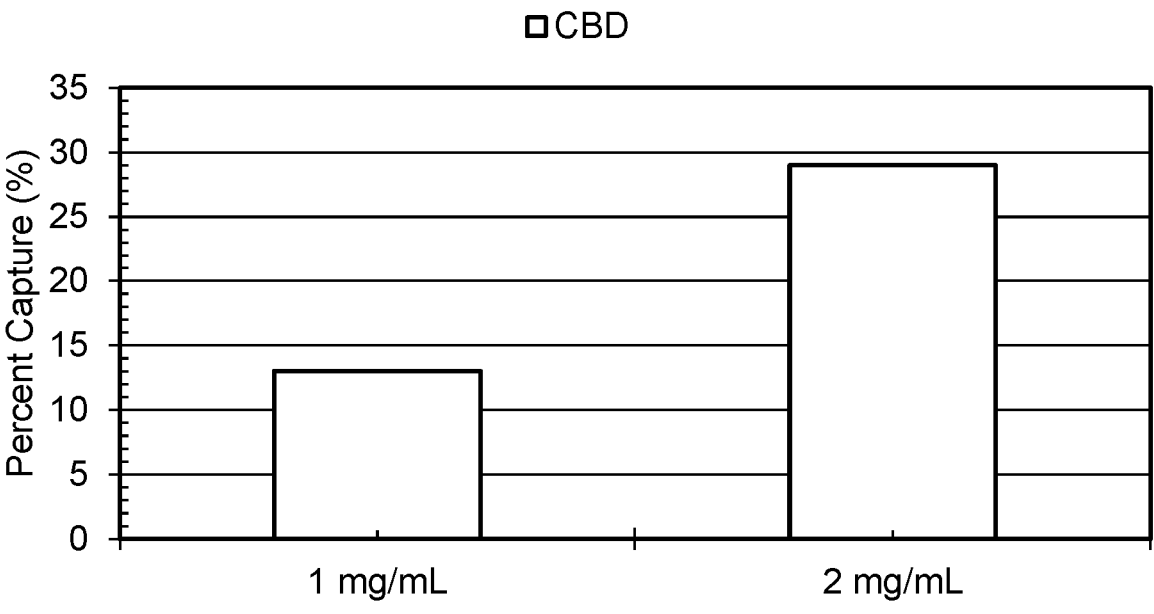
FIG. 57 shows percentage capture of CBD in Example 6.

FIG. 57 shows the percentage of CBD captured in batches 1 and 2.

Figure 58:
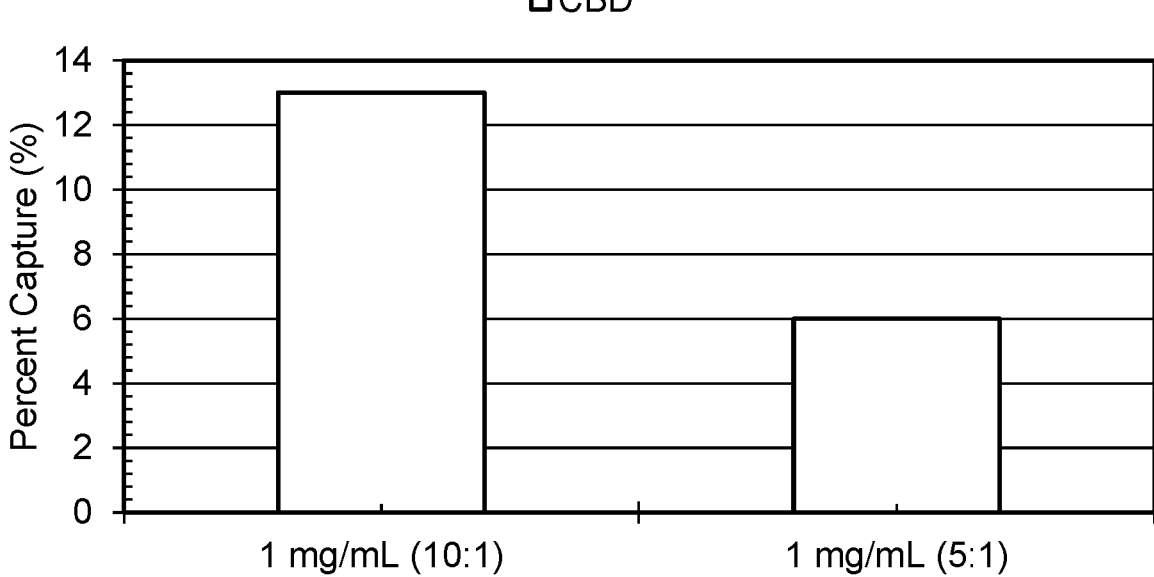
FIG. 58 shows percentage capture of CBD in Example 6.

FIG. 58 shows the percentage of CBD captured in batches 1 and 3.

Figure 59:
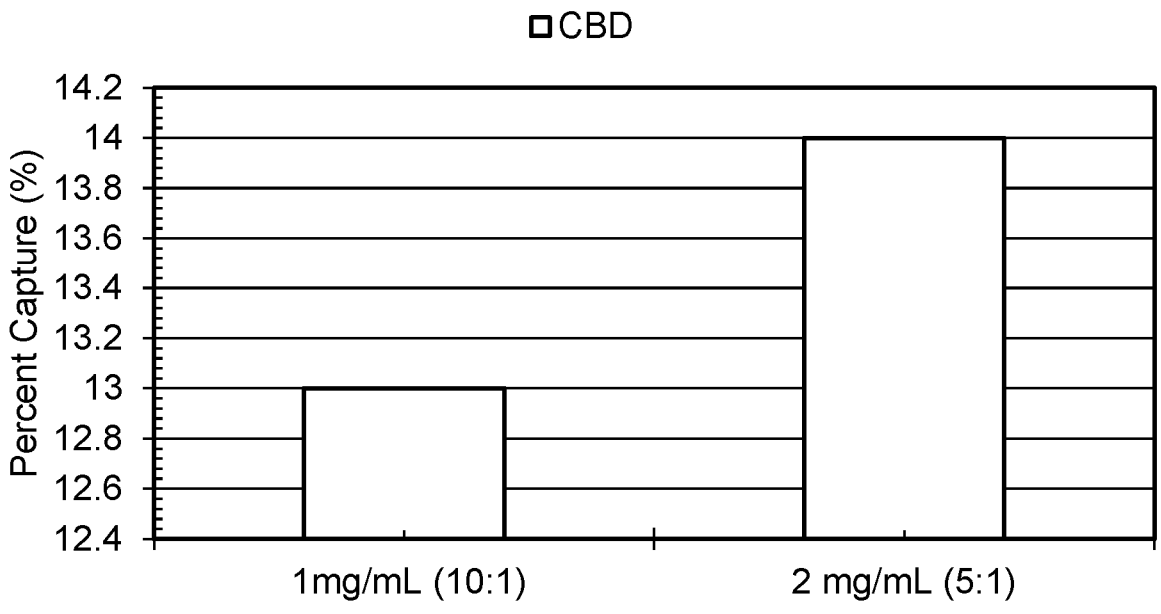
FIG. 59 shows percentage capture of CBD in Example 6.

FIG. 59 shows the percentage of CBD captured in batches 1 and 4.

Figure 60:
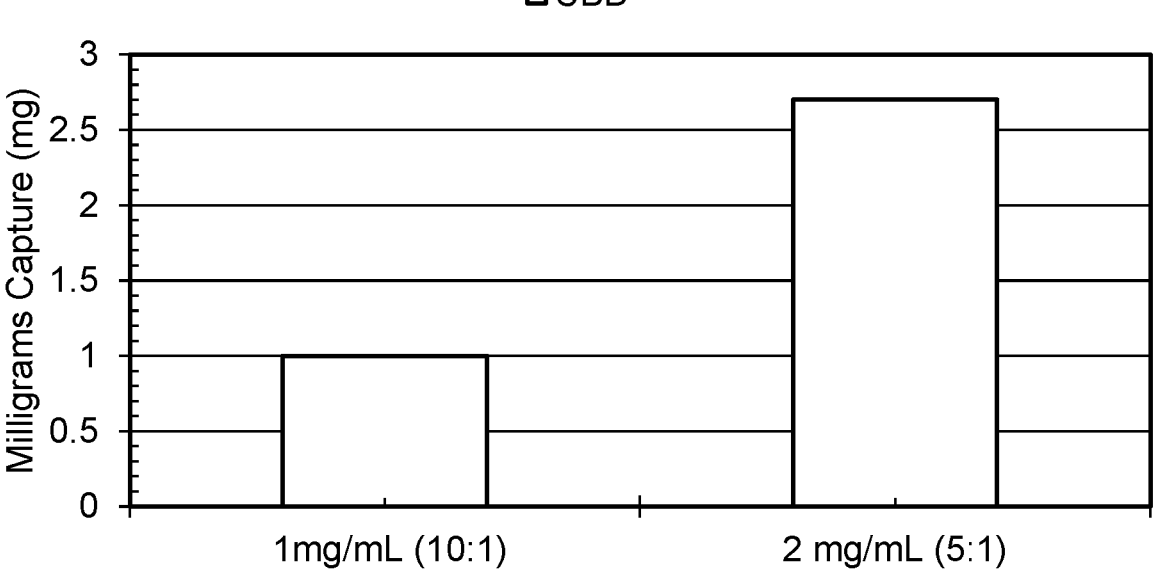
FIG. 60 shows percentage capture CBD in Example 6.

FIG. 60 shows the milligrams of CBD captured in batches 1 and 5 in milligrams.

Example 7

The protocol from Example 1 was followed for a first batch having an initial CBD concentration of 2 mg/mL (10 mg CBD in 5 mL 1:1 ethanol and water) and a 10:1 polymer to CBD ratio by mass. A second batch was prepared using the protocol from Example 1 having a concentration of 2 mg/mL (10 mg CBD in 5 mL 1:1 ethanol and water) and a 510:1 polymer to CBD ratio by mass. In Example 3 at 1 mg/mL, a 5× increased in polymer resulted in a 4 to 5 fold increased in percent CBD retention. In this case, at 2 mg/mL, only a 2.3 fold increase resulted, showing 68% recovery at 50:1 compared with 29% recovery at 10:1, suggesting that the saturation point of CBD in 1:1 ethanol:$H_2O$ was being reached.

Figure 61:
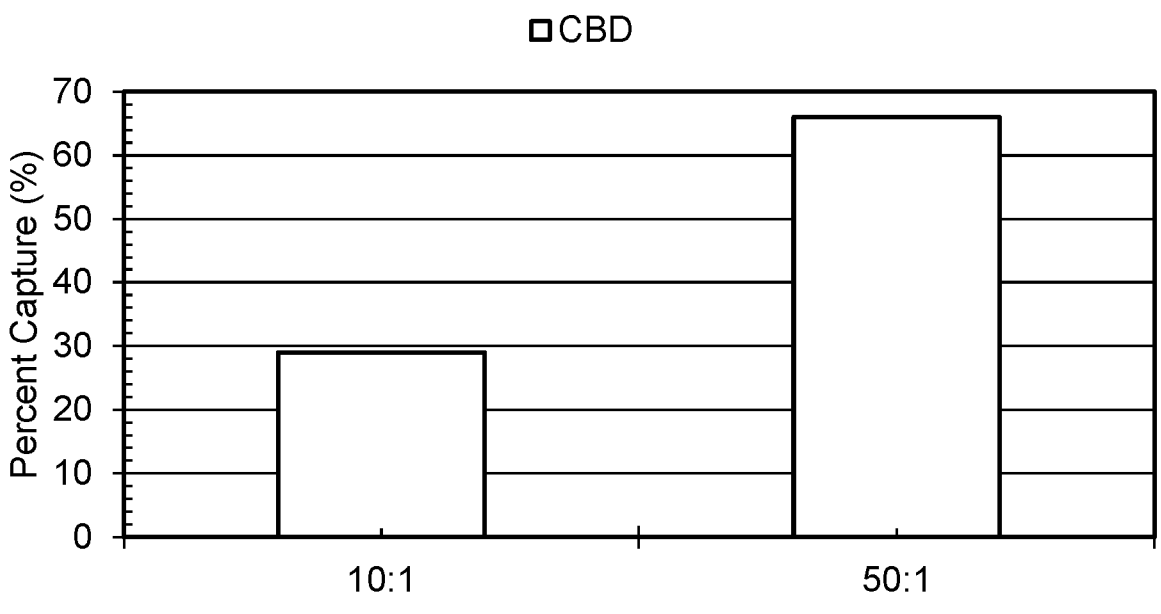
FIG. 61 shows the percentage capture of CBD in Example 7.

FIG. 61 shows the percentage of CBD captured for each batch.

Example 8

The protocol from Example 1 was followed for a first batch having an initial CBD concentration of 2 mg/mL in 1:1 ethanol and water. A second batch was prepared of the same concentration in ethanol only. A third batch was prepared with a CBD concentration of 4 mg/mL in ethanol only. Each batch used a 10:1 polymer to CBD ratio by mass. In this case, there was no significant capture in EtOH of either 2 mg/mL or 4 mg/mL.

Figure 62:
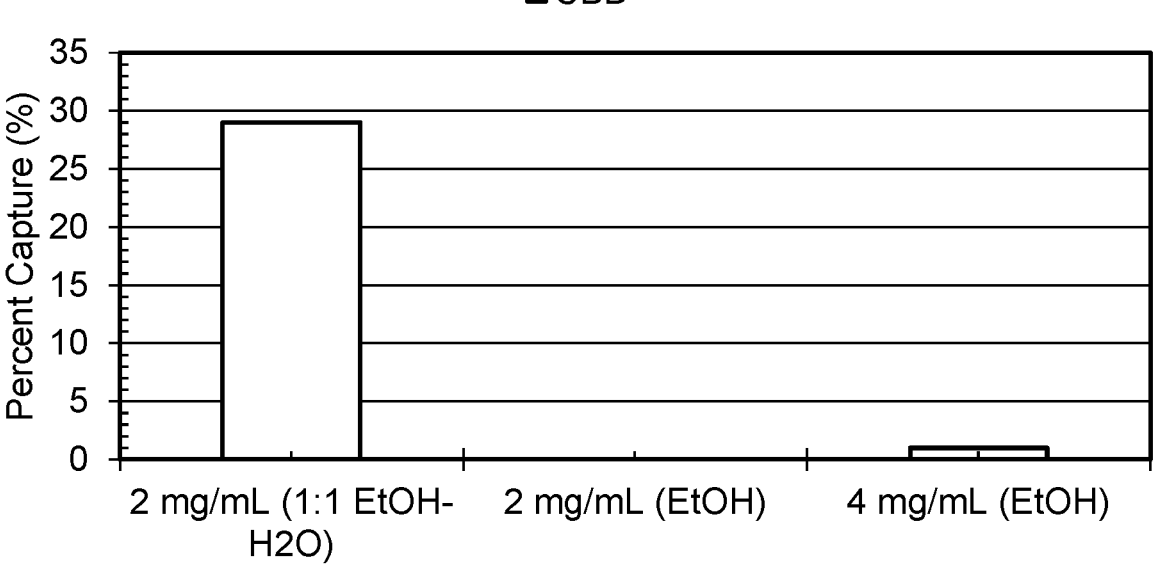
FIG. 62 shows the percentage capture of CBD in Example 8.

FIG. 62 shows the CBD percentage capture for each batch.

Example 9

Sixty milligrams of CBD were dissolved in a 30 mL mixture of 1:1 ethanol to water to produce a stock solution with a CBD concentration of 2 mg/mL. The stock solution was divided into 6 portions. One portion of the stock solution was then taken to calculate a baseline CBD concentration at t=0.

A cross-linked polymer was then combined with each of the remaining five portions for a polymer to CBD ratio of about 10:1 by mass. It was then stirred at room temperature. A plateau was reached at about 5 minutes.

The remaining portions were each filtered at a different time interval two minutes apart (one at t=2, another at t=4, another at t=6, etc.). CBD capture data was obtained from the supernatant fluid of these portions after filtration.

After filtration and recovery of the cross-linked polymer, the cross-linked polymer was flushed with DMSO.

Figure 63:
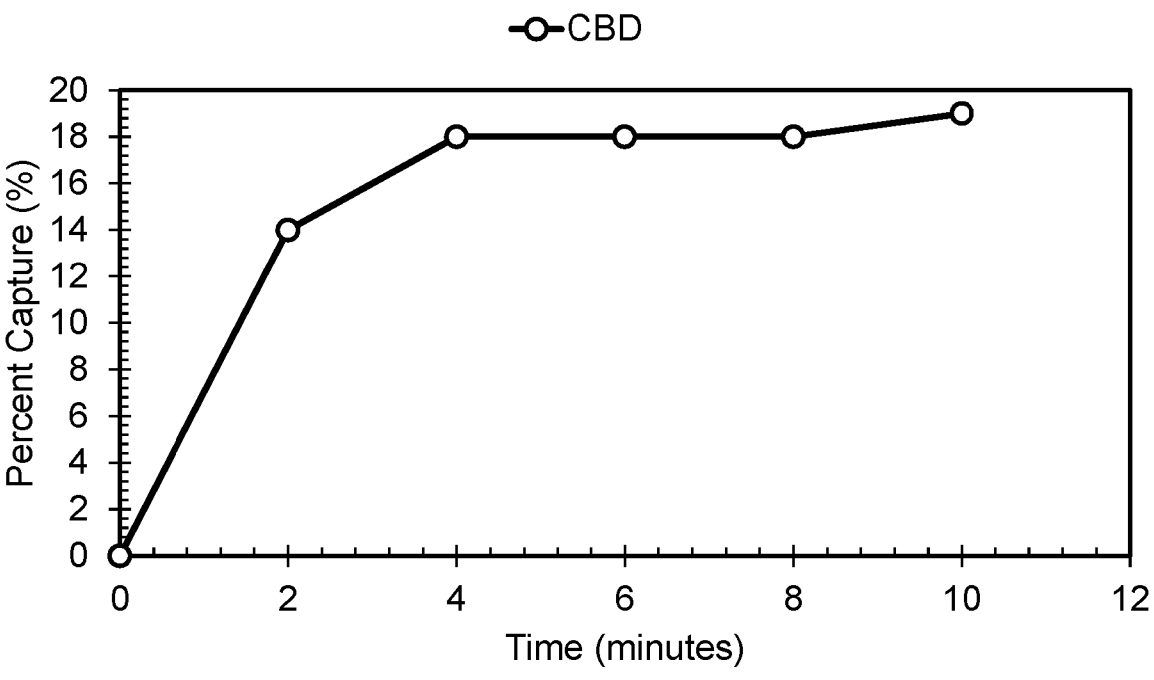
FIG. 63 shows percentage capture over time of CBD in Example 9.

FIG. 63 shows the CBD capture over time where each data point is derived from a different portion.

Example 10

The protocol of Example 9 was followed with the 60 mg initially dissolved in ethanol only. Water was then combined with each of the remaining five portions over the course of 2 to 5 minutes until the reaction mixture reached a target CBD concentration of 2 mg/mL. The remaining five portions were diluted to an ethanol to water ratio of 7:3, 6:4, 5:5, 4:6 or 3:7. The portions were then filtered to retrieve the cross-linked polymer.

At 50:50 EtOH:$H_2O$, CBD dissolves provided that EtOH is added first then $H_2O$. At 45:56 EtOH:$H_2O$, the 2 mg/mL CBD solution is cloudy. At 40:60 EtOH:$H_2O$, the 2 mg/mL CBD is not fully dissolved. Slowly adding $H_2O$ to the CBD, EtOH, polymer mixture results in very high capture of 98% at a 3:7 EtOH:$H_2O$. The S-shaped curve of FIG. 65 suggests insolubility-induced capture.

Figure 64:
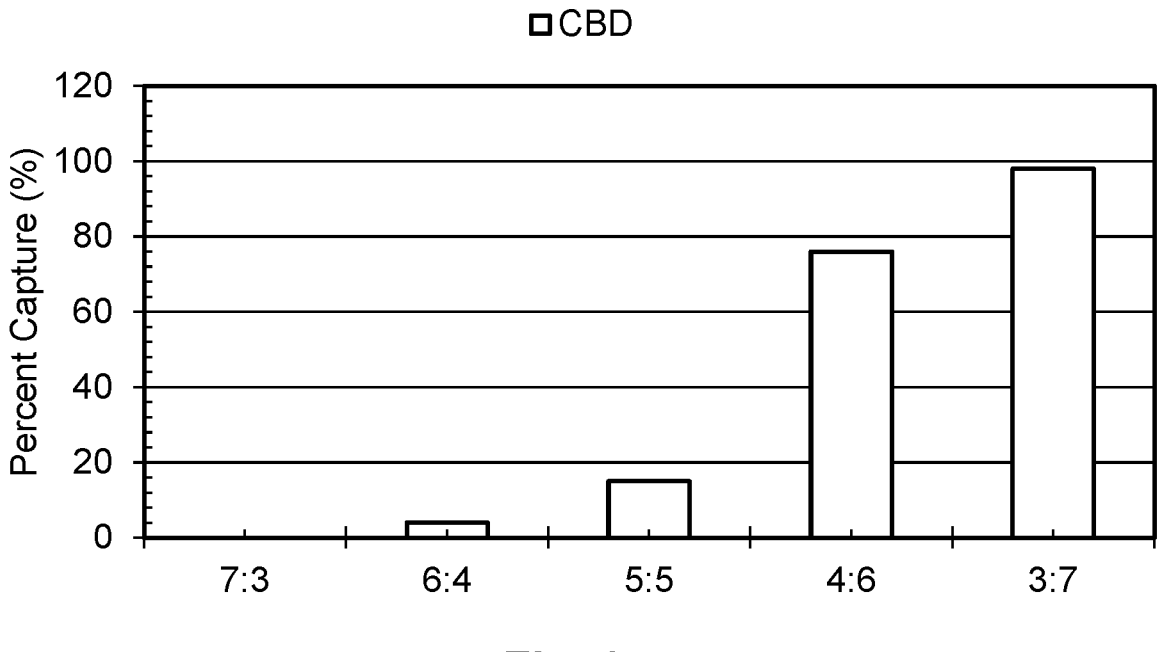
FIG. 64 shows percentage capture of CBD in Example 10.
Figure 65:
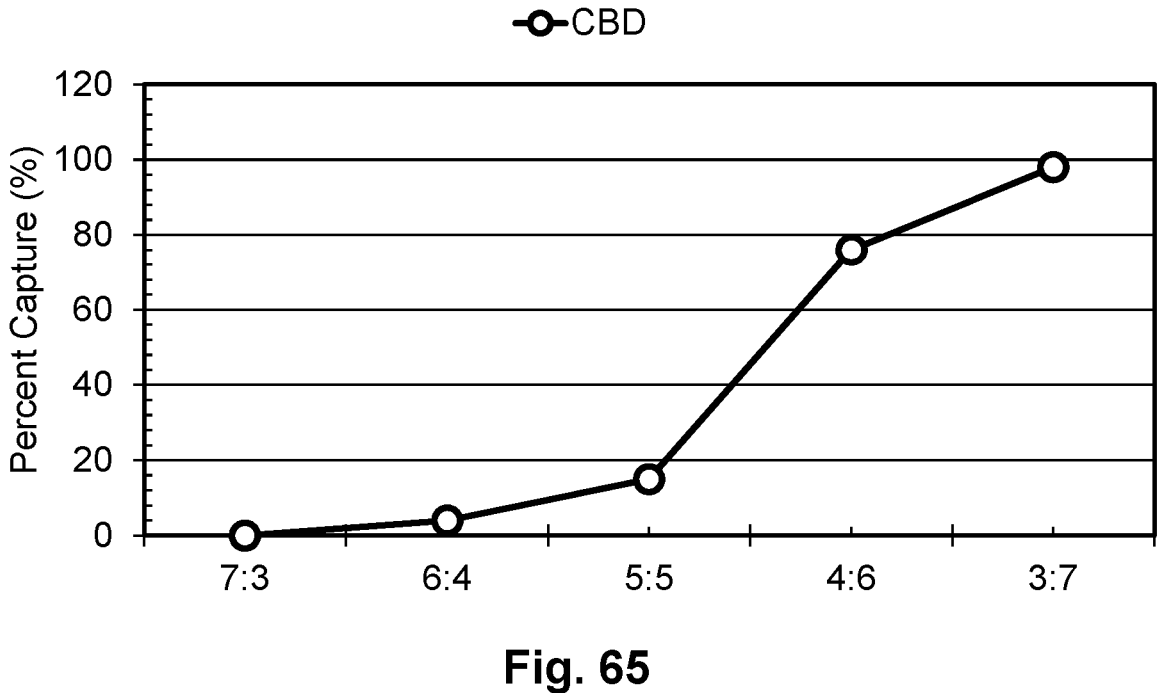
FIG. 65 shows CBD captured and released in Example 10.

FIGS. 64 and 65 show the percentage of CBD capture over different ethanol to water ratios.

Example 11

The protocol from Example 10 was followed, with filtration occurred a day after the diluted portions were prepared at EtOH:$H_2O$ ratios of 6:4, 5:5, 4:6 and 3:7. The cross-linked polymer retrieved after filtration was then flushed with DMSO in a second reaction vessel.

Figure 66:
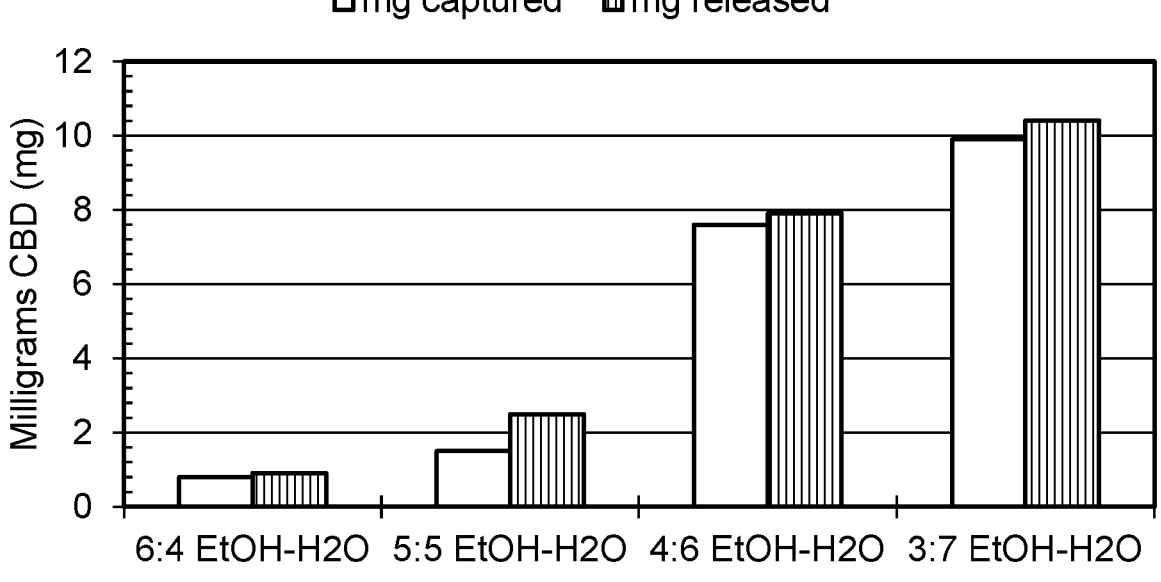
FIG. 66 shows the mg of CBD captured and released in Example 11.

FIG. 66 shows the milligrams of CBD captured and released for Example 11.

Example 12

Ten milligrams of CBD were dissolved in 5 mL of a mixture of 1:1 ethanol to water to produce a stock solution with a CBD concentration of 2 mg/mL. One portion of the stock solution was then taken to calculate a baseline CBD concentration at t=0. The remaining stock solution was then divided into three portions.

Fresh cross-linked polymer was then combined with the first portion of stock solution. Recycled polymer was combined with the second portion or stock solution. Fresh cross-linked polymer was also combined with the third portion of stock solution. The polymer was combined such that each portion had a polymer to CBD ratio of about 10:1 by mass. It was then stirred at room temperature.

Each portion was filtered by pipette filtration. Once retrieved, the cross-linked polymer was flushed with ethanol. The percent of CBD captured of fresh cross-linked polymer was (23%) was comparable to that of reconstituted cross-linked polymer (24%). A second run of the fresh cross-linked polymer showed a consistent performance of 25% capture. This a similar performance to the conditions in Example 7, which showed 29% capture.

Figure 67:
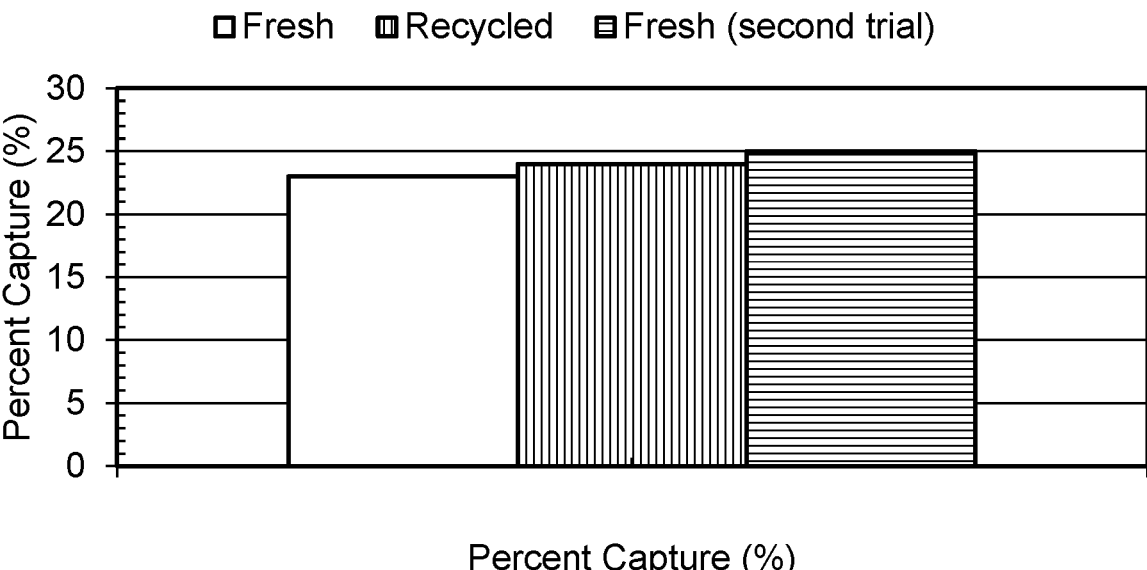
FIG. 67 shows percentage of CBD captured in Example 12.

FIG. 67 shows the milligrams of CBD captured for Example 12.

Example 13

Ten milligrams of CBD were dissolved in 5 mL of a mixture of 1:1 EtOH:H$_2$O to produce a first stock solution with a CBD concentration of 2 mg/mL.

A second reaction mixture was produced using a mass of CBD dissolved in a mixture of 1:1 EtOH:H$_2$O using sonication at room temperature to produce a stock solution with a CBD concentration of 4 mg/mL.

A third reaction mixture was produced using a mass of CBD was dissolved in a mixture of 1:1 EtOH:H$_2$O using sonication and heating to produce a stock solution with a CBD concentration of 6 mg/mL, but the solution did not dissolve.

One portion of each stock solution was then taken to calculate a baseline CBD concentration at t=0.

The first and second reaction mixtures were each divided into two batches. Cross-linked polymer was combined with the first batch of the first and second reaction mixtures in a ratio of 10:1 polymer to CBD by mass.

Cross-linked polymer was combined with the second batch of the first and second reaction mixtures in a ratio of 5:1 polymer to CBD by mass.

The batches were then filtered by pipette filtration and the recovered cross-linked polymer was flushed with ethanol as a dissociation solvent.

Figure 68:
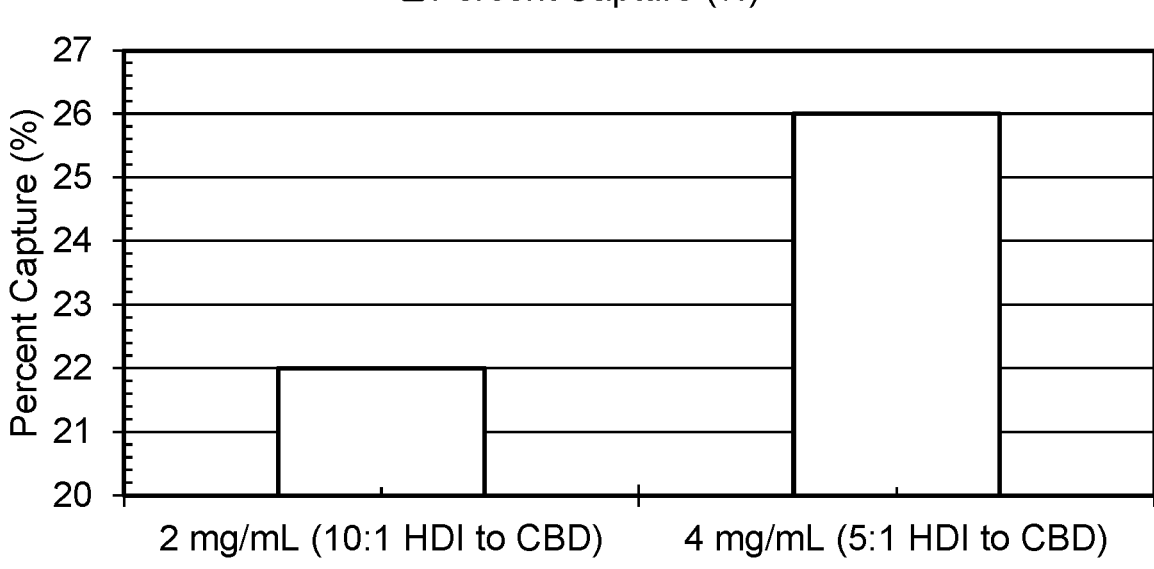
FIG. 68 shows percentage capture of CBD in Example 13.
Figure 69:
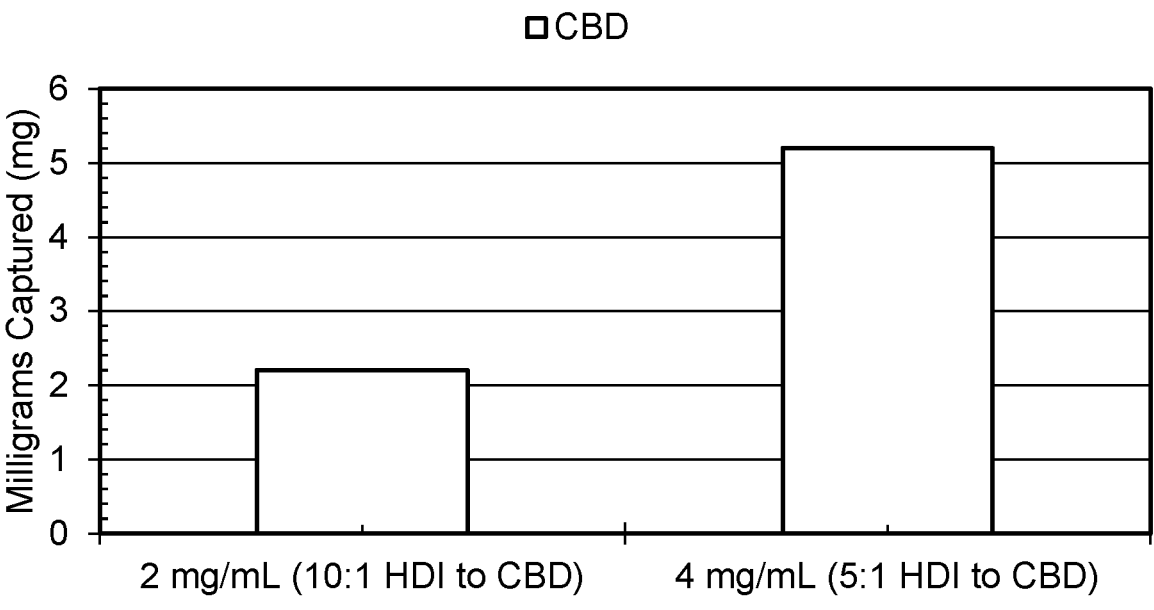
FIG. 69 shows mg of CBD captured in Example 13.

FIGS. 68 and 69 show the percentage and milligrams of CBD captured for Example 13.

Example 14

A stock solution with a CBD concentration of 2 mg/mL was prepared according to the protocol set out in Example 12. The stock solution was divided into five vials each containing 10 mg of CBD. Cross-linked polymer was combined with each vial to produce polymer to CBD ratios of 10:1, 8:1, 6:1, 4:1 and 2:1, respectively. The vial contents were then filtered by pipette filtration and the recovered cross-linked polymer flushed with ethanol.

The percent captured is reduced as the ratio of cross linked polymer is reduced. The mg captured did not reach a plateau. The mg of cross linked polymer to mg of CBD captured was close to 45:1, varying to 40:1 at 6:1 polymer: CBD and to 50:1 at a polymer:CBD ratio of 2:1.

Figure 70:
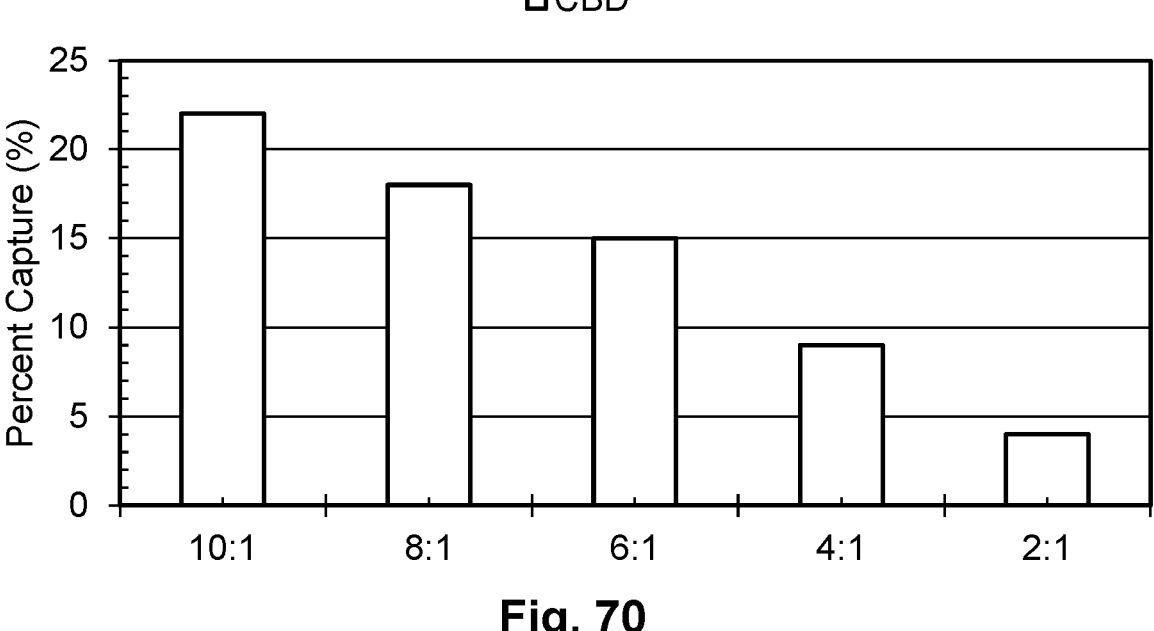
FIG. 70 shows percentage CBD captured in Example 14.
Figures 71, 72:
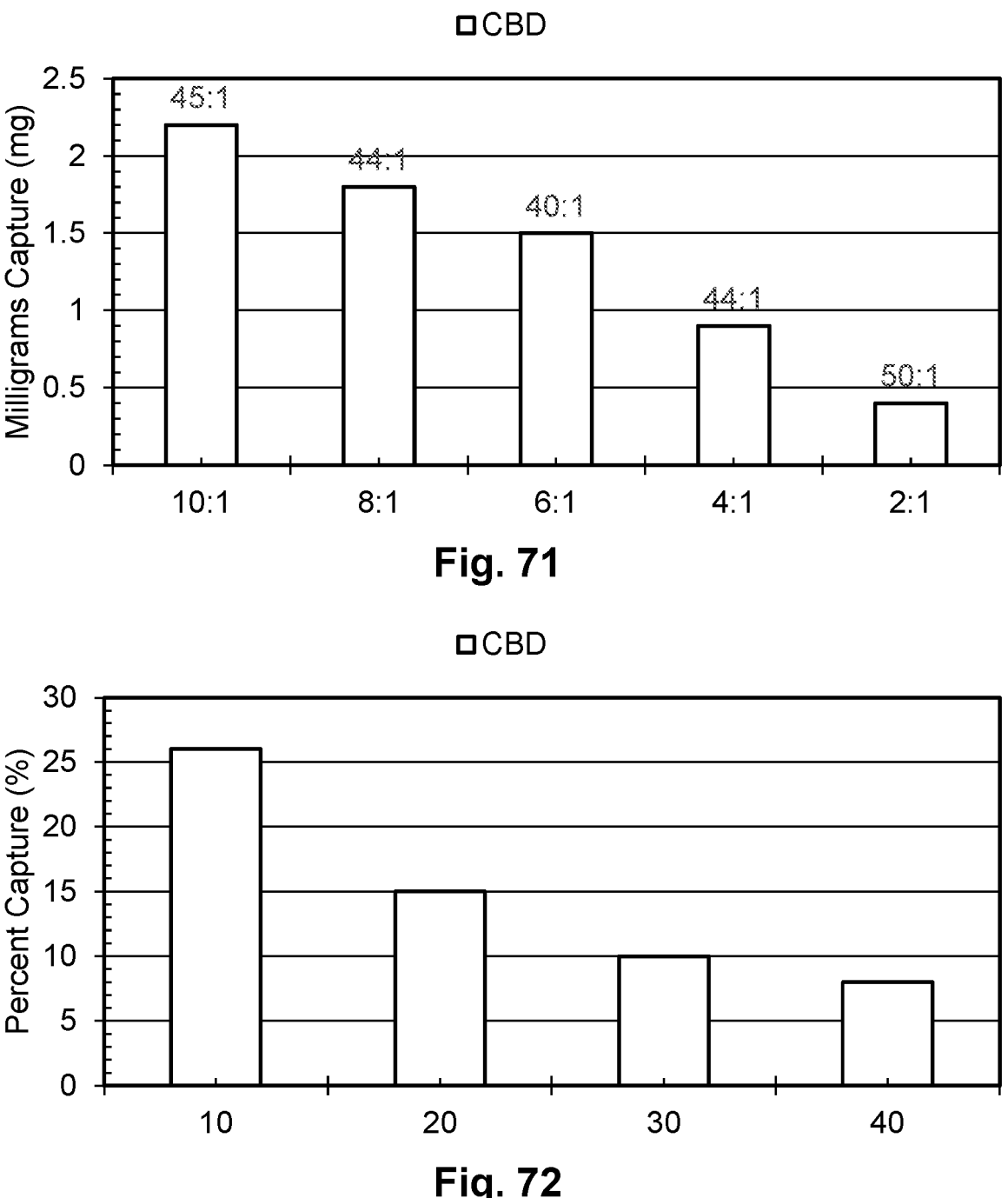
FIG. 71 shows mg CBD captured in Example 14.
FIG. 72 shows percentage of CBD captured in Example 15.

FIGS. 70 and 71 show the percentage and milligrams of CBD captured for Example 14, respectively. In FIG. 71, the ratio of cross-linked polymer to CBD captured is also shown on each data series.

Example 15

A stock solution with a CBD concentration of 2 mg/mL was prepared according to the protocol set out in Example 12. The stock solution was divided into four vials, the first containing 5 mL of solution, the second containing 10 mL of solution, the third containing 15 mL of solution and the fourth containing 20 mL of solution. One hundred milligrams of cross-linked polymer were then combined to each vial.

One hundred milligrams of cross-linked polymer was combined with each vial to produce polymer to CBD ratios of 10:1, 5:1, 3.3:1, and 2.5:1, respectively.

Figures 73, 74:
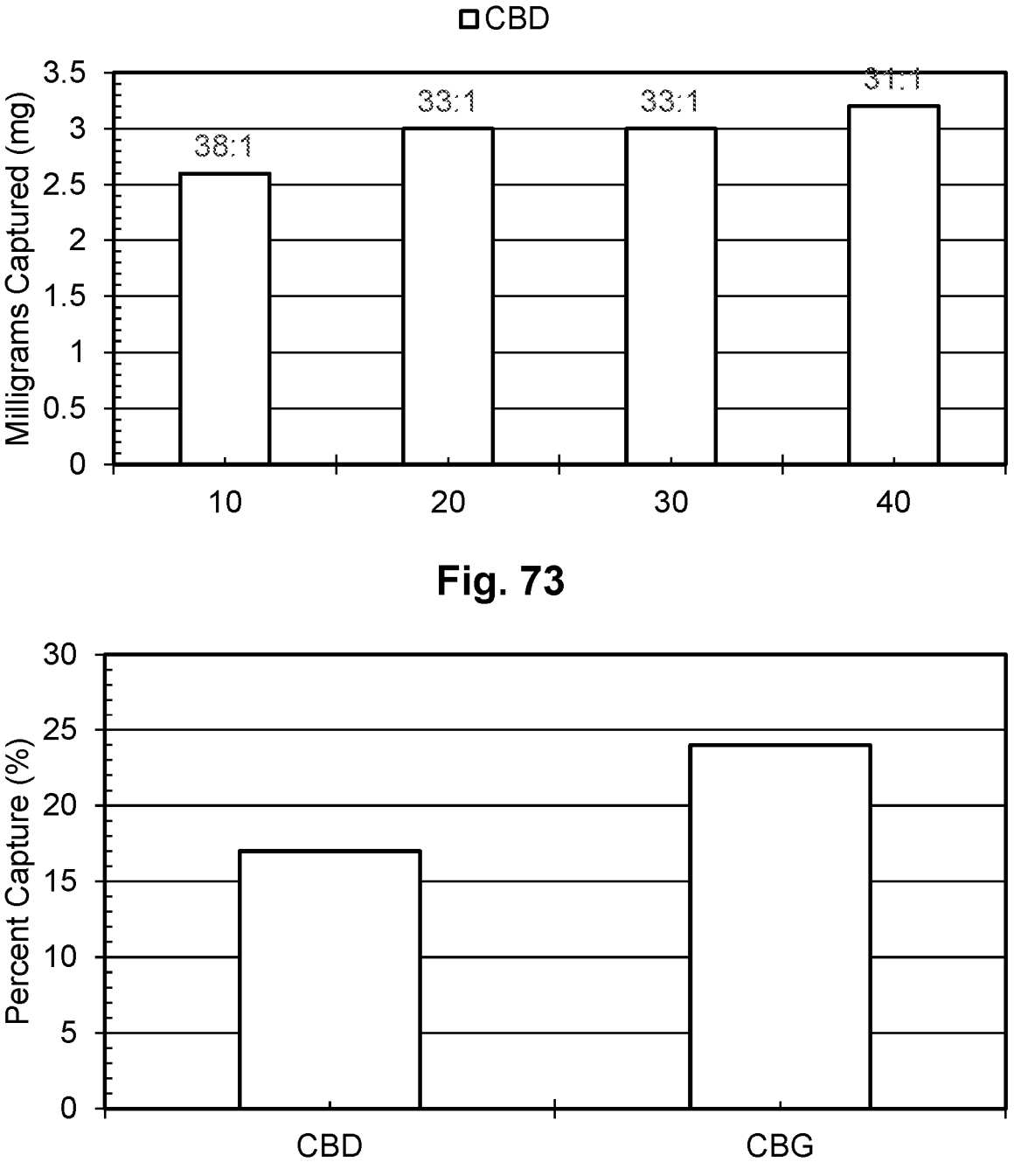
FIG. 73 shows mg of CBD captured in Example 15.
FIG. 74 shows percentage of CBD and CBG captured in Example 16.
Figure 75:
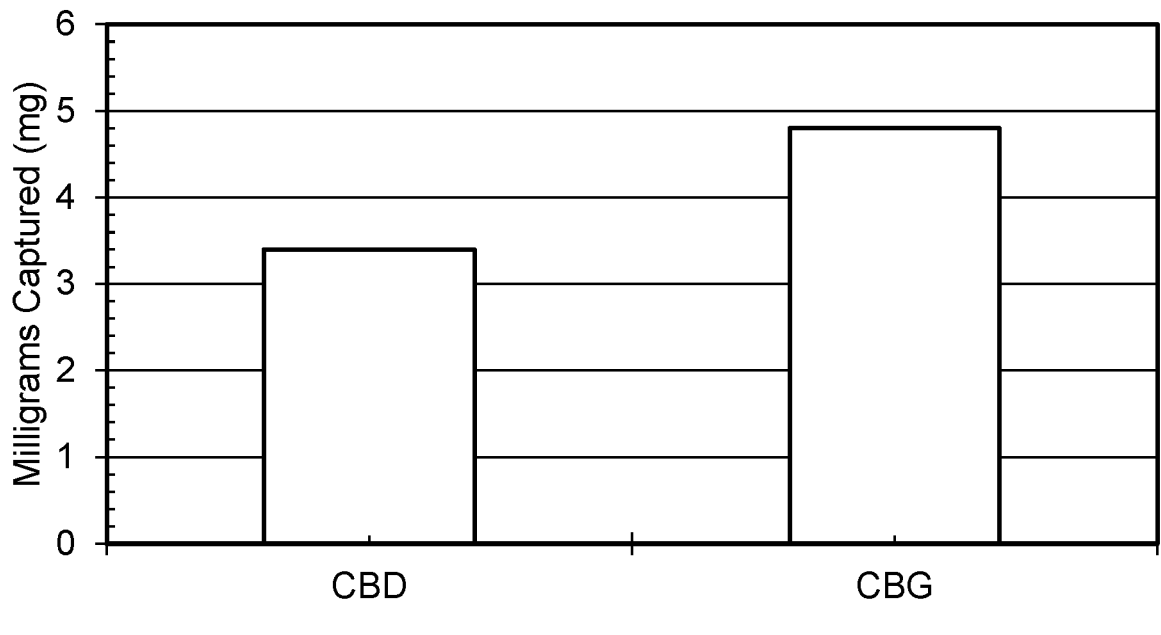
FIG. 75 shows mg of CBD and CBG captured in Example 16.

FIGS. 72 and 73 show the percentage and milligrams of CBD captured for Example 15, respectively. The percentage capture decrease as the amount of CBD increases, as expected. The mg captured reached a plateau at 3.2 mg. The mg of polymer to mg CBD was expected to plateau at 8:1.

Example 16

Twenty milligrams of CBD and 20 mg of CBG were dissolved in a 1:1 mixture of ethanol and water to a concentration of 2 mg/mL. One hundred milligrams of cross-linked polymer were then combined to achieve a ratio of 5:1 polymer to CBD and 5:1 polymer to CBG by mass. The solution was then stirred at room temperature.

The vial contents were then filtered by pipette filtration and the recovered cross-linked polymer flushed with ethanol. In Example 4, 45% of the CBD was recovered and 54% of the CBG was recovered, a ratio of 1:1.2. In this Example, 17% of the CBD and 24% of the CBG was recovered, a ratio of 1:1.5. In total, 3.4 mg CBD and 4.8 mg CBG for 8.2 mg phytocannabinoids recovered.

FIGS. 74 and 74 show the percentage and milligrams of CBD and CBG captured in Experiment 16.

Example 17

One hundred and twenty milligrams of CBD were dissolved in 18 mL in ethanol to form a stock solution.

The stock solution was divided into 1.5 mL portions. One portion of the stock solution was then taken to calculate a baseline CBD concentration at t=0. A cross-linked polymer was then combined with each of the remaining portions, each in a different quantity between 0 mg and 100 mg. The portions were stirred at room temperature. To all portions, 3.5 mL of water were then combined at a rate of 1 mL/minute.

The portions were filtered by pipette filtration to retrieve the cross-linked polymer. The cross-linked polymer was then flushed with DMSO. The saturation point was observed at a 2:1 polymer:CBD ratio. Ten percent of the CBD is not in solution when CBD in 3:7 EtOH:H$_2$O is used. The calculated cyclodextrin capacity within the polymer is 8:1 polymer:CBD. These results suggest that there are specific cyclodextrin encapsulated sites and also non-specific sites within the cyclodextrin polymer.

Figure 76:
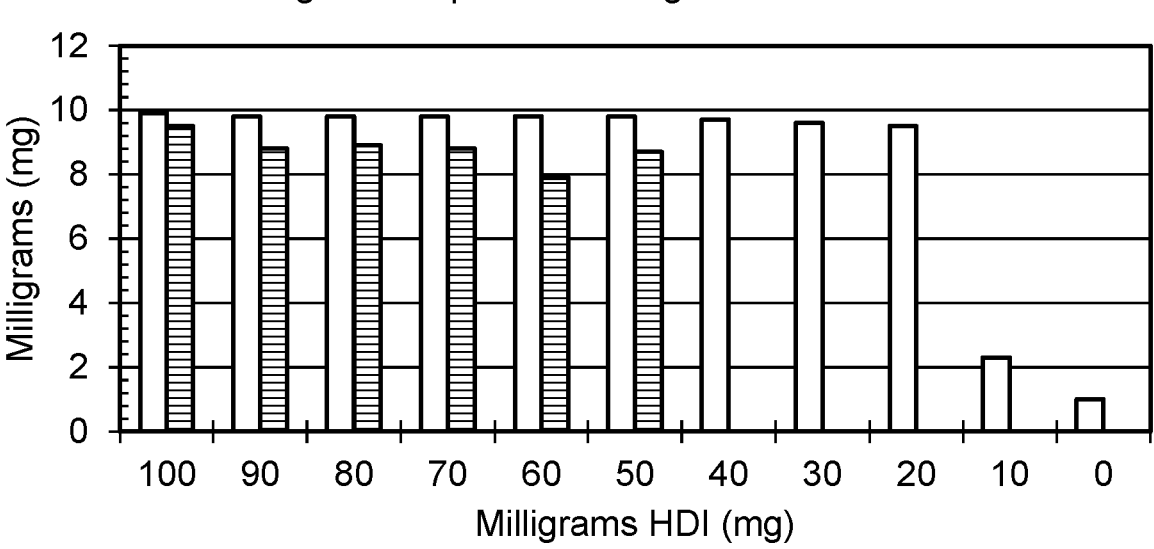
FIG. 76 shows mg of CBD captured and released in Example 17.

FIG. 76 shows the amount in milligrams of CBD captured and released in Example 17.

Example 18

As stock solution was prepared according to Example 17. The stock solution was divided into 1.5 mL portions. One portion of the stock solution was then taken to calculate a baseline CBD concentration at t=0. Additional CBD was then combined with each portion in differing amounts of either 10 mg, 12.5 mg, 15.0 mg, or 17.5 mg. One hundred milligrams of cross-linked polymer was then combined with each of the remaining portions. To all portions, 3.5 mL of water was then combined with the portions at a rate of 1 mL/minute. Further water was combined with the portions such that a CBD concentration of 2 mg/mL and an ethanol to water ratio of 3:7 was achieved.

The portions were filtered by pipette filtration to retrieve the cross-linked polymer. The cross-linked polymer was then flushed with DMSO. There was over 98% capture in all cases. The calculated polymer capacity is 12.7 mg. These results suggest that there are specific cyclodextrin encapsulated sites and also non-specific sites within the cyclodextrin polymer.

Figure 77:
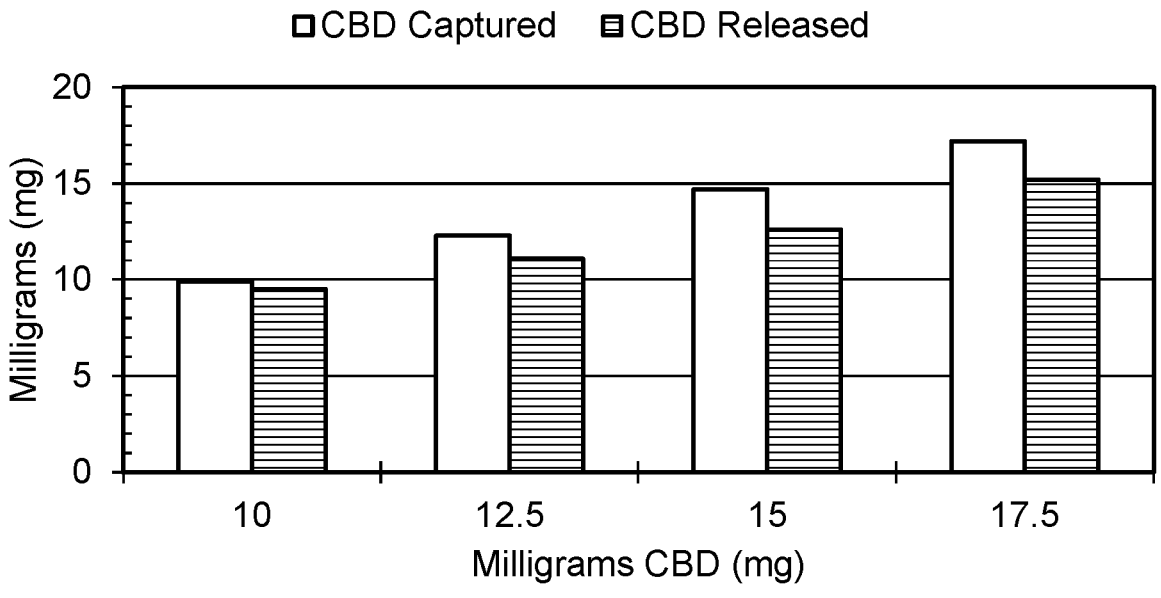
FIG. 77 shows mg of CBD captured and released in Example 18.

FIG. 77 shows the amount in milligrams of CBD captured and released in Example 18 as a function of the mg of CBD used.

Example 19

A protocol was followed as in Example 17. The cross-linked polymer was flushed with DMSO.

Figure 78:
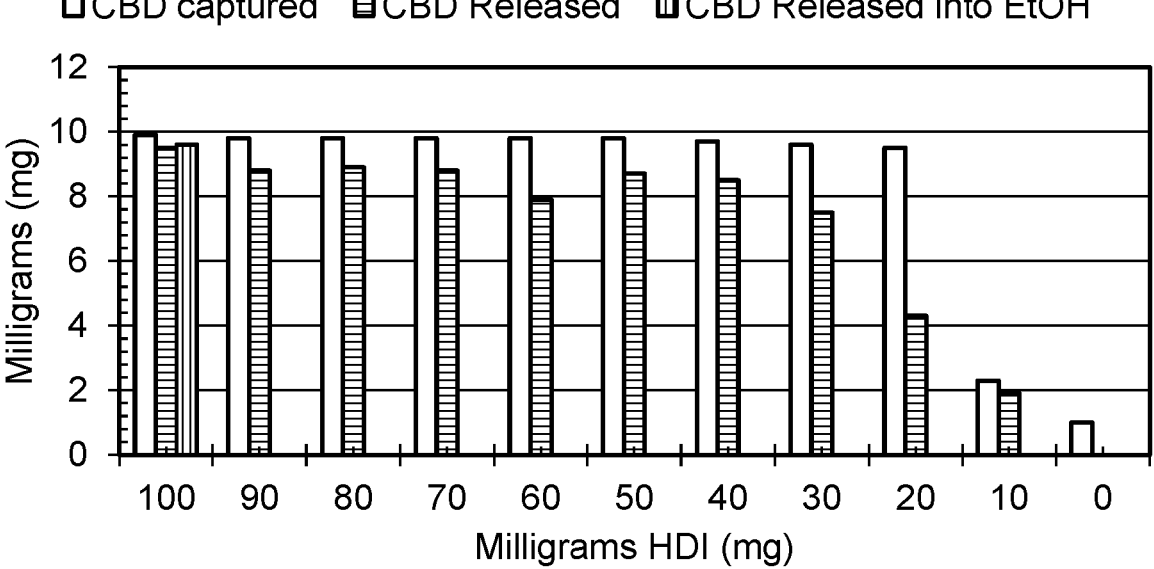
FIG. 78 shows mg of CBD captured, released and released into ethanol versus mg of polymer in Example 19.

FIG. 78 shows the amount in milligrams of CBD captured and released in Example 19.

Example 20

Hops were extracted using the protocol set out in *J. Inst. Brew.*, 1992, 98, 37-41. The extraction was performed using ethanol at a concentration of 300 g/L over 6 hours to produce a clear green solution. This ethanol extract of hops provides a simulated plant extract example.

One hundred milligrams of powdered hops were extracted using 5 mL of ethanol for thirty minutes, both at room temperature and with sonication to produce a clear green solution.

A protocol as in Example 17 was then followed using a polymer to CBD ratio of 10:1 by mass. The ethanol of Example 17 was replaced in two runs with the clear green solution of ethanol extract of hops that was obtained from the two hops extractions. The ethanol extract of hops showed 56% to 74% of the capture and about 52% of the release that was observed using pure ethanol, on a second trial about 50% of the release that was observed using pure ethanol. This result implies that there is some specificity of the cyclodextrin polymer for CBD over the compounds in hops at these concentrations.

Figure 79:
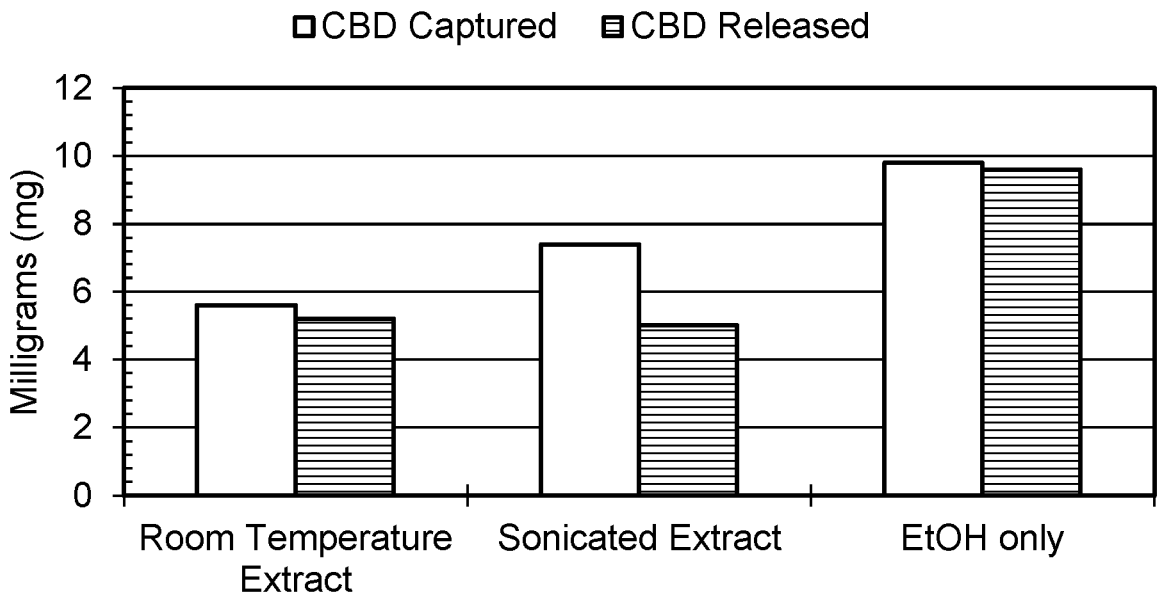
FIG. 79 shows mg of CBD captured and released in extract of hops in Example 20.

FIG. 79 shows the amount in milligrams of CBD captured and released in Example 20.

Example 21

Three grams of powdered hops were extracted using 100 mL of ethanol for thirty minutes and then concentrated. The concentrate was then diluted with 10 mL of ethanol, filtered by pipette filtration to produce a clear green solution.

A protocol as in Example 20 was then followed using a polymer to CBD ratio of 10:1 and using the clear green solution obtained from the hops extractions in place of ethanol as well as with ethanol only. With pure ethanol, about 9.8 mg of CBD was captured and was released. With the ethanol extract of hops, 9.6 mg was captured and 5.5 mg was released. This result implies that there is some specificity of the cyclodextrin polymer for CBD over the compounds in hops at these concentrations.

Filtered was done by pipette filtration and the recovered cross-linked polymer flushed with ethanol.

Figure 80:
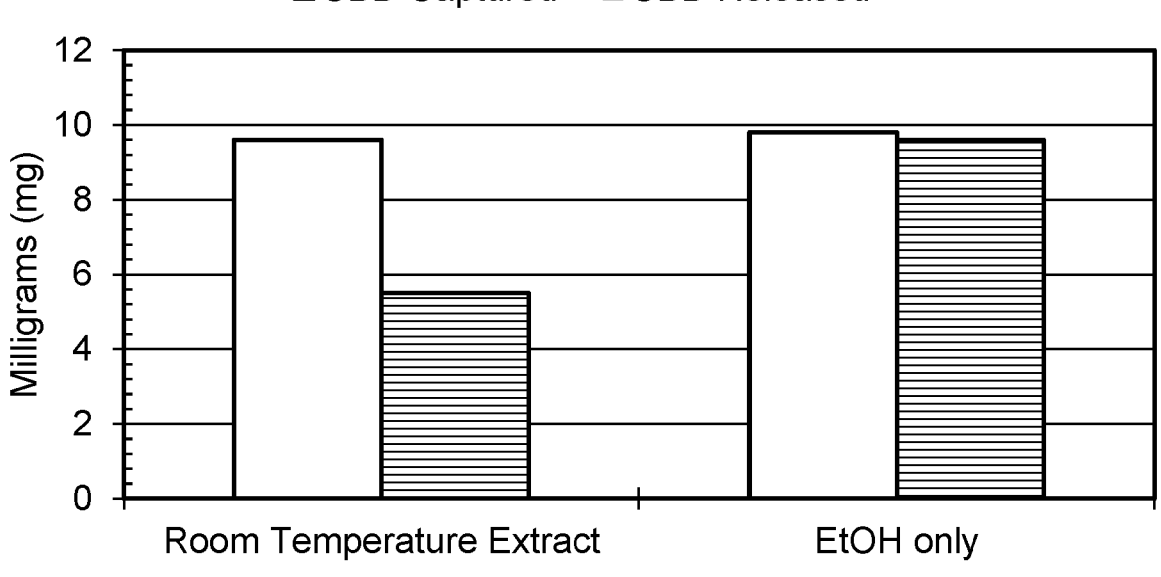
FIG. 80 shows mg of CBD captured and released in Example 21.

FIG. 80 shows the amount in milligrams of CBD captured and released in Experiment 21.

Example 22

Example 22 provide a protocol for removing colored impurities from ethanolic plant extracts prior to integration with the disclosed capturing method and protocol. It was visually observed that filtration through charcoal removed all detectable green pigments in the plant extract and the recovered hydrophobic compound was less colored in appearance by comparison with material obtained according to Example 20 that did not include a charcoal decolorization process.

Fifty milligrams of CBD were dissolved in 7.5 mL of an ethanol extract of hops according to the protocol set out in Example 20. Seventy milligrams of charcoal was loaded into a pipette column formed using a cotton plug followed by 150 mg of Celite® and the CBD solution was passed through the pipette in portions until all had been filtered. This stock solution was divided into 5 portions of 1.5 mL. A first portion of the stock solution was taken to calculate the baseline CBD concentration at t=0 by diluting with 3.5 mL of ethanol.

A second portion of the stock solution was transferred to a vial containing a stir bar and 100 mg of the cross-linked polymer derived from alpha-cyclodextrin. Water (3.5 mL) was then combined with the second portion over the course of 7 minutes at a rate of 0.5 mL/minute. The mixture was then stirred at room temperature for 30 minutes.

An aliquot was taken and filtered by pipette filtration to calculate the CBD concentration at t=30. The reaction mixture was then filtered to retrieve the cross-linked polymer. The cross-linked polymer retrieved after filtration was suspended in 5 mL ethanol. An aliquot was taken to determine released CBD concentration t=rel.

Figure 81:
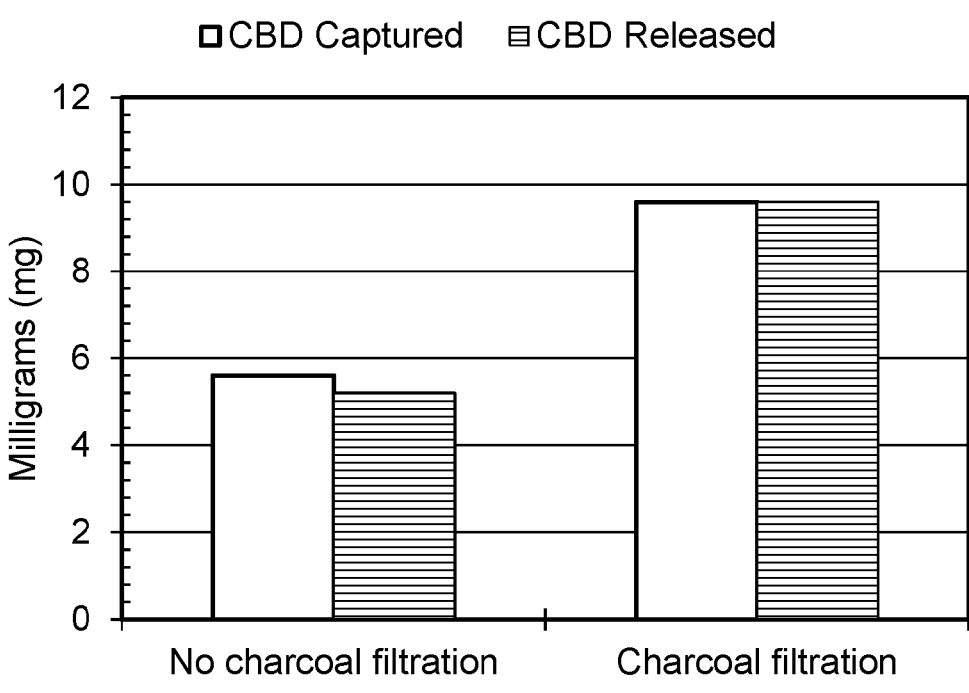
FIG. 81 shows mg of CBD captured and released in Example 22.

FIG. 81 shows the mass of captured and released CBD resulting from Example 22.

Example 23

Thirty milligrams of CBD were dissolved in 4.5 mL of methanol to produce a CBD-methanol stock solution according to the protocol set out in Example 17. The CBD-methanol stock solution was divided into 3 portions of 1.5 mL. A first portion of the CBD-methanol stock solution was taken to calculate the baseline CBD concentration at t=0 by diluting with 3.5 mL of methanol.

Thirty milligrams of CBD were dissolved in 4.5 mL of isopropanol to produce a CBD-isopropanol stock solution according to the protocol set out in Example 17. The CBD-isopropanol stock solution was divided into 3 portions of 1.5 mL. A first portion of the CBD-isopropanol stock solution was taken to calculate the baseline CBD concentration at t=0 by diluting with 3.5 mL of isopropanol.

One portion of each stock solution was transferred to two separate vials containing a stir bar and 100 mg of the cross-linked polymer. To each portion, water (3.5 mL) was then combined over the course of 7 minutes at a rate of 0.5 mL/minute. The mixture was then stirred at room temperature for 30 minutes.

From each portion, an aliquot was taken and filtered by pipette filtration to calculate the CBD concentration at t=30. The reaction mixture was then filtered to retrieve the cross-linked polymer. The cross-linked polymers were retrieved after filtration was suspended in 5 mL ethanol. From both portions, aliquots were taken to determine released CBD concentration t=rel.

Figure 82:
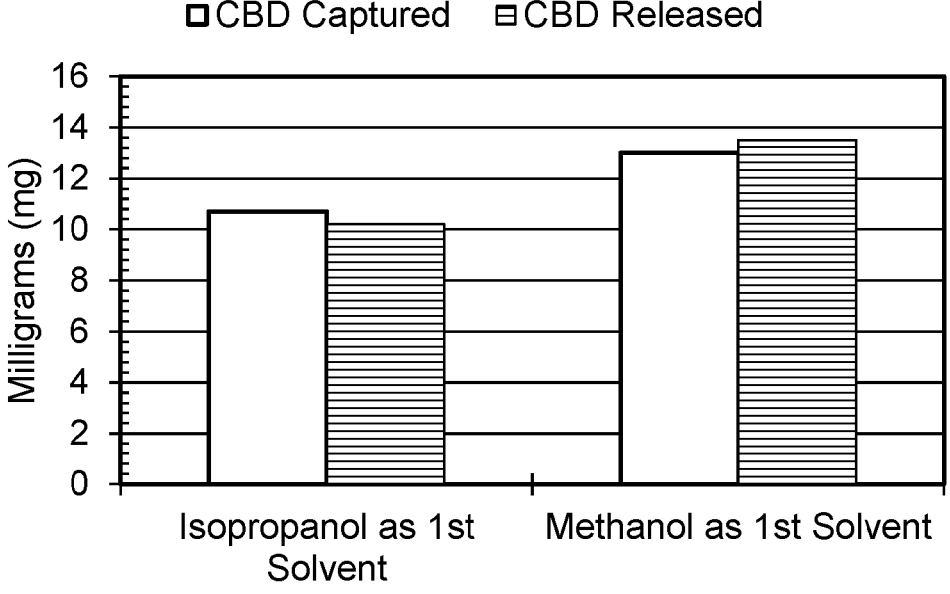
FIG. 82 shows mg of CBD captured and released in Example 23.

FIG. 82 shows the mass of captured and released of CBD resulting from Example 23.

These results imply that alcohols distinct from ethanol can be successfully used in conjunction with our capturing device to recover hydrophobic compounds.

Example 24

Thirty milligrams of CBD and thirty milligrams of CBG were dissolved in 4.5 mL of acetonitrile to produce a CBD-CBG-acetonitrile stock solution according to the protocol set out in Example 17. The CBD-CBG-acetonitrile stock solution was divided into 3 portions of 1.5 mL. One portion of the CBD-CBG-acetonitrile stock solution was taken to calculate the baseline CBD and CBG concentrations at t=0 by diluting with 3.5 mL of acetonitrile. One portion of the CBD-CBG-acetonitrile stock solution was transferred to a vial containing a stir bar and 100 mg of the cross-linked polymer.

Thirty milligrams of CBD and thirty milligrams of CBG were dissolved in 4.5 mL of acetone to produce a CBD-CBG-acetone stock solution according to the protocol set out in Example 17. The CBD-CBG-acetone stock solution was divided into 3 portions of 1.5 mL. One portion of the CBD-CBG-acetone stock solution was taken to calculate the baseline CBD and CBG concentrations at t=0 by diluting with 3.5 mL of acetone. One portion of the CBD-CBG-acetone stock solution was transferred to a vial containing a stir bar and 100 mg of the cross-linked polymer.

Thirty milligrams of CBD and thirty milligrams of CBG were dissolved in 4.5 mL of glycerol to produce a CBD-CBG-glycol stock solution according to the protocol set out in Example 17. The CBD-CBG-glycol stock solution was divided into 3 portions of 1.5 mL. One portion of the CBD-CBG-glycol stock solution was taken to calculate the baseline CBD and CBG concentrations at t=0 by diluting with 3.5 mL of glycerol. One portion of the CBD-CBG-glycol stock solution was transferred to a vial containing a stir bar and 100 mg of the cross-linked polymer.

To each of the above portions, water (3.5 mL) was then combined over the course of 7 minutes at a rate of 0.5 mL/minute. The mixtures were then stirred at room temperature for 30 minutes.

To each portion, an aliquot was taken and filtered by pipette filtration to calculate the CBD and CBG concentrations at t=30. The reaction mixtures were then filtered to retrieve the cross-linked polymer. The cross-linked polymer retrieved after filtration was suspended in 5 mL DMSO. An aliquot was taken to determine released CBD and CBG concentrations t=rel.

FIG. 83 shows the mass of captured and released of CBD and CBG resulting from Example 24. These results demonstrate that polar organic solvents other than ethanol, and specifically acetonitrile, acetone and glycerol, can be successfully used with the insoluble polysaccharides to recover the hydrophobic corn pounds.

Example 25

Thirty milligrams of CBD were dissolved in 4.5 mL of 1-butyl-3-methylimidazolium tetrafluoroborate, with considerable sonication due to viscosity, to produce a stock solution according to the protocol set out in Example 17. The stock solution was divided into 3 portions of 1.5 mL. A first portion of the stock solution was taken and diluted with 3.5 mL of ethanol to calculate the baseline CBD concentration at t=0.

A second portion of the stock solution was transferred to a vial containing a stir bar and 100 mg of the cross-linked polymer. Water (3.5 mL) was then combined with the second portion of the stock solution over the course of 7 minutes at a rate of 0.5 mL/minute. The reaction mixture was then stirred at room temperature for 30 minutes.

An aliquot of the reaction mixture was taken and filtered by pipette filtration to calculate the CBD concentration at t=30. The reaction mixture was then filtered to retrieve the cross-linked polymer. The cross-linked polymer retrieved after filtration was suspended in 5 mL ethanol. An aliquot was taken to determine released CBD concentration t=rel.

FIG. 84 shows the mass of captured and released of CBD resulting from Example 25.

These results demonstrate that solvents distinct from ethanol, specifically the ionic liquid 1-butyl-3-methylimidazolium tetrafluoroborate, can be successfully used as the first solvent for recovery of hydrophobic compounds.

Example 26

Sixty milligrams of CBD were dissolved in 9 mL of ethanol to produce a stock solution according to the protocol set out in Example 17. The stock solution was divided into 6 portions of 1.5 mL. A first portion of the stock solution was taken to calculate the baseline CBD concentration at t=0 by diluting with 3.5 mL of ethanol.

A second portion of the stock solution were transferred to a vial containing 100 mg of the cross-linked polymer derived from alpha-cyclodextrin. A third portion of the stock solution were transferred to a vial containing 100 mg of the cross-linked polymer derived from beta-cyclodextrin. A fourth portion of the stock solution were transferred to a vial containing 100 mg of the cross-linked polymer derived from gamma-cyclodextrin. To all portions, water (3.5 mL) was then combined with this portion over the course of 7 minutes at a rate of 0.5 mL/minute. The mixture was then stirred at room temperature for 30 minutes.

To all portions, an aliquot was taken from each vial and filtered by pipette filtration to calculate the CBD concentration at t=30. The reaction mixtures were then each filtered to retrieve the cross-linked polymers. The cross-linked polymers retrieved after filtration were suspended in 5 mL ethanol. An aliquot was taken to determine released CBD concentration t=rel.

Figure 85:
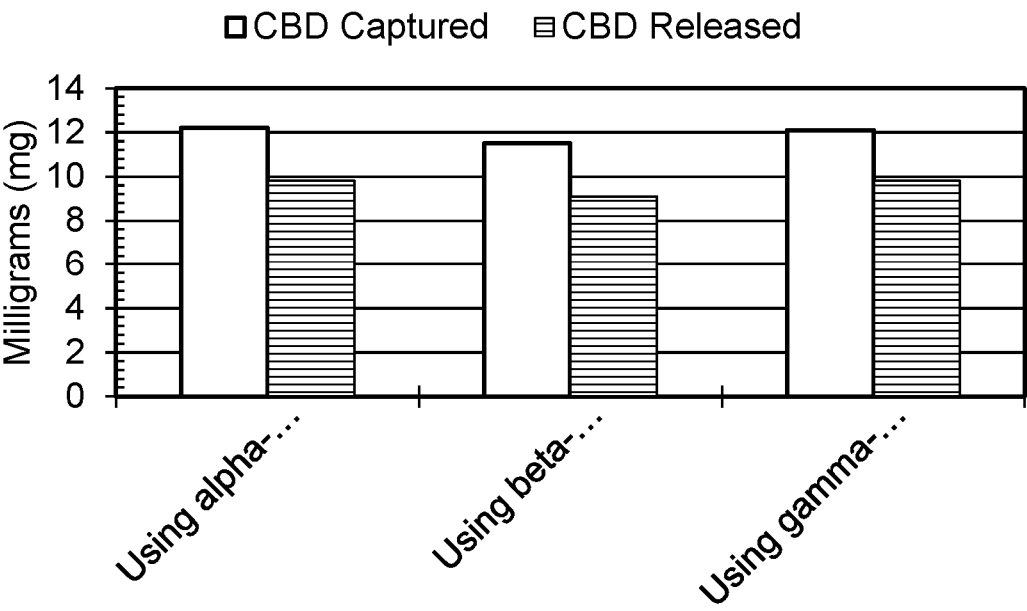
FIG. 85 shows mg CBD captured and released in Example 26.

FIG. 85 shows the mass of captured and released of CBD resulting from Example 26. These results demonstrate that HDI-CDP derived from cyclic oligosaccharides distinct from beta-cyclodextrin, specifically alpha-cyclodextrin and gamma-cyclodextrin, can be applied to recover hydrophobic compounds.

Example 27

Seventy milligrams of CBD were dissolved in 10.5 mL of ethanol to produce a stock solution according to the protocol set out in Example 17. The stock solution was divided into 7 portions of 1.5 mL. A first portion of the stock solution was taken to calculate the baseline CBD concentration at t=0 by diluting with 3.5 mL of ethanol.

Five portions of the stock solution were each transferred into a respective vial, each containing a stir bar and cross-linked polymer ground to various particles sizes ranging from <75, <178, <400, <1000, <4000 microns. To all portions, water (3.5 mL) was then combined over the course of 7 minutes at a rate of 0.5 mL/minute. The mixture was then stirred at room temperature for 30 minutes.

From all portions, an aliquot was taken and filtered by pipette filtration to calculate the CBD concentration at t=30. The reaction mixture was then filtered to retrieve the cross-linked polymer. The cross-linked polymer retrieved after filtration was suspended in 5 mL DMSO. An aliquot was taken to determine released CBD concentration t=rel.

Figure 86:
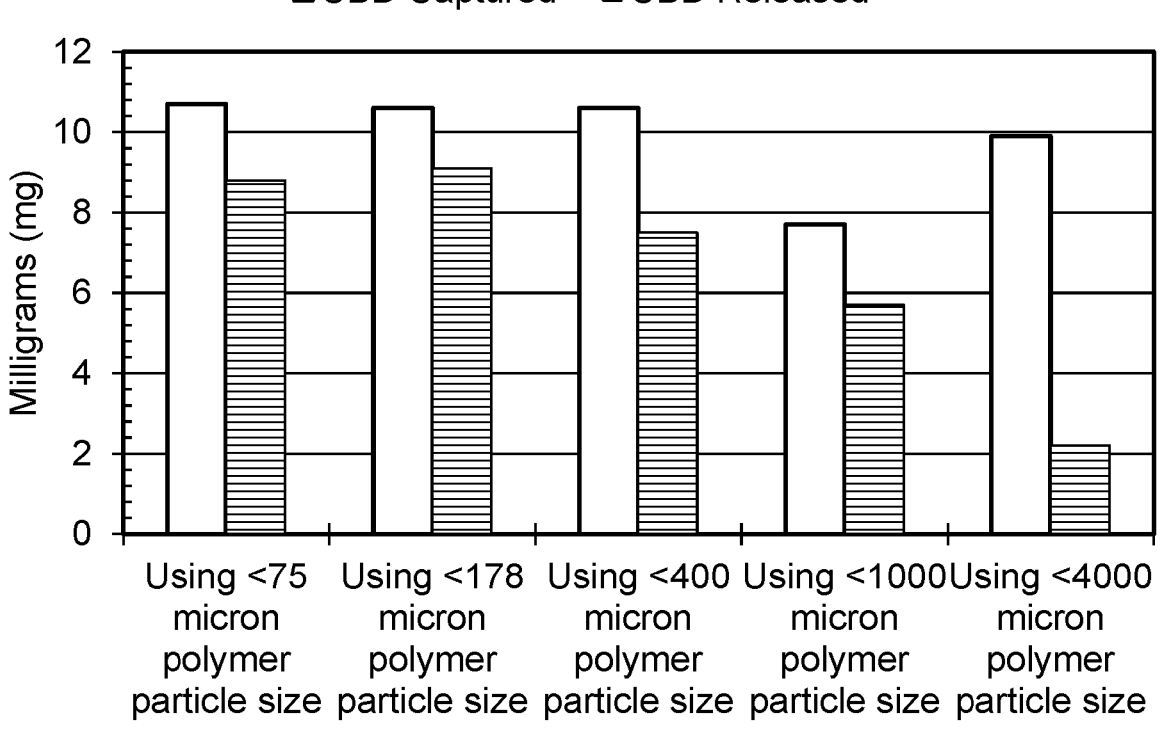
FIG. 86 shows mg CBD captured and released in Example 27.

FIG. 86 shows the concentration of captured and released CBD resulting from Example 27. These results demonstrate that the cross-linked polymer can be deployed successfully using the protocol outlined in Example 27 when in the form of finely ground powder or macroscopic beads to recover hydrophobic compounds. These results also demonstrate that smaller bead and particle sizes may have a greater hydrophobic compound recovery potential than larger particle sized polymer.

Example 28

Sixty milligrams of CBD were dissolved in 18.0 mL of ethanol to produce a stock solution according to the protocol set out in Example 17. The stock solution was divided into 6 portions of 3.0 mL. A first portion of the stock solution was taken to calculate the baseline CBD concentration at t=0 by diluting with 7.0 mL of ethanol.

Three portions of the stock solution were each transferred into three respective vials, the first containing 200 mg of the cross-linked polymer (400 micron mesh size) and an empty semi-permeable mesh bag, the second containing the same polymer housed within a semi-permeable mesh bag, the third containing the same polymer housed within a semi-permeable mesh netting connected to a string. To each portion, water (7 mL) was then combined with this portion over the course of 14 minutes at a rate of 0.5 mL/minute. The mixture was then stirred at room temperature for 30 minutes.

From each portion, an aliquot was taken and filtered by pipette filtration to calculate the CBD concentration at t=30. The cross-linked polymers were then retrieved by filtration. The mesh bag containing the cross-linked polymer was suspended in 10 mL ethanol. From each portion, an aliquot was taken to determine released CBD concentration t=rel.

Figure 87:
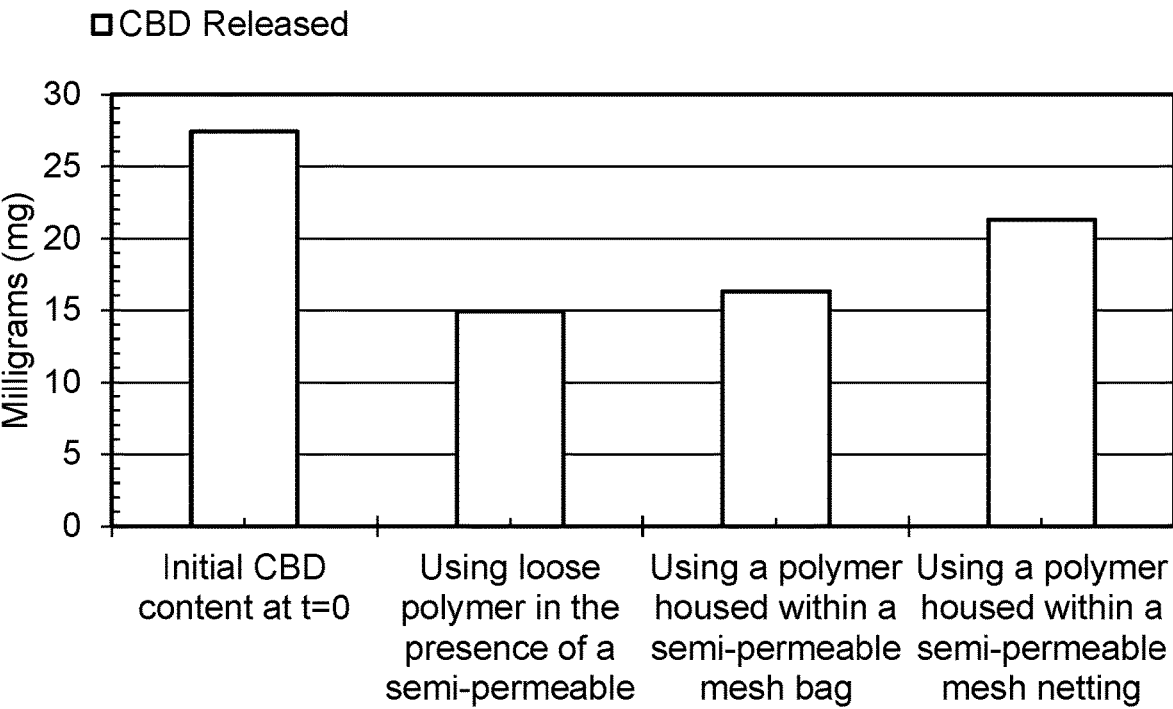
FIG. 87 shows mg CBD released in Example 28.

FIG. 87 shows the concentration of released CBD resulting from Example 28. These results demonstrate that one or more cross-linked polymers can be used while physically separated and housed within separate permeable mesh membranes.

Example 29

Thirty milligrams of CBD were dissolved in 4.5 mL of ethanol to produce a stock solution according to the protocol set out in Example 17. The stock solution was divided into 3 portions of 1.5 mL. A first portion of the stock solution was taken to calculate the baseline CBD concentration at t=0 by diluting with 3.5 mL of ethanol.

A second portion of the stock solution was transferred to a vial containing a stir bar. The second portion was diluted using 3.5 mL of water to create a turbid suspension. 100 mg of the cross-linked polymer was combined with the reaction mixture. It was then stirred at room temperature for 30 minutes.

An aliquot was taken and filtered by pipette filtration to calculate the CBD concentration at t=30. The reaction mixture was then filtered to retrieve the cross-linked polymer. The cross-linked polymer retrieved after filtration was suspended in 5 mL DMSO. An aliquot was taken to determine released CBD concentration t=rel.

Figure 88:
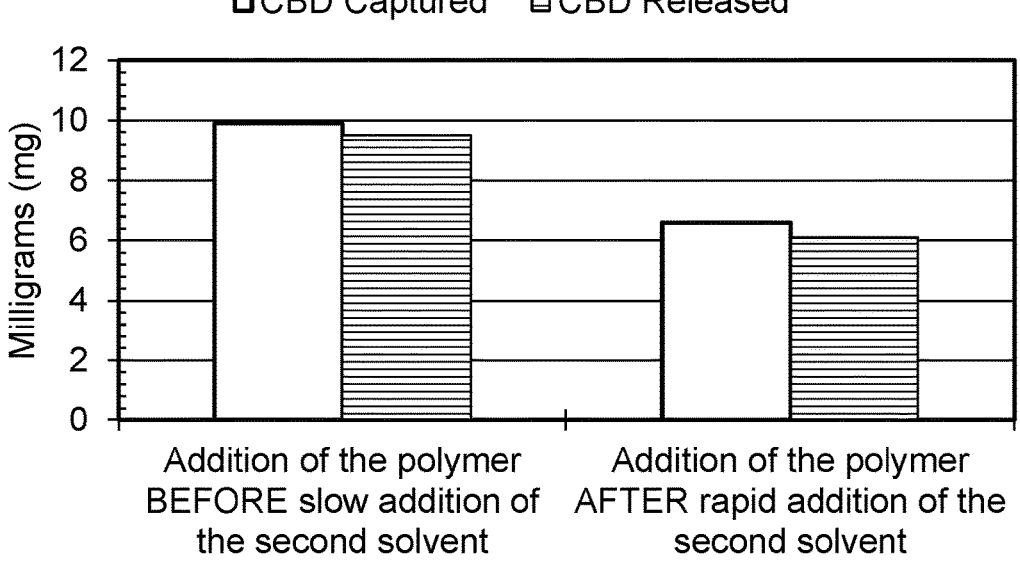
FIG. 88 shows mg CBD captured and released in Example 29.

FIG. 88 shows the mass of captured and released CBD resulting from Example 29. These results demonstrate application to turbid suspensions of target compounds successfully. These data also demonstrate that slow addition of the second solvent to induce capture by the polymer may be more efficient than rapid addition.

Example 30

Twenty milligrams of CBD were dissolved in 0.3 mL of ethanol and applied directly to a pipette column plugged with cotton and preloaded with 300 mg of a cross-linked polymer (<75 micron mesh size).

Water (5 mL) was applied to the column in five portions and collected in a single container following the application of compressed air to facilitate flow. An aliquot of this sample was taken to determine CBD concentration.

An ethanol-water mixture (2:8 EtOH:H$_2$O, 5 mL) was applied to the column in five portions and collected in a single container following the application of compressed air to facilitate flow. An aliquot of this sample was taken to determine CBD concentration.

An ethanol-water mixture (4:6 EtOH:H$_2$O, 5 mL) was applied to the column in five portions and collected in a single container following the application of compressed air to facilitate flow. An aliquot of this sample was taken to determine CBD concentration.

Ethanol (5 mL) was applied to the column in five portions and collected in a single container following the application of compressed air to facilitate flow. An aliquot of this sample was taken to determine CBD concentration.

Figure 89:
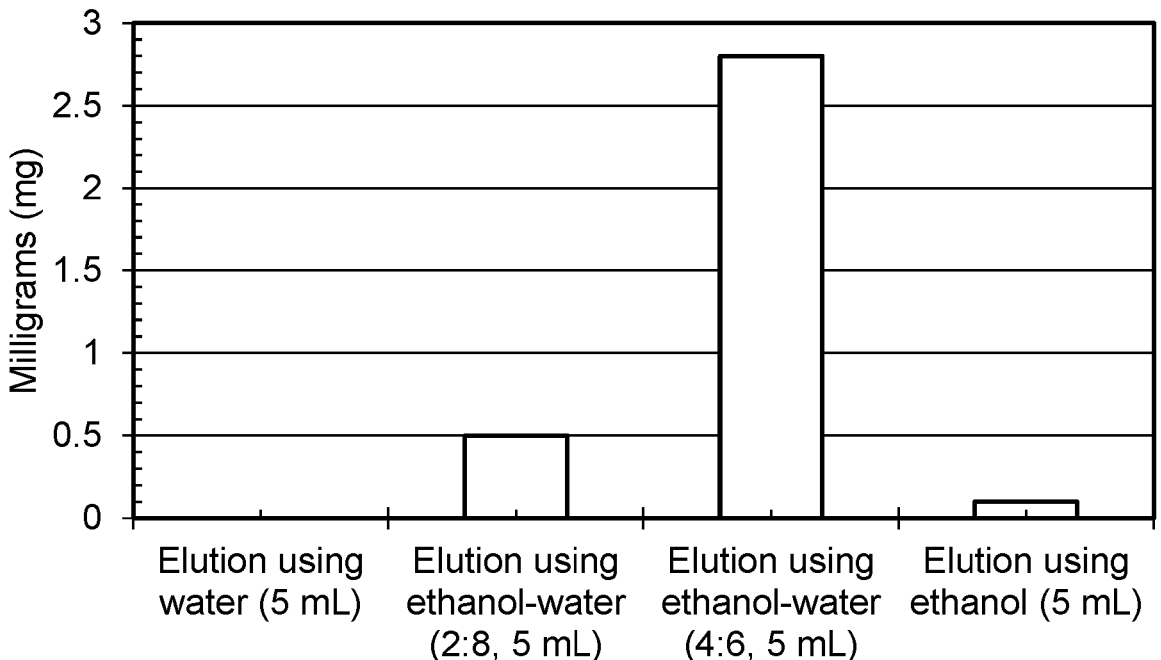
FIG. 89 shows mg CBD captured versus eluent in Example 30.

FIG. 89 shows the mass of released CBD resulting from Example 30. These results demonstrate use of the insoluble polysaccharide as a chromatography medium with gradient elution to retain and recover hydrophobic compounds. These results also demonstrate that ethanol-water mixtures may be used to elute hydrophobic substances from the cross-linked polymeric chromatography medium.

Example 31

Fifty milligrams of CBD were dissolved in 7.5 mL of an ethanol extract of hops according to the protocol set out in Example 20. The stock solution was divided into 5 portions of 1.5 mL. A first portion of the stock solution was taken to calculate the baseline CBD concentration at t=0 by diluting with 3.5 mL of ethanol.

Three portions of the stock solution were each transferred to three respective vials each containing a stir bar and 100 mg of the cross-linked polymer. To the first portion, water (3.5 mL) was added over the course of 7 minutes at a rate of 0.5 mL/minute. To the second portion, a sodium chloride solution in water (1 M, 3.5 mL) was added over the course of 7 minutes at a rate of 0.5 mL/minute. To the third solution, a trisodium citrate solution in water (1 M, 3.5 mL) was added over the course of 7 minutes at a rate of 0.5 mL/minute. The mixtures was then stirred at room temperature for 30 minutes.

From each portion, an aliquot was taken and filtered by pipette filtration to calculate the CBD concentration at t=30. The reaction mixture was then filtered to retrieve the cross-linked polymer. The cross-linked polymer retrieved after filtration each suspended in 5 mL ethanol. From each portion, an aliquot was taken to determine released CBD concentration t=rel.

Figure 90:
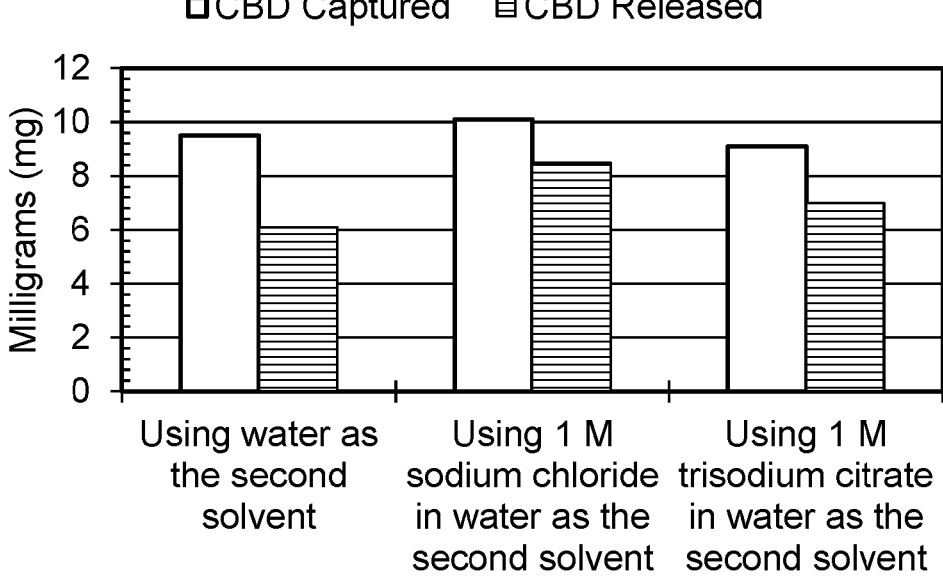
FIG. 90 shows mg CBD captured in Example 31.

FIG. 90 shows the mass of captured and released CBD resulting from Example 31. These results demonstrate that water-salt solutions may be used as the second solvent. These results also imply that a second solution with greater ionic strength may improve efficiency of hydrophobic compound recovery. In addition, it was observed visually that hydrophobic compound samples recovered using a brine solution as the second solvent contained fewer colored impurities.

Example 32

Sixty milligrams of CBD were dissolved in 9.0 mL of an ethanolic hops extract according to the protocol set out in Example 20. The stock solution was divided into 6 portions of 1.5 mL. One portion of the stock solution was taken to calculate the baseline CBD concentration at t=0 by diluting with 3.5 mL of ethanol.

Four portions of the stock solution were transferred to four separate vials each containing a stir bar and 100 mg of a structurally distinct cross-linked polymer derived from reaction of beta-cyclodextrin and a different diisocyanate as cross-linking agent. The first portion was added to a vial containing polymer prepared using hexamethylene diisocyanate (HDI-CDP). The second portion was added to a vial containing polymer prepared using isophorone diisocyanate (IPI-CDP). The third portion was added to a vial containing polymer prepared using 4,4'-methylenebis(phenyl isocyanate) (MPI-CDP). The fourth portion was added to a vial containing polymer prepared using tolylene-2,4-diisocyanate (TDI-CDP).

To each portion, brine (1.0 M, 3.5 mL) was added over the course of 7 minutes at a rate of 0.5 mL/minute. The mixtures were then stirred at room temperature for 30 minutes. From each portion, an aliquot was taken and filtered by syringe filtration to calculate the CBD concentration at t=30. The reaction mixtures were then filtered to retrieve the cross-linked polymers. The cross-linked polymer retrieved after filtration each suspended in 5 mL ethanol. From each portion, an aliquot was taken to determine released CBD concentration t=rel.

Figure 91:
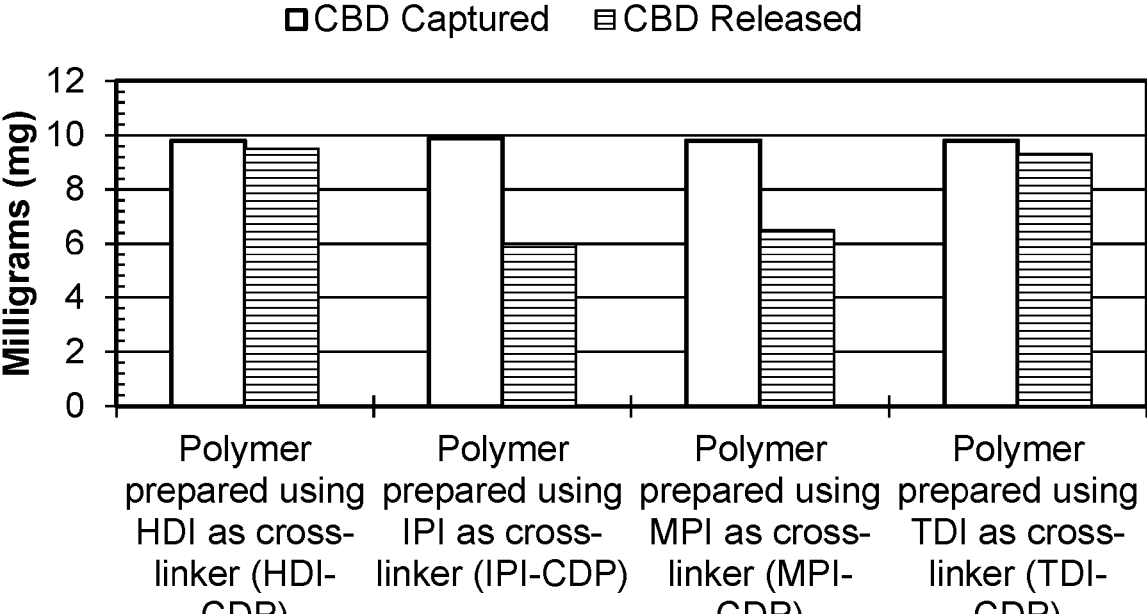
FIG. 91 shows mg CBD captured and released in Example 32.

FIG. 91 shows the mass of captured and released CBD resulting from Example 32. These results demonstrate that cross-linking agents other than hexamethylene diisocyanate can be employed to prepare insoluble polysaccharides for hydrophobic compound recovery. This data also demonstrates that the efficacy of compound recovery may have structure-activity dependence and that the polymer prepared using hexamethylene diisocyanate was more effective than the three other cross-linking agents used in Example 32.

Example 33

Fifty milligrams of CBD were dissolved in 7.5 mL of an ethanolic hops extract according to the protocol set out in Example 20. The stock solution was divided into 5 portions of 1.5 mL. One portion of the stock solution was taken to calculate the baseline CBD concentration at t=0 by diluting with 3.5 mL of ethanol.

Three portions of the stock solution were transferred to three separate vials each containing a stir bar and 100 mg of a cross-linked polymer derived from reaction of beta-cyclodextrin and hexamethylene diisocyanate at different CD:HDI molar ratios. The first portion was added to a vial containing polymer prepared using 1:8 CD to HDI. The second portion was added to a vial containing polymer prepared using 1:4 CD to HDI. The third portion was added to a vial containing polymer prepared using 1:2 CD to HDI.

To each portion, brine (1.0 M, 3.5 mL) was added over the course of 7 minutes at a rate of 0.5 mL/minute. The mixtures were then stirred at room temperature for 30 minutes. From each portion, an aliquot was taken and filtered by syringe filtration to calculate the CBD concentration at t=30. The reaction mixtures were then filtered to retrieve the cross-linked polymers. The cross-linked polymer retrieved after filtration each suspended in 5 mL ethanol. From each portion, an aliquot was taken to determine released CBD concentration t=rel.

Figure 92:
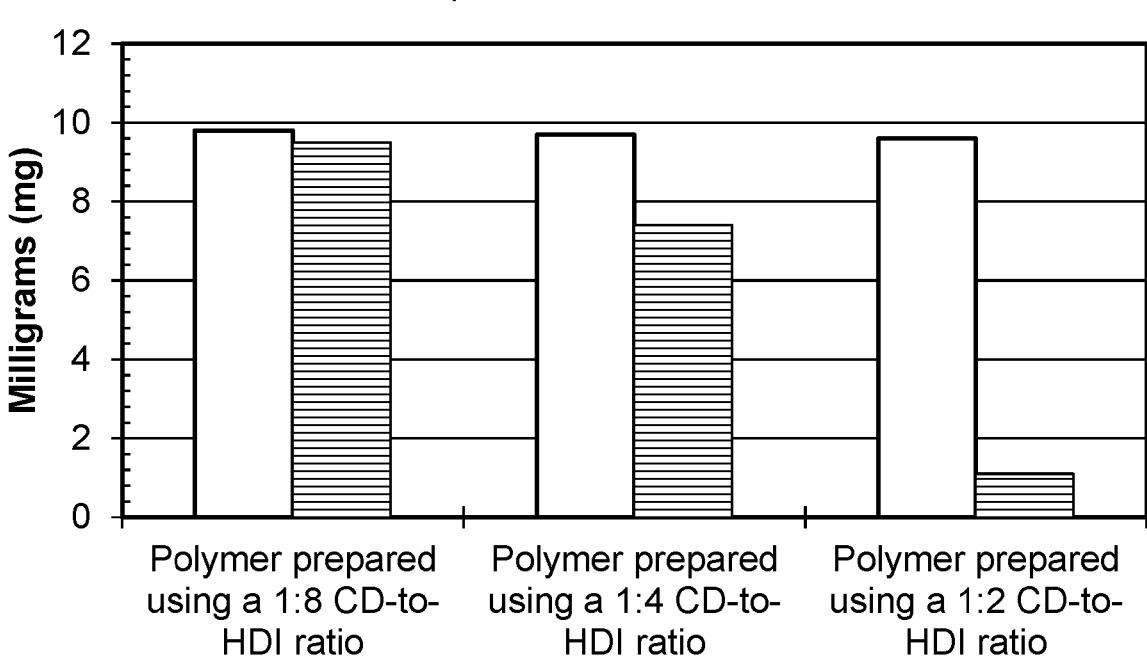
FIG. 92 shows mg CBD captured and released in Example 33.

FIG. 92 shows the mass of captured and released CBD resulting from Example 33. These results demonstrate that the molar proportion of cross-linking agent used in preparation of the polymer relative to the cyclodextrin may influence hydrophobic compound recovery. Specifically, the efficacy of hydrophobic compound recovery was shown to be optimal at 1:8 CD-to-HDI ratio relative to 1:4 or 1:2 ratios of CD-to-HDI.

Example 34

Dried plant material (4% moisture content) from the Carmagnola cultivar of *cannabis* hemp was determined to contain 2.69% total CBD (CBDA+CBD). Fresh plant matter (50.86 g, 72.5% moisture content) consisting of flower, buds, leaves, and small stems from the same source was finely chopped using shears and subsequently blended for 10 minutes in the presence of ethanol (250 mL) to produce a deep green solution and plant pulp.

The deep green solution and plant pulp was transferred to a round-bottomed flask fitted with a condenser and a stir bar. The mixture was heated to 70° C. and stirred at this temperature for a further 60 minutes before gradual cooling to room temperature. The mixture was filtered through filter paper using Büchner funnel, rinsing the residual plant material with additional ethanol to a final total volume of 340 mL to produce a stock solution.

From the stock solution, 6.0 mL was transferred to a vial containing 200 mg of the cross-linked polymer and a stir bar. Brine (1.0 M, 14.0 mL) was then combined with this portion over the course of 14 minutes at a rate of 1.0 mL/minute. The mixture was then stirred at room temperature for 30 minutes.

The reaction mixture was then filtered to retrieve the cross-linked polymer. The cross-linked polymer retrieved after filtration was suspended in 5 mL ethanol. An aliquot was taken to determine released total CBD concentration t=rel and compared with the theoretic maximum of recoverable total CBD based on dried plant matter analysis, adjusting for moisture content.

Figure 93:
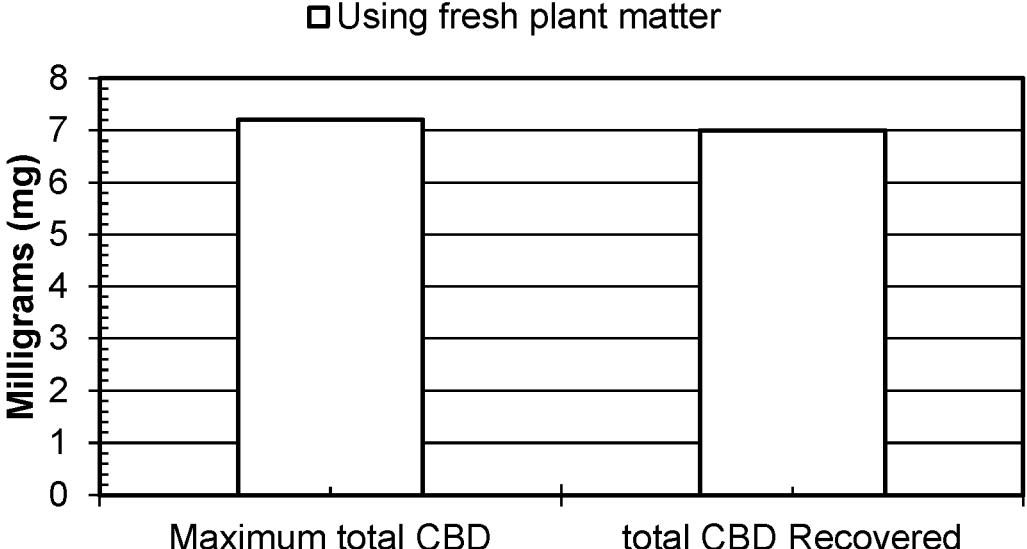
FIG. 93 shows mg CBD recoverable and recovered in Example 34.

FIG. 93 shows the maximum total CBD recoverable and total CBD recovered using fresh plant matter. These results demonstrate that influence of moisture in fresh plant matter did not negatively affect the removal of CBD and CBDA from the biomass into ethanol when facilitated by vigorous blending, stirring, and application of heat.

Example 35

Fifty milligrams of CBD were dissolved in 7.5 mL of an ethanolic hops extract according to the protocol set out in Example 20. The stock solution was divided into 5 portions of 1.5 mL. One portion of the stock solution was taken to calculate the baseline CBD concentration at t=0 by diluting with 3.5 mL of ethanol.

Three portions of the stock solution was transferred to three separate vials each containing a stir bar and 100 mg of the cross-linked polymer. To the first portion, an EDTA solution in water (1.0 M, 3.5 mL) was added over the course of 7 minutes at a rate of 0.5 mL/minute. To the second portion, EGTA solution in water (1 M, 3.5 mL) was added over the course of 7 minutes at a rate of 0.5 mL/minute. To the third solution, a citrate acid solution in water (1 M, 3.5 mL) was added over the course of 7 minutes at a rate of 0.5 mL/minute. The reaction mixtures were then stirred at room temperature for 30 minutes.

From each reaction mixture, an aliquot was taken and filtered by pipette filtration to calculate the CBD concentration at t=30. Each reaction mixture was then filtered to retrieve the cross-linked polymer. The cross-linked polymer retrieved after filtration each suspended in 5 mL ethanol.

From each portion, an aliquot was taken to determine released CBD concentration t=rel.

Figure 94:
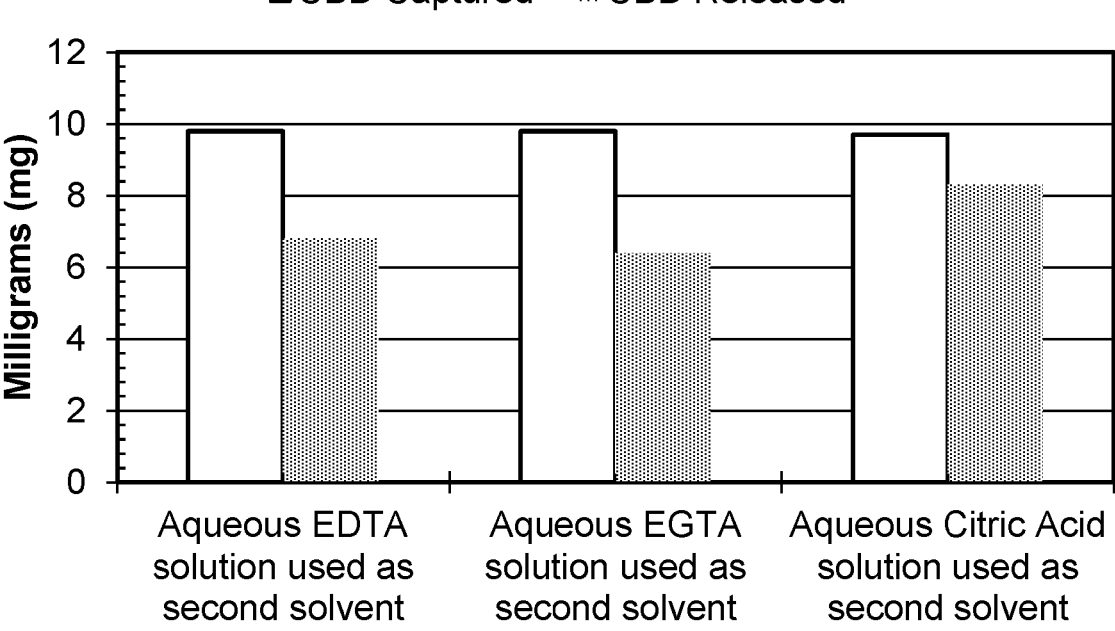
FIG. 94 shows mg CBD captured and released in Example 35.

FIG. 94 shows the mass of captured and released CBD resulting from Example 35. These results demonstrate that aqueous solutions of chelating agents may be used in place of water as the second solvent. These results also demonstrate that chelating agents influence the efficiency of hydrophobic compound recovery in a structure-dependent manner and that citric acid was optimal within the range demonstrated above. In addition, it was observed visually that hydrophobic compound samples recovered using an aqueous chelating agent solution as the second solvent contained fewer colored impurities when compared with using water alone.

Example 36

A deep eutectic solvent mixture was formed using equimolar portions of acetic acid and (±)-menthol by heating to 70° C. for one hour. Sixty milligrams of CBD were dissolved in 9.0 mL of the deep eutectic solvent mixture and heating was maintained while dissolution occurred to form a stock solution. The stock solution was divided into 4 portions of 1.5 mL. One portion of the stock solution was taken to calculate the baseline CBD concentration at t=0 by diluting with 3.5 mL of ethanol.

One portion of the stock solution was transferred to vial each containing a stir bar and 100 mg of the cross-linked polymer. With the continuation of heating to 70° C. and stirring, water (3.5 mL) was added over the course of 7 minutes at a rate of 0.5 mL/minute. The reaction mixtures were then stirred at 30 minutes with continued heating.

An aliquot was taken and filtered using a syringe filter then used to calculate the CBD concentration at t=30. The reaction mixture was then filtered to retrieve the cross-linked polymer. The cross-linked polymer retrieved after filtration each suspended in 5 mL ethanol. An aliquot was taken to determine released CBD concentration t=rel.

Figure 95:
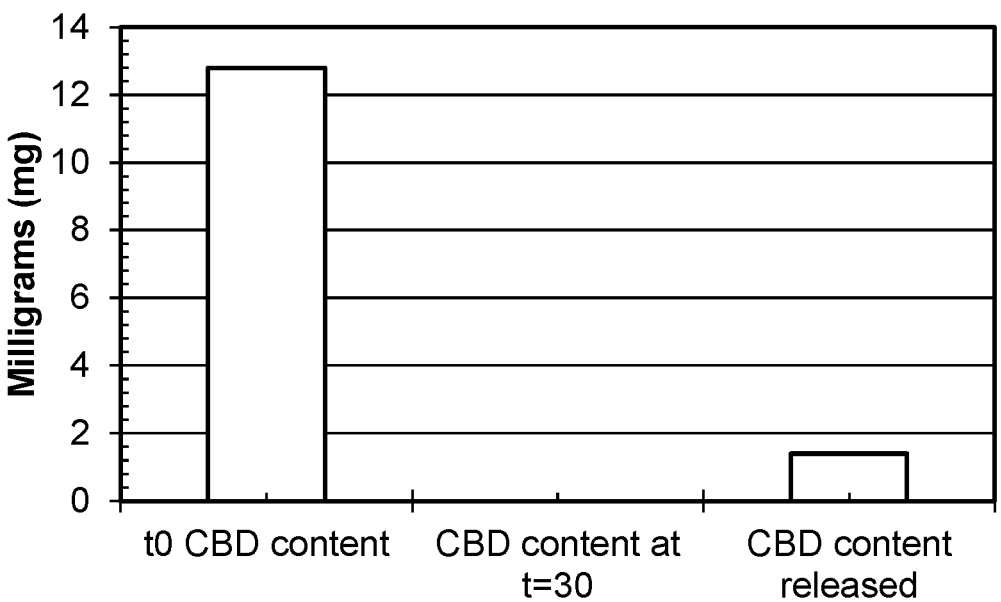
FIG. 95 shows mg CBD in solution at different time points in Examples 36 and 43.

FIG. 95 shows the CBD content recovered resulting from Example 36. These results demonstrate that non-conventional solvents including a deep eutectic solvent derived from (±)-menthol-acetic acid may be used in place of ethanol as the hydrophobic solvent.

Example 37

One hundred and fifty milligrams of CBD were dissolved in 20 mL of an ethanol extract of hops according to the protocol set out in Example 20 to produce a stock solution. This stock solution was divided into 4 portions of 4.0 mL each. One portion of the stock solution was taken to calculate the baseline CBD concentration at t=0 by diluting with 9.0 mL of ethanol.

One portion of the stock solution was transferred to a vial containing a stir bar and three portions of 100 mg of cross-linked polymer derived from α-, β- and γ-cyclodextrin (<125 micron particle size). Water (9.0 mL) was then combined with this portion over the course of 9 minutes at a rate of 1.0 mL/minute. The mixture was then stirred at room temperature for 30 minutes.

A chromatography column was packed with 1.5 g of coarsely-ground (125-250 micron particle size) cyclodextrin polymers (comprising a mixture of equal proportions of polymers derived from α-, β- and γ-cyclodextrin) to a height of 3.5 cm with diameter 1 cm.

The chromatography medium was flushed with 20 mL ethanol followed by 20 mL water. The first reaction mixture was poured onto the chromatography medium, rinsing the vial with 30 mL water. The liquid was entirely forced through the media using a gentle application of compressed gas. A 10 mL portion of ethanol was added to the top of the column, and the liquid entirely forced through the media in the same manner and collected in a separate receptacle. Using additional portions of ethanol this process was repeated a total of eight times.

The CBD content of each fraction was determined and the eluents combined to a total of 100 mL ethanol. The CBD content of combined ethanol fractions was determined.

Figure 96:
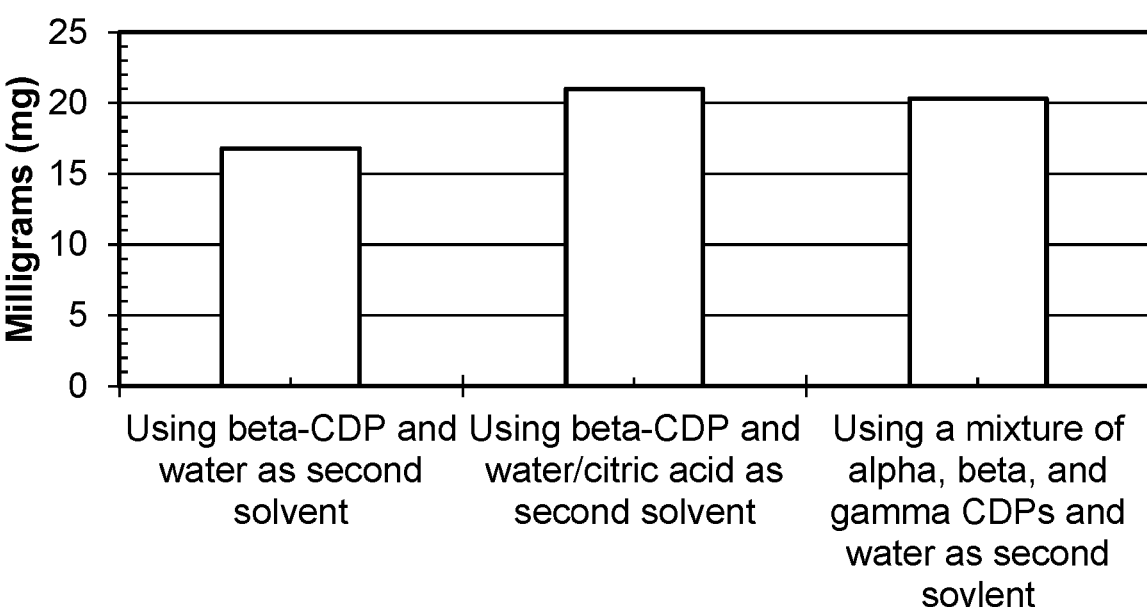
FIG. 96 shows mg total CBD recovered in Examples 37 and 38.

FIG. 96 shows total CBD recovered with different second solvents. These results demonstrate that polymers derived from α-, β- and γ-cyclodextrins may all be used for recovery of hydrophobic compounds.

Example 38

One hundred and fifty milligrams of CBD were dissolved in 20 mL of an ethanol extract of hops according to the protocol set out in Example 20 to produce a stock solution. The stock solution was divided into 4 portions of 4.0 mL each. One portion of the stock solution was taken to calculate the baseline CBD concentration at t=0 by diluting with 9.0 mL of ethanol.

One portion of the stock solution was transferred to a vial containing a stir bar and 300 mg of the cross-linked polymer derived from β-cyclodextrin (<125 micron particle size). Water (9.0 mL) was then combined with this portion over the course of 9 minutes at a rate of 1.0 mL/minute. The mixture was then stirred at room temperature for 30 minutes.

One portion of the stock solution was transferred to a vial containing a stir bar and 300 mg of the cross-linked polymer derived from β-cyclodextrin (178-400 micron particle size). An aqueous solution of citric acid (1.0 M, 9.0 mL) was then combined with this portion over the course of 9 minutes at a rate of 1.0 mL/minute to produce a reaction mixture. The reaction mixture was then stirred at room temperature for 30 minutes.

A chromatography column was packed with 1.5 g of the coarsely-ground cyclodextrin polymer (178-400 micron particle size) to height of 3.5 cm with diameter 1 cm. The chromatography medium was flushed with 20 mL ethanol followed by 20 mL water. The first reaction mixture was poured onto the chromatography medium, rinsing the vial with 30 mL water. The liquid was entirely forced through the media using a gentle application of compressed gas. A 10 mL portion of ethanol was added to the top of the column, and the liquid entirely forced through the media in the same manner and collected in a separate receptacle. Using additional portions of ethanol this process was repeated a total of four times.

The CBD content of each fraction was determined and the eluents combined to a total of 70 mL ethanol. The CBD content of combined ethanol fractions was determined. The second reaction mixture was subjected to the same chromatography protocol.

FIG. 96 shows, in addition to the data of Example 37, the total CBD recovered resulting from Example 38. These results demonstrate that a chelating agent can be utilized in the second solvent in addition to water was demonstrated to yield greater recovery of the hydrophobic target compound relative to water without a chelating agent and was visually observed to be less colored following the above chromatographic fractionation.

These results imply that solvents distinct from ethanol, specifically ionic liquid 1-butyl-3-methylimidazolium tetrafluoroborate, can be successfully used in conjunction with our capturing device and protocol to recover hydrophobic compounds.

Example 39

Sixty milligrams of CBD were dissolved in 9.0 mL of ethanol according to the protocol set out in Example 17. This stock solution was divided into six portions of 1.5 mL each. One portion of the stock solution was taken to calculate the baseline CBD concentration at t=0 by diluting with 3.5 mL of ethanol.

One portion of the stock solution was transferred to a vial containing a stir bar and 100 mg of the cross-linked polymer derived from beta-cyclodextrin (<125 micron particle size). Three portions of the stock solution were transferred to a vial containing a stir bar and 300 mg of the cross-linked polymer.

Water (3.5 mL) was then combined with the first vial over the course of 7 minutes at a rate of 0.5 mL/minute. Water (10.5 mL) was added to the second vial over the course of 10.5 minutes at a rate of 1.0 mL/minute.

Each vial was transferred to a rotary evaporator and the organic component was removed under reduced pressure. This process was performed slowly over the course of 30 minutes until all volatile organics had been removed a small quantity of aqueous material was observed to be distilling.

The reaction mixtures were then filtered to retrieve the cross-linked polymers. The cross-linked polymer retrieved after filtration of the first vial was suspended in 5 mL ethanol. An aliquot was taken to determine released CBD concentration t=rel.

The cross-linked polymer retrieved after filtration of the second vial was poured onto a chromatography column containing 300 mg cross-linked polymer (<125 micron particle size) that was previously packed using water and dried with compressed air. The column was flushed with water (20 mL) and pumped dry with compressed air. The column was flushed with DMSO (15 mL) to recover the CBD and an aliquot was taken to determine released CBD concentration t=col.

Sixty milligrams of CBD were dissolved in 9.0 mL of acetonitrile according to the protocol set out in Example 17. This stock solution was divided into six portions of 1.5 mL each. One portion of the stock solution was taken to calculate the baseline CBD concentration at t=0 by diluting with 3.5 mL of acetonitrile.

One portion of the stock solution was transferred to a vial containing a stir bar and 100 mg of the cross-linked polymer derived from beta-cyclodextrin (<125 micron particle size). Three portions of the stock solution were transferred to a vial containing a stir bar and 300 mg of the cross-linked polymer.

Water (3.5 mL) was then combined with the first vial over the course of 7 minutes at a rate of 0.5 mL/minute. Water (10.5 mL) was added to the second vial over the course of 10.5 minutes at a rate of 1.0 mL/minute.

Each vial was transferred to a rotary evaporator and the organic component was removed under reduced pressure. This process was performed slowly over the course of 30 minutes until all volatile organics had been removed a small quantity of aqueous material was observed to be distilling.

The reaction mixtures were then filtered to retrieve the cross-linked polymers. The cross-linked polymer retrieved after filtration of the first vial was suspended in 5 mL ethanol. An aliquot was taken to determine released CBD concentration t=rel.

The cross-linked polymer retrieved after filtration of the second vial was poured onto a chromatography column containing 300 mg cross-linked polymer (<125 micron particle size) that was previously packed using water and dried with compressed air. The column was flushed with water (20 mL) and pumped dry with compressed air. The column was flushed with ethanol (50 mL) to recover the CBD. The solution of CBD was subsequently concentrated to a total volume of 15 mL and an aliquot was taken to determine released CBD concentration t=col.

The process was repeated using dichloromethane and also hexane as the initial solvent.

Figure 97:
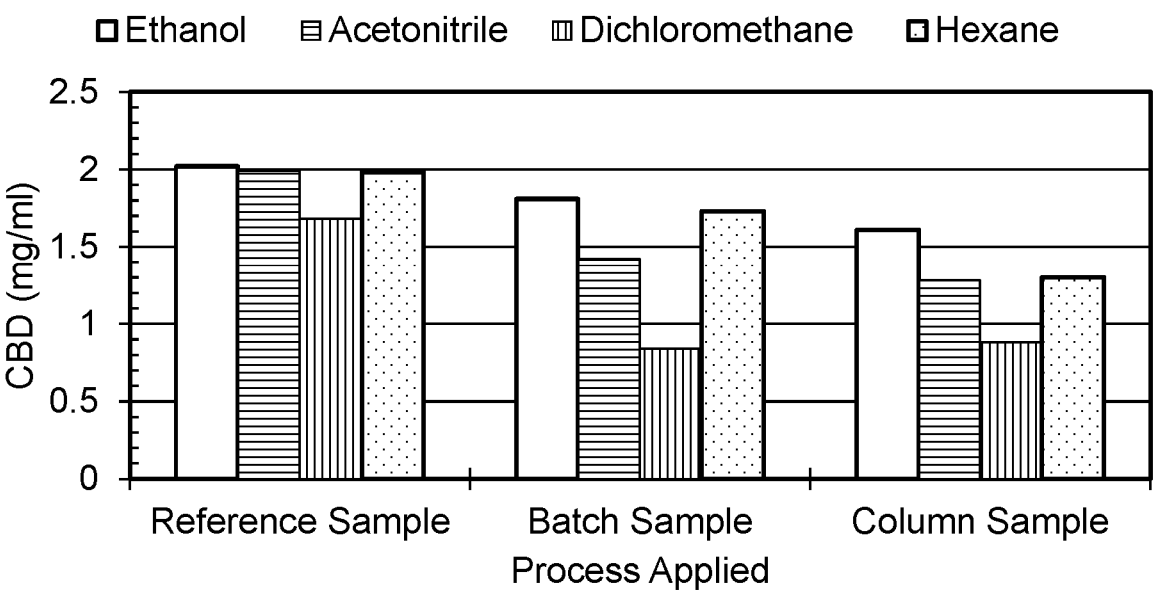
FIG. 97 shows mg/ml CBD recovered in Example 39.

FIG. 97 shows the CBD concentration resulting from Example 39. These results demonstrate that recovery of a hydrophobic target molecule can be achieved using the cross-linked polymer by gradual evaporation of a hydrophobic solvent from an aqueous mixture. By contrast with the 'standard' batch protocol, this technique has been employed using both water-miscible and water-immiscible solvents. In addition, these findings demonstrate that hydrophobic compounds captured following this technique can be eluted from a chromatography column following dry-loading of the polymer after the capture phase. Specifically, elution is not observed when flushing with a hydrophilic media but is eluted when flushing with more hydrophobic solvents.

Example 40

Eighty-six milligrams of CBD were dissolved in 10 mL of ethanol to produce a stock solution according to the protocol set out in Example 17. One 1.5 mL portion of the stock solution was taken to calculate the baseline CBD concentration at t=0 by diluting with 3.5 mL of ethanol.

One 7.5 ml portion stock solution above was transferred a glass reactor vessel called a peptide synthesis vessel, with an internal separating wall of sintered glass and a closed tap below, containing a stir bar and 100 mg of the cross-linked polymer, and held at a 45 degree angle. Water (17.5 mL) was then combined with this portion over the course of 17.5 minutes at a rate of 1 mL/minute. The mixture was then stirred at room temperature for 30 minutes.

The reaction mixture was then filtered at t=30 to retrieve the cross-linked polymer, by attaching the reaction vessel to Büchner flask under vacuum, and opening the rector tap. An aliquot was taken from the filtrate to calculate the CBD concentration at t=30. The reactor vessel tap was closed and The cross-linked polymer was resuspended in 5 mL DMSO and stirred for 30 minutes before filtering in the same manner. An aliquot was then taken from the filtrate to determine released CBD concentration t=rel.

This process of capture and release was then repeated 4 time without taking aliquots, and then a fifth time while taking aliquots. This set of five capture-release cycles was repeated twice, a total eleven capture-release cycles, including the initial cycle. Aliquots of capture and release after cycles 1, 6 and 11 showed the cross-linked polymer continued to capture and release CBD after uses.

Figure 98:
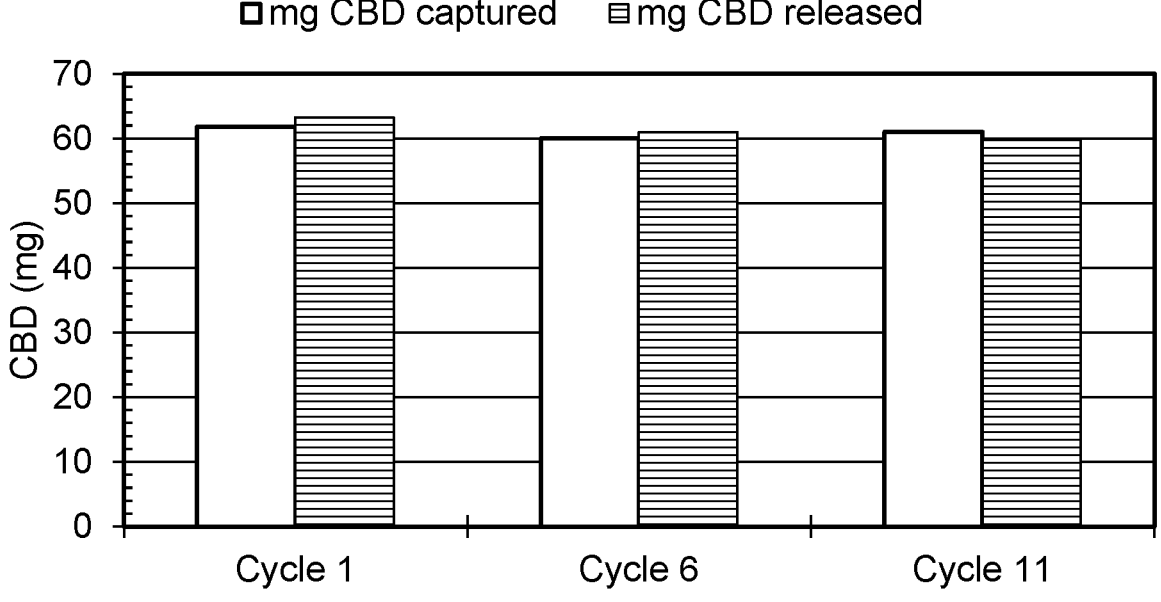
FIG. 98 shows mg CBD captured and released in Example 40.

FIG. 98 shows the total CBD captured and released resulting from Example 40. These results demonstrate that that capture of insoluble polysaccharides can be used repeatedly after regeneration to recover hydrophobic compounds in a closed system.

Example 41

Eighty-six milligrams of CBD were dissolved in 10 mL of ethanol to produce a stock solution according to the protocol set out in Example 17. One 1.5 mL portion of the stock solution was taken to calculate the baseline CBD concentration at t=0 by diluting with 3.5 mL of ethanol.

One 7.5 ml portion stock solution above was transferred a 50 mL round bottom flask, containing a stir bar and 100 mg of the cross-linked polymer. Water (17.5 mL) was then combined with this portion over the course of 17.5 minutes at a rate of 1 mL/minute. The mixture was then stirred at room temperature for 30 minutes.

An aliquot was taken and filtered through a glass pipette with cotton wool to calculate the CBD concentration at t=30. The cross-linked polymer was then filtered from the reaction mixture, washed with water, resuspended in 25 mL DMSO and stirred for 30 minutes before taking an aliquot and filtering in the same manner.

This process of capture and release was then repeated 4 times without taking aliquots, and then a fifth time while taking aliquots. This set of five capture-release cycles was repeated twice, a total eleven capture-release cycles, including the initial cycle. Aliquots of capture and release after cycles 1, 6 and 11 showed the cross-linked polymer continued to capture and release CBD after uses.

Figure 99:
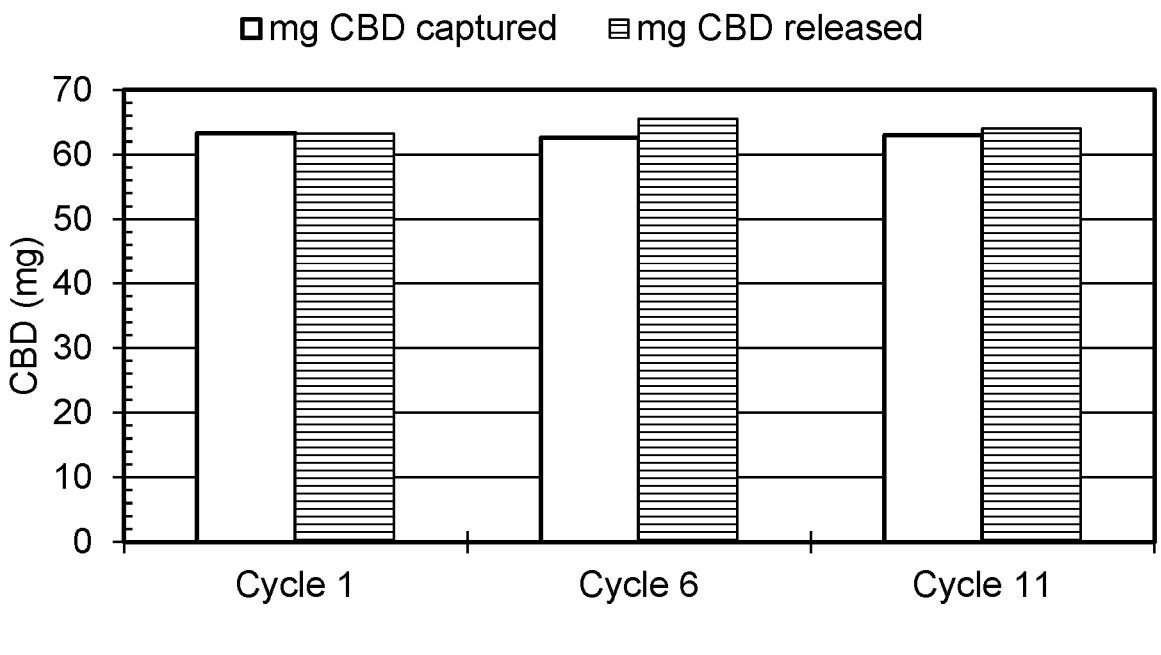
FIG. 99 shows mg CBD captured and released in Example 41.

FIG. 99 shows the total CBD captured and released resulting from Example 41.

Example 42

Eighty-six milligrams of CBD were dissolved in 10 mL of ethanol to produce a stock solution according to the protocol set out in Example 17. One 1.5 mL portion of the stock solution was taken to calculate the baseline CBD concentration at t=0 by diluting with 3.5 mL of ethanol.

One 7.5 ml portion stock solution above was transferred a glass reactor vessel called a peptide synthesis vessel, with an internal separating wall of sintered glass and a closed tap below, containing a stir bar and 100 mg of the cross-linked polymer, and held at a 45 degree angle. Water (17.5 mL) was then combined with this portion over the course of 17.5 minutes at a rate of 1 mL/minute. The mixture was then stirred at room temperature for 30 minutes.

The reaction mixture was then filtered at t=30 to retrieve the cross-linked polymer, by attaching the reaction vessel to Buchner flask under vacuum, and opening the rector tap. An aliquot was taken from the filtrate to calculate the CBD concentration at t=30. The reactor vessel tap was closed and the cross-linked polymer was resuspended in 25 mL DMSO and stirred for 30 minutes before filtering in the same manner. An aliquot was then taken from the filtrate to determine released CBD concentration t=rel.

Figure 100:
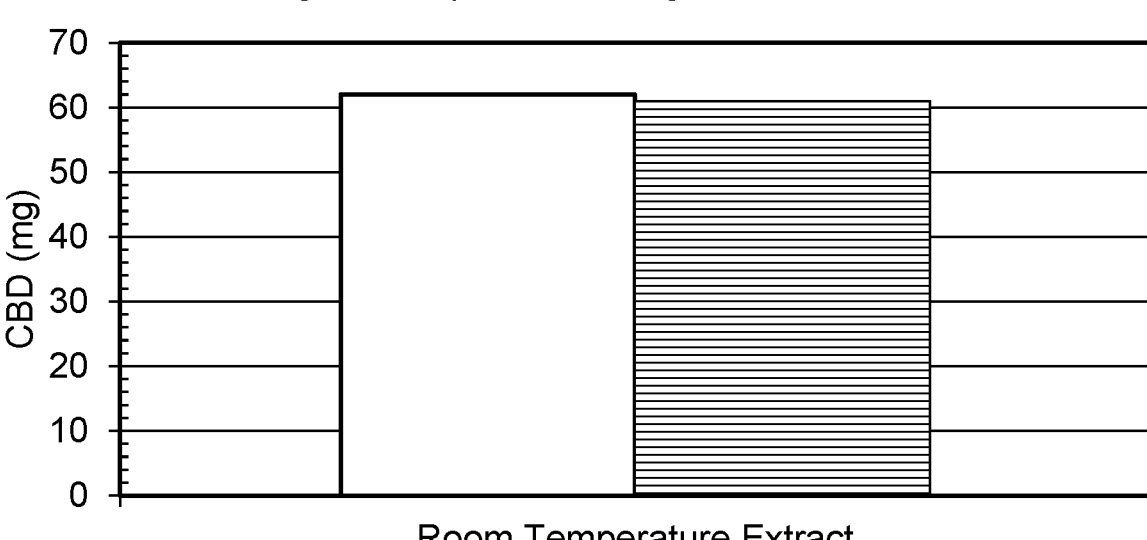
FIG. 100 shows mg CBD captured and released in Example 42.

FIG. 100 shows the total CBD captured and released resulting from Example 42.

Example 43

Thirty milligrams of CBD were dissolved in 4.5 mL of glucose syrup and stirring until dissolution occurred. This stock solution was divided into 3 portions of 1.5 mL. One portion of the stock solution was taken to calculate the baseline CBD concentration at t=0 by diluting with 3.5 mL of ethanol.

One portion of the stock solution was transferred to vial containing a stir bar and 100 mg of the cross-linked polymer. Water (3.5 mL) was added over the course of 7 minutes at a rate of 0.5 mL/minute. The mixtures was then stirred at 30 minutes with continued heating.

An aliquot was taken and filtered using a syringe filter then used to calculate the CBD concentration at t=30. The reaction mixture was then filtered to retrieve the cross-linked polymer. The cross-linked polymer retrieved after filtration each suspended in 5 mL ethanol. An aliquot was taken to determine released CBD concentration at release.

FIG. 95, in addition to Example 36, shows the mass of CBD resulting from Example 43. This data demonstrate that deep eutectic solvents including a commercial sugar syrup can be employed as the first solvent.

Example 44

Two hundred and fifty milligrams samples of cross-linked polymer were suspended in a series of buffer solutions and strong acids and bases: pH0 1M HCl, pH1 0.1M HCl/KCl buffer, pH3 0.1M Glycine/HCl buffer, pH4 0.1M citrate buffer, pH5 0.1M acetate buffer, pH7 0.1M phosphate buffer, pH9 0.1M Glycine/NaOH buffer, pH10 0.1M carbonate/bicarbonate buffer, pH13 0.1M NaOH/NaCl buffer, pH14 1M NaOH.

In each case, the polymer was stirred in a vial containing 25 mL of buffer solution for seven days. Samples were then filtered, washed with water and dried, and then analyzed by Fourier transform infrared spectroscopy for structural or chemical changes. No substantial differences were found between the FTIR spectra of the exposed polymers and that of the untreated polymer across the range of pHs and concentrations investigated.

A standard capture and release protocol as demonstrated in claim 17 was performed on the exposed sampled, which performed to the same standard as the untreated polymer, such as shown in FIG. 85. These results imply that a capturing device can be used to recover hydrophobic compounds following exposure to acidic and basic conditions.

Example 45

250 mg cross-linked polymer was heated in an oven at 120 degrees Celsius for 24 hours. The sample was cooled and analyzed by FTIR spectroscopy for structural or chemical changes. No substantial differences were found between the FTIR spectra of the heated polymer and that of the unheated polymer.

A standard capture and release protocol as demonstrated in claim 17 was performed on the heated sample, which performed to the same standard as the unheated polymer, such as shown in FIG. 85.

Example 46

Dried *cannabis* hemp plant material (2.02 g, 8.5% moisture content; 4.49% CBDA; 0.26% CBD; 0.19% THCA; <0.02% THC) was heated to 110° C. for 40 minutes in a convection oven. The recovered plant material (1.81 g) was transferred to a centrifuge tube containing activated charcoal (200 mg) and a stir bar. Ethanol (30 mL) was added and the mixture stirred vigorously for 3 hours at room temperature. The mixture was centrifuged for 30 minutes at 350 rpm and the amber colored liquid decanted by pipette transfer to a separate container.

From the above stock solution, 6.0 mL was transferred to a vial containing 200 mg of the insoluble polysaccharide and a stir bar. Brine (1.0 M, 14.0 mL) was then combined with this portion over the course of 28 minutes at a rate of 0.5 mL/minute. The mixture was then stirred at room temperature for 30 minutes.

The reaction mixture was then filtered to retrieve the cross-linked polymer. The cross-linked polymer retrieved after filtration was suspended in 6 mL ethanol. An aliquot was taken to determine released phytocannabinoid concentration and composition with comparison to the phytocannabinoid composition of the ethanolic *cannabis* extract.

Figure 101:
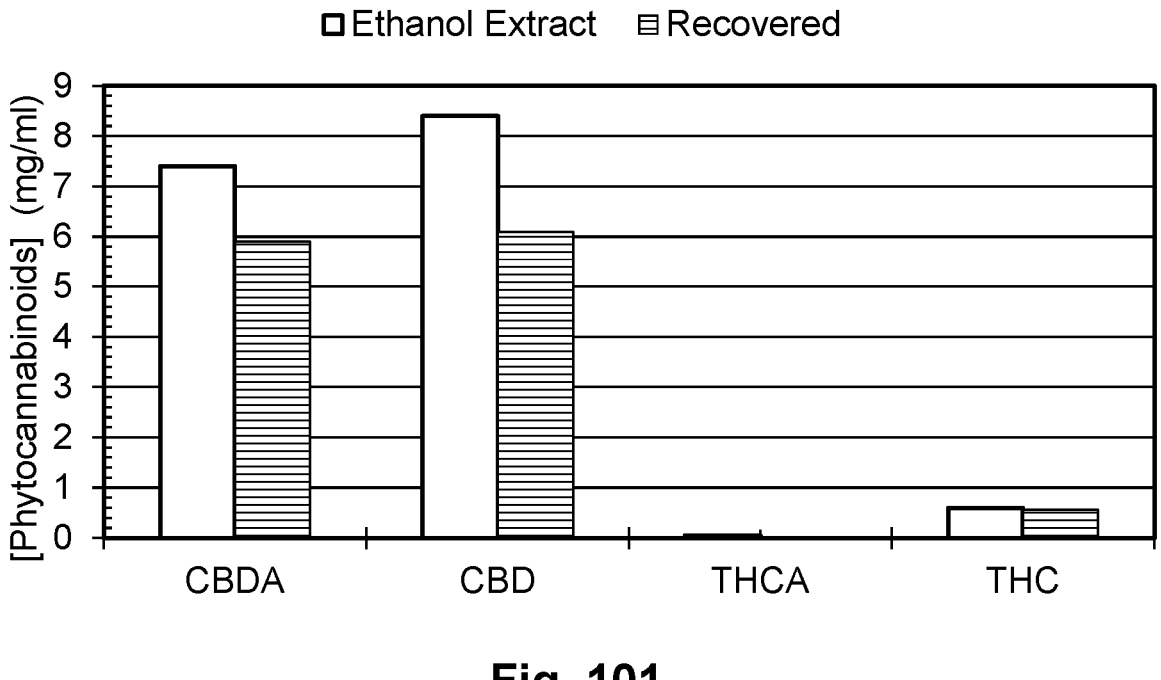
FIG. 101 shows mg/ml phytocannabinoids captured and released in Example 46.

FIG. 101 shows recovery of CBDA, CBD, THCA and THC of Example 46. This data demonstrates that partially decarboxylated *cannabis* hemp can be recovered using insoluble polysaccharides. This data also demonstrates that CBD and THC can be captured using insoluble polysaccharides and that some selectivity of capture is observed compared with the respective phytocannabinoid acid forms.

Example 47

130 milligrams of CBD were dissolved in 19.5 mL of ethanol according to the standard protocol. Two portions of 7.5 mL of the stock solution were transferred to two vials each containing 0.5 g of the insoluble polysaccharide polymer and a stir bar.

To each portion, water (17.5 mL) was added over the course of 17 minutes at a rate of 0.5 mL/minute. The mixtures were then stirred at room temperature for 30 minutes. Each reaction mixture was then filtered to retrieve the cross-linked polymers. Each polymer was transferred to a pipette plugged with cotton wool and purged of residual water using a flow of argon for 1 minute.

To the first pipette, butane gas was passed through in a constant stream that was maintained for 10 minutes. The butane having passed through the polymer was collected using a round bottomed flask and spontaneously evaporated under atmospheric pressure to provide the recovered CBD. The mass of the collected CBD was measured (18.6 mg) and the sample dissolved in ethanol (25.0 mL) to verify CBD quantity by HPLC.

To the second pipette, mixture of liquidized gases containing various linear, branched, cyclic, and aromatic hydrocarbons as well as carbon dioxide was passed through in a constant stream that was maintained for 10 minutes. The gases having passed through the polymer were collected using a round bottomed flask and evaporated rapidly under atmospheric pressure to provide the recovered CBD. The mass of the collected CBD was measured (36.3 mg) and the sample dissolved in 25.0 mL ethanol to verify CBD quantity by HPLC.

One 1.5 mL portion of the stock solution was subjected to the standard protocol for slurry batch capture and release using ethanol (5.0 mL) as the releasing solvent. The determined CBD concentration used as a reference comparison.

Figure 102:
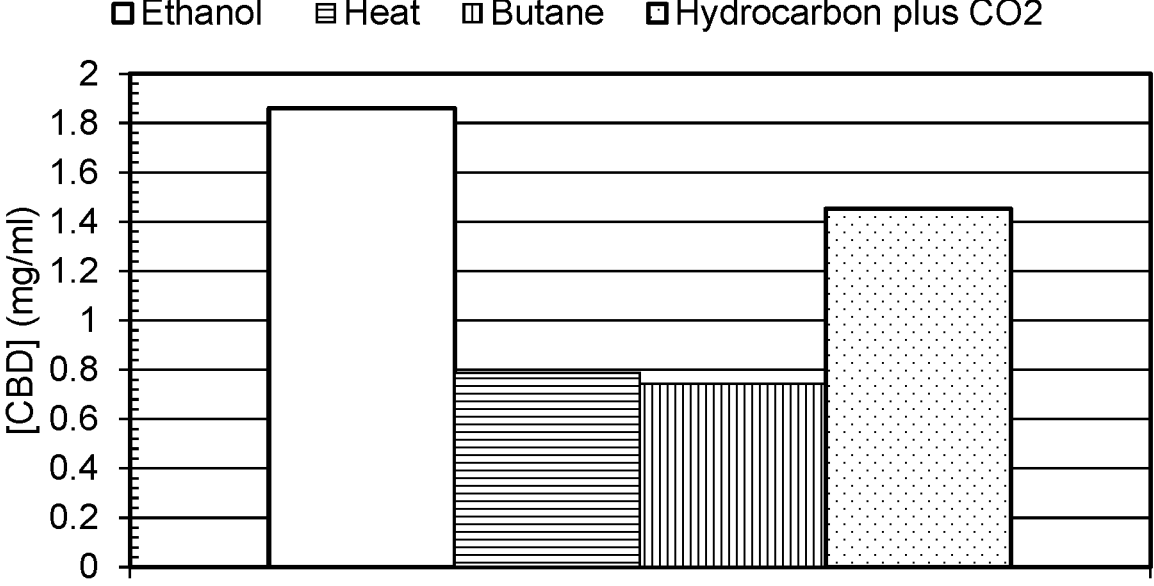
FIG. 102 shows mg/ml CBD captured and released in Examples 47 and 48.

FIG. 102 shows concentrations of CBD recovered using solvent driven or gas-driven CBD release in Example 47. This data demonstrates that liquidized gases with hydrophobic properties can be employed to promote the release of hydrophobic compounds bound to the insoluble polysaccharide. Furthermore, the rapid evaporation of the liquidized can be allow isolation of the hydrophobic compound from the polymeric polysaccharide in a solventless form.

Example 48

130 milligrams of CBD were dissolved in 19.5 mL of ethanol according to the standard protocol. 15 mL of the stock solution was transferred to a vial containing 1.0 g of the insoluble polysaccharide polymer and a stir bar.

Water (45.5 mL) was combined with this portion over the course of 45 minutes at a rate of 1.0 mL/minute. The mixture was then stirred at room temperature for 30 minutes. The reaction mixture was then filtered to retrieve the cross-linked polymer.

The polymer was transferred to a round bottomed flask fitted with a short-path distillation receiving bulb. The system was evacuated under reduced pressure and rotation was initiated. Conventional distillation treatment was applied, whereby the flask containing the polymer was heated and the receiving flask cooled until condensate was observed in the receiving flask.

The mass of the collected CBD was measured (39.4 mg) and the sample dissolved in 50.0 mL ethanol to verify CBD quantity by HPLC. One 1.5 mL portion of the stock solution was subjected to the standard protocol for slurry batch capture and release using ethanol (5.0 mL) as the releasing solvent. The determined CBD concentration used as a reference comparison.

FIG. 102 shows concentrate of CBD recovered using solvent driven or heat-driven CBD release in Example 48. This data also demonstrates that heat can be used to promote the release of hydrophobic compounds bound to the insoluble polysaccharide polymer. Furthermore, a conventional short path distillation setup can be employed to isolate the hydrophobic compound from the polymeric polysaccharide in a solventless form.

Example 49

FTIR and capture-release data demonstrate that recovery of hydrophobic target compounds after exposure of the insoluble polysaccharide to temperatures up to 120° C. performed to the same standard as the unheated polymer, such as shown in FIG. 85.

Example 50

FIG. 79 shows the amount in milligrams of CBD captured and released in Example 20. Samples of the captured hydrophobic target compounds were resolved on HPLC and measured using UV absorption at 254 nm.

FIGS. 103 and 104 show the chemical structures of xanthumol and flavanone, respectively. Xanthumol and flavanone are structural isomers and have the same molecular weight.

FIGS. 105 and 106 are time-course UV absorption graphs of the reaction mixture before the addition of the cross-linked polymer, and after filtration and flushing of the cross-linked polymer, respectively. The time-course UV spectra show resolution of compounds by HPLC.

In the UV spectra, CBD was visible prior to capture and release at about 12.6 min (FIG. 105). In addition to CBD, other peaks were lowered in FIG. 106, showing collection of other compounds by the polymer as shown by the presence of a larger xanthumol/flavanone peak at about 10.3 min in FIG. 105 than in FIG. 106.

REFERENCES

Ahmed, S. A.; Ross, S. A.; Slade, D.; Radwan, M. M.; Zulfigar, F.; ElSohly, M. A. *J. Nat. Prod.* 2008, 71(4), 536-542.

Ameh, S. J.; Obodozie, O. O.; Babalola, P. C.; Gamaniel, K. S. Br. *J. Pharmacol. Res.* 2011, 1(4), 99-123.

Anderson, R. P.; Zechar, K. *Respir. Med. Case Rep.* 2019, 26, 171-173; Al-Zouabi, I.; Stogner, J. M.; Miller, B. L.; Lane, E. S. *Subst. Abuse Rehabil.* 2018, 9, 91-101.

Arslan, M.; Sayin, S.; Yilmaz, M. *Tetrahedron: Asymmetry* 2013, 24, 982-989.

Azmir, J.; Zaidul, I. S. M.; Rahman, M. M.; Sharif, K. M.; Mohammed, A.; Sahena, F.; Jahurul, M. H. A.; Ghafoor, K.; Norulaini, N. A. N.; Omar, A. K. M. *J. Food Eng.* 2013, 117, 426-436.

Berman, P.; Futoran, K.; Lewitus, G. M.; Mukha, D.; Benami, M.; Shlomi, T.; Meiri, D. *Sci. Rep.* 2018, 8(1), 1-15.

Braganca de Carvalho, L.; Carvalho, T. G.; Margriotis, Z. M.; de Castro Ramalho, T.; de Maltos Alves Pinto, L. J. *Incl. Phenom. Macrocycl. Chem.* 2014, 78, 77-87.

Cai, C.; Yu, W.; Wang, C.; Liu, L.; Li, F.; Tan, Z. *J. Mol. Liq.* 2019, 287, 110957.

Cordier, C. J.; Morton, D.; Murrison, S.; Nelson, A. S.; O'Leary-Steele, C. *Nat. Prod. Rep.* 2008, 25, 719-737; (b) Morton, D.; Leach, S.; Cordier, C. J.; Warriner, S.; Nelson, A. *Angew. Chem. Int. Ed.* 2008, 48, 104-109.

Claude, B.; Morin, P.; Lafosse, M.; Belmont, A.-S., Haupt, K. Talanta, 2008, 75, 344-350.

Crini, G. *Chem. Rev.* 2014, 114(21), 10940-10975.

Davison, E. K.; Brimble, M. A. *Curr. Opin. Chem. Biol.* 2019, 52, 1-8.

Del Valle, E. M. M. *Process Biochem.* 2004, 39(9), 1033-1046.

Doorenbos, N. J.; Fetterman, P. S.; Quimby, M. W.; Turner, C. E. *Ann. N. Y. Acad. Sci.* 1971, 191, 3-14; (b) Sexton, M.; Shelton, K.; Haley, P.; West, M. *Planta Med.* 2018, 84(4), 234-41.

Gaoni, Y.; Mechoulam, R. *J. Am. Chem. Soc.* 1971, 93, 217-224.

Gilbert, B.; Alves, L. F. *Curr. Med. Chem.* 2003, 10(1), 13-20.

Grof, C. P. L. *Br. J. Clin. Pharmacol.* 2018, 84, 2463-2467.

Hazekamp, A.; Verpoorte, R. *Eur. J. Pharm. Sci.* 2006, 29, 340-47.

Krizek, T.; Bursova, M.; Horsley, R.; Kuchar, M.; Tuma, P.; Cabala, R.; Hlozek, T. *J. Cleaner Production* 2018, 193, 391-396.

Lewis, M. M.; Yang, Y.; Wasilewski, E.; Clarke, H. A.; Kotra, L. P. *ACS Omega* 2017, 2, 6091-6103.

Li, G.; Lou, H.-X. *Med. Res. Rev.* 2017, 38(4), 1255-1294.

Loftsson, T.; Brewster, M. E. *J. Pharm. Sci.* 1996, 85(10), 1017-1025.

Loomis, W. D.; Battaile, J. *Phytochemistry,* 1966, 5, 423-438.

Machado, B. A. S.; Pereira, C. G.; Nunes, S. B.; Padilha, F. F.; Umsza-Guez, M. A. *Sep. Sci. Technol.* 2013, 48(18), 2741-2760.

Mannila, J.; Jarvinen, T.; Jarvinen, K.; Jarho, P. *J. Pharm. Sci.* 2007, 96, 312-319.

Morin-Crini, N.; Winterton, P.; Fourmentin, S.; Wilson, L. D.; Fenyvesi, E.; Crini, G. *Progress in Polymer Science,* 2018, 78, 1-23.

Moulahcene, L.; Skiba, M.; Bounoure, F.; Benamor, M.; Milon, N.; Hallouard, F.; Lahiana-Skiba, M. *Int. J. Environ. Res. Public Health* 2019, 16, 414.

Ogawa, N.; Takahashi, C.; Yamamoto, H. *J. Pharm. Sci.* 2015, 104(3), 942-954.

Otta K., Zsadon B., Faragó J., Szejtli J., Tüdös F. (1988) *Cyclodextrin—Cellulose Copolymers.* In: Huber O., Szejtli J. (eds) Proceedings of the Fourth International Symposium on Cyclodextrins. Advances in Inclusion Science, vol 5. Springer, Dordrecht.

Peng, X.; Duan, M.-H.; Yao, X.-H.; Zhao, C.-J.; Zu, Y.-G.; Fu, Y.-J. *Separation and Purification Technol.* 2016, 157, 249-257.

Philippova, O.; Barabanova, A.; Molchanov, V.; Khokhlov A. *Eur. Pol. J.* 2011, 47, 542-559.

Pushpangadan, P.; George, V. *Handbook of Herbs and Spices* (Second Edition), Volume 1, 2012.

Radosevic, K.; Curko, N.; Srcek, V. G.; Bubalo, M. C.; Tomasevic, M.; Ganic, K. K.; Redovnikovic, I. R. *LWT* 2016, 73,45-51.

Rajewski, R. A.; Stella, V. J. *J. Pharm. Sci.* 1996, 85(11), 1142-1169.

Rates, S. M. K. *Toxicon* 2001, 39, 603-613.

Rovetto, L. J.; Aieta, N. V. *J. Supercrit. Fluids* 2017, 129, 16-27.

Ruesgas-Ramon, M.; Figueroa-Espinoza, M. C.; Durand, E. *J. Agric. Food Chem.* 2017, 65, 3591-3601.

Russo, E. B. *Br. J. Pharm.* 2011, 163(7), 1344-1364.

Starmans, D. A. J.; Nijhuis, H. H. *Trends in Food Science and Technology* 1996, 7(6), 191-197.

Still, C. W.; Kahn, M.; Mitra, A. *J. Org. Chem.* 1978, 14, 2923-2925.

Turner, C. E.; Cheng, P. C.; Lewis, G. S.; Russell, M. H.; Sharma, G. K. *Planta Med.* 1979, 37(11), 217-225.

Ventura, S. P. M.; e Silva, F. A.; Quental, M. V.; Mondal, D.; Freire, M. G.; Coutinho, J. A. P. *Chem. Rev.* 2017, 117, 6984-7052.

Yamasaki, H.; Makihata, Y.; Fukunaga, K. *J. Chem. Technol. Biotechnol.* 2006, 81, 1271-1276.

Yamasaki, H.; Makihata, Y.; Fukunaga, K. *J. Chem. Technol. Biotechnol.* 2008, 83, 991-997.

Ying, Z.; Shufen, L.; Xiwen, W.; Xing, Z. Chin. *J. Chem. Eng.* 2007, 15(6), 872-876.

Yue, D.; Yang, L.; Liu, S.; Li, J.; Li, W.; Ma, C. *Molecules,* 2016, 21, 204-217.

Zainal-Abidin, M. H.; Hayyan, M.; Hayyan, A.; Jayakumar, N. S. *Anal, Chim. Acta.* 2017, 979, 1-23.

Zulfigar, F.; Ross, S. A.; Slade, D.; Ahmed, S. A.; Radwan, M. M.; Ali, Z.; Khan, I. A.; ElSohly, M. A. *Tetrahedron Lett.* 2012, 53(28), 3560-3562.

In the preceding description, for purposes of explanation, numerous details are set forth in order to provide a thorough understanding of the embodiments. However, it will be apparent to one skilled in the art that these specific details are not required.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

The invention claimed is:

1. A method of selectively recovering a phytocannabinoid, the method comprising:

providing a solution comprising the phytocannabinoid in an organic solvent;

combining cyclodextrin with the solution, the cyclodextrin being insoluble in the solution;

combining a hydrophilic solvent with the solution, the hydrophilic solvent being less hydrophobic than the organic solvent for facilitating binding of the cyclodextrin with the phytocannabinoid;

isolating the cyclodextrin from the solution; and combining a hydrophobic dissociation solvent with the cyclodextrin for solubilizing the phytocannabinoid;

wherein the cyclodextrin is added to the solution before combining the hydrophilic solvent with the solution.

2. The method of claim 1, wherein providing the solution comprises combining bulk plant material from *Cannabis sativa* with the organic solvent and separating the bulk plant material from the organic solvent.

3. The method of claim 1, wherein the organic solvent is selected from the group consisting of acetone, acetonitrile, tetrahydrofuran, glycerol, DMSO, dichloromethane, and chloroform.

4. The method of claim 1, wherein the organic solvent comprises an alcohol.

5. The method of claim 4, wherein the alcohol is selected from the group consisting of methanol, ethanol, n-propyl alcohol, and isopropyl alcohol.

6. The method of claim 1, wherein the organic solvent comprises a hydrocarbon.

7. The method of claim 6, wherein the hydrocarbon is selected from the group consisting of n-hexane, butane, and propane.

8. The method of claim 1, wherein the hydrophilic solvent comprises water.

9. The method of claim 1, wherein the hydrophilic solvent comprises a chelating agent.

10. The method of claim 1, wherein combining the hydrophilic solvent with the solution comprises evaporating at least a portion of the organic solvent prior to combining the hydrophilic solvent with the solution.

11. The method of claim 1, wherein the cyclodextrin is selected from the group consisting of a-cyclodextrin, β-cyclodextrin, and y-cyclodextrin.

12. The method of claim 1, wherein the cyclodextrin is cross-linked with hexamethylene diisocyanate.

13. The method of claim 1, wherein the phytocannabinoid is selected from the group consisting of CBD, CBDA, THC, THCA, and CBG.

14. The method of claim 1, wherein the ratio of the phytocannabinoid to the cyclodextrin in the solution after combining the hydrophilic solvent with the solution is between 1:3 and 1:10.

15. The method of claim 1, wherein the cyclodextrin comprises a powder that is insoluble in the solution.

16. The method of claim 1, wherein:

the cyclodextrin is sequestered within an immersion filter by a pore size of the immersion filter that is smaller than the cyclodextrin; and the immersion filter is sized to receive filtrate that passes through the immersion filter.

17. The method of claim 16, wherein isolating the cyclodextrin from the solution comprises removing the immersion filter from the solution.

18. The method of claim 16, wherein combining the dissociation solvent with the cyclodextrin for recovering the phytocannabinoid comprises immersing the immersion filter in the dissociation solvent.

19. The method of claim 1, wherein the dissociation solvent is more hydrophobic than the organic solvent.

20. The method of claim 19, wherein the dissociation solvent is selected from the group consisting of methanol, ethanol, n-propyl alcohol and isopropyl alcohol, other alcohols, acetone, acetonitrile, tetrahydrofuran, glycerol, DMSO, dichloromethane, chloroform, other organic solvents, n-hexane, butane, propane, other hydrocarbons, glucose syrup, acetic acid mixed with menthol, other eutectic solvents, 1-butyl-3-methylimidazolium tetrafluoroborate, and other ionic liquids.

21. The method of claim 1, wherein combining the hydrophilic solvent with the solution comprises slowly adding the hydrophilic solvent to the solution to gradually decrease the solubility of the phytocannabinoid in the solution, until a target ratio of the organic solvent to the hydrophilic solvent is reached, for facilitating binding of the cyclodextrin with the phytocannabinoid.

22. The method of claim 21, wherein the target ratio of the organic solvent to the hydrophilic solvent is 4:6.

23. The method of claim 21, wherein the target ratio of the organic solvent to the hydrophilic solvent is 3:7.

24. The method of claim 21, wherein slowly adding the hydrophilic solvent to the solution comprises adding a volume of the hydrophilic solvent equal to $\frac{1}{20}$ the starting volume of the organic solvent in the solution each minute until the target ratio of the organic solvent to the hydrophilic solvent is reached.

25. The method of claim 21, wherein slowly adding the hydrophilic solvent to the solution comprises adding a volume of the hydrophilic solvent equal to $\frac{2}{15}$ the starting volume of the organic solvent in the solution each minute until the target ratio of the organic solvent to the hydrophilic solvent is reached.

26. The method of claim 21, wherein slowly adding the hydrophilic solvent to the solution comprises adding a volume of the hydrophilic solvent equal to $\frac{1}{6}$ the starting volume of the organic solvent in the solution each minute until the target ratio of the organic solvent to the hydrophilic solvent is reached.

27. The method of claim 21, wherein slowly adding the hydrophilic solvent to the solution comprises adding a volume of the hydrophilic solvent equal to $\frac{1}{3}$ the starting volume of the organic solvent in the solution each minute until the target ratio of the organic solvent to the hydrophilic solvent is reached.

28. The method of claim 21, wherein slowly adding the hydrophilic solvent to the solution comprises adding a volume of the hydrophilic solvent equal to $\frac{2}{3}$ the starting volume of the organic solvent in the solution each minute until the target ratio of the organic solvent to the hydrophilic solvent is reached.

29. The method of claim 21, wherein slowly adding the hydrophilic solvent to the solution comprises adding the hydrophilic solvent over a period of between 2 and 5 minutes.

30. The method of claim 1, wherein additional cyclodextrin is added to the solution after combining the hydrophilic solvent with the solution.

\* \* \* \* \*